United States Patent [19]

Harpold et al.

[11] Patent Number: 5,876,958
[45] Date of Patent: Mar. 2, 1999

[54] ASSAYS OF CELLS EXPRESSING HUMAN CALCIUM CHANNELS CONTAINING $\alpha_1\beta$ SUBUNITS

[75] Inventors: Michael M. Harpold; Steven B. Ellis, both of San Diego; Mark E. Williams, Carlsbad; Daniel H. Feldman, San Diego; Ann F. McCue, La Mesa, all of Calif.; Robert Brenner, Austin, Tex.

[73] Assignee: SIBIA Neurosciences, Inc., La Jolla, Calif.

[21] Appl. No.: 311,363

[22] Filed: Sep. 23, 1994

Related U.S. Application Data

[63] Continuation of Ser. No. 745,206, Aug. 15, 1991, Pat. No. 5,429,921, which is a continuation-in-part of Ser. No. 482,384, Feb. 20, 1990, Pat. No. 5,386,025, Ser. No. 603,751, filed as PCT/US89/01408, Apr. 4, 1989, abandoned, and Ser. No. 620,250, Nov. 30, 1990, abandoned, which is a continuation-in-part of Ser. No. 176,899, Apr. 4, 1988, abandoned.

[51] Int. Cl.[6] .................. C12Q 1/02; C12N 15/12
[52] U.S. Cl. .................. 435/29; 435/7.2; 435/7.21; 435/69.1
[58] Field of Search .................. 435/7.2, 29, 69.1, 435/7.21; 536/23.5

[56] References Cited

U.S. PATENT DOCUMENTS

| | | | |
|---|---|---|---|
| 4,788,135 | 11/1988 | Davis et al. | 435/6 |
| 4,912,202 | 3/1990 | Campbell et al. | 530/387 |
| 4,954,436 | 9/1990 | Froehner et al. | 435/7 |
| 5,024,939 | 6/1991 | Gorman | 435/69.1 |
| 5,051,403 | 9/1991 | Miljanich et al. | 514/12 |
| 5,189,020 | 2/1993 | Miljanich et al. | 514/12 |
| 5,264,371 | 11/1993 | Miljanich et al. | 436/503 |
| 5,424,218 | 6/1995 | Miljanich et al. | 436/503 |

FOREIGN PATENT DOCUMENTS

| | | |
|---|---|---|
| 2085502 | of 0000 | Canada . |
| 0507170 | 3/1992 | European Pat. Off. . |
| 0556651 | 4/1993 | European Pat. Off. . |
| 8907608 | 8/1989 | WIPO . |
| 8909834 | 10/1989 | WIPO . |
| 9113077 | 9/1991 | WIPO . |
| 9202639 | 2/1992 | WIPO . |
| 9304083 | 3/1993 | WIPO . |
| 9308469 | 4/1993 | WIPO . |
| 9402511 | 2/1994 | WIPO . |
| 9504144 | 2/1995 | WIPO . |

OTHER PUBLICATIONS

Powers, et al., "Assignment of the human gene for the $\alpha_1$ subunit of the cardiac DHP–sensitive $Ca^{2+}$ channel (CCHL1A1) to Chromosome 12p12–pter," *Genomics* 10:835–839 (1991).

Kim, et al., "IgG from patients with Lambert–Eaton syndrome blocks voltage–dependent calcium channels," *Science* 239:405–408 (1988).

Claudio, et al., "Genetic reconstitution of functional acetylcholine receptor channels in mouse fibroblasts," *Science* 238:1688–1694 (1987).

Tanabe, et al., "Primary structure of the receptor for calcium channel blockers from skeletal muscle," *Nature* 328:313–318 (1987).

Vaghy, et al., "Identification of a novel 1,4–dihydropyridine– and phenylalkylamine–binding polypeptide in calcium channel preparations," *J. Biol. Chem.* 262(29):14337–14342 (1987).

Nakayama, et al., "Purification of a putative $Ca^{2+}$ channel protein from rabbit skeletal muscle," *J. Biol. Chem.* 262:6572–6576 (1987).

Leung, et al., "Structural characterization of the 1,4–dihydropyridine receptor of the voltage–dependent $Ca^{2+}$ channel from rabbit skeletal muscle," *J. Biol. Chem.* 262(17):7943–7946 (1987).

Sharp, et al., "Identification and characterization of the dihydropyridine–binding subunit of the skeletal muscle dihydropyridine receptor," *J. Biol. Chem.* 62(25):12309–12315 (1987).

Takahashi, et al., "Subunit structure of dihydropyridine–sensitive calcium channels from skeletal muscle," *Proc. Natl. Acad. Sci. (USA)* 84:5478–5482 (1987).

Morton et al. "Monoclonal antibody identifies a 200–kDA subunit of the dihydropyridine–sensitive calcium channel," *J. Biol. Chem.* 262(25):11904–11907 (1987).

Barhanin, et al., "The calcium channel antagonists receptor from rabbit skeletal muscle: reconstitution after purification and subunit characterization," *Eur. J. Biochem.* 164:525–531 (1987).

Sieber, et al., "The 165–kDa peptide of the purified skeletal muscle dihydropyridine receptor contains the known regulatory sites of the calcium channel," *Eur. J. Biochem.* 167:117–122 (1987).

Lang, et al., "The effect of myasthenic syndrome antibody on presynaptic calcium channels in the mouse," *J. Physiol.* 390:257–270 (1987).

Curran and Morgan, "Barium modules c–fos expression and post–translational modification," *Proc. Natl. Acad. Sci.* 83:3521–8524 (1986).

Fisch, et al., "c–fos sequences necessary for basal expression and induction by epidermal growth factor, 12–O–tetradecanoyl phorbol–13–acetate, and the calcium inophore," *Mol. Cell. Biol.* 7(10):3490–3502 (1987).

Noda, et al., "Existence of distinct sodium channel messenger RNAs in rat brain," *Nature* 320:188–192 (1986).

Noda, et al., "Expression of functional sodium channels from cloned cDNA," *Nature* 322:826–828 (1986).

(List continued on next page.)

*Primary Examiner*—David L. Fitzgerald
*Attorney, Agent, or Firm*—Stephanie L. Seidman; Brown Martin Haller & McClain LLP

[57] ABSTRACT

Human calcium channel $\alpha_1$-, $\alpha_2$-, $\beta$- and $\gamma$-subunit encoding cDNAs, and related compositions and methods, are provided.

4 Claims, 14 Drawing Sheets

OTHER PUBLICATIONS

Mierendorf, et al., "Gene isolation by screening Kgtll libraries with antibodies," *Methods in Enz.* 152:458–469 (1986).

Gustin, et al., "Ion channels in yeast," *Science* 233:1195–1197 (1986).

Striessnig, et al., "Photoaffinity labelling of the phenylalkylamine receptor of the skeletal muscle transverse–tubule calcium channel," *FEBS Letters* 212(2):247–253 (1987).

Froehner, "New insights into the molecular structure of the dihydropyridine–sensitive calcium channel," *TINS* 11(3):90–92 (1988).

Catterall, et al., "Molecular properties of dihydropyridine–sensitive calcium channels in skeletal muscle," *J. Biol. Chem.* 263(8):3535–3538 (1988).

Curtis, et al., "Purification of the calcium antagonist receptor of the voltage–sensitive calcium channel from skeletal muscle transverse tubules," *Biochemistry* 23(10):2113–2118 (1984).

Borsotto, et al., "The 1,4–dihydropyridine receptor associated with the skeletal muscle voltage–dependent $Ca^{2+}$ channel," *J. Biol. Chem.* 260(26):14255–14263 (1985).

Cooper, et al., "Purification and characterization of the dihydropyridine–sensitive voltage–dependent calcium channel from cardiac tissue," *J. Biol. Chem.* 262(2):509–512 (1987).

Wood, "Gene cloning based on long oligonucleotide probes," *Methods in Enzymology* 152:443–447 (1987).

Schmid, et al., "Immunochemical analysis of subunit structure of 1,4–dihydropyridine receptors associated with voltage–dependent $Ca^{2+}$ channels in skeletal, cardiac, and smooth muscles," *Biochemistry* 25:3492–3495 (1986).

Mishina, et al., "Location of functional regions of acetylcholine receptor α–subunit by site–directed mutagenesis," *Nature* 313:364–369 (1985).

Hamill, et al., "Improved patch–clamp techniques for high–resolution current recording from cells and cell–free membrane patches," *Pfluger Archiv.European Journal of Physiology* 391:85–100 (1981).

Hess, et al., "Different modes of Ca channel gating behavior favored by dihydropyridine Ca agonist and antagonists," *Nature* 311:538–544 (1984).

Leung, et al., "Biochemical and ultrastructural characterization of the 1,4–dihydropyridine receptor from rabbit skeletal muscle," *J. of Biol. Chem.* 263(2):994–1001 (1988).

Imagawa, et al., "Phosphorylation of the 1,4–dihydropyridine receptor of the voltage–dependent $Ca^{2+}$ channel by an intrinsic protein kinase in isolated triads from rabbit skeletal muscle," *J. of Biol. Chem.* 262(17):8333–8339 (1987).

Miller, "Multiple calcium channels and neuronal function," *Science* 235:46–52 (1987).

Kozak, "An analysis of 5'–noncoding sequences from 699 vertebrate messenger RNAs," *Nucleic Acids Research* 15(20):8125–8148 (1987).

von Heijne, "Signal sequences: the limits of variation," *Jour. of Mol. Biol.* 184:99–105 (1985).

Hubbard, et al., "Synthesis and processing of asparagine–linked oligosaccharides[1,2]," *Ann. Rev. Biochem.* 50:555–583 (1981).

Feramisco, et al., "Optimal spatial requirements for the location of basic residues in peptide substrates for the cyclic AMP–dependent protein kinase," *Journal of Biological Chemistry* 255(9):4240–4245 (1980).

Takahashi, et al., "Identification of an α subunit of dihydropyridine–sensitive brain calcium channels," *Science* 236:88–91 (1987).

Hofmann, et al., "Regulation of the L–type calcium channel," *TINS* 8:393–398 (1987).

Curtis, et al., "Reconstitution of the voltage–sensitive calcium channel purified from skeletal muscle transverse tubules," *Biochemistry* 25:3077–3083 (1986).

Smith, et al., "Calcium channel activity in a purified dihydropyridine–receptor preparation of skeletal muscle," *Biochemistry* 26:7182–7188 (1987).

Meshi, et al., "Nucleotide sequence of the 30K protein cistron of cowpea strain of tobacco mosaic virus," *Nucleic Acids Research* 10(19):6111–6117 (1982).

Nikaido, et al., "Molecular cloning of cDNA encoding human interleukin–2 receptor," *Nature* 311:631–636 (1984).

Roberts, et al., "Paraneoplastic myasthenic syndrome IgG inhibits $^{45}Ca^{2+}$ flux in a human small cell carcinoma line," *Nature* 317:737–739 (1985).

Starr, et al., "Primary structure of a calcium channel that is highly expressed in rat cerebellum," *Proc. Natl. Acad. Sci. USA* 88:5621–5625 (1991).

Snutch, et al., "Distinct calcium channels are generated by alternative splicing and are differentially expressed in the mammalian CNS," *Neuron* 7:45–57 (1991).

Hui, et al., "Molecular cloning of multiple sybtypes of a novel rat brain isoform of the $a_1$ subunit of the voltage–dependent calcium channel," *Neuron* 7:35–44 (1991).

Bean et al., "Classes of calcium channels in vertebrate cells," *Annu. Rev. Physiol.* 51:367–384 (1989).

Swandulla, et al., "Do calcium channel classifications account for neuronal calcium channel diversity?" *TINS* 14(2):46–51 (1991).

Ruth, et al., "Primary structure of the α subunit of the DHP–sensitive calcium channel from skeletal muscle," *Science* 245:1115–1118 (1989).

Mikami, et al., "Primary structure and functional expression of the cardiac dihydropyridine–sensitive calcium channel," *Nature* 340:230–233 (1989).

Biel, et al., "Primary structure and functional expression of a high voltage activiated calcium channel from rabbit lung," *FEBS Letters* 269(2):409–412 (1990).

Mori, et al., "Primary structure and functional expression from complementary DNA of a brain calcium channel," *Nature* 350:398–402 (1991).

Snutch, et al., "Rat brain expresses a heterogeneous family of calcium channels," *Proc. Natl. Acad. Sci. USA* 87:3391–3395 (1990).

Perez–Reyes, et al., "Molecular diversity of L–type calcium channels," *J. of Biol. Chem.* 265(33):20430–20436 (1990).

Perez–Reyes, et al., "Induction of calcium currents by the expression of the $α_1$–subunit of the dihydropyridine receptor from skeletal muscle," *Nature* 340:233–236 (1989).

Koch, et al., "Characterization of cDNA clones encoding two putative isoforms of the $α_1$–subunit of the dihydropyridine–sensitive voltage–dependent calcium channel isolated from rat brain and rat aorta," *FEBS Letters* 250(2):386–388 (1989).

Slish, et al., "Evidence for the existence of a cardiac specific isoform of the $α_1$–subunit of the voltage dependent calcium channel," *FEBS Letters* 250(2):509–514 (1989).

Varadi, et al., "Development regulation of expression of the $α_1$ and $α_2$ subunits mRNAs of the voltage–dependent calcium channel in a differentiating myogenic cell line," *FEBS Letters* 250(2)CE:515–518 (1989).

Jongh, et al., "Subunits of purified calcium channels: a 212–kDa form of $\alpha_1$ and partial amino acid sequence of a phosphorylation site of an independent β–subunit," *Proc. Natl. Acad. Sci. USA* 86:8585–8589 (1989).

Hamilton, et al., "Subunit composition of the purified dihydropyridine binding protein from skeletal muscle," *Biochemistry* 28:7820–7828 (1989).

Nunoki, et al., "Activation of purified calcium channels by stoichiometric protein phosphorylation," *Proc. Natl. Acad. Sci. USA* 86:6816–6820 (1989).

Ichida, et al., "Photoaffinity labeling with dihyropyridine derivatives of crude membranes from rat skeletal, cardiac, ileal, and uterine muscles and whole brain," *J. Biochem.* 105:767–774 (1989).

Sharp and Campbell, "Characterization of the 1,4–dihydropyridine receptor using subunit–specific polyclonal antibodies," *J. Biol. Chem.* 264(5):2816–2825 (1989).

Campbell, et al., "The biochemistry and molecular biology of the dihydropyridine–sensitive calcium channel," *TINS* 11(10):425–430 (1988).

Pelzer, et al., "Properties and regulation of calcium channels in muscle cells," *Rev. Physiol. Biochem. Pharmacol.* 114:107–207 (1990).

Kim, et al., "Studies on the structural requirements for the activity of the skeletal muscle dihydropyridine receptor/slow $Ca^{2+}$ channel," *J. Biol. Chem.* 11858–11863 (1990).

Lotan, et al., "Specific block of calcium channel expression by a fragment of dihydropyridine receptor cDNA," *Science* 243:666–669 (1989).

Rampe, et al., "[$^3$H]Pn200–110 binding in a fibroblast cell line transformed with the $\alpha_1$ subunit of the skeletal muscle L–type $Ca^{2+}$ channel," *Biochem. and Biophys.Research Communications* 169(3):825–831 (1990).

Adams, et al., "Intramembrane charge movement restored in dysgenic skeletal muscle by injection of dihydropyridine receptor cDNAs," *Nature* 346:569–572 (1990).

Tanabe, et al., "Cardiac–type excitation–contraction coupling in dysgenic skeletal muscle injected with cardiac dihydropyridine receptor cDNA," *Nature* 344:451–453 (1990).

Tanabe, et al., "Regions of the skeletal muscle dihydropyridine receptor critical for excitation–contraction coupling," *Nature* 346:567–569 (1991).

Regulla, et al., "Identification of the site of interaction of the dihydropyridine channel blockers nitrendipine and azidopine with the calcium–channel $\alpha_1$ subunit," *EMBO Journal* 10(1):45–49 (1991).

Sher, et al., "Voltage–operated calcium channels in small cell lung carcinoma cell lines: pharmacological, functional, and immunological properties," *Cancer Research* 5:3892–3896 (1990).

Sher, et al., "w–Conotoxin binding and effects on calcium channel function in human neuroblastoma and rat pheochromocytoma cell lines," *FEBS Letters* 235(1,2):178–182 (1988).

Koch, et al., "cDNA cloning of a dihydropyridine–sensitive calcium channel from rat aorta," *J. of Biol.Chem.* 265(29):17786–17791 (1990).

Bosse, et al., "The cDNA and deduced amino acid sequence of the γ subunit of the L–type calcium channel from rabbit skeletal muscle," *FEBS* 267(1):153–156 (1990).

Burns, et al., "Calcium channel activity of purified human synexin and structure of the human synexin gene," *Proc. Natl. Acad. Sci.* 86:3798–3802 (1989).

Campbell, et al., "32,000–Dalton subunit of the 1,4–dihydropyridine receptor," *Ann. N.Y. Acad. Sci.* 560:251–257 (1989).

Dascal, N., "The use of Xenopus oocytes for the study of ion channels," *CRC Critical Rev. Biochem.* 22(4):317–387 (1987).

DeJongh, et al., "Subunits of purified calcium channels," *J. Biol. Chem.* 265(25):14738–14741 (1990) (best available copy submitted).

Jay, et al., "Primary Structure of the γ subunit of the DHP–sensitive calcium channel from skeletal muscle," *Science* 248:490–492 (1990).

Jay, et al., "Structural characterization of the dihydropyridine–sensitive calcium channel $\alpha_2$–subunit and the associated δ peptides," *J. Biol. Chem.* 266(5):3287–3293 (1991).

Leung, et al., "Monoclonal antibody characterization of the 1,4–dihydropyridine receptor of rabbit skeletal muscle," *Ann. N.Y. Acad. Sci.* 522:43–46 (1988).

Vaghy, et al., "Mechanism of action of calcium channel modulator drugs," *Ann. N.Y. Acad. Sci.* 522:176–186 (1988).

Ahlijanian, et al., "Subunit structure and localization of dihydropyridine–sensitive calcium channels in mammalian brain, spinal cord, and retina," *Neuron* 4:819–832 (1990).

Blount, et al., "Assembly intermediates of the mouse muscle nicotinic Acetylcholine receptor in stably transfected fibroblasts," *J. Cell. Biol.* 111:2601 (1990).

Carbone, et al., "Ca currents in human neuroblastoma IMR32 cells: kinetics, permeability and pharmacology," *Pfluegers Arch.* 416:170–179 (1990) (best available copy submitted).

Dascal, et al., "Expression of modulation of voltage–gated calcium channels after RNA injection in Xenopus oocytes," *Science* 231:1147–1150 (1986).

Hess, et al., "Calcium channels in vertebrate cells," *Ann. Rev. Neurosci.* 13:337–356 (1990).

Stanley, et al., "Characterization of a calcium current in a vertebrate cholinergic presynaptic nerve terminal," *J. Neurosci.* 11:985 (1991).

Wei, et al., "Heterologous regulation of the cardiac $Ca^{2+}$ channel $\alpha_1$ subunit by skeletal muscle β and γ subunits," *J. Biol. Chem.* 266:21943–21947 (1991).

Claudio, T., "Stable expression of transfected Torpedo acetylocholine receptor α subunits in mouse fibroblast L cells," *Proc. Natl. Acad. Sci.* 84:5967–5971 (1987).

Seagar, et al., "Molecular properties of dehydropyrine–sensitive calcium channels," *Ann. N.Y. Acad. Sci.* 552:162–175 (1988).

Takahashi and Catterall, "Dihydropyridine–sensitive calcium channels in cardiac and skeletal muscle membranes: studies with antibodies against the α–subunits," *Biochemistry* 26(17):1518–1526 (1987).

Cruz et al., "Characterization of ω–Conotoxin Target. Evidence for Tissue–Specific Heterogeneity ion Calcium Channel Types", *Biochem. J.* 26:820 (1987).

Breitbart et al.,, "Alternatvie Splicing: A Ubiquitous Mechanism for the Generation of Multiple Protein Isoforms From Single Genes", *Ann. Rev. Biochem.* 56:467–495 (1984).

Spedding et al., "Calcium Antgonists': A Class of Drugs with a Bright Future. Part II. Determination of Basic Pharmacological Properties," *Life Sciences* 35:575–587 (1984).

Pragnell, et al., "Cloning and tissue–specific expression of the brain calcium channel β–subunit," *FEBS Letters,* 291:253 (1991).

Ellis, et al., "Sequence and Expression of mRNAs Encoding the $\alpha_1$ and $\alpha_2$ Subunits of DHP–Sensitive $Ca^{++}$ Channels," *Science* 241:1661–1664 (1988).

Williams, et al., "Structure and functional expression of $\alpha_1$, $\alpha_2$ and $\beta$ subunits of a novel human neuronal calcium channel subtype," *Neuron* 8:71–84 (1992).

Olivera, et al., "Conotoxins," *J. of Biol. Chem.* 266(33):22067–22070 (1991).

Kasai, H., "Tonic inhibition and rebound facilitation of a neuronal calcium channel by a GTP–binding protein," *Proc. Natl.Acad.Sci. USA* 88:8855–8859 (1991).

Cohen, et al., "Distribution of $Ca^{2+}$ channels on frog motor nerve terminals revealed by fluorescent w–conotoxin," *J. of Neuroscience* 11(4):1032–1039 (1991).

Ahlijanian, et al., "Phosphorylation of an α1–like subunit of an ω–conotoxin–sensitive brain calcium channel by cAMP–dependent protein kinase and protein kinase C," *J. Biol. Chem.* 266:20192 (1991).

Sakamoto, et al., "A monoclonal antibody to the $\beta$ subunit of the skeletal muscle dihydropyridine receptor immunoprecipitates the brain ω–conotoxin GVIA receptor," *J. Biol. Chem.* 266:18914 (1991).

Tsien, et al., "Molecular diversity of voltage–dependent $Ca^{2+}$ channels," *Trends in Pharmacol. Sci.* 12:349–353 (1991).

Williams et al., "Structure and Functional Expression of an ω–Conotoxin–Sensitive Human N–Type Calcium Channel", *Science* 257:389–395 (1992).

Brust, *Neuropharmacology* 32(11):1089–1102 (1993).

Williams, et al., "Structure and Functional Characterization of Neuronal $\alpha_{1E}$ Calcium Channel Subtypes," *J. Biol. Chem.* 269(35):22347–22357 (1994).

```
R.Sk    GTGGTAACGAGAGATGACTAACTTAGCCTTTGAACTTAGAGAGCCCCTTAGAGACTTAGAGAGGACGAGAGGCAGAGCTCGGTGAGCAG
         |||||||||||||| |||||||||||||||||||| |||||||||||||||||| |||  ||||||||||||||||||||||||||
H.Sk    GTGGTAATGAAATGACTAACTTAGCCTTTGAACTTAGAGACCCCCTAGAGTTAGAGAGGAAGAGGCTGAGCTTGGTGAGCAG
         ||  ||
H.Br    GTGCCAAACAGAAGCAGAAGTCG..................................
         || ||
H.Aor   GT......................................................

R.Sk    AGCGGGCTCTGCCAAGACTAGCGTTAGCAGTGTCACCACCCCGCCACCCCACGGCACACGCATCCCCCTTCTTTAAGAAGAC
         || || ||||||||||||||||||  |||||||||||||||||||  ||||| |||||||  |||||||||||||||||
H.Sk    AGTGGCTCTGCCAAGACTAGTGTTAGCAGTGTCACCACCCCGCCACCCCATGGCAAACGCATCCCCCTTCTTTAAGAAGAC
                                                                                        ..AC
H.Br    ..............................................................................
                                                                                        .GAC
H.Aor   ..............................................................................
```

FIG. 7A

| | | | | | | | | |
|---|---|---|---|---|---|---|---|---|
| R.SK($\beta_1$) | PPASG | NEMTNLAFEL | EPLDLEEDEA | ELGEQSGSAK | TSVSSVTTPP | PHGTRIPFFK | KTEHV |
| H.SK($\beta_1$) | PPASG | NEMTNLAFEL | DPLELEEEA | ELGEQSGSAK | TSVSSVTTPP | PHGKRIPFFK | KTEHV |
| H.BR($\beta_2$) | PPASA | KQKQKS..... | .......... | .......... | .......... | .......... | .TEHV |
| H.AO($\beta_4$) | PPAS. | .......... | .......... | .......... | .......... | .......... | .TEHV |

FIG. 7B ent molecular mass of 52–65 kD (as determined by SDS-
ASSAYS OF CELLS EXPRESSING HUMAN CALCIUM CHANNELS CONTAINING $\alpha_1\beta$ SUBUNITS This application is a continuation of application Ser. No. 07/745,206, filed 15 Aug. 1991, now U.S. Pat. No. 5,429,921, which is a continuation-in-part of application Ser. No. 07/620,250, filed 30 Nov. 1990, now abandoned, which is in turn a continuation-in-part of application Ser. No. 07/176,899, filed 4 Apr. 1988, now abandoned. Application Ser. No. 07/745,206 is also a continuation-in-part of application Ser. No. 07/482,384, filed 20 Feb. 1990, now U.S. Pat. No. 5,386,025, and a continuation-in-part of application Ser. No. 07/603,751, filed 8 Nov. 1990, now abandoned, which is the national stage (35 U.S.C. § 371) of international application Ser. No. PCT/US89/01408, filed 4 Apr. 1989.

TECHNICAL FIELD

The present invention relates to molecular biology and pharmacology.

More particularly, the invention relates to calcium channel compositions and methods of making and using same.

BACKGROUND OF THE INVENTION

Calcium channels are membrane-spanning, multi-subunit proteins that allow controlled entry of $Ca^{2+}$ ions into cells from the extracellular fluid. Cells throughout the animal kingdom, and at least some bacterial, fungal and plant cells, possess one or more types of calcium channel.

The most common type of calcium channel is voltage dependent. In a voltage-dependent channel, the "opening" to allow an influx of $Ca^{2+}$ ions into the cells to begin, requires a depolarization to a certain level of the potential difference between the inside of the cell bearing the channel and the extracellular medium bathing the cell. The rate of influx of $Ca^{2+}$ into the cell depends on this potential difference. All "excitable" cells in animals, such as neurons of the central nervous system, peripheral nerve cells, and muscle cells, including those of skeletal muscles, cardiac muscles, and venous and arterial smooth muscles, have voltage-dependent calcium channels.

Calcium channels are physiologically important because the channels have a central role in regulating intracellular $Ca^{2+}$ levels. These levels are important for cell viability and function. Thus, intracellular $Ca^{2+}$ concentrations are implicated in a number of vital processes in animals, such as neurotransmitter release, muscle contraction, pacemaker activity, and secretion of hormones and other substances.

The rabbit skeletal muscle calcium channel is the most well-characterized of the calcium channels identified to date. Biochemical analysis of the calcium channel purified from rabbit skeletal muscle revealed that it consists of two large subunits, of between about 130 and about 200 kilodaltons ("kD") in molecular weight, and a number (generally thought to be one to three) of different smaller subunits, of less than about 60 kD in molecular weight. At least one of the larger subunits and possibly some of the smaller are glycosylated. Some of the subunits are capable of being phosphorylated.

The two large subunits of voltage-dependent calcium channels are designated herein the "$\alpha_1$-subunit" and the "$\alpha_2$-subunit".

The rabbit skeletal muscle calcium channel $\alpha_1$-subunit is not detectably changed in molecular weight when treated with dithiothreitol ("DTT") or with enzymes which catalyze removal of N-linked sugar groups from glycosylated proteins. The $\alpha_1$-subunit has a molecular weight of about 150 to about 170 kD when analyzed by sodium dodecylsulfate ("SDS")-polyacrylamide gel electrophoresis ("PAGE") after isolation from mammalian muscle tissue and has specific binding sites for various 1,4-dihydropyridines ("DHPs") and phenylalkylamines.

The molecular weight of the $\alpha_2$-subunit of the rabbit skeletal muscle calcium channel is at least about 130–150 kD, as determined by SDS-PAGE analysis in the presence of DTT after isolation from muscle tissue. However, in SDS-PAGE under non-reducing conditions (in the presence of N-ethylmaleimide), the $\alpha_2$-subunit migrates with a band of about 160–190 kD. The smaller fragments (of about 30 kD), which appear to be released upon reduction, are derived from the primary translation product of the $\alpha_2$ subunit transcript. There is evidence that the $\alpha_2$-subunit and the corresponding fragment produced under reducing conditions are glycosylated with at least N-linked sugars and do not have specified binding sites for 1,4-dihydropyridines and phenylalkylamines that are known to bind to the $\alpha_1$-subunit.

The $\beta$-subunit of the rabbit skeletal muscle calcium channel has recently been characterized as having an apparent molecular mass of 52–65 kD (as determined by SDS-PAGE analysis). It is comprised of consensus phosphorylation sites and has been shown by biochemical methods to be phosphorylated. This subunit is insensitive to reducing conditions.

The $\gamma$-subunit of the calcium channel has not been observed in all purified preparations, depending on the source of material analyzed, the investigating laboratory, and so on. The native material appears to be a glycoprotein with an apparent molecular mass of 30–33 kD, as determined by SDS-PAGE analysis. The native protein is believed to be glycosylated since its apparent molecular mass decreases after digestion with neuraminidase followed by endoglycosidase F.

Multiple types of calcium channels have been detected based on electrophysiological and pharmacological studies of various mammalian cells from various tissues (e.g., skeletal muscle, cardiac muscle, lung, smooth muscle and brain) [Bean, B. P., *Annu. Rev. Physiol.* 51:367–384 (1989) and Hess, P., *Annu. Rev. Neurosci.* 56:337 (1990)). These different types of calcium channels have been broadly categorized into four classes, L-, T-, N-, and P-type, distinguished by current kinetics, holding potential sensitivity and sensitivity to calcium channel agonists and antagonists. Four subtypes of neuronal voltage-dependent calcium channels have been proposed [Swandulla, D. et al., *Trends Neurosci* 14:46 (1991)].

Characterization of a particular type of calcium channel by analysis of whole cells is severely restricted by the presence of mixed populations of different types of calcium channels in the majority of cells. This hindrance is also a drawback in attempting to discern whether a calcium current with properties that preclude categorization on the basis of these four broad classes is generated by a new type or subtype of calcium channel or a previously classified channel that is obscured by contaminating currents. Although single-channel recording methods can be used to examine individual calcium channels, such analysis reveals nothing about the molecular structure or biochemical composition of the channel. Furthermore, in this type of analysis, the channel is isolated from other cellular constituents that might be important for natural functions and pharmacological interactions.

Structural features of calcium channels can also be used in evaluation and characterization of different types of calcium channels. However, large amounts of pure channel protein are required to understand, at the molecular level, the nature of the subunits and their various interactions, for example, with one another, with the cell membranes across which the channels allow $Ca^{2+}$ ions to pass, with $Ca^{2+}$ and other ions, and with low molecular weight compounds such as drugs (pharmacological agents) that affect channel function. Due to the complex nature of these multi-subunit proteins, the varying levels of calcium channels in tissue sources of the protein, the presence of mixed populations of calcium channels in tissues, and the modifications of the native protein that can occur during the isolation procedure, it is extremely difficult to obtain large amounts of highly purified, completely intact calcium channel protein.

Characterization of the gene or genes encoding calcium channels provides another means of characterization of different types of calcium channels. The amino acid sequence determined based on the complete nucleotide sequence of the coding region of a gene encoding a calcium channel protein represents the actual primary structure of the protein. Furthermore, secondary structure of the calcium channel protein and the relationship of the protein to the membrane may be predicted based on analysis of the primary structure. For instance, hydropathy plots of the αl subunit protein of the rabbit skeletal muscle calcium channel indicate that it contains four internal repeats, each containing six putative transmembrane regions. [Tanabe, T. et al., *Nature* 328:313 (1987).]

The cDNA and corresponding amino acid sequences of the α1, α$_2$, β and γ subunits of the rabbit skeletal muscle have been determined [see Tanabe et al., *Nature* 328:313–318 (1987), Ellis et al., PCT Application No. WO 89/09834, Ruth et al., *Science* 245:1115–1118 (1989), and U.S. patent application Ser. No. 482,384, filed Feb. 20, 1990, (the disclosure of which is hereby incorporated by reference), respectively]. In addition, the cDNA and corresponding amino acid sequences of αl subunits of rabbit cardiac muscle [Mikami, A. et al., *Nature* 340:230–233 (1989)] and lung [Biel, M., *FEBS Letters* 269:409–412 (1990)] calcium channels have been determined. Recently, a rabbit brain calcium channel (designated the BI channel) cDNA was isolated [Mori, Y. et al., *Nature* 350:398–402 (1991)]. The amino acid sequences deduced from the rabbit skeletal muscle, rabbit cardiac muscle, and rabbit lung cDNAs and the rabbit brain BI cDNA indicate that these proteins share some general structural features. However, the sequences share, at most, ~60% homology and appear to be encoded by a minimum of three distinct genes. These findings correlate with the varied intensities of hybridization of the rabbit skeletal muscle calcium channel αl subunit cDNA to rabbit genomic DNA fragments as reported by Ellis et al., *Science* 241:1661–1664 (1988).

Interestingly, partial cDNAs encoding portions of several different subtypes of the calcium channel αl subunit have been isolated from rat brain [Snutch, T. et al., *Proc. Natl. Acad. Sci USA* 87:3391–3395 (1990)]. These are referred to as rat brain class A, B, C and D cDNAs. More recently full-length rat brain class A [Starr, T. et al., *Proc. Natl. Acad. Sci. USA* 88:5621–5625 (1991)] and class C [Snutch, T. et al., *Neuron* 7:45–57 (1991)] cDNAs have been reported. Although the amino acid sequence encoded by the rat brain class C cDNA is approximately 95% identical to that encoded by the rabbit cardiac muscle calcium channel α1 subunit cDNA, the amino acid sequence encoded by the rat brain class A cDNA shares only 33% sequence identity with the amino acid sequences encoded by the rabbit skeletal or cardiac muscle α1 subunit cDNAs. A cDNA encoding another calcium channel α1 subunit was also recently reported [Hui, A. et al., *Neuron* 7:35–44 (1991)]. The amino acid sequence encoded by this cDNA is ~70% homologous to the proteins encoded by the rabbit skeletal and cardiac muscle calcium channel cDNAs.

A cDNA closely related to the rat brain class C α1 subunit cDNA and partial cDNA sequences closely related to other cDNAs encoding apparently different calcium channel α1 subunits have also been described [see Snutch, T. et al., *Neuron* 7:45–57 (1991), Perez-Reyes, E., Wei, X., Castellano, A. and Birnbaumer, L.,*J. Biol. Chem.* 265:20430 (1990), and Hui, A. et al, *Neuron* 7:35–44 (1991)]. Evidence suggests that the closely related cDNA sequences, which are identical to some of the previously isolated αl subunit cDNAs except in certain limited areas, represent variants generated by alternative splicing of a primary gene transcript.

Although the existence of numerous types and subtypes of calcium channel α1 subunits with a broad range of homologies is of interest, this information may be of limited utility in the absence of the knowledge of the functional characteristics of the calcium channels containing these different α1 subunits. Insufficient information is available to predict or discern, based on the primary structure of the $\alpha_1$ subunits, the functional or pharmacological properties of voltage-dependent calcium channels containing the different $\alpha_1$ subunits. Therefore, attempts to recombinantly express mammalian calcium channel α1 subunits have been reported.

To date, successful recombinant expression has been reported for only three of the six or seven different rabbit or rat $\alpha_1$ subunit cDNAs referred to in the preceding paragraphs. Perez-Reyes et al., *Nature* 340:233–236 (1989) have described the presence of voltage-dependent calcium currents in murine L cells transfected with the rabbit skeletal muscle calcium channel α1 subunit cDNA. These currents were enhanced in the presence of Bay K8644 (a known calcium channel agonist). Bay K8644-sensitive $Ba^{2+}$ currents have been detected in oocytes injected with in vitro transcripts of the rabbit cardiac muscle calcium channel α1 subunit cDNA [Mikami, A. et al., *Nature* 340:230–233 (1989)]. These currents were substantially reduced in the presence of the calcium channel antagonist nifedipine. Significantly, the barium currents of an oocyte co-injected with transcripts of the rabbit cardiac muscle calcium channel α1 subunit cDNA and the rabbit skeletal muscle calcium channel α2 subunit cDNA were more than 2-fold larger than those of oocytes injected with transcripts of the rabbit cardiac calcium channel α1 subunit cDNA. Similar results were obtained when oocytes were co-injected with transcripts of the rabbit lung calcium channel α1 subunit cDNA and the rabbit skeletal muscle calcium channel α2 subunit cDNA, i.e., the barium current was enhanced relative to that detected in oocytes injected with transcripts of the rabbit lung calcium channel α1 subunit cDNA only [Biel, M. et al, *FEBS Letters* 269:409–412 (1990)]. Most recently, Mori et al., *Nature* 350:398–402 (1991) report the presence of inward barium currents in oocytes injected with in vitro transcripts of the rabbit brain BI channel cDNA. These currents were increased by two orders of magnitude when in vitro transcripts of the rabbit skeletal muscle calcium channel α2-, β-, or α2-, β-and γ-subunits were co-injected with transcripts of the BI cDNA. Barium currents in oocytes co-injected with transcripts of the BI cDNA and the rabbit skeletal muscle calcium channel α2 and β cDNAs were unaffected by the calcium channel antagonists nifedipine or ψ-CgTx and inhibited by Bay K8644 and crude venom from *Agelenopsis aperta*. of rabbit calcium channel α1 subunit cDNAs and transcripts of the cDNAs indicate that the α1 subunit forms the pore through which calcium enters cells. However, the relevance of the barium currents generated in these recombinant cells to the actual current generated by calcium channels containing as one component the respective α1 subunits in vivo is unclear. Because addition of in vitro transcripts of rabbit skeletal muscle calcium channel α2 and/or β and γ cDNAs significantly enhanced the barium currents in the recombinant cells, it appears that to completely and accurately characterize and evaluate different calcium channel types, it is essential to examine the functional properties of recombinant channels consisting of all the subunits as found in vivo. However, cDNAs encoding α2-, β-and γ-subunits from any of the rabbit or rat tissues besides rabbit skeletal muscle tissue are not available for use in such studies. The usefulness of rabbit skeletal muscle calcium channel α2- and β-subunit cDNAs in attempting to recombinantly evaluate different calcium channel types is extremely limited. Although others have suggested that the β- and α2-subunits of rabbit calcium channels from different tissues are essentially identical [Mori, Y. et al., *Nature* 350:398 (1991)], as described herein, different forms of α2-and β-subunits, arising from alternative splicing of the corresponding genes, are expressed in human brain, skeletal muscle and aorta. Therefore, in evaluating specific calcium channel types by examination of recombinantly expressed channels, it is most valuable to express cDNAs encoding calcium channel subunits from the same type of tissue.

It appears that calcium channels, specifically human calcium channels, can be relevant in certain disease states. A number of compounds useful in treating various cardiovascular diseases in animals, including humans, are thought to exert their beneficial effects by modulating functions of voltage-dependent calcium channels present in cardiac and/ or vascular smooth muscle. Many of these compounds bind to calcium channels and block, or reduce the rate of, influx of $Ca^{2+}$ into the cells in response to depolarization of the cell membrane.

An understanding of the pharmacology of compounds that interact with calcium channels in other organ systems, such as the central nervous system ("CNS"), and the ability to rationally design compounds that will interact with these specific subtypes of human calcium channels to have desired therapeutic, e.g., treatment of neurodegenerative disorders, effects have been hampered by an inability to independently determine how many different types of calcium channels exist or the molecular nature of individual subtypes, particularly in the CNS, and the unavailability of pure preparations of specific channel subtypes, i.e., systems to evaluate the specificity of calcium channel-effecting compounds.

SUMMARY OF THE INVENTION

In accordance with the present invention, we have discovered, isolated and purified DNAs which encode $α_1$-subunits of voltage-dependent human calcium channels (type II, type III and type IV, hereinafter VDCC II, VDCC III and VDCC IV); DNAs which encode $α_2$-subunits of human calcium channels; DNAs which encode β-subunits of human calcium channels; and DNAs which encode γ-subunits of human calcium channels.

In accordance with one aspect of the present invention there is provided for the first time the isolation and characterization of full length cDNAs (and corresponding RNAs) encoding $α_1$ VDCC III-, $α_2$- and β-subunits of human calcium channels. Also provided are cDNAs encoding significant portions of $α_1$ VDCC II-, α1 VDCC IV-, and γ-subunits of voltage-dependent human calcium channels from which full length cDNAs encoding types II and IV $α_1$- and γ-subunits may be readily isolated, cloned and used, for example, to express recombinant human calcium channels. In still another aspect the invention concerns nucleic acid probes comprising at least about 14 contiguous nucleotides of an $α_1$ VDCC III-, $α_1$ VDCC II-, $α_1$ VDCC IV-, $α_2$-, β- or γ-subunit DNA of the invention which may be used for the isolation and cloning of additional calcium channel subunit encoding cDNAs, including splice variants within tissues and inter-tissue variants.

In another aspect of the invention there is provided a eukaryotic cell which is transfected or injected with DNA or transcripts of DNA comprising at least one or more of the novel subunit-encoding cDNAs of the invention which are expressed such that the cell possesses a calcium channel comprising at least one or more human calcium channel subunits of the present invention. These eukaryotic cells of the invention have functional, heterologous calcium channels (hereinafter referred to as "foreign" or "heterologous" or "recombinant" calcium channels) which are capable of gating the passage of calcium channel selective ions and/or binding a compound, present at a physiological concentration, which is capable of affecting the ability of the recombinant calcium channel to pass such ions. The heterologous calcium channels of such cells are distinguishable from endogenous calcium channels of the host cell. In one aspect, the invention includes a eukaryotic cell which is transfected with a cDNA (or injected with RNA transcripts thereof) encoding a human calcium channel $α_1$-subunit of the invention, preferably an $α_1$ VDCC III subunit, and more preferably additional cDNAs encoding human β, $α_2$ or γ-subunits, such that the cell expresses a recombinant calcium channel which is capable of regulating the passage of calcium channel selective ions and is sensitive to compounds which are agonists or antagonists of human calcium channel activity. In other aspects, the invention entails a eukaryotic cell stably or transiently transfected with any combination of one, two, three or four of the subunit-encoding cDNAs of the present invention (e.g., $α_1$, $α_1+β$, $α_1+β+α_2$, etc.) which cells may be used in functional assays of the invention or, in the case of cells transformed with fewer subunit-encoding nucleic acids than necessary to constitute a functional recombinant human calcium channel, such cells may be employed as intermediates in the production of cells having additional sub units of the invention, the additional sub units being provided by subsequently transfecting such a cell with one or more cDNAs encoding a human calcium channel subunit of which the transfected cell is devoid.

In an especially preferred embodiment, the invention entails a eukaryotic cell comprising a recombinant calcium channel consisting essentially of human sub units, said recombinant channel being capable of binding agonist or antagonist compounds and/or passing calcium channel selective ions. In another of its aspects the invention employs a eukaryotic cell which expresses on its surface functional heterologous calcium channels of the invention in methods for identifying agonists and antagonists of calcium channel activity in humans and/or assessing the contribution of the various calcium channel sub units to the transport and regulation of calcium ions.

In still another aspect the invention is a purified human calcium channel subunit which is obtained from a eukaryotic cell transfected with a DNA comprising a cDNA of the invention which encodes the subunit.

BRIEF DESCRIPTION OF THE FIGURES

FIG. 7A–B present a comparison of a portion of the nucleic acid sequences and deduced amino acid sequences of (1) a rabbit skeletal muscle β subunit, (2) a human skeletal muscle β-subunit, (3) a human neuronal β-subunit, and (4) a human aortic β-subunit;

DETAILED DESCRIPTION OF THE INVENTION

Figure 1:
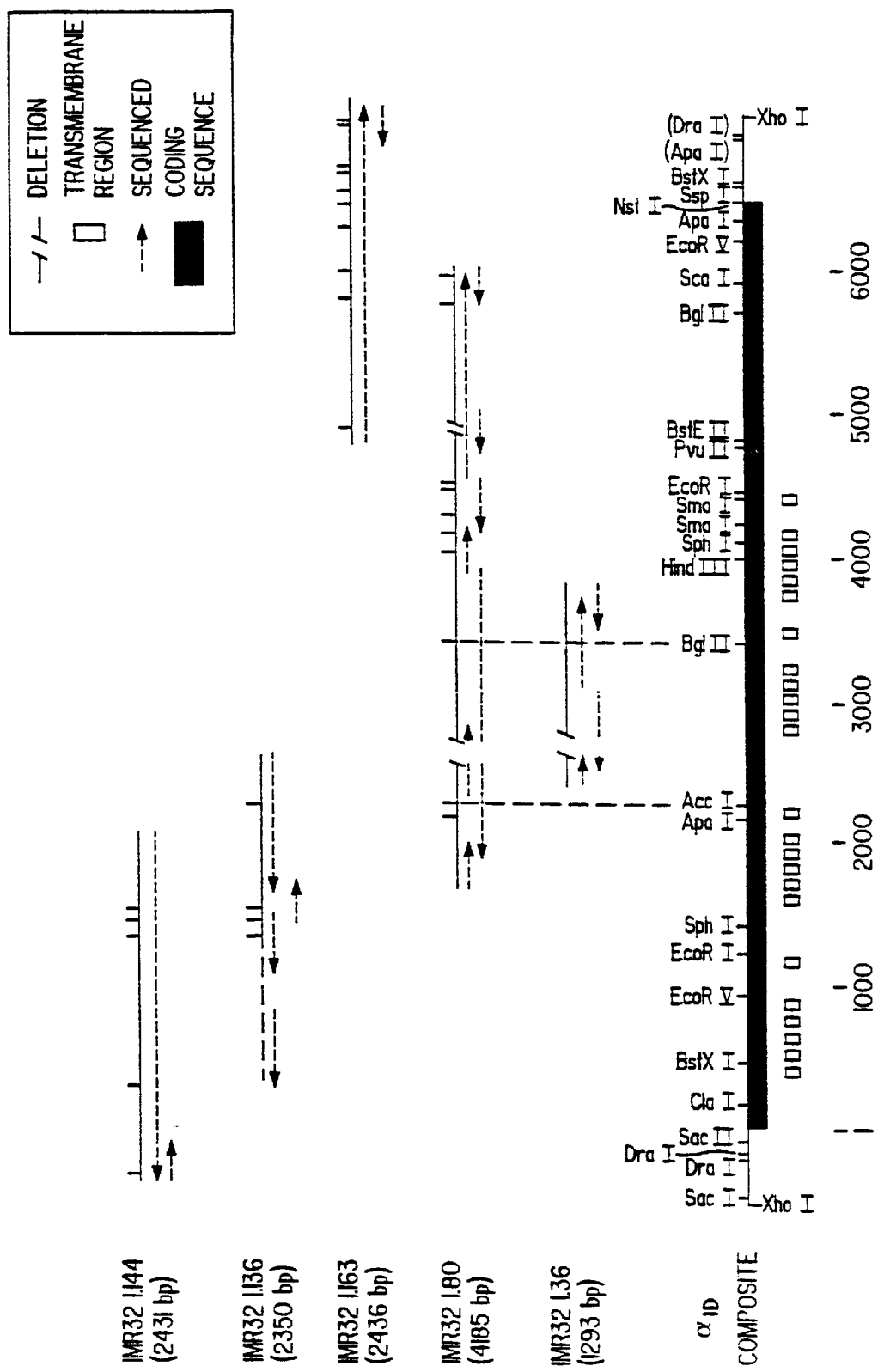
FIG. 1 represents a restriction map of a nucleic acid sequence encoding a human neuronal $\alpha_1$ calcium channel subunit (VDCC III), and the DNA sequencing strategy of various partial cDNAs used to derive the complete coding sequence.

For the first time there is provided DNAs for making recombinant human calcium channels and in vitro methods for testing compounds for calcium channel agonist and antagonist activity using eukaryotic cells that express such recombinant human calcium channels. The DNAs of the present invention and eukaryotic cells expressing these DNAs allow for the first time drug screening assays for calcium channel agonists and antagonists which are specific for human calcium channels expressed in a controlled system. The assay methods of the invention are highly accurate for predicting the relative efficacy of a compound in humans. Such assays may be advantageously used, for example, in screening methods used in conjunction with "designing" agonists and antagonists where it is important to accurately predict efficacy, with human calcium channels, between test compounds which differ slightly in structure (e.g., stereoisomers, etc.). The compositions and recombinant cells of the inventions thus allow the study of human calcium channel functions in recombinant cell systems.

Moreover, there are provided $\alpha_1$-sub units of voltage-dependent calcium channels types II, III and IV, and subtypes thereof, which types (and subtypes thereof) differ with respect to their sensitivity to known classes of calcium channel agonists and antagonists such as dihydropyridines, phenylalkylamines, omega conotoxin and pyrazonoylguanidines. Further provided are variant forms of human calcium channel $\alpha_2$ and β sub units, some of which appear to be tissue-specific variants. Thus, the present invention advantageously allows human calcium channel subtype specific drugs to be identified.

Thus, in one of its aspects, the invention is a DNA which comprises a cDNA which codes for an $\alpha_1$-subunit of a human calcium channel, and the RNA, coding for such a subunit, made upon transcription of such a DNA according to the invention.

In another of its aspects, the invention is a DNA which comprises a cDNA which codes for an $\alpha_2$-subunit of a human calcium channel, and the RNA, coding for such a subunit, made upon transcription of such a DNA according to the invention.

In a further of its aspects, the invention is a DNA which comprises a cDNA which codes for a β-subunit of a human calcium channel, and the RNA, coding for such a subunit, made upon transcription of such a DNA according to the invention.

In another of its aspects, the invention is a DNA which comprises a cDNA which codes for a γ-subunit of a human calcium channel, and the RNA, coding for such a subunit, made upon transcription of such a DNA according to the invention.

In a further of its aspects, the invention is a eukaryotic cell comprising at least one heterologous DNA selected from the group consisting of: a DNA which comprises a nucleotide sequence which can be expressed to make an $\alpha_1$-subunit of a human calcium channel; a DNA which comprises a nucleotide sequence which can be expressed to make an $\alpha_2$-subunit of a human calcium channel; a DNA which comprises a nucleotide sequence which can be expressed to make a β-subunit of a human calcium channel; and a DNA which comprises a nucleotide sequence which can be expressed to make a γ-subunit of a human calcium channel. Preferably, said nucleotide sequence is comprised of a cDNA. cDNAs having nucleotide sequences which code for divergent, but nearly identical, amino acid sequences of a subunit of the invention are referred to herein as "splice variants." A splice variant refers to differential processing of a primary transcript of the genomic DNA to give more than one type of mRNA. Splice variants may be found within a single tissue type or between tissues (tissue-specific variants).

In particularly preferred aspects, the invention entails a recombinant eukaryotic cell comprising at least one heterologous DNA which comprises a cDNA which can be expressed to make a subunit of the present invention which at least one subunit, when expressed in the host cell, provides recombinant functional calcium channel activity of a calcium channel type that is absent from the untransfected host cell or that is of a magnitude not exhibited in the untransfected cell. "Functional" as used herein in reference to a recombinant or heterologous calcium channel means that the channel is able to provide for and regulate entry of calcium channel selective ions (e.g., $Ca^{2+}$ or $Ba^{2+}$) in response to a stimulus and/or bind ligands with affinity for the channel, and that such calcium channel activity is distinguishable (e.g., electrophysiologically, pharmacologically, etc.) from any identified endogenous calcium channel activity that might be present in the host cell. In accordance with one preferred embodiment of the invention the at least one heterologous DNA which comprises a cDNA which can be expressed to make a subunit of the present invention encodes a human calcium channel $\alpha_1$-subunit By the term "calcium channel selective ion" is meant an ion that is capable of flowing through, or being blocked from flowing through, a calcium channel which spans a cellular membrane under conditions which would substantially similarly permit or block the flow of $Ca^{2+}$. $Ba^{2+}$ is an example of an ion which is a calcium channel selective ion.

In another of its aspects, the invention entails a eukaryotic cell with an heterologous calcium channel, said cell made by a process comprising administering to said cell a first which composition, which comprises at least one RNA which is translatable in said cell for the expression of the corresponding at least one subunit of a human calcium channel. Preferably said at least one RNA encodes an $\alpha_1$-subunit of a human calcium channel. More preferably said composition comprising at least one RNA is a composition which contains an RNA which encodes an $\alpha_1$-subunit of a human calcium channel and further comprises (1) an RNA which encodes a $\beta$ subunit of a human calcium channel and/or (2) an RNA which encodes an $\alpha_2$-subunit of a human calcium channel. Especially preferred is the administration to such cell of an RNA encoding an $\alpha_1$-, an RNA encoding a $\beta$- and an RNA encoding an $\alpha_2$-human calcium channel subunit of the invention, and, optionally, an RNA encoding a $\gamma$-subunit of a human calcium channel. Preferred cells for expressing RNAs which, when expressed in combination, yield functional heterologous human calcium channels are Xenopus laevis oocytes.

Methods employed in making cells of the invention, i.e., transforming a eukaryotic cell with suitable heterologous DNAS, to be maintained in the cell as episomes or (preferably) integrated into chromosomal DNA of the cell, and then culturing transformants or subculturing (or passaging, in the case of mammalian cells) from such a culture or a subculture thereof, or injecting a eukaryotic cell with transcripts of the heterologous DNAs to be translated within the cell, are well known to those of ordinary skill. Preferred as host cells for preparing cells of the present invention which express heterologous calcium channels are cells of mammalian origin, such as COS cells, mouse L cells, CHO cells (e.g., DG44 cells), human embryonic kidney cells (e.g., HEK293 cells), African green monkey cells and the like, amphibian cells, such as *Xenopus laevis* oocytes, or those of yeast such as *S. cerevisiae* or *P. pastoris*.

Preferred among such cells of the invention is a recombinant eukaryotic cell with a functional heterologous calcium channel, said calcium channel made by a process comprising expressing a first cDNA, which can be expressed to make an $\alpha_1$-subunit of a human calcium channel, more preferably further comprising expressing, along with said first cDNA, a second cDNA, which can be expressed to make a $\beta$-subunit of a human calcium channel and/or a third cDNA which can be expressed to make an $\alpha_2$-subunit of a human calcium channel. Especially preferred is the expression in such a recombinant cell of each of the $\alpha_1$-, $\beta$- and $\alpha_2$-subunit-encoding cDNAs, and optionally a fourth cDNA encoding a $\gamma$-subunit of a human calcium channel, or transcripts of heterologous DNAs encoding these four sub units. Preferred host cells for expressing such cDNAs are mammalian cells such as COS cells, mouse L cells, CHO cells (e.g., DG44 cells), human embryonic kidney cells (e.g., HEK293 cells), African green monkey cells and the like, and yeast cells such as *S. cerevisiae* or *P. pastoris*.

In another of its aspects, a method of the invention entails a ligand binding assay for testing a compound for capacity to specifically bind to a calcium channel which method comprises contacting the cell membrane of a eukaryotic cell of the invention which expresses at least one subunit of a human calcium channel, preferably at least an $\alpha_1$-subunit of a human calcium channel, with the test compound and measuring the capacity of the test compound to specifically bind to the membrane. More preferably such an assay employs a recombinant cell which has a calcium channel comprising an $\alpha_1$-subunit of a human calcium channel in combination with a $\beta$-subunit of a human calcium channel and/or an $\alpha_2$-subunit of a human calcium channel. Especially preferred for use in such an assay is a recombinant cell expressing heterologous calcium channels comprising each of the $\alpha_1$-, $\beta$- and $\alpha_2$-human sub units of the invention, and, optionally, a $\gamma$-subunit of a human calcium channel.

In another of its aspects, a method of the invention entails a functional assay for testing a compound for calcium channel agonist or antagonist activity which method comprises measuring the calcium channel activity of a eukaryotic cell of the invention having a heterologous, functional calcium channel (that is, the amount of current which flows through the recombinant channel in response to a stimulus) when such cell is exposed to a solution containing the compound being tested for agonist or antagonis activity, and comparing the measured calcium channel activity to the calcium channel activity of the same cell or a substantially identical control cell in a solution not containing the test compound. In the method, such a cell is maintained in a solution having a concentration of calcium channel selective ions sufficient to provide an inward current when the channels open. Especially preferred for use is a recombinant cell expressing calcium channels comprising each of the $\alpha_1$-, $\beta$- and $\alpha_2$-human sub units of the invention, and, optionally, a $\gamma$-subunit of a human calcium channel. For similar methods applied with Xenopus laevis oocytes and acetylcholine receptors, see e.g., Mishina et al., *Nature* 313:364 (1985) and, with such oocytes and sodium channels, see Noda et al., *Nature* 322:826–828 (1986). Such a cell having heterologous functional calcium channels is thus employed in the method of the invention to measure functionally (e.g., electrophysiologically) the ability of the test compound to potentiate or antagonize the magnitude and duration of the flow of calcium channel selective ions, such as $Ca^{++}$ or $Ba^{++}$, through the heterologous functional channel. For similar studies which have been carried out with the acetylcholine receptor, see Claudio et al., *Science* 238:1688–1694 (1987). The amount of current which flows through the recombinant calcium channels of a cell may be determined directly, electrophysiologically or by monitoring an independent reaction which occurs intracellularly and which is directly influenced in a calcium (or other) ion dependent manner.

In one embodiment of the method for testing a compound for calcium channel agonist or antagonist activity, in which method the amount of current is measured by its modulation of a reaction which is sensitive to calcium channel selective ions, a eukaryotic cell of the present invention further comprises another heterologous gene, which comprises a transcriptional control element linked operatively for expression to a structural gene for an indicator protein. The transcriptional control element employed to drive transcription of the indicator gene is responsive in the cell to a calcium channel selective ion (e.g., $Ca^{2+}$). Such methods for testing a compound for ion channel activity are disclosed in commonly owned U.S. Ser. No. 563,751, filed Aug. 7, 1990, now U.S. Pat. No. 5,401,629, and in commonly-owned PCT International Patent Application No. WO 92/02639, filed Aug. 7, 1991, which claims priority to U.S. Ser. No. 563, 751, field Aug. 7, 1990, now U.S. Pat. No. 5,401,629, the contents of which applications are hereby incorporated by reference herein.

As clearly understood by those skilled in the art, assay methods for determining whether a compound is an agonist or an antagonist of a given functional activity requires comparison to a control. One type of a "control" cell or "control" culture is a cell or culture that is, and is treated, substantially the same as the culture exposed to the compound being assayed except that the control culture is not exposed to the compound being assayed. Another type of a "control" cell or "control" culture is a cell or a culture of cells which are identical to the cells according to the invention, except the cells employed for the control culture do not express functional calcium channels. In this situation, the response of test cell to the compound being assayed is compared to the response (or lack of response) of the receptor-negative cell to the compound being assayed, when cells or cultures of each type of cell are exposed to substantially the same reaction conditions in the presence of the compound being assayed. In methods of the invention utilizing patch clamp electrophysiological procedures, the same cell can be tested in the presence and absence of the test compound, by changing the external solution bathing the cell as known in the art.

In yet another of its aspects, the invention is a substantially pure subunit of a human calcium channel selected from the group consisting of an $\alpha_1$-subunit of a human calcium channel, an $\alpha_2$-subunit of a human calcium channel, a $\beta$-subunit of a human calcium channel and a $\gamma$-subunit of a human calcium channel.

By a "substantially pure" subunit or protein is meant a subunit or protein that is sufficiently free of other polypeptide contaminants to be considered homogeneous by SDS-PAGE or to be unambiguously sequenced.

In yet another aspect the invention entails immunoglobulins obtained from the serum of an animal immunized with a substantially pure preparation of a human calcium channel subunit (or epitope containing fragment thereof) of the present invention or monoclonal antibodies produced using a calcium channel subunit of the invention (or epitope containing fragment thereof) as immunogen. E.coli fusion proteins comprising a fragment of a human calcium channel subunit may also be used as immunogen. Such fusion proteins may consist of e.g., E.coli TrpE protein fused to a peptide based on selected nucleotide sequences of a subunit cDNA of the invention. The immunoglobulins of the present invention have among other properties the ability to specifically bind and/or cause the immunoprecipitation of a human calcium channel or a subunit thereof which may be present in a biological sample or a solution derived from such a biological sample. Another aspect of the invention is a diagnostic method for determining the presence of Lambert Eaton Syndrome (LES) in a human based on immunological reactivity of LES immunoglobulin G (IgG) with a human calcium channel subunit of the present invention or a eukaryotic cell of the invention which expresses a recombinant human calcium channel a subunit of the invention.

In a still further aspect, the invention is an immunoassay method for diagnosing Lambert-Eaton Syndrome in a person, which method comprises combining serum from the person (test serum) with $\alpha_1$-subunit of a human calcium channel and $\alpha_2$-subunit of a human calcium channel and ascertaining whether antibodies in the test serum react with one or both of the sub units, or a recombinant cell of the invention which expresses one or both of the sub units to a greater extent than antibodies in control serum (e.g., from a person or group of persons known to be free of the Syndrome). Any immunoassay procedure known in the art for detecting antibodies against a given antigen in serum can be employed in the method.

The invention entails also a labeled (e.g., radioactively or enzymatically labeled) RNA or single-stranded DNA of at least 14 bases in length in a sequence which comprises a sequence of at least 14 (preferably at least 30) contiguous bases of a nucleic acid which encodes at least a portion of a human calcium channel subunit, the sequence of which nucleic acid corresponds to a segment of a nucleic acid sequence of the present invention disclosed herein by reference to a Sequence ID No. Such nucleic acid segments may be used as probes. See, generally, Sambrook et al., *Molecular Cloning: A Laboratory Manual*, 2d, Cold Spring Harbor Laboratory Press, 1989.

Finally, the invention entails a method to identify DNA encoding $\alpha_1$-, $\alpha_2$-, $\beta$- or $\gamma$-sub units of human calcium channels. This is accomplished by hybridizing, under appropriate hybridization conditions (e.g., high stringency), restriction enzyme-digested human DNA with a labeled probe having at least 14 nucleotides and derived from any contiguous sequence taken from the sequences set forth herein by sequence identification number. Once a fragment of interest is identified in the hybridization reaction, it can be cloned employing standard cloning techniques which are known by those of skill in the art. This method can be employed to identify varying transcripts encoding human calcium channel sub units (i.e., splice variants) generated by alternative splicing of the primary transcript of the genomic subunit DNA. For instance, a subunit cDNA isolated by hybridization to a DNA sequence of the invention can be characterized (e.g., restriction mapping, DNA sequencing) and compared to cDNAs of the invention to identify heterogeneity or divergences in the sequences indicative of alternative splicing of the transcript from which the cDNAs were derived. Oligonucleotides corresponding to divergent sequences can be used to isolate, by hybridization, the full-length splice variant cDNA. In addition, nucleic acid amplification techniques, which are well known in the art, can be used to locate splice variants of calcium channel sub units by employing oligonucleotides based on DNA sequences surrounding the divergent sequence of a cDNA as primers to amplify human RNA or genomic DNA. Size and sequence determinations of the amplification products can reveal splice variants. Furthermore, isolation of human genomic DNA sequences by hybridization to cDNAs of the invention can yield DNAs containing multiple exons, separated by introns, that correspond to different splice variants of transcripts encoding human calcium channel sub units.

A preferred strategy for cloning cDNAs encoding an $\alpha_1$-, $\alpha_2$-, $\beta$- or $\gamma$-sub units of voltage-dependent human calcium channels is to screen human cDNA libraries prepared from isolated poly A+ mRNA from cell lines or tissue of human origin having such calcium channels. Among the sources of such cells or tissue for obtaining mRNA are brain tissue or a cell line having neural origin such as a neuroblastoma cell line, human skeletal muscle or smooth muscle cells, and the like. Methods of preparing cDNA libraries are well known in the art [see generally Ausubel et al., *Current Protocols in Molecular Biolory*, Wiley-Interscience, New York (1987); and Davis et al., *Basic Methods in Molecular Biology*, Elsevier Science Publishing Co., New York (1986)].

With respect to each of the respective sub units of a human calcium channel ($\alpha_1$-, $\alpha_2$-, $\beta$- or $\gamma$), once a channel subunit is found by a nucleic acid screening method, the clone may be used for further screening to identify overlapping clones. These cloned DNA fragments can be subcloned into an appropriate vector such as pIBI24/25 (IBI, New Haven, Conn.) or M13mp18/19, pGEM4, pGEM3, pGEM7Z, pSP72 or the like, and characterized by DNA sequencing and restriction enzyme mapping. A sequential series of overlapping clones may be thus generated for each of the sub units until a full-length clone can be prepared as determined by identification of translation initiation (start) and translation termination (stop) codons. Also, the 5' non-coding sequence of such a clone may be replaced with an efficient ribosome binding site as known in the art. Examples II–VI below describes in detail the cloning of each of the various sub units of the present invention as well as subtypes and splice variants, including tissue-specific variants thereof. And, where partial sequences of a subunit are disclosed, it is well within the skill of art, in view of the teaching herein to obtain the corresponding full-length nucleotide sequence encoding the subunit, subtype or splice variant thereof.

Briefly, as pertains to the isolation of the VDCC III $\alpha_1$-subunit cDNA, fragments of the rabbit skeletal muscle calcium channel $\alpha_1$-subunit cDNA were used as a probe to screen a cDNA library of the human neuroblastoma cell line, IMR32 to obtain clone $\alpha$1.36. This clone was used as a probe to screen additional IMR32 cell cDNA libraries to obtain overlapping clones, which overlapping clones were then employed in screening until a sufficient series of clones to span the length of the nucleotide sequence encoding the human VDCC III $\alpha_1$ subunit was obtained. Full-length VDCC III cDNAs were constructed by, inter alia ligating portions of partial VDCC III clones as described in Example I. The various cDNA clones from which the coding sequence for the $\alpha_1$-subunit was derived are set forth in FIG. 1. In the Figure, the heavy line represents the $\alpha_1$ coding sequence. Overlapping clones from which the complete sequence was derived are shown above the composite restriction map. The shows the sequence of an alternative exon encoding the IS6 transmembrane domain is included in portions of the sequences of IMR32 1.157 (nt 57 to 89, Sequence ID #9; nt 1 to 67, Sequence ID #6), IMR32 1.66 (nt 100 to 132, Sequence ID #8; nt 1 to 67, Sequence ID #6), and the rabbit lung CaCB-receptor sequence, nt −33 to 67 [M. Biel. et al., (1990) FEBS Lett. 269, 409][see Tanabe, T., et al. (1987). Nature 328:313–318 for a description of transmembrane domain terminology of the VDCC III -subunit.

Sequence ID No. 1 shows the 7,125 nucleotide sequence of the cDNA encoding the VDCC III $\alpha_1$-subunit. There is a 6,483 nucleotide sequence reading frame which encodes a sequence of 2,161 amino acids (as shown in Sequence ID No. 1).

Sequence ID No. 2 shows the 2,161 amino acid 30 sequence deduced from the cDNA of the VDCC III $\alpha_1$ subunit of the human neuronal calcium channel. The complete sequence yields a calculated Mr of 245,163 for the VDCC III $\alpha_1$ protein. The amino acid sequence determined and reported here is about 70% identical to that described by Tanabe et al., supra. The VDCC III $\alpha_1$-subunit of the calcium channel contains four putative internal repeated sequence regions. Four internally repeated regions represent twenty-four putative transmembrane segments and the amino- and carboxyl-termini extend intracellularly.

A description of the cloning of cDNAs encoding portions of $\alpha_1$ VDCC II and a VDCC IV sub units of the invention are given in Example I. A VDCC II $\alpha_1$ subunit is encoded by a nucleotide sequence which encodes an amino acid sequence comprising the sequence represented by sequence ID No. 7 or sequence ID No. 11; and a VDCC IV $\alpha_1$ subunit is encoded by a nucleotide sequence which encodes an amino acid sequence comprising sequences represented by sequence ID No. 15 and/or sequence ID No. 17.

With respect to the $\beta$ subunit, a human hippocampus cDNA library was plated with an appropriate strain of *E. coli* and 3×10$^5$ plaques were screened by hybridization to a cDNA sequence encoding rabbit skeletal muscle calcium channel $\beta$ subunit to identify a positive clone which was in turn used to isolate overlapping clones until the entire sequence for the human calcium channel $\beta$ subunit was determined. The cDNA sequence encoding $\beta$ subunit of rabbit skeletal muscle calcium channel is disclosed in commonly owned U.S. application Ser. No. 482,384, filed Feb. 20, 1990, the contents of which are incorporated herein by reference. A detailed example of the cloning of cDNAs which encode human neuronal calcium channel $\beta$ sub units is given in Example III.

Sequence ID No. 18 shows the nucleotide sequence of a cDNA encoding one variant of the $\beta$-subunit. Sequence ID No. 22 represents the sequence of a cDNA encoding the major portion including a unique exon which is included in another splice variant of a $\beta$-subunit. Both of these splice variants encode human neuronal $\beta$-sub units. A cDNA sequence distinctive for a portion of a $\beta$-subunit of a human aortic calcium channel is shown in Sequence ID No. 31.

A cDNA encoding a human neuronal calcium channel $\alpha_2$-subunit was isolated in a manner substantially similar to that used for isolating $\alpha_1$ subunit cDNAs, except that a human genomic DNA library was probed under low and high stringency conditions with a fragment of the rabbit skeletal muscle calcium channel $\alpha_2$ subunit cDNA having the sequence corresponding to the nucleotide sequence between nucleotides 43 and 272 inclusive of rabbit back skeletal muscle calcium channel $\alpha_2$ subunit cDNA as disclosed in PCT International Patent Application Publication No. WO 89/09834, incorporated herein by reference. Example IV describes in detail the isolation of cDNA clones encoding an $\alpha_2$ subunit of a human calcium channel from a human DNA library using genomic DNA and cDNA identified by hybridization to the genomic DNA as probes.

Sequence ID No. 24 shows a cDNA sequence encoding the $\alpha_2$-subunit. As described in Example V, PCR analysis of RNA from human skeletal muscle, brain tissue and aorta using oligonucleotide primers specific for a region of the human neuronal $\alpha_2$-subunit cDNA that diverges from the rabbit skeletal muscle calcium channel $\alpha_2$-subunit cDNA (which divergence was discoverable only by first obtaining novel human calcium channel $\alpha_2$-subunit cDNAs) identified novel splice variants of the human calcium channel $\alpha_2$-subunit transcript.

A cDNA encoding a human neuronal calcium channel $\gamma$-subunit may be isolated as described in detail in the Example VI. Sequence ID No. 29 shows the nucleotide sequence at the 3'-end of this DNA which has a reading frame encoding a sequence of 43 amino acid residues.

A nucleotide sequence disclosed herein which encodes at least a portion of a subunit of a human calcium channel, (e.g., a tissue-specific exon) may be used to clone a full length gene encoding said human calcium channel subunit, which can then be expressed in a host cell, using methods described in the following examples or other procedures well known to those ordinarily skilled in the art. Incorporation of a cloned gene into a suitable expression vector, transfection of eukaryotic cells with a plasmid vector or a combination of plasmid vectors, each encoding one or more distinct genes, and selection of transfected cells are also well known in the art. (See, Sambrook, et al., *Molecular Cloning: A Laboratory Manual, Second Edition* (Cold Spring Harbor Laboratory Press (1989).) Cloned full-length cDNAs encoding any of the sub units of a human calcium channel of the present invention may be introduced into a plasmid vector for expression in a eukaryotic cell. Such a vector is an example of a DNA which comprises a cDNA with a sequence which codes for a subunit of a human calcium channel. Host cells may be transfected with one or a combination of said vectors, each of which encodes a calcium channel subunit. While the DNAs of the invention may be expressed in any eukaryotic cell including yeast cells such as *Pichia pastoris* (see e.g., Cregg, et al., *Bio/Technology* 5, 479 (1987)) it is preferred to use mammalian expression systems for expression of the calcium channel sub units of the present invention because of the ability of such expression systems to effect post-translational modifications such as glycosylation, phosphorylation, specific proteolysis and the like.

Furthermore, in vitro transcription of a cloned gene and injection of the resulting RNA into eukaryotic cells are also well known in the art. Transcripts of any of the full-length cDNAs encoding any of the sub units of a human calcium channel of the present invention may be injected alone or in combination into eukaryotic cells for expression in said cells. Amphibian oocytes are particularly preferred for expression of in vitro transcripts of the human calcium channel subunit cDNAs of the present invention.

Among the uses for eukaryotic cells which recombinantly express one or more sub units of the present invention are assays for determining whether a test compound has calcium channel agonist or antagonist activity. Desirably, a host cell for the expression of calcium channel sub units of the present invention will not produce endogenous calcium channel sub units of the type or in an amount that will substantially interfere with the detection of heterologous calcium channel sub units in ligand binding assays or detection of heterologous calcium channel function (e.g., generation of calcium current) in functional assays.

With respect to ligand binding assays, the host cells preferably should not produce endogenous calcium channels which are able to bind a ligand having, at physiological concentrations (e.g., nanomolar or picomolar amounts), affinity for one or a combination of the heterologous calcium channel sub units of the present invention. Preferred among the mammalian host cells which may be employed to express one or more of the human calcium channel sub units of the present invention for such expression are Chinese hamster ovary (CHO) cells, COS cells, mouse L cells, human embryonic kidney (HEK) cells.

With respect to ligand binding assays for identifying a compound which has affinity for calcium channels, cells are employed which express, preferably, at least a heterologous $\alpha_1$ subunit. Transfected eukaryotic cells of the present invention which express at least an $\alpha_1$-subunit of the invention may be used to determine the capacity of a test compound to specifically bind to, and likely affect the function of, a calcium channel. Such ligand binding assays may be performed on intact transfected cells or membranes prepared therefrom.

The capacity of a test compound to bind to membranes comprising heterologous calcium channels or sub units thereof may be determined by any appropriate competitive binding analysis (e.g., Scatchard plots), wherein the binding capacity of such membranes is determined in the presence and absence of one or more concentrations a compound having known affinity for the calcium channel. As a control, these results may be compared to an identically treated membrane preparation from host cells which were not transfected with one or more subunit-encoding nucleic acids (i.e., a negative control).

Stably or transiently transfected cells or injected cells of the present invention which express voltage-dependent human calcium channels comprising one or more of the sub units of a human calcium channel desirably may be used in functional assays to identify agents which are agonists or antagonists of calcium channel activity. Functionally testing activity of test compounds, including compounds having unknown activity, for calcium channel agonist or antagonist activity to determine if a test compound can potentiate or inhibit the flow of calcium through a human calcium channel entails a method which comprises (a) maintaining a eukaryotic cell which is transformed or injected to express a heterologous functional calcium channel capable of regulating the flow of calcium channel selective ions into the cell in a medium comprising calcium channel selective ions (i) in the presence of and (ii) in the absence of a test compound; (b) maintaining the cell under conditions such that the heterologous calcium channels are substantially closed and endogenous calcium channels of the cell are substantially inhibited (c) depolarizing the membrane of the cell maintained in step (b) to an extent and for an amount of time sufficient to cause (preferably, substantially only) the heterologous calcium channels to become permeable to the calcium channel selective ions; and (d) comparing the amount and duration of current flow into the cell in the presence of the test compound to that of the current flow into the cell, or a substantially similar cell, in the absence of the test compound.

Functional calcium channels as used herein may preferably comprise at least an $\alpha_1$ subunit and a $\beta$-subunit of a human calcium channel. Eukaryotic cells expressing these two sub units have exhibited voltage dependent calcium channel activity. The $\alpha_2$-subunit may potentiate calcium channel function (i.e., eukaryotic cells expressing heterologous calcium channels comprising an $\alpha_2$ subunit in addition to the $\alpha_1$ subunit and $\beta$ a subunit have been shown to exhibit increased calcium selective ion flow across the cellular membrane in response to depolarization). Eukaryotic cells which express heterologous calcium channels comprising at least a human $\alpha_1$-subunit, a human $\beta$-subunit and a human $\alpha_2$-subunit are preferred eukaryotic cells of the present invention. However, eukaryotic cells transformed with a composition consisting essentially of a cDNA-containing vector or an RNA of the invention which encodes an $\alpha_1$-subunit alone or in combination with a $\beta$-and/or an $\alpha_2$ subunit may be used to give functional calcium channels. Since recombinant cells expressing human calcium channels consisting essentially of human sub units are especially preferred, it is desirable to inject or transform such host cells with a sufficient concentration of the subunit-encoding nucleic acids of the invention to promote expression of calcium channels consisting essentially of human sub units.

With respect to measurement of functional heterologous calcium channels, preferably, endogenous ion channel activity and hybrid channel activity of a host cell can be inhibited to a significant extent by chemical (i.e., pharmacological) and/or electrophysiological means (e.g., differential holding potential) to increase the S/N ratio of the measured heterologous calcium channel activity.

Particularly preferred vectors for transfection of mammalian cells are the pSV2dhfr expression vectors (which comprises the SV40 early promoter, mouse dhfr gene, SV40 polyadenylation and splice sites and sequences necessary for maintaining the vector in bacteria), pCDNA1 or pCMV-based vectors which comprise the cytomegalovirus promoter or MMTV promoter-based vectors or the vector pCMV. A cloned calcium channel subunit gene of the present invention may be inserted in the vector pCDNA1 at a position immediately following the CMV promoter. The expression of functional, voltage-dependent calcium channels in HEK 293 cells transfected with calcium channel subunit cDNAs contained in vector pCDNA1 is described in Example VII.

Stably transfected mammalian cells may be made as known in the art by transfecting cells with an expression vector having a selectable marker gene such as the gene for thymidine kinase, dihydrofolate reductase, neomycin resistance or the like, and growing the transfected cells under conditions selective for cells expressing the marker gene.

Electrophysiological procedures for measuring the current across an ion-selective membrane of a cell are well known. A preferred method for the determination of the amount and duration of the flow of calcium selective ions through heterologous calcium channels of a recombinant cell of the invention employs electrophysiological recordings using a voltage clamp, such as the whole-cell patch clamp technique. It is known to eliminate non-calcium currents and, preferably, substantially reduce calcium currents resulting from endogenous calcium channels (i.e., pharmacologically, electrophysiologically) when measuring calcium currents through recombinant channels.

A further aspect of the invention provides for a diagnostic assay for Lambert Eaton Syndrome (LES). LES is an autoimmune disease characterized by an insufficient release of acetylcholine from motor nerve terminals which normally are responsive to nerve impulses. A recent publication (Kim and Neher, *Science* 239, 405–408 (1988)) demonstrates that IgGs from LES patients block individual voltage-dependent calcium channels and thus prevent function. A diagnostic assay for LES based on immunological reactivity of LES IgG with calcium channel $\alpha_1$-subunit alone or in combination with β-subunit is thus provided for. For example, such an assay may be based on immunoprecipitation of LES IgG by the calcium channel sub units of the invention.

The invention will now be described in greater detail by reference to the following non-limiting examples.

EXAMPLE I cDNA LIBRARIES USED TO ISOLATE cDNAs ENCODING HUMAN NEURONAL VOLTAGE-DEPENDENT CALCIUM CHANNEL SUB UNITS

A. RNA Isolation

1. IMR32 cells

IMR32 cells were obtained from the American Type Culture Collection (ATCC #CCL127, Rockville, Md.) and grown in DMEM, 10% fetal bovine serum, 1% penicillin/streptomycin (GIBCO, Grand Island, N.Y.) plus 1.0 mM dibutyryl cAMP (dbcAMP) for ten days. Total RNA was isolated from the cells according to the procedure described by H. C. Birnboim [*Nucleic Acids Research* 16:1487–1497 (1988)]. Poly(A$^+$) RNA was selected according to standard procedures (see J. Sambrook, E. F. Fritsch, T. Maniatis, in: *Molecular Cloning, A Laboratory Manual*, Cold Spring Harbor Laboratory Press, 1989; pg. 7.26–7.29).

2. Human thalamus tissue

Human thalamus tissue (2.34 g), obtained from the National Neurological Research Bank, Los Angeles, Calif., that had been stored frozen at −70° C. was pulverized using a mortar and pestle in the presence of liquid nitrogen and the cells were lysed in 12 ml of lysis buffer (5M guanidinium isothiocyanate, 50 mM TRIS, pH 7.4, 10 mM EDTA, 5% β-mercaptoethanol). Lysis buffer was added to the lysate to yield a final volume of 17 ml. N-laurylsarcosine and CsCl were added to the mixture to yield final concentrations of 4% and 0.01 g/ml, respectively, in a final volume of 18 ml.

The sample was centrifuged at 9,000 rpm in a Sorvall SS34 rotor for 10 min at room temperature to remove the insoluble material as a pellet. The supernatant was divided into two equal portions and each was layered onto a 2-ml cushion of a solution of 5.7M CsCl, 0.1M EDTA contained in separate centrifuge tubes to yield approximately 9 ml per tube. The samples were centrifuged in an SW41 rotor at 37,000 rpm for 24 h at 20° C.

After centrifugation, each RNA pellet was resuspended in 3 ml ETS (10 mM TRIS, pH 7.4, 10 mM EDTA, 0.2% SDS) and combined into a single tube. The RNA was precipitated with 0.25M NaCl and two volumes of 95% ethanol.

The precipitate was collected by centrifugation and resuspended in 4 ml PK buffer (0.05M TRIS, pH 8.4, 0.14M NaCl, 0.01M EDTA, 1% SDS). Proteinase K was added to the sample to a final concentration of 200 μg/ml. The sample was incubated at 22° C. for 1 h, followed by extraction with an equal volume of phenol:chloroform:isoamylalcohol (50:48:2) two times, followed by one extraction with an equal volume of chloroform: isoamylalcohol (24:1). The RNA was precipitated with ethanol and NaCl. The precipitate was resuspended in 400 μl of ETS buffer. The yield of total RNA was approximately 1.0 mg. Poly A$^+$ RNA (30 μg) was isolated from the total RNA according to standard methods as stated in Example I.A.1.

B. cDNA Library Construction

Double strand cDNA was synthesized according to standard methods (J. Sambrook, E. F. Fritsch, T. Maniatis, IN: *Molecular Cloning, A Laboratory Manual*, Cold Spring Harbor Laboratory Press, 1989, Chapter 8). Differences occurred in the construction of the cDNA libraries due to 1) the oligonucleotide used to prime the first strand cDNA synthesis, 2) the adapters that were attached to the double strand cDNA, 3) the method used to remove the free or unused adapters, and 4) the size of the fractionated cDNA ligated into the λ phage vector. Each cDNA library constructed is described below with these points highlighted.

1. IMR32 cDNA library #1

Single strand cDNA was synthesized using IMR32 poly (A$^+$) RNA (Example I.A.1.) as a template. The synthesis was primed using oligo (dT)$_{12-18}$ (Collaborative Research Inc., Bedford, Mass.). The single strand cDNA was converted to double strand cDNA and the yield was approximately 2 μg. EcoRI adapters,

```
5'-AATTCGGTACGTACACTCGAGC-3' = 22-mer
3'-     GCCATGCATGTGAGCTCG-5' = 18-mer,
``` also containing SnaBI and XhoI restriction sites were then added to the double strand cDNA according to the following procedure.

a. Phosphorylation of 18-mer

The 18-mer was phosphorylated by combining the following reagents and incubating at 37° C. for 15 minutes:

| | |
|---|---|
| 225 pmoles 18 mer plus water = | 6.8 µl |
| 10x kinase buffer* | 1.2 µl |
| [$^{32}$P]γ-ATP (7000 Ci/mmole) | 1.0 µl |
| kinase (2 U/µl) | 1.0 µl |
| | 10 µl |

*See J. Sambrook et al., (supra).

The following two reagents were added to the above mixture and incubated at 37° C. for 15 minutes:

| | |
|---|---|
| 10 mM ATP | 1 µl |
| kinase (2 U/ml) | *p1326X1 µl |
| | 12 µl (total) |

The enzyme was then inactivated by boiling for 10 minutes.

b. Hybridization of 22-mer

The 22-mer was hybridized to the phosphorylated 18-mer by addition of 225 pmoles of the 22-mer (plus water to bring volume to 15 µl), and incubation at 65° C. for 5 minutes. The reaction was then allowed to slow cool to room temperature.

The adapters were thus present at a concentration of 15 pmoles/µl, and were ready for cDNA-adapter ligation.

c. Ligation of adapters to cDNA

The following were combined: Double-strand cDNA (collected as a pellet by ethanol precipitation)

| | |
|---|---|
| Double-strand cDNA | 16 µl |
| (collected as a pellet by ethanol precipitation) | |
| plus | |
| hybridized adapters (15 pmol/µl) excess | 50-fold molar |
| plus | over ds cDNA |
| water = | |
| 10x ligase buffer* | 2 µl |
| ligase (10 U/µl) | 2 µl |
| | 20 µl |

*See J. Sambrook et al., (supra).

The reaction was incubated at 37° C. for 60 minutes.

After the EcoRI, SnaBI, XhoI adapters were added to the double strand cDNA by incubating for 60 minutes, the ligase was inactivated by heating the mixture to 72° C. for 15 minutes. The following reagents were added to the cDNA ligation reaction and heated at 37° C. for 30 minutes:

| | |
|---|---|
| cDNA ligation reaction | 20 µl |
| water | 24 µl |
| 10x kinase buffer | 3 µl |
| 10 mM ATP | 1 µl |
| kinase (2 U/µl) | 2 µl |
| | 50 µl |

The reaction was stopped by the addition of 2 µl 0.5M EDTA, followed by one phenol/chloroform extraction and one chloroform extraction.

d. Size Selection and Packaging of cDNAs

The double strand cDNA with the EcoRI, naBI, XhoI adapters ligated was purified away from the free or nligated adapters using a 5 ml Sepharose CL-4B column (Sigma, St. Louis, Mo.). 100 µl fractions were collected and those containing the cDNA, determined by monitoring the radioactivity, were pooled, ethanol precipitated, resuspended in TE buffer and loaded onto a 1% agarose gel. After the electrophoresis, the gel was stained with ethidium bromide and the 1 to 3 kb fraction was cut from the gel. The cDNA embedded in the agarose was eluted using the "Geneluter Electroelution System" (Invitrogen, San Diego, Calif.). The eluted cDNA was collected by ethanol precipitation and resuspended in TE buffer at 0.10 pmol/µl. The cDNA was ligated to 1 µg of EcoRI digested, dephosphorylated λt11 in a 5 µreaction volume at a 2- to 4- fold molar excess ratio of cDNA over the λgt11 vector. The ligated λgt11 containing the cDNA insert was packaged into λ phage virions in vitro using the Gigapack (Stratagene, La Jolla, Calif.) kit. The packaged phage were plated on an *E. coli* Y1088 bacterial lawn in preparation for screening.

2. IMR32 cDNA library #2

This library was prepared as described (Example I.B.1.) with the exception that 3 to 9 kb cDNA fragments were ligated into the λgt11 phage vector rather than the 1 to 3 kb fragments.

3. IMR32 cDNA library #3

IMR32 cell poly(A$^+$) RNA (Example I.A.1.) was used as a template to synthesize single strand cDNA. The primers for the first strand cDNA synthesis were random primers (hexadeoxy-nucleotides [pd(N)$_6$] Cat #5020-1 Clontech, Palo Alto, Calif.). The double strand cDNA was synthesized (Example I.B.1.), EcoRI, SnaBI, XhoI adapters were added to the cDNA (Example I.B.1.), the unligated adapters were removed (Example I.B.1.), and the double strand cDNA with the ligated adapters was fractionated on an agarose gel (Example I.B.1.). The cDNA fraction greater than 1.8 kb was eluted from the agarose (Example I.B.1.), ligated into λgt11, packaged, and plated into a bacterial lawn of Y1088 (Example I.B.1.).

4. IMR32 cDNA library #4

IMR32 cell poly(A$^+$) RNA (Example I.A.1.) was used as a template to synthesize single strand cDNA. The primers for the first strand cDNA synthesis were oligonucleotides 89–365a specific for the VDCC III type $\alpha_1$-subunit (see Example II.A.) coding sequence (the complementary sequence of nt 2417 to 2446, Sequence ID #1), 89–495 specific for the VDCC II type $\alpha_1$-subunit (see Example II.B.) coding sequence (the complementary sequence of nt 852 to 873, Sequence ID #6), and 90–12 specific for the VDCC II type $\alpha_1$-subunit coding sequence (the complementary sequence of nt 2496 to 2520, Sequence ID #6). The cDNA library was then constructed as described (Example I.B.3) with the exception that the cDNA size-fraction greater than 1.5 kb was eluted from the agarose rather than the greater than 1.8 kb fraction.

5. IMR32 cDNA library #5

The cDNA library was constructed as described (Example I.B.3.) with the exception that the size-fraction greater than 1.2 kb was eluted from the agarose rather than the greater than 1.8 kb fraction.

6. Human thalamus cDNA library 16

Human thalamus poly (A$^+$) RNA (Example I.A.2.) was used as a template to synthesize single strand cDNA. Oligo (dT) was used to prime the first strand synthesis (Example I.B.1.). The double strand cDNA was synthesized (Example I.B.1.) and EcoRI, KpnI, NcoI adapters of the following sequence 5'CCATGGTACCTTCGTTGACG3' = 20 mer
3'GGTACCATGGAAGCAACTGCTTAA5' = 24 mer were ligated to the double strand cDNA as described (Example I.B.1.) with the 20-mer replacing the 18-mer and the 24-mer replacing the 22-mer. The unligated adapters were removed by passing the cDNA-adapter mixture through a 1 ml Bio Gel A-50 (Bio-Rad Laboratories, Richmond, Calif.) column. Fractions (30 μl) were collected and 1 μl of each fraction in the first peak of radioactivity was electrophoresed on a 1% agarose gel. After electrophoresis, the gel was dried on a vacuum gel drier and exposed to x-ray film. The fractions containing cDNA fragments greater than 600 bp were pooled, ethanol precipitated, and ligated into λgt11 (Example I.B.1.). The construction of the cDNA library was completed as described (Example I.B.1.).

C. Hybridization and Washing Conditions

Hybridization of radiolabelled nucleic acids to immobilized DNA for the purpose of screening cDNA libraries, DNA Southern transfers, or northern transfers was routinely performed in standard hybridization conditions [5× SSPE, 5× Denhardt's, 50% deionized formamide, 200 μg/ml sonicated herring sperm DNA (Cat #223646, Boehringer Mannheim Biochemicals, Indianapolis, Ind.)]. The recipes for SSPE and Denhart's and the preparation of deionized formamide are described by J. Sambrook et al. (Example I.A.1. provides the complete reference). In some hybridizations, lower stringency conditions were used in that 10% deionized formamide replaced 50% deionized formamide described for the standard hybridization conditions.

The washing conditions for removing the non-specific probe from the filters was either high, medium, or low stringency as described below:

1) high stringency: 0.1× SSPE, 0.1% SDS, 65° C.
2) medium stringency: 0.2× SSPE, 0.1% SDS, 50° C.
3) low stringency: 1.0× SSPE, 0.1% SDS, 50° C.

EXAMPLE II

HUMAN NEURONAL CALCIUM CHANNEL α₁ SUBUNIT cDNAS

At least three voltage-dependent calcium channel α₁-subunit genes are expressed in the human central nervous system. These genes have been designated VDCC II, VDCC III and VDCC IV (VDCC: voltage-dependent calcium channel). Human neuronal cDNA sequences corresponding to all three VDCC genes have been isolated. The isolation and characterization of sequences corresponding to the three human neuronal VDCC α₁ subunit genes are described in detail in this example.

A. VDCC III cDNAs

1. Reference list of partial VDCC III cDNAs

Numerous VDCC III-specific cDNAs were isolated in order to characterize the complete VDCC III coding sequence plus portions of the 5' and 3' untranslated sequences. Sequence ID #1 shows the complete VDCC III DNA coding sequence, plus 642 nucleotides of 3' untranslated sequence. Also shown in Sequence ID #1 is the deduced amino acid sequence. Sequence ID #3 shows 510 nucleotides of VDCC III 5' untranslated sequence ending in the guanidine nucleotide adjacent to the adenine nucleotide of the proposed initiation of translation. Shown below is a list of partial cDNAs used to characterize the VDCC III sequence and the nucleotide position of each clone relative to the full-length VDCC III cDNA sequence (i.e., sequence ID No. 1). Restriction maps of the partial VDCC III cDNAs are shown in FIG. 1. The isolation and characterization of these clones are described below (Example II.A.2.).

| IMR32   | 1.144 | nt. 1 to 510 of 5' untranslated sequence, nt. 1 to 1921, | Sequence ID #3 Sequence ID #1 |
| IMR32*  | 1.136 | nt. 1117 to 2478, nt. 1 to 104 of, additional exon, | Sequence ID #1 Sequence ID #4 |
| IMR32@  | 1.80  | nt. 1573 to 5958, | Sequence ID #1 |
| IMR32#  | 1.36  | nt. 2347 to 3771, | Sequence ID #1 |
| IMR32   | 1.163 | nt. 4690 to 7125, | Sequence ID #1 |

*5' of nt 1117, IMR32 1.136 encodes an intron and an additional exon described in Example II.A.2.d.
@IMR32 1.80 contains two deletions, nt 2474 to 2621 and nt 4793 to 4839 (Sequence ID #1). The 148 nt deletion (nt. 2474 to 2621) was corrected by performing a polymerase chain reaction described in Example II.A.3.b.
IMR32 1.36 contains a 132 nt deletion (nt. 2571 to 2702).

2. Isolation and characterization of individual clones listed in Example II.A.1.

a. IMR32 1.36

Two million recombinants of the IMR32 cDNA library #1 (Example I.B.1.) were screened in duplicate at a density of approximately 200,000 plaques per 150 mm plate using a mixture of radiolabelled fragments of the coding region of the rabbit skeletal muscle calcium channel α1 cDNA (for the sequence of the rabbit skeletal muscle calcium channel α1 subunit cDNA, see, Tanabe et al. (1987). *Nature* 328:313–318]:

| Fragment   | Nucleotides   |
|------------|---------------|
| Kpn-EcoRI  | −78 to 1006   |
| EcoRI-XhoI | 1006 to 2653  |
| ApaI-ApaI  | 3093 to 4182  |
| BglII-SacI | 4487 to 5310  |

The hybridization was performed using low stringency hybridization conditions (Example I.C.) and the filters were washed under low stringency (Example I.C.). Only one VDCC III-specific recombinant (IMR32 1.36) of the two million screened was identified. IMR32 1.36 was plaque purified by standard methods (J. Sambrook et al., supra) subcloned into pGEM3 (Promega, Madison, Wis.) and characterized by DNA sequencing.

b. IMR32 1.80

Approximately 1×10⁶ recombinants of the IMR32 cDNA library #2 (Example I.B.2.) were screened in duplicate at a density of approximately 100,000 plaques per 150 mm plate using the IMR32 1.36 cDNA fragment (II.A.1) as a probe. Standard hybridization conditions were used (Example I.C), and the filters were washed under high stringency (Example I.C.). Three positive plaques were identified one of which was IMR32 1.80. IMR32 1.80 was plaque purified by standard methods, restriction mapped, subcloned, and characterized by DNA sequencing.

c. IMR32 1.144

Approximately 1×10⁶ recombinants of the IMR32 cDNA library #3 (Example I.B.3) were screened with the EcoRI-PvuII fragment (nt 1573 to 2008, Sequence ID #1) of IMR32 1.80. The hybridization was performed using standard hybridization conditions (Example I.C.) and the filters were washed under high stringency (Example I.C.). Three positive plaques were identified one of which was IMR32 1.144. IMR32 1.144 was plaque purified, restriction mapped, and the cDNA insert was subcloned into pGEM7Z (Promega, Madison, Wis.) and characterized by DNA sequencing. This characterization revealed that IMR32 1.144 has a series of ATG codons encoding seven possible initiating methionines (nt 1 to 21, Sequence ID #1). PCR analysis, and DNA sequencing of cloned PCR products encoding these seven ATG codons confirmed that this sequence is present in the VDCC III transcript expressed in dbcAMP-induced IMR32 cells.

d. IMR32 1.136

Approximately 1×10$^6$ recombinants of the IMR32 cDNA library #4 (Example I.B.4) were screened with the EcoRI-PvuII fragment (nt 1573 to 2008, Sequence ID #1) of IMR32 1.80 (Example II.A.1.). The hybridization was performed using standard hybridization conditions (Example I.C.) and the filters were washed under high stringency (Example I.C.). Six positive plaques were identified one of which was IMR32 1.136. IMR32 1.136 was plaque purified, restriction mapped, and the cDNA insert was subcloned into a standard plasmid vector, e.g., pSP72 (Promega, Madison, Wis.), and characterized by DNA sequencing. This characterization revealed that IMR32 1.136 encodes an incompletely spliced VDCC III transcript. The clone contains nucleotides 1117 to 2478 of Sequence ID #1 preceded by an approximate 640 bp intron. This intron is then preceded by a 104 nt exon (Sequence ID #4) which is an alternative exon encoding the IS6 transmembrane domain [see Tanabe et al. (1987) *Nature* 328:313–318 for a description of the IS1 to IVS6 transmembrane terminology] of the VDCC III α$_1$ subunit and is proposed to be capable of replacing nt 1117 to 1220, Sequence ID #1, in a completely spliced VDCC III transcript.

e. IMR32 1.163

Approximately 1×10$^6$ recombinants of the IMR32 cDNA library #3 (I.B.3.) were screened with the NcoI-XhoI fragment of IMR32 1.80 (Example II.A.1.) containing nt 5301 to 5958 (Sequence ID #1). The hybridization was performed using standard hybridization conditions (Example I.C.) and the filters were washed under high stringency (Example I.C.). Three positive plaques were identified one of which was IMR32 1.163. IMR32 1.163 was plaque purified, restriction mapped, and the cDNA insert was subcloned into a standard plasmid vector, e.g., pSP72 (Promega, Madison, Wis.), and characterized by DNA sequencing. This characterization revealed that IMR32 1.163 contains the VDCC III termination codon, nt 6484 to 6486 (Sequence ID #1).

3. Construction of a full-length VDCC III cDNA [pVDCC III (A)]

VDCC III cDNA clones IMR32 1.144, IMR32 1.136, IMR32 1.80, and IMR32 1.163 (Example II.A.2.) overlap to comprise the entire VDCC III coding sequence, nt 1 to 6483 (Sequence ID #1), with the exception of a 148 bp deletion, nt 2474 to 2621 (Sequence ID #1). Portions of these partial cDNAs were ligated to generate a full-length VDCC III cDNA contained within a eukaryotic expression vector. The resulting vector was called pVDCCIII(A). The construction of pVDCCIII(A) was performed in four steps described in detail below: (1) the construction of pVDCCIII/5' using portions of IMR32 1.144, IMR32 1.136, and IMR32 1.80, (2) the construction of pVDCCIII/5'.3 that corrects the 148 nt deletion in the IMR32 1.80 portion of pVDCCIII/5', (3) the construction of pVDCCIII/3'.1 using portions of IMR32 1.80 and IMR32 1.163, and (4) the ligation of a portion of the pVDCCIII/5'.3 insert, the insert of pVDCCIII/3'.1, and pcDNA1 (Invitrogen, San Diego, Calif.) to form pVDCCIII (A). pcDNA1 is a eukaryotic expression vector containing a cytomegalovirus (CMV) promoter which is a constitutive promoter that can be used to control the recombinant expression of a VDCC III cDNA in mammalian host cells.

Each of the DNA fragments used in preparing the full-length construct was purified by electrophoresis through an agarose gel onto DE81 filter paper (Whatman, Clifton, N.J.) and elution from the filter paper using 1.0M NaCl, 10 mM TRIS, pH 8.0, 1 mM EDTA. The ligations routinely were performed in a 10 μl reaction volume with an equal molar ratio of insert fragment and a two-fold molar excess of the total insert relative to the vector. The mass of DNAs used was normally 50 ng to 100 ng.

a. pVDCC III/5'

To construct pVDCC III/5', IMR32 1.144 (Example II.A.2. c.) was digested with XhoI and EcoRI and the fragment containing the vector (pGEM7Z), VDCC III nt 1 to 510 (Sequence ID #3), and VDCC III nt 1 to 1222 (Sequence ID #1) was isolated by gel electrophoresis. The EcoRI-ApaI fragment of IMR32 1.136 (Example II.A.2. d.) nucleotides 1222 to 2157 (Sequence ID #1) was isolated, and the ApaI-HindIII fragment of IMR32 1.80 (Example II.A.2. b.), nucleotides 2157 to 3982 (Sequence ID #1) was isolated. The three DNAs were ligated together to form PVDCC III/5' containing nt 1 to 510 (5' untranslated sequence; Sequence ID #3) and nt 1 to 3982 (Sequence ID #1).

b. pVDCCIII/5'.3

At the time pVDCCIII/5' was being constructed, a comparison of the IMR32 1.36 and IMR32 1.80 DNA sequences revealed that these two cDNAs differ through the VDCC III coding sequence, nucleotides 2474 to 2702. PCR analysis of IMR32 1.80 and dbcAMP-induced (1.0 mM, 10 days) IMR32 cytoplasmic RNA (isolated according to Ausubel, F. M. et al. (1988) (Eds) *Current Protocols in Molecular Biology*, John Wiley and Sons, New York) revealed that IMR32 1.80 had a 148 nt deletion, nt 2474 to 2621 (Sequence ID #1), and that IMR32 1.36 had a 132 nt deletion, nt 2571 to 2702. To perform the PCR analysis, amplification was primed with VDCC III-specific oligonucleotides 112 (nt 2038 to 2062, Sequence ID #1) and 311 (the complementary sequence of nt 3418 to 3447, Sequence ID #1). These products were then reamplified using VDCC III-specific oligonucleotides 310 (nt 2073 to 2098 Sequence ID #1) and 312 (the complementary sequence of nt 3373 to 3399). Contained within this reamplified product are AccI and BglII restriction sites (FIG. 1). The reamplified PCR product was restriction digested with AccI and BglII and the AccI-BglII fragment, nt 2254 to 3380 (Sequence ID #1) was cloned into AccI-BglII digested pVDCCIII/5' to replace the AccI-BglII pVDCCIII/5' fragment that had the deletion. This new construct was named pVDCCIII/5'.3. DNA sequence determination of pVDCC III/5'.3 through the amplified region confirmed the 148 nt deletion in IMR32 1.80.

c. pVDCCIII/3'.1

To construct pVDCCIII/3'.1, the cDNA insert of IMR32 1.163 (Example II.A.2. e.) was subcloned into pBluescript II (Stratagene, La Jolla, Calif.) as an XhoI fragment. The XhoI sites on the cDNA fragment were furnished by the adapters used to construct the cDNA library (I.B.3.). The insert was oriented such that the translational orientation of the insert of IMR32 1.163 was p390X opposite to that of the lacZ gene present in the plasmid, as confirmed by analysis of restriction enzyme digests of the resulting plasmid. This was done to preclude the possibility of expression of α1 sequences in DH5α cells transformed with this plasmid due to fusion with the lacZ gene. This plasmid was then digested with HindIII and BglII and the HindIII-BglII fragment (the HindIII site comes from the vector and the BglII site is at nt 5710, Sequence ID #1) was removed, thus deleting nt 4690 to 5710 (Sequence ID #1) of the IMR32 1.163 clone and releasing the 3' BglII-XhoI fragment, nt 5710 to 7125 (Sequence ID #1). pVDCCIII/3'.1 was then made by splicing together the HindIII-PvuII fragment from IMR32 1.80 (nucleotides 3982–4784, Sequence ID #1), the PvuII-BglII fragment of IMR32 1.163 (nucleotides 4784 to 5710, Sequence ID #1) and the HindIII-BglII-digested pBluescript plasmid containing the 3' BglII/XhoI IMR32 1.163 fragment (nt 5710 to 7125, Sequence ID #1).

d. pVDCCIII(A): the full-length VDCC III construct

To construct pVDCCII(A), the DraI-HindIII fragment (5' untranslated sequence nt 327 to 510, Sequence ID #3 and coding sequence nt 1 to 3982, Sequence ID #1) of pVDCCIII/5'.3 (Example II.A.3. b.) was isolated; the HindIII-XhoI fragment pf pVDCCIII/3'.1 (containing nt 3982 to 7125, Sequence ID #1, plus the XhoI site of the adapter) (Example II.A.3. c.) was isolated; and the plasmid vector, pcDNA1, was digested with EcoRV and XhoI and isolated on an agarose gel. These three DNAs were ligated together and MC1061-P3 (Invitrogen, San Diego, Calif.) was transformed. Isolated clones were analyzed by restriction mapping and DNA sequencing and pVDCCIII(A) was identified which had the fragments correctly ligated together: DraI-HindIII, HindIII-XhoI, XhoI-EcoRV with the blunt-end DraI and EcoRV site ligating together to form the circular plasmid.

Due to the unusual primary structure of the aminoterminus of the VDCC III subunit, which is encoded by the seven consecutive 5' methionine codons (nt 1 to 21, Sequence ID #1), this 5' nt sequence plus nt 22 to 27, encoding two lysine residues, were deleted from pVDCCIII (A) and replaced with an efficient ribosomal binding site (5'-ACCACC-3') to form pVDCCIII.RBS (A). Expression experiments in which transcripts of this construct were injected into *Xenopus laevis* oocytes did not result in an enhancement in the recombinant voltage-dependent calcium channel expression level relative to the level of expression in oocytes injected with transcripts of pVDCCIII(A).

B. VDCC II cDNAs

1. Reference List of Partial VDCC II cDNAs

Figure 2:
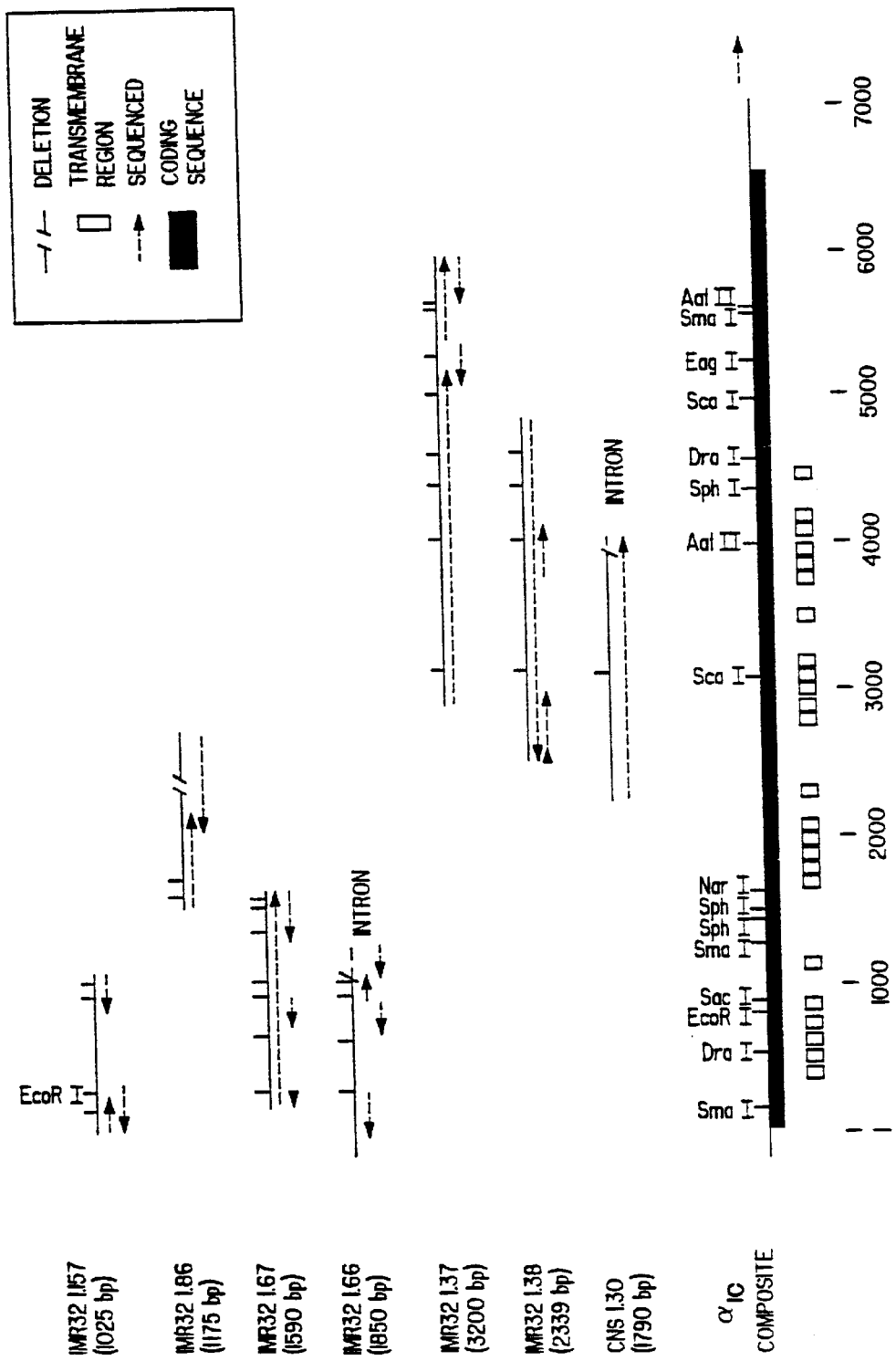
FIG. 2 represents a restriction map of a nucleic acid sequence encoding the majority of a human neuronal $\alpha_1$ calcium channel subunit (VDCC II), and the DNA sequencing strategy of various cDNA clones used to derive the coding sequence.

Numerous VDCC II-specific cDNAs were isolated in order to characterize the VDCC II coding sequence, the VDCC II initiation of translation, and an alternatively spliced region of VDCC II. Sequence ID #6 shows the characterized VDCC II coding sequence (nt 1 to 5904). Also shown in Sequence ID #6 is the deduced amino acid sequence. Sequence ID #8 and #9 encode two possible amino terminal ends of the VDCC II protein. Sequence ID #10 encodes an alternative exon for the IV S3 transmembrane domain. Shown below is a list of clones used to characterize the VDCC II sequence and the nucleotide position of each clone relative to the characterized VDCC II sequence (Sequence ID #6). Restriction maps of the partial VDCC II cDNAs are shown in FIG. 2. The isolation and characterization of these cDNAs are described below (Example II.B.2).

| IMR32 | 1.66 | nt 1 to 916, | Sequence ID #6 |
|---|---|---|---|
| | | nt 1 to 132, | Sequence ID #8 |
| IMR32 | 1.157 | nt 1 to 873, | Sequence ID #6 |
| | | nt 1 to 89, | Sequence ID #9 |
| IMR32 | 1.67 | nt 50 to 1717, | Sequence ID #6 |
| *IMR32 | 1.86 | nt 1366 to 2583, | Sequence ID #6 |
| @1.16G | | nt 758 to 867, | Sequence ID #6 |
| IMR32 | 1.37 | nt 2804 to 5904, | Sequence ID #6 |
| CNS | 1.30 | nt 2199 to 3903, | Sequence ID #6 |
| | | nt 1 to 84 of alternative exon, | Sequence ID #10 |
| IMR32 | 1.38 | nt 2448 to 4702, | Sequence ID #6 |
| | | nt 1 to 84 of alternative exon, | Sequence ID #10 |

*IMR32 1.86 has a 73 nt deletion compared to the rabbit cardiac muscle calcium channel $\alpha_1$-subunit cDNA sequence.
@1.16G is a VDCC II genomic clone.

2. Isolation and characterization of individual cDNAs and DNAs listed in Example II.B.1.

a. CNS 1.30

Approximately one million recombinants of the human thalamus cDNA library #6 (Example I.B.6.) were screened with fragments of the rabbit skeletal muscle calcium channel α1 cDNA described in Example II.A.2.a. The hybridization was performed using standard hybridization conditions (Example I.C.) and the filters were washed under low stringency (Example I.C.). Six positive plaques were identified, one of which was CNS 1.30. CNS 1.30 was plaque purified, restriction mapped, subcloned, and characterized by DNA sequencing. CNS 1.30 encodes VDCC II-specific sequence nt 2199 to 3903 (Sequence ID #6) followed by nt 1 to 84 of one of two identified alternative VDCC II exons (Sequence ID #10). 3' of Sequence ID #10, CNS 1.30 contains an intron and, thus, CNS 1.30 encodes a partially spliced VDCC II transcript.

b. 1.16G

Approximately one million recombinants of a λEMBL3-based human genomic DNA library (Cat # HL1006d Clontech Corp., Palo Alto, Calif.) were screened using a rabbit skeletal muscle cDNA fragment (nt -78 to 1006, Example II.A.2. a.). The hybridization was performed using standard hybridization conditions (Example I.C.) and the filters were washed under low stringency (Example I.C.). Fourteen positive plaques were identified, one of which was 1.16G. Clone 1.16G was plaque purified, restriction mapped, subcloned, and portions were characterized by DNA sequencing. DNA sequencing revealed that 1.16G encodes VDCC II-specific sequence as described in Example II.A.1.

c. IMR32 1.66 and IMR32 1.67

Approximately one million recombinants of IMR32 cDNA library #5 (Example I.B.5.) were screened with a 151 bp KpnI-SacI fragment of 1.16G (Example II.B.2.b.) encoding VDCC II sequence (nt 758 to 867, Sequence ID #6). The hybridization was performed using standard hybridization conditions (Example I.C.). The filters were then washed in 0.5× SSPE at 65° C. Of the positive plaques, IMR32 1.66 and IMR32 1.67 were identified. The hybridizing plaques were purified, restriction mapped, subcloned, and characterized by DNA sequencing. Two of these cDNAs, IMR32 1.66 and 1.67, encode VDCC II sequences as described (Example II.A.1.). In addition, IMR32 1.66 encodes a partially spliced VDCC II transcript marked by a GT splice donor dinucleotide beginning at the nucleotide 3' of nt 916 (Sequence ID #6). The intron sequence within 1.66 is 101 nt long. IMR32 1.66 encodes the VDCC II initiation of translation, nt 1 to 3 (Sequence ID #6) and 132 nt of 5' untranslated sequence (Sequence ID #8) precede the start codon in IMR32 1.66.

d. IMR32 1.37 and IMR32 1.38

Approximately two million recombinants of IMR32 cDNA library #1 (Example I.B.1.) were screened with the CNS 1.30 cDNA fragment (Example II.B.2.a.). The hybridization was performed using low stringency hybridization conditions (Example I.C.) and the filters were washed under low stringency (Example I.C.). Four positive plaques were identified, plaque purified, restriction mapped, subcloned, and characterized by DNA sequencing. Two of these characterized cDNAs were IMR32 1.37 and IMR32 1.38 encoding VDCC II-specific sequence as described in Example II.B.1.

Figure 3:
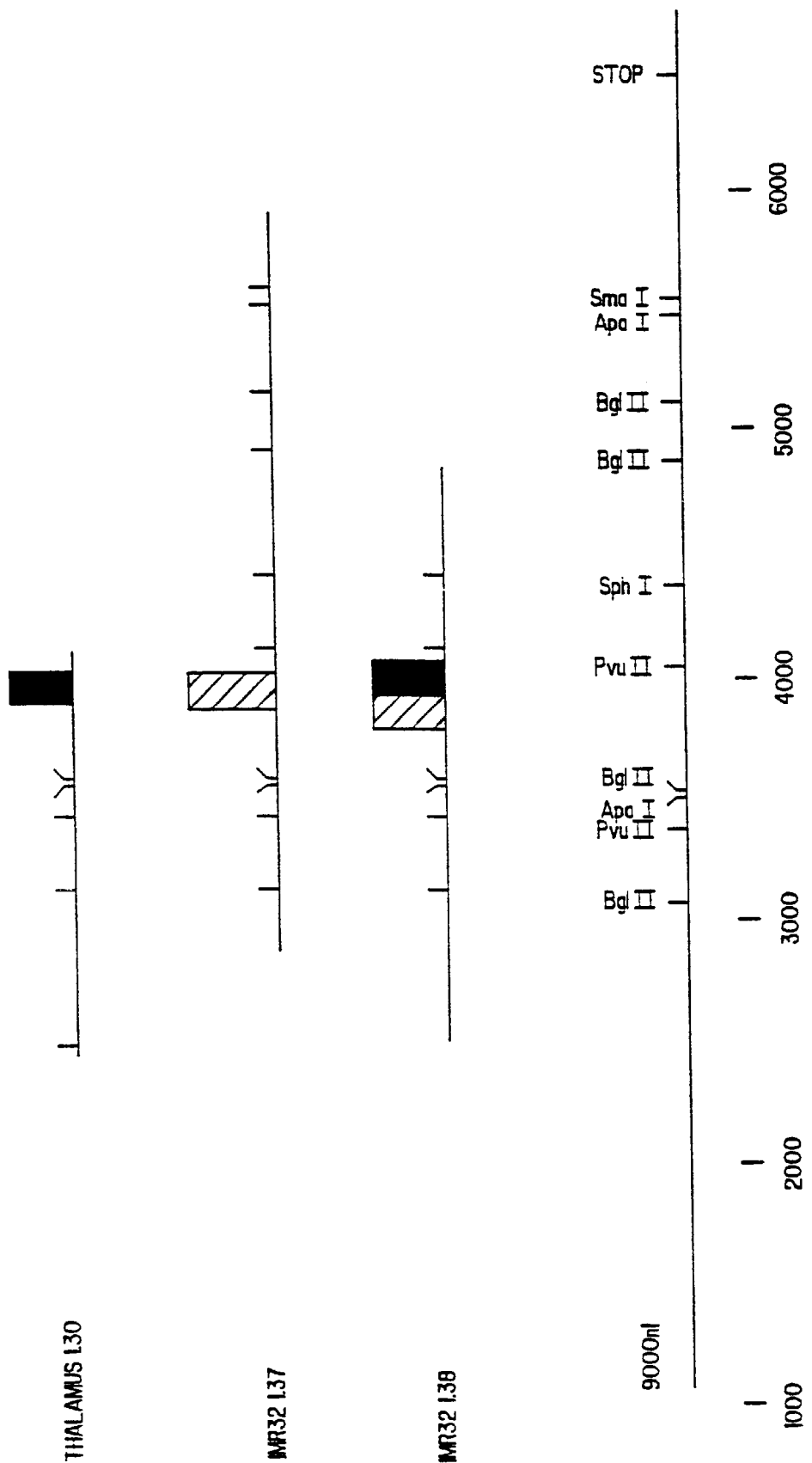
FIG. 3 depicts an alternative splicing strategy of a nucleic acid sequence encoding a human neuronal $\alpha_1$ calcium channel subunit (VDCC II)

DNA sequence comparison of IMR32 1.37 and IMR32 1.38 revealed that the VDCC II transcript has two exons that encode the IVS3 transmembrane domain. IMR32 1.37 has a single exon, nt 3904 to 3987 (Sequence ID #6) and IMR32 1.38 appears to be anomolously spliced to contain both exons juxtaposed, nt 3904 to 3987 (Sequence ID #6) followed by nt 1 to 84 (Sequence ID #10). The alternative splice of the VDCC II transcript to contain either of the two exons encoding the IVS3 region was confirmed by comparing the CNS 1.30 sequence to the IMR32 1.37 sequence. CNS 1.30 contains nt 1 to 84 (Sequence ID #10) preceded by the identical sequence contained in IMR32 1.37 for nt 2199 to 3903 (Sequence ID #6). Described in Example II.B.2. a., an intron follows nt 1 to 84 (Sequence ID #10). Regardless, two alternative exons have been spliced adjacent to nt 3903 (Sequence ID #6) represented by CNS 1.30 and IMR32 1.37. The alternative splicing of this region is schematically depicted in FIG. 3. The solid box represents nt 1 to 84 (Sequence ID #10) and the striped box represents nt 3904 to 3987 (Sequence ID #6).

e. IMR32 1.86

IMR32 cDNA library #1 (Example I.B.1.) was screened in duplicate using oligonucleotide probes 90–9 (nt 1462 to 1491, Sequence ID #6) and 90–12 (nt 2496 to 2520, Sequence ID #6). These oligonucleotide probes were chosen in order to isolate a clone that encodes the VDCC II sequence between the 3' end of IMR32 1.67 (nt 1717, Sequence ID #6) and the 5' end of CNS 1.30 (nt 2199, Sequence ID #6). The hybridization conditions were standard hybridization conditions (Example I.C.) with the exception that the 50% deionized formamide was reduced to 20%. The filters were washed under low stringency (Example I.C.). Three positive plaques were identified one of which was IMR32 1.86. IMR32 1.86 was plaque purified, subcloned, and characterized by restriction mapping and DNA sequencing. IMR32 1.86 encodes VDCC II sequences as described in Example II.B.1. Characterization by DNA sequencing revealed that IMR32 1.86 contains a 73 nt deletion when compared to the rabbit cardiac muscle calcium channel $\alpha_1$ subunit cDNA sequence [A. Mikami et al., Nature 340:230 (1989)], nt 2191 to 2263. These missing nucleotides correspond to nt 2176–2248 of Sequence ID #6. Because the 5'-end of CNS 1.30 overlaps the 3'-end of IMR32 1.86, some of these missing nucleotides, i.e., nt 2205–2248 of Sequence ID #6, are accounted for by CNS 1.30. The remaining missing nucleotides of the 73 nucleotide deletion in IMR32 1.86 (i.e., nt 2176–2204 Sequence ID #6) are represented by the letter "N" in Sequence ID #6. The 73 nt deletion is a frame-shift mutation and, thus, needs to be corrected. This can be accomplished by screening either IMR32 cDNA libraries or human CNS cDNA libraries with oligonucleotides 90–9 and 90–12, described above and isolating and characterizing positive plaques. The exact human sequence through this region then can be determined and the deletion can be corrected by standard methods, e.g., replacement of a restriction fragment or site-directed mutagenesis.

f. IR32 1.157

One million recombinants of IMR32 cDNA library #4 (Example I.B.4.) were screened with an XhoI-EcoRI fragment of IMR32 1.67 encoding VDCC II nt 50 to 774 (Sequence ID #6). The hybridization was performed using standard hybridization conditions (Example I.C.). The filters were washed under high stringency (Example I.C.). One of the positive plaques identified was IMR32 1.157. This plaque was purified, the insert was restriction mapped and subcloned to a standard plasmid vector (ei., pGEM7Z, Madison, Wis.). The cDNA was characterized by DNA sequencing. IMR32 1.157 possibly encodes an alternative 5' portion of the VDCC II sequence beginning with nt 1 to 89 (Sequence ID #9) which is then followed by nt 1 to 873 (Sequence ID #6). Analysis of the 1.66 and 1.157 5' sequence is described below (Example II.B.3.).

3. Characterization of the VDCC II initiation of translation

The human sequences represent possible alternative 5' ends of the VDCC II transcript encoding the region of initiation of translation. IMR32 1.66 closely matches the CaCB-receptor sequence and diverges from the CaCB-receptor sequence in the 5' direction beginning at nt 122 (Sequence ID #8). The start codon identified in the CaCB-receptor sequence is enclosed in a box and is the same start codon used to describe the VDCC II coding sequence, nt 1 to 3 (Sequence ID #6). The functional significance of the IMR32 1.157 sequence, nt 1 to 89 (Sequence ID #9), is unknown, however, chimeric sequence between 1.157 and the VDCC II coding sequence 1.158 and the VDCC II coding sequence can be constructed and functional differences can be tested. IMR32 1.157 does not contain an initiation codon, however, one can cloned by screening IMR32 cell cDNA libraries using probes corresponding to Sequence ID #9.

C. VDCC IV cDNAs

Five VDCC IV-specific cDNAs were isolated in order to characterize portions of the VDCC IV coding sequence. Sequence ID #12 shows the VDCC IV sequence characterized. The deduced amino acid sequence of VDCC IV (Sequence ID #12) revealed two regions, Sequence ID #14 and Sequence ID #16, with noteworthy sequence homology to the rabbit BI-2 deduced amino acid sequence [Mori et al., Nature 350:398 (1991)]. The deduced amino acid sequence shown in Sequence ID #14 (corresponding to nt 144–2612 of Sequence ID #12) is 80.3% identical to the rabbit BI-2 sequence (amino acid 1 to 827). The deduced amino acid sequence shown in Sequence ID #16 (corresponding to nt 3855–4811 of Sequence ID #12) is 85.8% identical to the rabbit BI-2 sequence (amino acid 1343 to 1660). The reading frame of the deduced amino acid sequences shown as Sequence ID #14 and Sequence ID #16 begins with the adenine nucleotide at position 144 (Sequence ID #12). Beginning at nt 144 (Sequence ID #12) an open reading frame is not maintained through the remaining 5323 nucleotides. Fourteen termination codons are contained in the region of Sequence ID #12 between nucleotides encoding Sequence ID #14 and Sequence ID #16 (i.e., between nt 2612–3855 of Sequence ID #12). Several possibilities exist for the absence of an open reading frame through this region. It could be the result of a partially spliced transcript and, thus, a portion of this region could encode an intron; it could be a cloning artifact or bacterial rearrangement of the sequence during purification of the cDNA; or it could simply be a sequence error. These possibilities can be pursued by using nucleotides encoding Sequence ID #14 and #16 as probes to isolate independent cDNAs. The nucleotide sequence 3' of nt 4811 (Sequence ID #12) residue 1556 also encodes several termination codons. Independent isolates of VDCC IV cDNAs encoding this region can be characterized for the reasons described above.

Figure 4:
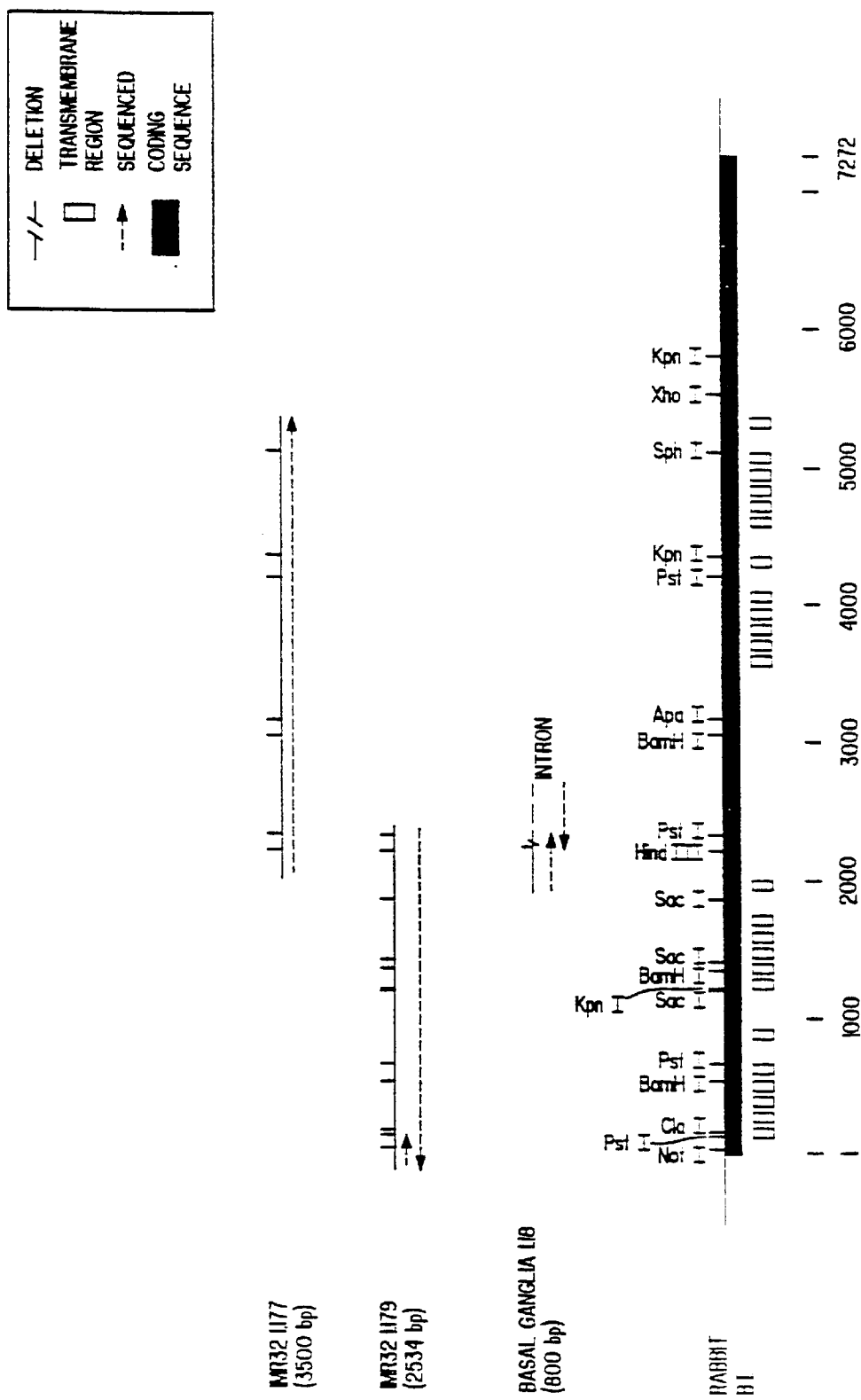
FIG. 4 presents restriction maps of a cDNA encoding the majority of a human neuronal $\alpha_1$ calcium channel VDCC IV as compared to a restriction map of the rabbit BI cDNA coding sequence.

Restriction maps of the partial VDCC IV cDNAs are shown in FIG. 4. The isolation and characterization of these clones are described below (Example II.C.2.).

| CNS | 1.18 | contains an approximately 800 bp insert beginning at nt 2012 of Sequence ID #12 |
|---|---|---|
| *IMR32 | 1.179 | nt 1 to 2537 Sequence ID #12 |
| IMR32 | 1.177 | nt 2154 to 5467 Sequence ID #12 |
| *IMR32 | 1.177 | contains a CAG triplet between nt 2410 and nt 2414 of Sequence ID #12 that is not contained in IMR32 1.179. Therefore, IMR32 1.179 is actually 2534 nt long. |

2. Isolation and characterization of VDCC IV cDNAs a. CNS 1.18

A human basal ganglia cDNA library obtained from the American Type Culture Collection (ATCC #37433, Rockville, Md.) were screened with the rabbit skeletal muscle $\alpha_1$-subunit cDNA fragments (see Example II.A.2. a. for description of fragments). The hybridization and washing conditions were low stringency (Example I.C.). CNS 1.18 was one of the positive clones identified. Restriction mapping and DNA sequencing revealed that it contains an approximate 800 bp insert beginning at nt 2012 (Sequence ID #12). CNS 1.18 represents a partially spliced VDCC IV transcript with the intron beginning after nt 2410 (Sequence ID #12).

b. IMR32 1.177

Approximately $1\times10^6$ recombinants of IMR32 cDNA library #3 (Example I.B.3.) were screened with an EcoRI-HindIII fragment of CNS 1.18 (nt 2012 to 2338). The hybridization was performed under high stringency (Example I.C.), and the filters were washed under high stringency (Example I.C.). One of the positive plaques identified was IMR32 1.177. The plaque was purified, subcloned, and sequenced. DNA sequence characterization revealed that IMR32 1.177 encoded nt 2154 to 5467 (Sequence ID #12).

C. IMR32 1.179

IMR32 1.179 was identified and characterized as described in Example II.C.2. b. DNA sequence characterization revealed that it encodes nt 1 to 2537 (Sequence ID #12).

EXAMPLE III

ISOLATION OF cDNAS ENCODING THE HUMAN NEURONAL CALCIUM CHANNEL β-subunit

Figure 5:
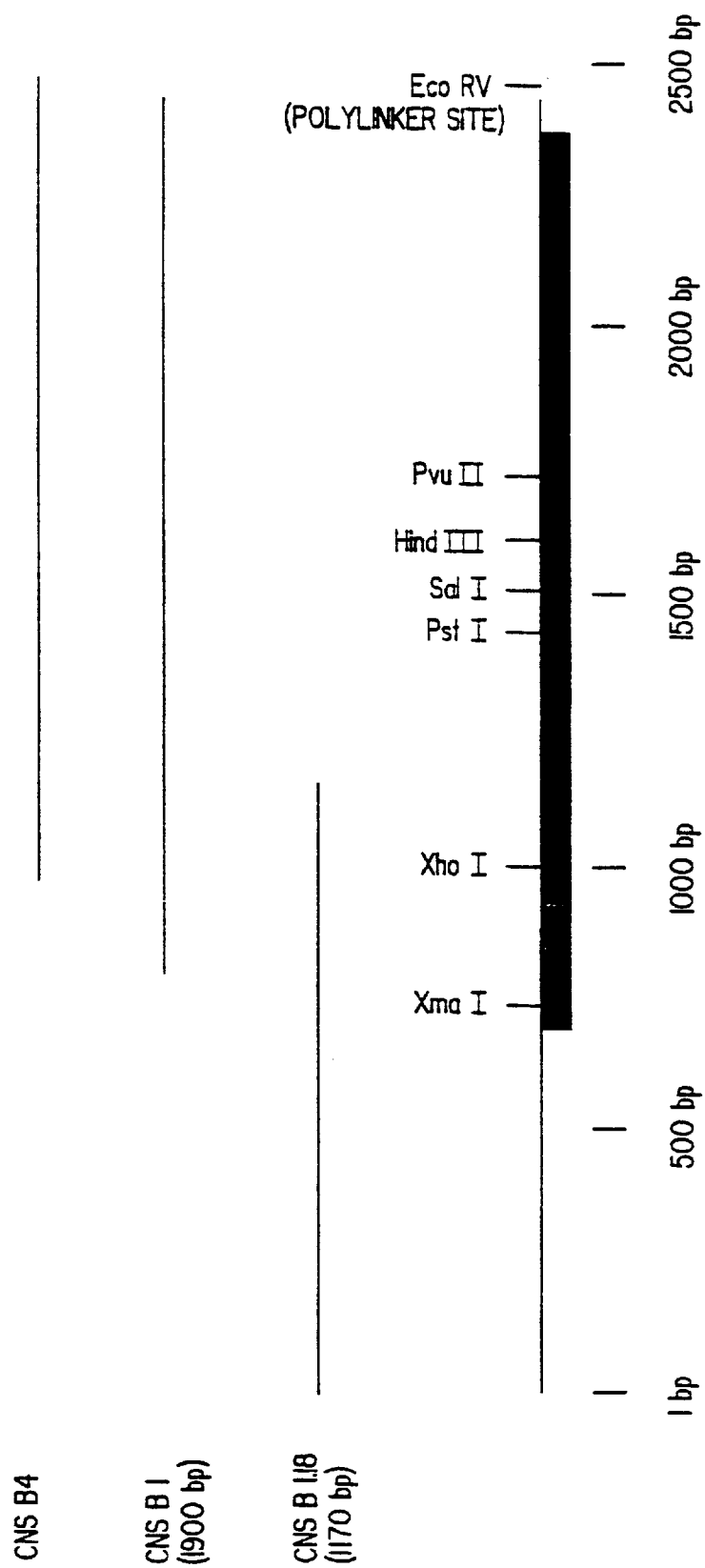
FIG. 5 is a restriction map of a nucleic acid sequence encoding a human neuronal calcium channel β-subunit, and the various cDNA clones used to derive the complete coding sequence.

The results of cDNA cloning, PCR analysis, and DNA sequencing have identified four alternatively spliced forms of the human calcium channel β-subunit transcript. These forms are designated $\beta_1$ expressed in skeletal muscle; $\beta_2$, expressed in the central nervous system; $\beta_3$, a second β form found in the CNS; and $\beta_4$, expressed in aorta tissue. Described in this example is the characterization of these forms and the construction of a full-length cDNA encoding the complete $\beta_2$ coding sequence. Restriction maps of the partial human neuronal cDNAs are shown in FIG. 5. Shown in FIG. 6 (Example V) is the result of PCR analysis that identifies the $\beta_1$, $\beta_2$, and $\beta_4$ alternative forms.

A. Reference List of Partial Subunit cDNAs

| CNS β1 | nt 69 to 1546 | Sequence ID #18 |
|---|---|---|
|  | nt 1 to 448 | Sequence ID #21 |
| CNS β1.18 | nt 1 to 65 | Sequence ID #20 |
|  | nt 1 to 325 | Sequence ID #18 |
| CNS β4 | nt 216 to 1515 | Sequence ID #18 |

The full-length $\beta_2$ coding sequence plus a portion of the 3' untranslated sequence is shown as Sequence ID #18. A portion of the 5' untranslated sequence is shown as Sequence ID #20. Encoded in CNS β1 is a 448 nt intron shown as Sequence ID #21. CNS β4 encodes an alternative splice form of the human neuronal β transcript. Nucleotides 1 to 1086 of CNS cDNA B4 (Sequence ID #22) are identical to nucleotides 246–1332 of CNS cDNA BI (Sequence ID #18). However, CNS cDNA β4 then diverges from CNS cDNA β1 at nt 1087–1515 (Sequence ID #22).

B. Isolation and Characterization of Individual Clones Listed in Example III.A.

1. CNS β1 and CNS β4

Approximately 300,000 plaques of a human hippocampus cDNA library obtained from Stratagene (CAT #936205, La Jolla, Calif.) were plated on agar plates as described by the supplier and screened with the rabbit skeletal muscle calcium channel β-subunit cDNA fragment (nt 441 to 1379) [for isolation and sequence of the rabbit skeletal muscle calcium channel β-subunit cDNA, see U.S. patent application Ser. No. 482,384 or Ruth et al. (1989) Science 245:1115]. The hybridization was performed using standard hybridization conditions (Example I.C.), and the filters were washed under low stringency (Example I.C.). Several positive plaques were identified, plaque purified and excised from the phage vector via the in vivo excision method performed according to the supplier's (Stratagene) instructions to yield cDNAs contained in the pBluescript II plasmid vector. The cDNA inserts were characterized by restriction mapping and DNA sequencing and compared to the rabbit skeletal muscle calcium channel β-subunit cDNA sequence.

a. CNS β1

CNS β1 encodes nt 69 to 1546(Sequence ID #18). CNS β1 represents a partially spliced β2 transcript that encodes a 448 bp intron (Sequence ID #21) inserted between nucleotides 1146 and 1147 of Sequence ID #18 and shown schematically in FIG. 5. This 448 bp intron was deleted via site-directed mutagenesis as described by J. Sambrook et al. (see Example I.A. for complete reference). The mutagenic oligonucleotide used to accomplish this mutagenesis encoded nt 1128 to 1165 (Sequence ID #18) and this construct was designated pβ1(−) encoding nucleotides 69 to 1546(Sequence ID #18).

b. CNS 84

DNA sequence characterization of CNS β4 showed that the first 1086 nt of β4 (Sequence ID #22) are identical to nt 246 to 1332 of β1 (Sequence ID #18). β4 then diverges at nt 1087 to 1515 (Sequence ID #22). CNS β4 represents an alternative splice form of the β transcript $\beta_3$) expressed in the CNS. The translation termination codon has not been identified.

2. CNS β1.18

Approximately $2\times10^6$ recombinants of the human hippocampus cDNA library (Example III.B.1.) were screened with a 5' PstI fragment of CNS $\beta_1$ (nucleotide 69 to 511 Sequence ID #18). The hybridization was performed using standard hybridization conditions (Example I.C.) and the filters were washed under high stringency (Example I.C.). Twenty-six positive plaques were purified and characterized as described in Example III.B.1. One clone was identified as CNS β1.18 and shown to represent ~800 bp of 5' untranslated sequence that contains nt 1 to 65 (Sequence ID #20) followed by nt 1 to 325 (Sequence ID #18) followed by additional, seemingly unrelated sequence.

3. Construction of a full-length $\beta_2$-subunit cDNA a. pβ1-1.18

A full-length $p_2$-subunit cDNA containing the CNS β1 intron was constructed. Plasmid CNS β1.18 was digested with EcoRI and XhoI and the approximately 1100 bp fragment (approximately 800 bp of 5' untranslated sequence plus nt 1 to 282 Sequence ID #18) was isolated from an agarose gel. Plasmid CNS β1 was digested with XhoI and EcoRI and the approximately 1730 bp fragment (beginning at nucleotide 277 of the coding sequence; see Sequence ID #18) was isolated from an agarose gel. The approximately 1100 bp EcoRI-XhoI fragment of CNS β1.18 was ligated to the approximately 1730 bp XhoI-EcoRI fragment of CNS β1 and cloned into the EcoRI site of pGEM7Z (Promega, Madison, Wis.). The resulting plasmid was designated pβ1-1.18. The 5' end of the full-length $\beta_2$-subunit cDNA was proximal to the T7 promoter in pGEM7Z.

b. pβ1-1.18RBS pβ1-1.18 contains ~800 bp of 5' untranslated sequence. This sequence was replaced with an efficient ribosome binding site as follows.

A double-stranded adapter was synthesized that consists of an EcoRI site, sequence encoding a ribosome binding site, and nucleotides 1 to 25 (5' half of SmaI site) of the 62$_2$ coding sequence (see Sequence ID #18):

This adapter was ligated to SmaI digested pβ1-1.18. The products of the ligation were then digested with EcoRI and the ~2000 bp EcoRI fragment containing the EcoRI adapter, the efficient ribosomal binding site (RBS) and nt 1 to 1546 of 62$_2$ sequence (Sequence ID #18) plus the intron (Sequence ID #21) was cloned into a plasmid vector and designated pβ1-1.18RBS.

c. pHBCaCHβ1bA

The 5' EcoRI-XhoI fragment of pβ1-1.18RBS (Example III. B.3. b.) was ligated to the 3' XhoI-EcoRI fragment of pβ1(−), nt 282 to 1547 (Sequence ID #18) (Example III.B.1.a.), and subcloned into the pcDNA1 expression vector (Invitrogen, San Diego, Calif.) with the initiation of translation proximal to the CMV promoter.

EXAMPLE IV

Figure 6:
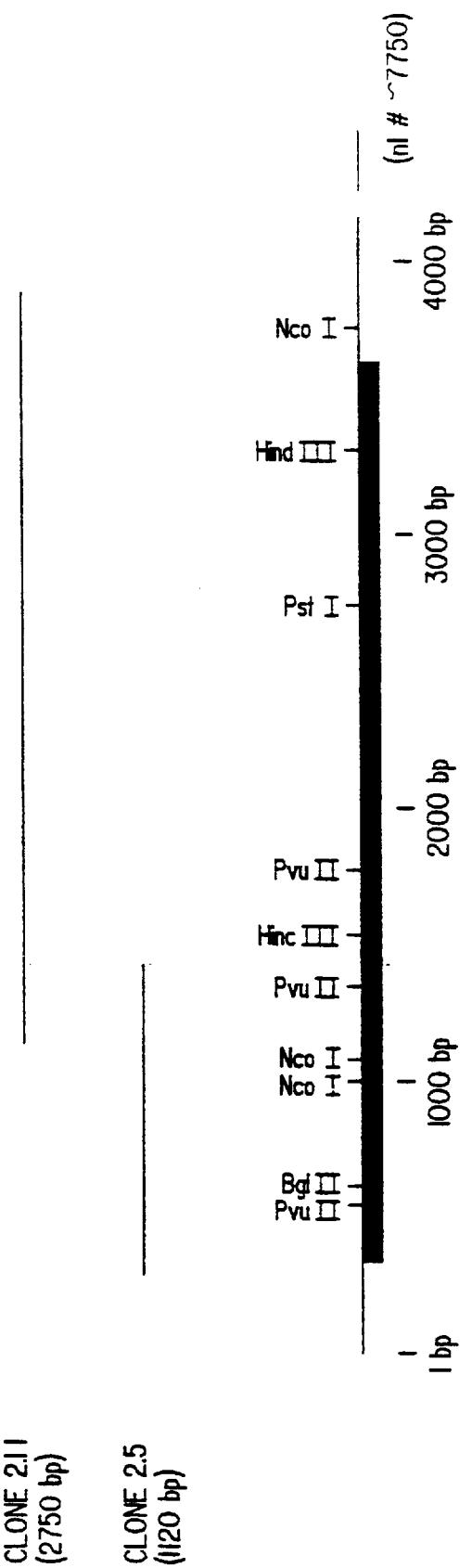
FIG. 6 is a restriction map a nucleic acid sequence encoding a human neuronal $\alpha_2$ calcium channel subunit, and the various cDNA clones used to derive the complete coding sequence.
Figure 8A:
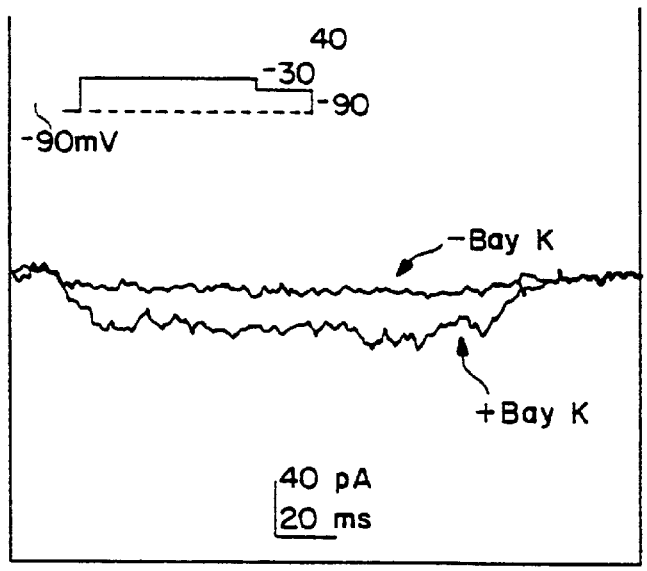
FIG. 8A–G show recordings and IV curve depicting currents measured in an HEK cell transiently transfected with $\alpha_1$-, $\alpha_2$-, and β-subunit-encoding cDNAs.
Figure 8B:
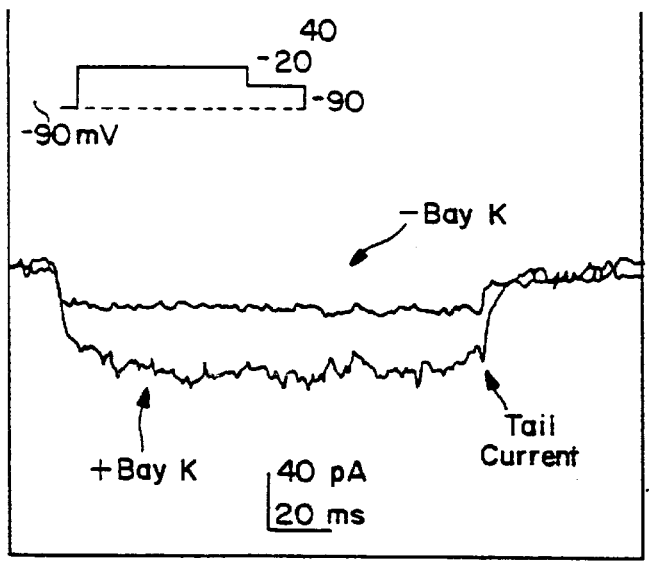
Figure 8C:
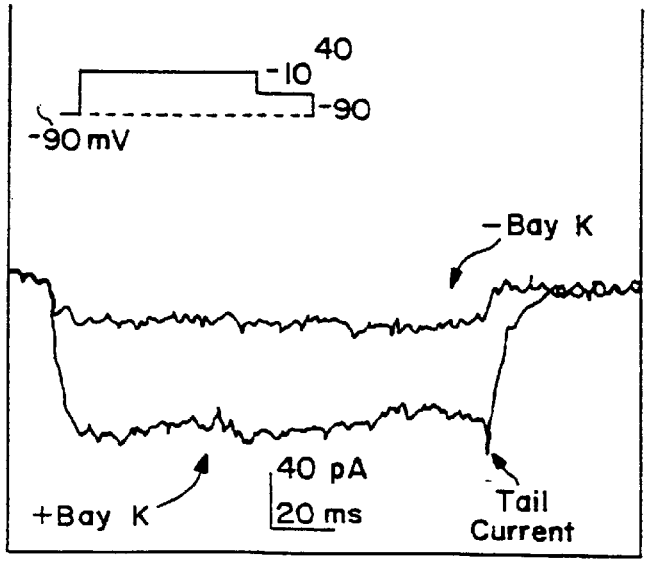
Figure 8D:
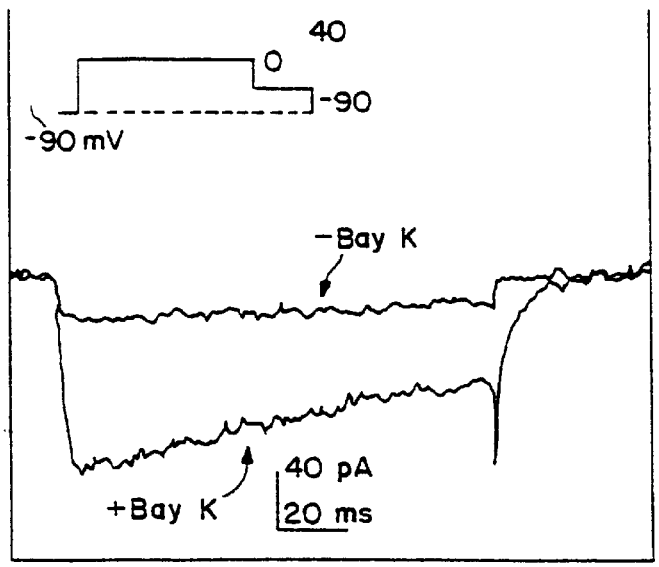
Figure 8E:
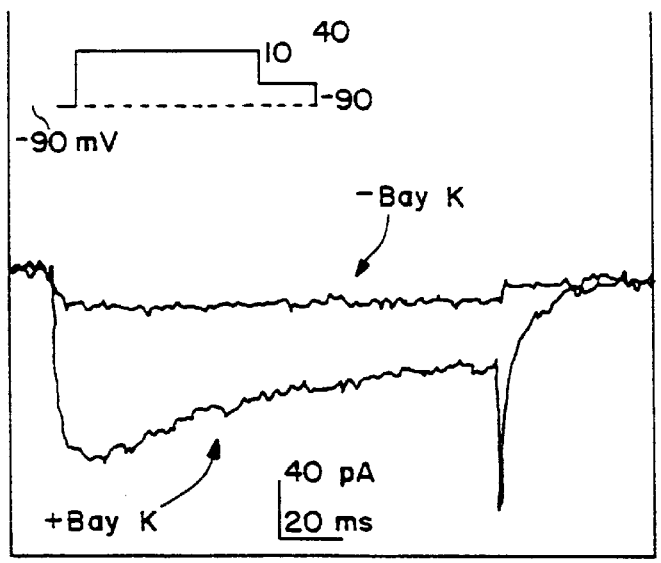
Figure 8F:
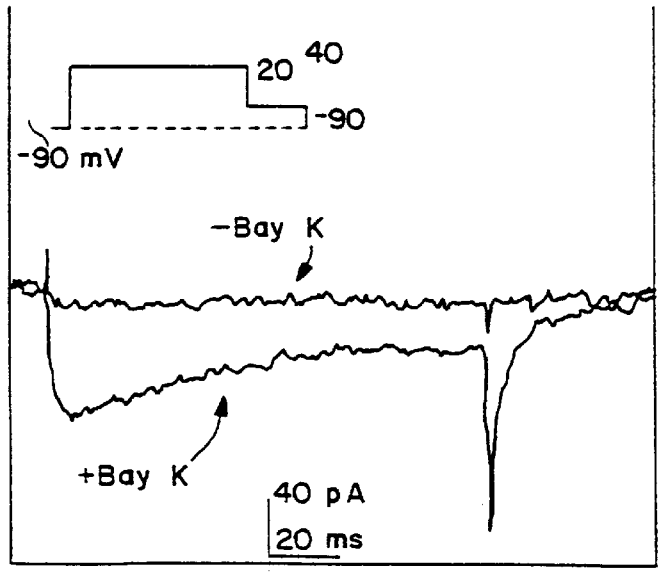
Figure 8G:
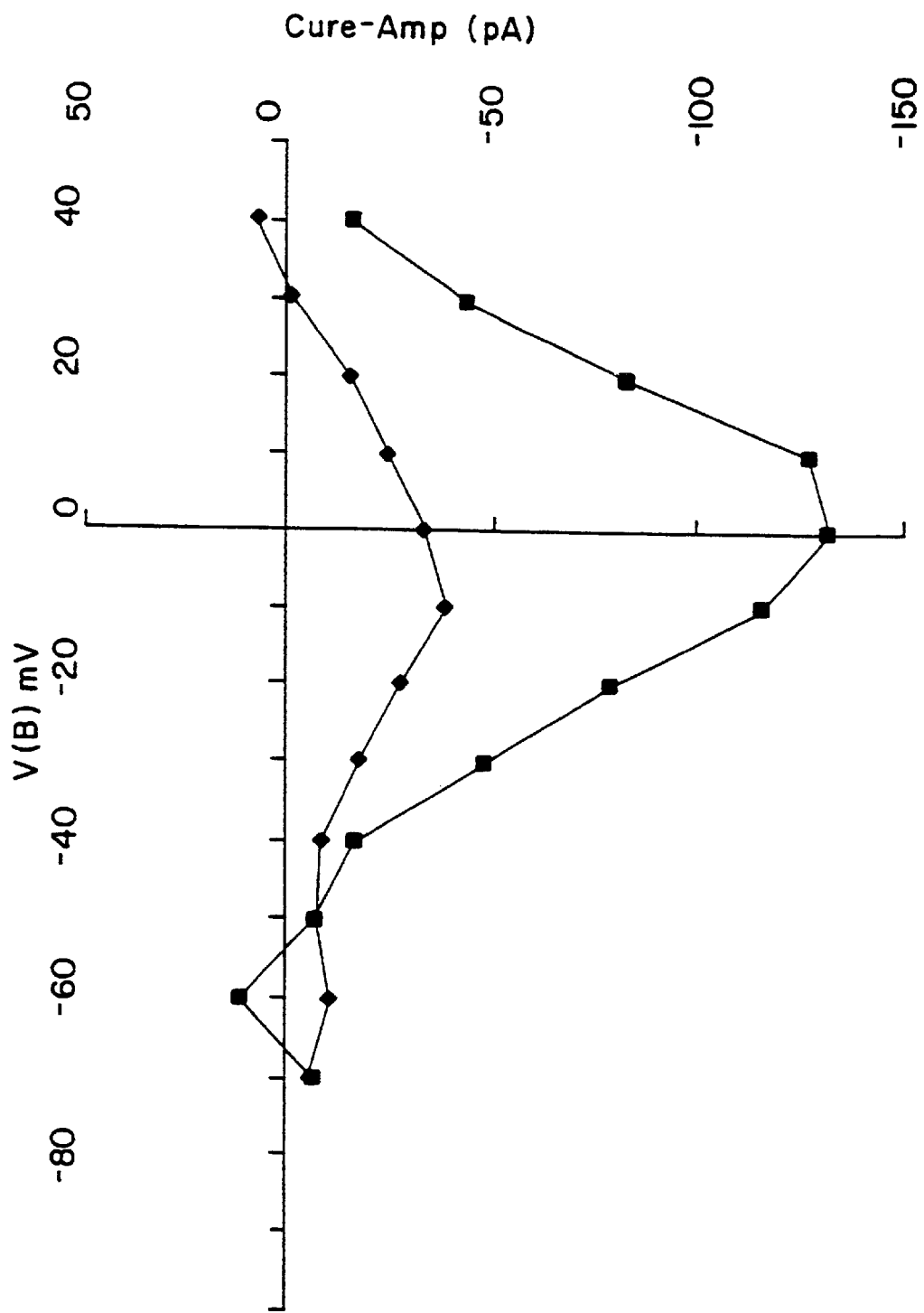

ISOLATION OF cDNAS ENCODING THE HUMAN NEURONAL CALCIUM CHANNEL $\alpha_2$-subunit A. Isolation of cDNAs Shown in FIG. 6 is a schematic of human neuronal calcium channel $\alpha_2$-subunit cDNAs that overlap to encode the complete coding sequence. The complete human neuronal $\alpha_2$ coding sequence plus a portion of the 3' untranslated sequence is shown as Sequence ID #24 (nt 1 to 3566). A portion of the 5' untranslated sequence, nt 1 to 34 is shown as Sequence ID #26.

To isolate human neuronal $\alpha_2$ cDNAs, human $\alpha_2$ genomic clones first were isolated by probing human genomic Southern blots using a rabbit skeletal muscle calcium channel $\alpha_2$-subunit cDNA fragment (nt 43 to 272, Ellis et al., (1988) *Science* 240:1661). Human genomic DNA was digested with EcoRI, electrophoresed, blotted, and probed with the rabbit skeletal muscle probe using standard hybridization conditions (Example I.C.) and low stringency washing conditions (Example I.C.). Two restriction fragments were identified, 3.5 kb and 3.0 kb. These EcoRI restriction fragments were cloned by preparing a λgt11 library containing human genomic EcoRI fragments ranging from 2.2 kb to 4.3 kb. The library was screened as described above using the rabbit $\alpha_2$ probe, the clones were isolated and characterized by DNA sequencing. HGCaCHα2.20 contained the 3.5 kb fragment and HGCaCHα2.9 contained the 3.0 kb fragment.

Restriction mapping and DNA sequencing revealed that HGCaCHα2.20 contains an 82 bp exon (nt 96 to 177 of the human β$_2$ coding sequence, Sequence ID #24) on a 650 bp PstI-XbaI restriction fragment and that HGCaCHβ2.9 contains 105 bp of an exon (nt 178 to 282 of the coding sequence, Sequence ID #24) on a 750 bp XbaI-BglII restriction fragment. These restriction fragments were used to screen the human basal banglia cDNA library (Example II.C.2. a.). HBCaCHα2.1 was isolated (nt 1 to 6, Sequence ID #26 and nt 1 to 1129, Sequence ID #24) and used to screen a human brain stem cDNA library obtained from the American Type Culture Collection (ATCC #37432). Two clones were isolated, HBCaCHα2.5 (nt 1 to 34, Sequence ID #26 and nt 1 to 1128, Sequence ID #24) and HBCaCHα2.8 (nt 680 to 1528, Sequence ID #24, followed by 1600 nt of intervening sequence). A 2400 bp fragment of HBCaCHα2.8 (beginning at nt 725 of Sequence ID #24 and ending at a SmaI site in the intron) was used to rescreen the brain stem library and to isolate HBCaCHα2.11 (nt 845 to 3566, Sequence ID #24). Clones HBCaCHα2.5 and HBCaCHα2.11 overlap to encode the entire human brain $\alpha_2$ protein.

B. Construction of pHBCaCHα2A

To construct pHBCaCHα$_2$A containing a full-length human calcium channel $\alpha_2$ cDNA, an (EcoRI)-PvuII fragment of HBCaCHα2.5 (nt 1 to 34, Sequence ID #26 and nt 1 to 1027, Sequence ID #24 EcoRI adapter, PvuII partial digest) and a PvuII-PstI fragment of HBCaCHα2.11 (nt 1027 to 2390 Sequence ID #24; PvuII partial digest) were ligated together into EcoRI-PstI digested pIBI24 (Stratagene, La Jolla, Calif.). Subsequently, an (EcoRI)-PstI fragment (nt 1 to 34 Sequence ID #26 and 1 to 2390 Sequence ID #24) was isolated and ligated to a PstI-(EcoRI) fragment (nt 2390 to 3566 Sequence ID #24) of HBCaCHc2.11 in EcoRI digested pIBI24 to create a full-length human brain $\alpha_2$ cDNA, HBCaCHα2. The 3600 bp EcoRI insert of HBCaCHα2 (nt 1 to 34, Sequence ID #26 and nt 1 to 3566, Sequence ID #24) was subcloned into pcDNA1 (pHBCaCHα2A) with the methionine initiating codon proximal to the CMV promoter. The 3600 bp EcoRI insert of HBCaCHα2 was also subcloned into pSV2dHFR [Subramani, et al. (1981). *Mol. Cell. Biol.* 1:854–864] which contains the SV40 early promoter, mouse dihydrofolate reductase (dhfr) gene, SV40 polyadenylation and splice sites and sequences required for maintenance of the vector in bacteria.

EXAMPLE V

DIFFERENTIAL PROCESSING OF TEE HUMAN β TRANSCRIPT AND THE HUMAN $\alpha_2$TRANSCRIPT

A. β

A comparison of the amino acid sequences encoded by the human neuronal and rabbit skeletal muscle calcium channel β-subunit cDNAs revealed a deletion of 45 amino acids in the human sequence (corresponding to nucleotides 628–782 of the rabbit skeletal muscle calcium channel β-subunit cDNA) relative to the rabbit sequence. This deletion is confirmed by the sequence of β4.

To determine if this difference between the rabbit and human sequences is a result of differential processing, human skeletal muscle and aorta poly(A$^+$) RNAs were characterized by PCR analysis and DNA sequencing.

PCR products of human skeletal muscle and human aorta poly(A$^+$) RNAs were synthesized by standard methods (PCR Protocols, *A Guide to Methods and Applications*, Ginnis, M., Gelfand, D., Sniasky, J. and White, T., eds. Acadamic Press, San Diego, Calif.) using β$_2$ oligonucleotide primers, nt 541 to 560 and the complement of nt 953 to 972 (Sequence ID #18). The PCR products were purified on an agarose gel and cloned in pcr1000 (Invitrogen, San Diego, Calif.).

Shown in FIG. 7A–B are the comparisons of the nucleotide sequence and deduced amino acid sequence through a 156 nt (52 amino acid) region of the rabbit skeletal muscle β-subunit transcript, designated R.SK(β$_1$), that is deleted from the human aorta and CNS β transcripts. The human skeletal muscle sequence (Sequence ID #27), designated H.SK(β$_1$), is very similar to the rabbit skeletal muscle sequence (Ruth et αl (1988) *Science* 245:1115) through the analyzed region. In contrast, the human brain β$_2$ sequence (Sequence ID #18), designated H.BR(β$_2$), lacks 156 nt of the human skeletal muscle sequence, nt 1 to 156 (Sequence ID

27) and, furthermore, has an insertion relative to the skeletal muscle sequence, nt 628 to 648 (Sequence ID #18). The human aorta transcript (designated H.AO($\beta_4$)), lacks the entire 156 nt region, nt 1 to 156 (Sequence ID #27). These results indicate that this 156 nt region is comprised of at least three exons that are differentially processed between the CNS, skeletal muscle, and aorta transcripts.

B. $\alpha_2$

A comparison of the amino acid sequences encoded by the human neuronal and rabbit skeletal muscle calcium channel $\alpha_2$-subunit cDNAs revealed a 19 amino acid deletion in the human sequence compared to the rabbit sequence (rabbit residues Pro 507 to Gln 525) which corresponds to a deletion between nt 1590 and 1591 of the human sequence (Sequence ID #24). Furthermore, a seven amino insertion was identified in the human sequence compared to the rabbit sequence (human residue Lys$^{626}$ to Asp$^{632}$) encoded by nt 1876 to 1896 (Sequence ID #24).

PCR analysis of this region using human neuronal $\alpha_2$ oligonucleotides, nt 1455 to 1479 and the complement of nt 1931 to 1955 (Sequence ID #24) to prime PCR assays of human skeletal muscle, aorta, and CNS poly(A+) RNAs showed that this region is alternatively spliced. The predicted size of the PCR products was 539 bp for the skeletal muscle reaction and 501 bp for the CNS reaction. An approximate 539 bp band was observed in the skeletal muscle reaction and an approximate 500 bp band was observed in the CNS reaction. An approximate 460 bp band also was observed in the aorta reaction plus at least two additional, larger bands, approximately 470 and 480 bp, suggesting additional alternative splicing.

EXAMPLE VI

ISOLATION OF A CALCIUM CRANNEL $\gamma$-subunit cDNA FROM A HUMAN BRAIN cDNA LIBRARY A human hippocampus cDNA library was screened as described in this example to determine if human brain tissue expresses a transcript that encodes a protein homologous to a calcium channel $\gamma$-subunit.

A. Isolation of cDNAs

Appoproximately 1×10$^6$ recombinants from a $\lambda$gt11-based human hippocampus cDNA library (Clontech catalog #HL1088b, Palo Alto, Calif.) were screened by hybridization to a 484 bp sequence of the rabbit skeletal muscle calcium channel $\gamma$-subunit cDNA (nucleotides 621–626 of the coding sequence plus 438 nucleotides of 3'-untranslated sequence) contained in vector $\gamma$J10 [Jay, S., et al. (1990). Science 248:490–492]. Hybridization was performed using moderate stringency conditions (20% deionized formamide, 5× Denhardt's; 6× SSPE, 0.2% SDS, 20 $\mu$g/ml herring sperm DNA, 42° C.) and the filters were washed under low stringency (see Example I.C.). A plaque that hybridized to this probe was purified and insert DNA was subcloned into pGEM7Z. This cDNA was designated $\gamma$1.4.

B. Characterization of $\gamma$1.4

$\gamma$1.4 was confirmed by DNA hybridization and characterized by DNA sequencing. The 1500 bp SstI fragment of $\gamma$1.4 hybridized to the rabbit skeletal muscle calcium channel $\gamma$-subunit cDNA YJ10 on a Southern blot. Sequence analysis of this fragment revealed that it consists of approximately 500 nt of human DNA sequence and ~1000 nt of $\lambda$gt11 sequence (included due to apparent destruction of one of the EcoRI cloning sites in $\lambda$gt11). The human DNA sequence consists of 129 nt of coding sequence followed immediately by a translational STOP codon and 3' untranslated sequence (Sequence ID #29).

To isolate the remaining 5' sequence of the human $\gamma$-subunit cDNA, human CNS cDNA libraries and/or preparations of mRNA from human CNS tissues can first be assayed by PCR methods using oligonucleotide primers based on the $\gamma$ cDNA-specific sequence of $\gamma$1.4. Additional human neuronal $\gamma$-subunit cDNAs could be isolated from cDNA libraries that, based on the results of the PCR assay, contain $\gamma$-specific amplifiable cDNA or, alternatively, cDNA libraries could be constructed from mRNA preparations that, based on the results of PCR assays, contain $\gamma$-specific amplifiable transcripts. cDNA libraries could be constructed by standard methods using oligo dT to prime first-strand cDNA synthesis from poly A$^+$ RNA (see Example I.B.). Alternatively, first-strand cDNA could be specified by priming first-strand cDNA synthesis with a $\gamma$ cDNA-specific olionucleotide based on the human DNA sequence in $\gamma$1.4. A cDNA library would then be constructed based on this first-strand synthesis. The libraries would be screened with the $\gamma$-specific portion of $\gamma$1.4.

EXAMPLE VII

RECOMBINANT EXPRESSION OF HUMAN NEURONAL CALCIUM CHANNEL SUBUNIT cDNAS AND TRANSCRIPTS PREPARED IN VITRO FROM THE cDNAS IN MAMMALIAN CELLS

A. Recombinant Expression of the Human Neuronal Calcium Channel $\alpha_2$-subunit cDNA in DG44 Cells 1. Stable transfection of DG44 cells DG44 cells [dhfr$^-$ Chinese hamster ovary cells; see Urlaub, G. et al. (1986). Som. Cell Molec Genet. 12:555–566] obtained from Lawrence Chasin at Columbia University were stably transfected by CaPO$_4$ precipitation methods [Wigler et al. (1979) Proc. Natl. Acad. Sci. USA 76:1373–1376] with pSV2dhfr vector containing the human neuronal calcium channel $\alpha_2$-subunit cDNA (see Example IV) for polycistronic expression/selection in transfected cells. Transfectants were grown on 10% DMEM medium without hypoxanthine or thymidine in order to select cells that had incorporated the expression vector. Twelve transfectant cell lines were established as indicated by their ability to survive on this medium.

2. Analysis of $\alpha_2$-subunit cDNA expression in transfected DG44 cells

Total RNA was extracted according to the method of Birnboim [Nuc. Acids Res. 16:1487–1497 (1988)] from four of the DG44 cell lines that had been stably transfected with pSV2dhfr containing the human neuronal calcium channel $\alpha_2$-subunit cDNA. RNA (~15 $\mu$g per lane) was separated on a 1% agarose formaldehyde gel, transferred to nitrocellulose and hybridized to the random-primed human neuronal calcium channel $\alpha_2$ cDNA (hybridization: 50% formamide, 5× SSPE, 5× Denhardt's, 42° C.; wash:0.2× SSPE, 0.1% SDS, 65° C.). Northern blot analysis of total RNA from four of the DG44 cell lines that had been stably transfected with pSV2dhfr containing the human neuronal calcium channel $\alpha_2$-subunit cDNA revealed that one of the four cell lines contained hybridizing mRNA the size expected for the transcript of the $\alpha_2$-subunit cDNA (5000 nt based on the size of the cDNA) when grown in the presence of 10 mN sodium butyrate for two days. Butyrate nonspecifically induces transcription and is often used for inducing the SV40 early promoter [Gorman, C. and Howard, B. (1983). Nuc. Acids Res. 11:1631]. This cell line, 44$\alpha_2$-9, also produced mRNA species smaller (several species) and larger (6800 nt) than the size expected for the transcript of the $\alpha_2$ cDNA (5000 nt) that hybridized to the $\alpha_2$ cDNA-based probe. The 5000- and 6800-nt transcripts produced by this transfectant should contain the entire $\alpha_2$-subunit coding sequence and therefore should yield a full-length $\alpha_2$-subunit protein. A weakly hybridizing 8000-nucleotide transcript was present in both untransfected and transfected DG44 cells. Apparently, DG44 cells transcribe a calcium channel $\alpha_2$-subunit or similar gene at low levels. The level of expression of this endogenous $\alpha_2$-subunit transcript did not appear to be affected by exposing the cells to butyrate before isolation of RNA for northern analysis.

Total protein was extracted from three of the DG44 cell lines that had been stably transfected with pSV2dhfr containing the human neuronal calcium channel $\alpha_2$-subunit cDNA. Approximately $10^7$ cells were sonicated in 300 µl ×50 mM HEPES, 1 mM EDTA, 1MM PMSF. An equal volume of 2× loading dye [Laemmli, U.K. (1970). *Nature* 227:680] was added to the samples and the protein was subjected to electrophoresis on an 8% polyacrylamide gel and then electrotransferred to nitrocellulose. The nitrocellulose was incubated with polyclonal guinea pig antisera (1:200 dilution) directed against the rabbit skeletal muscle calcium channel α-subunit (obtained from K. Campbell, University of Iowa) followed by incubation with [$^{125}$I]-protein A. The blot was exposed to X-ray film at −70° C. Reduced samples of protein from the transfected cells as well as from untransfected DG44 cells contained immunoreactive protein of the size expected for the $\alpha_2$-subunit of the human neuronal calcium channel (130–150 kDa). However, the level of this immunoreactive protein was higher in 44$\alpha_2$-9 cells that had been grown in the presence of 10 mM sodium butyrate than in 44$\alpha_2$-9 cells that were grown in the absence of sodium butyrate. These data correlate well with those obtained in northern analyses of total RNA from 44$\alpha_{2-9}$ and untransfected DG44 cells. Cell line 44$\alpha_2$-9 also produced a 110-kDa immunoreactive protein which may be either a product or a proteolytic degradaton of the full-length $\alpha_2$-subunit or a product of translation of one of the shorter (<5000 nt) mRNAs produced in this cell line that hybridized to the $\alpha_2$-subunit cDNA probe.

B. Recombinant Expression of Human Neuronal Calcium Channel $\alpha_1$, $\alpha_2$ and β-subunit cDNAs in HEK 293 Cells Human embryonic kidney cells (HEK 293 cells) were transiently and stably transfected with human neuronal calcium channel subunit cDNAs. Individual transfectants were analyzed electrophysiologically for the presence of voltage-activated barium currents indicative of the presence of functional recombinant voltage-dependent calcium channels.

1. Transfection of NEK 293 cells

Separate expression vectors containing cDNAs encoding human neuronal calcium channel $\alpha_1$ (VDCC III), $\alpha_2$ and β-subunits, vectors pVDCCIII(A), pHBCaCHα2A, and pB1-1.18, respectively, were constructed as described in Examples II.A.3, IV.B. and III.B.3. , respectively. These three vectors were used to transiently co-transfect HEK 293 cells. For stable transfection of HEK 293 cells, vector pHBCaCHβ$_1$bA (Example III.B.3.) was used in place of pB1-1.18 to introduce the β-subunit cDNA into the cells along with pVDCCIII(A) and pHBCaCHα$_2$A.

a. Transient transfection

Expression vectors pVDCCIII (A), pHBCaCHα2A and pB1-1.18 were used in two sets of transient transfections of HEK 293 cells (ATCC #CRL1573). In one transfection procedure, HEK 293 cells were transiently cotransfected with the $\alpha_1$-subunit cDNA expression vector, the $\alpha_2$-subunit cDNA expression vector, the β-subunit cDNA expression vector and vector pCMVβgal (Clontech Laboratories, Palo Alto, Calif.). Vector pCMVβgal contains the lacZ gene (encoding *E. coli* β-galactosidase) fused to the cytomegalovirus (CMV) promoter and was included in this transfection as a marker gene for monitoring the efficiency of transfection. In the other transfection procedure, HEK 293 cells were transiently co-transfected with the $\alpha_1$-subunit cDNA expression vector pVDCCIII(A) and pCMVβgal. In both transfections, 2–4×10$^6$ HEK 293 cells contained in a 10-cm tissue culture plate were transiently co-transfected with 5 µg of each of the vectors included in the experiment according to standard CaPO$_4$ precipitation transfection procedures (Wigler et al., supra). The transfectants were analyzed for β-galactosidase expression by direct staining of the product of a reaction involving β-galactosidase and the X-gal substrate [Jones, J. R. (1986). *EMBO* 5:3133–3142] and by measurement of β-galactosidase activity [Miller, J. H. (1972). Experiments in Molecular Genetics, pp. 352–355, Cold Spring Harbor Press]. To evaluate subunit cDNA expression in these transfectants, the cells were analyzed for subunit transcript production (northern analysis), subunit protein production (immunoblot analysis of cell lysates) and functional calcium channel expression (electrophysiological analysis).

b. Stable transfection

HEK 293 cells were transfected using the calcium phosphate transfection procedure [*Current Protocols in Molecular Biology*, Vol. 1, Wiley Inter-Science, Supplement 14, Unit 9.1.1–9.1.9 (1990)]. Ten-cm plates, each containing one-to-two million HEK 293 cells, were transfected with 1 ml of DNA/calcium phosphate precipitate containing 5 µg pVDCCIII(A), 5 µg pHBCaCHα$_2$A, 5 µg pHBCaCHβ$_1$bA, 5 µg pCMVBgal and 1 µg pSV2neo (as a selectable marker). After 10–20 days of growth in media containing 500 µg G418, colonies had formed and were isolated using cloning cylinders.

2. Analysis of HEK 293 cells transiently transfected with cDNAs encoding human neuronal calcium channel sub units a. Analysis of β-galactosidase expression Transient transfectants were assayed for β-galactosidase expression by β-galactosidase activity assays (Miller, J. H., supra) of cell lysates (prepared as described in Example V.A. 2) and staining of fixed cells (Jones, J. R. supra). The results of these assays indicated that approximately 30% of the HEK 293 cells had been transfected.

b. Northern analysis

PolyA+ RNA was isolated using the Invitrogen Fast Trak Kit (InVitrogen, San Diego, Calif.) from HEK 293 cells transiently transfected with α$_1$, α$_2$ and β-subunit cDNAs and the lacZ gene or the α$_1$-subunit cDNA and the lacZ gene. The RNA was subjected to electrophoresis on an agarose gel and transferred to nitrocellulose. The nitrocellulose was then hybridized with one or more of the following radiolabeled probes: lacZ gene, human neuronal calcium channel α$_1$ (VDCC III) subunit cDNA, human neuronal calcium channel α$_2$-subunit cDNA or human neuronal calcium channel β-subunit cDNA. Two transcripts that hybridized with the α$_1$-subunit cDNA were detected in HEK 293 cells transfected with the α$_1$, α$_2$, and β-subunit cDNAs and the lacZ gene as well as in HEK 293 cells transfected with the α$_1$-subunit cDNA and the lacZ gene. One mRNA species was the size expected for the transcript of the α$_1$-subunit cDNA (8000 nucleotides). The second RNA species was smaller (4000 nucleotides) than the size expected for this transcript. RNA the size expected for the transcript of the lacZ gene was detected in cells transfected with the α$_1$, α$_2$ and β-subunit cDNAs and the lacZ gene and in cells transfected with the α$_1$-subunit cDNA and the lacZ gene by hybridization to the lacZ gene sequence.

RNA from cells transfected with the $\alpha_1$, $\alpha_2$ and $\beta$-subunit cDNAs and the lacZ gene was also hybridized with the $\alpha_2$ and $\beta$-subunit cDNA probes. Two mRNA species hybridized to the $\alpha_2$-subunit cDNA probe. One species was the size expected for the transcript of the $\alpha_2$-subunit cDNA (4000 nucleotides). The other species was larger (6000 nucleotides) than the expected size of this transcript. Multiple RNA species in the cells co-transfected with $\alpha_1$, $\alpha_2$ and $\beta$-subunit cDNAs and the lacZ gene hybridized to the $\beta$-subunit cDNA probe. Multiple $\beta$-subunit transcripts of varying sizes were not unexpected since the $\beta$-subunit cDNA expression vector contains two potential polyA$^+$ addition sites. Differential processing of the 3' end of the $\beta$-subunit transcript at these multiple polyA$^+$ addition sites could result in multiple $\beta$-subunit transcripts of varying sizes. It is unlikely that any of these multiple $\beta$-subunit transcripts contained the intron sequence that was present in the $\beta$-subunit cDNA used to transfect these HEK 293 cells since HEK 293 cells should be capable of recognizing the splice donor and acceptor sites on the 5' and 3' ends of the intron, respectively, and removing the intron from the primary transcript.

c. Electrophysiological analysis

Individual transiently transfected HEK 293 cells were assayed for the presence of voltage-dependent barium currents using the whole-cell variant of the patch clamp technique (Hamill, O. P., Marty, A., Neher, E., Sakmann, B. and Sigworth, F. J. (1981). Pflugers Arch. 391:85–100]. HEK 293 cells transiently transfected with pCMV$\beta$gal only were assayed for barium currents as a negative control in these experiments. The cells were placed in a bathing solution that contained barium ions to serve as the current carrier. Choline chloride, instead of NaCl or KCl, was used as the major salt component of the bath solution to eliminate currents through sodium and potassium channels. The bathing solution contained in 1 mM MgCl$_2$ and was buffered at pH 7.3 with 10 mM HEPES (pH adjusted with sodium or tetraethylammonium hydroxide). Patch pipettes were filled with a solution containing 135 mM CsCl, 1 mM MgCl$_2$, 10 mM glucose, 10 mM EGTA, 4 mM ATP and 10 mM HEPES (pH adjusted to 7.3 with tetraethylammonium hydroxide). Cesium and tetraethylammonium ions block most types of potassium channels. Pipettes were coated with Sylgard (Dow-Corning, Midland, Mich.) and had resistances of 1–4 megohm. Currents were measured through a 500 megohm headstage resistor with the Axopatch IC (Axon Instruments, Foster City, Calif.) amplifier, interfaced with a Labmaster (Scientific Solutions, Solon, Ohio) data acquisition board in an IBM-compatible PC. PClamp (Axon Instruments) was used to generate voltage commands and acquire data. Data were analyzed with pClamp or Quattro Professional (Borland International, Scotts Valley, Calif.) programs.

To apply drugs, "puffer" pipettes positioned within several micrometers of the cell under study were used to apply solutions by pressure application. The drugs were used to apply solutions by pressure application. The drugs used for pharmacological characterization were dissolved in a solution identical to the bathing solution. Samples of a 10 mM stock solution of Bay K 8644 (RBI, Natick, Mass.), which was prepared in DMSO, were diluted to a final concentration of 1 $\mu$M in 15 mM Ba$^{2+}$-containing bath solution before they were applied.

Twenty-one negative control HEK 293 cells (transiently transfected with the lacZ gene expression vector pCMV$\beta$gal only) were analyzed by the whole-cell variant of the patch clamp method for recording currents. only one cell diplayed a discernable inward barium current which was not affected by the presence of 1 $\mu$M Bay K 8644. In addition, application of Bay K 8644 to four cells that did not display Ba$^{2+}$ currents did not result in the appearance of any currents.

Two days after transient transfection of HEK 293 cells with $\alpha_1$, $\alpha_2$ and $\beta$-subunit cDNAs and the lacZ gene, individual transfectants were assayed for voltage-dependent barium currents. The currents in nine transfectants were recorded. Because the efficiency of transfection of one cell can vary from the efficiency of transfection of another cell, the degree of expression of heterologous proteins in individual transfectants varies and some cells do not incorporate or express the foreign DNA. Therefore, it was not unexpected that seven of these nine transfectants did not display a voltage-dependent inward barium current. However, inward barium currents were detected in two of these nine transfectants. In these assays, the holding potential of the membrane was –90 mV. The membrane was depolarized in a series of voltage steps to different test potentials and the current in the presence and absence of 1 $\mu$M Bay K 8644 was recorded. The current tracings for one of the two cells are shown in FIG. 8A–G The inset in each tracing panel indicates the test potential to which the membrane was depolarized. The inward barium current in this cell was significantly enhanced in magnitude by the addition of Bay K 8644. The largest inward barium current (~160 pA) was recorded when the membrane was depolarized to 0 mV in the presence of 1 $\mu$Bay K 8644. The data shown in the current tracings are also presented in FIG. 8A–G as an I-V curve generated by plotting the largest current recorded after each depolarization versus the depolarization voltage. A comparison of the I-V curves corresponding to recordings conducted in the absence and presence of Bay K 8644 illustrates the enhancement of the voltage-activated current in the presence of Bay K 8644.

It has been reported [Hess, J. B., et al. (1984), Nature 311: 538–544] that the dihydropyridine Bay K 8644 specifically enhances L-type calcium channel function by increasing the duration of the open state of the channels.

Prolonged opening of the channels results in calcium currents of increased magnitude and duration. The generation of prolonged calcium currents and Bay K "tails" in whole-cell patch claim recordings of L cells transfected with the rabbit skeletal muscle calcium channel $\alpha$1-subunit cDNA that were treated with Bay K 8644 has also been described [Perez-Reyes, E., et al. (1989). Nature 340:233–236]. Tail currents can be observed upon repolarization of the cell membrane after activation of ion channels by a depolarizing voltage command. The opened channels require a finite time to close or "deactivate" upon repolarization, and the current that flows through the channels during this period is referred to as a tail current. Because Bay K 8644 prolongs opening events in calcium channels, it tends to prolong these tail currents and make them more pronounced. As shown in FIG. 8A–G, pronounced tail currents were detected in the tracings of currents generated in the presence of Bay K 8644 in this HEK 293 cell transfected with $\alpha_1$, $\alpha_2$ and $\beta$-subunit cDNAs and the lacZ gene. Therefore, the recombinant calcium channels responsible for the voltage-activated barium currents recorded in this transfected appear to be DHP sensitive.

The second of the two transfected cells that displayed inward barium currents expressed a ~50 pA current when the membrane was depolarized from –90 mV. This current was nearly completely blocked by 200 $\mu$M cadmium, an established calcium channel blocker.

Ten cells that were transiently transfected with the $\alpha_1$-subunit cDNA and the lacZ gene were analyzed by whole-cell patch clamp methods two days after transfection. One of these cells displayed a 30 pA inward barium current. This current amplified 2-fold in the presence of 1 μM Bay K 8644. Furthermore, small tail currents were detected in the presence of Bay K 8644. These data indicate that expression of the human neuronal calcium channel VDCC III $\alpha_1$-subunit cDNA in HEK 293 yields a functional DHP-sensitive calcium channel.

3. Analysis of HEX 293 cells stably transfected with cDNAs encoding human neuronal calcium channel subunits Individual stably transfected HEK 293 cells were assayed electrophysiologically for the presence of voltage-dependent barium currents as described for electrophysiological analysis of transiently transfected HEK 293 cells (see Example VII.B.2. c). In an effort to maximize calcium channel activity via cyclic-AMP-dependent kinase-mediated phosphorylation [Pelzer, et al. (1990) *Rev.*

Physiol. Biochem. Pharmacol. 114:107–207], cAMP (Na salt, 250 μM) was added to the pipet solution and forskolin (10 μM) was added to the bath solution in some of the recordings. Qualitatively similar results were obtained whether these compounds were present or not.

Figure 9A:
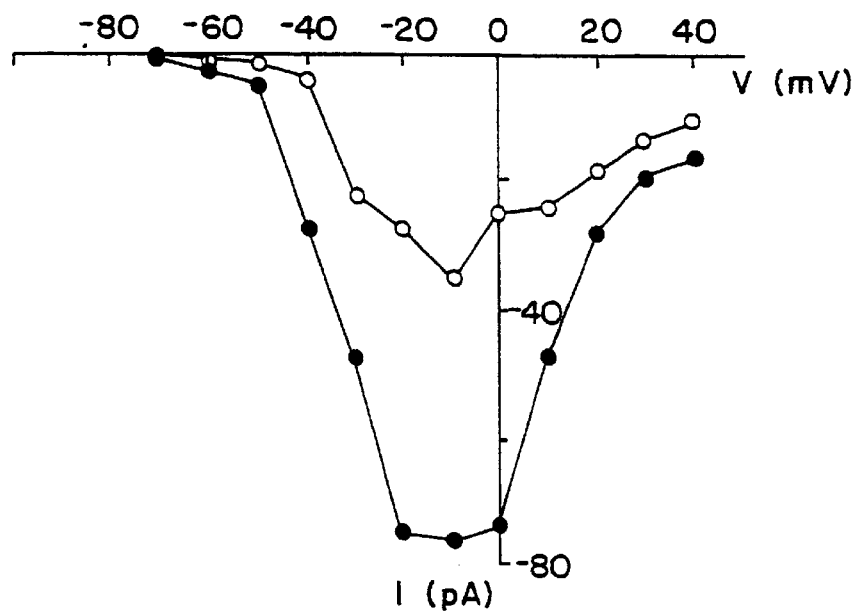
FIG. 9A–B show recordings and IV curve depicting currents measured in an HEK cell stably transfected with α1-, α2-, and β-subunit-encoding cDNAs.
Figure 9B:
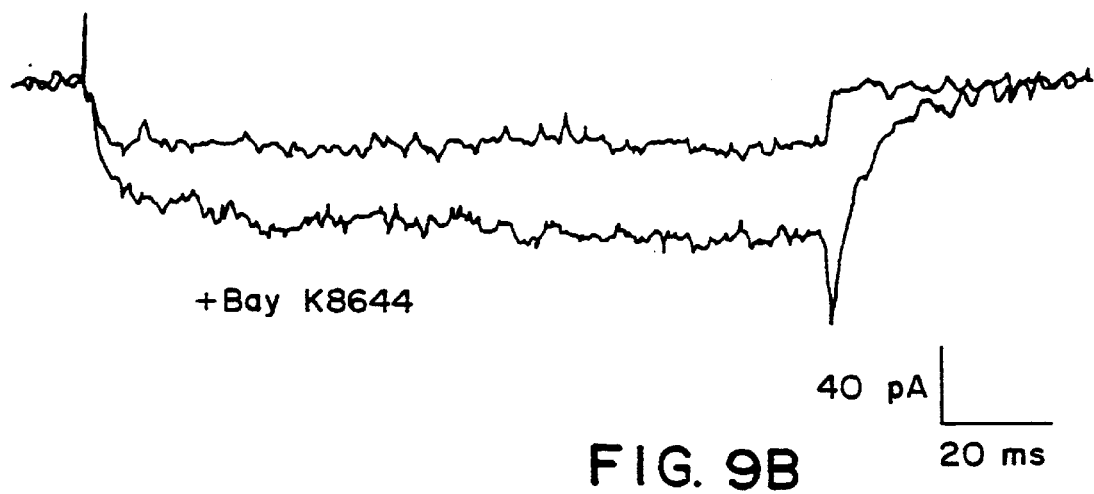

Barium currents recorded from stably transfected cell in the absence and presence of Bay K 8644 (1 μM) are shown in FIG. 9A–B. When the cell was depolarized to −10 mV from a holding potential of −90 mV in the absence of Bay K 8644, a current of approximately 35pA with a rapidly deactivating tail current was recorded. During application of Bay K 8644, an identical depolarizing protocol elicited a current of approximately 75 pA, accompanied by an augmented and prolonged tail current. The current-voltage relations also shown in FIG. 9A–B summarize the peak magnitude of currents recorded from this same cell at a series of depolarizing voltages. The responses in the presence of Bay K 8644 (closed circles) are not only increased, but the entire current-voltage relation is shifted about −10 mV. Thus, three typical hallmarks of Bay K 8644 action, namely increased current magnitude, prolonged tail currents, and negatively shifted activation voltage, were observed, clearly indicating the expression of a DHP-sensitive calcium channel in these stably transfected cells. No such effects of Bay K 8644 were observed in untransfected HEK 293 cells, either with or without cAMP or forskolin.

C. Use of pCMV-vs. pcDNA1-Based Vectors for Recombinant Expression of Human Neuronal Calcium Channel Subunit cDNAs 1. Preparation of Constructs To determine if the levels of recombinant expression of human calcium channel subunit cDNAs in host cells could be enhanced by using pCMV-based instead of pcDNA1-based expression vectors, additional expression vectors were constructed. The full-length VDCC III cDNA from pVDCCIII (A) (see Example II.A.3. d), the full-length $\alpha_2$ cDNA, contained on a 3600 bp EcoRI fragment from HBCaCH$\alpha_2$ (see Example IV.B) and a full-length β-subunit cDNA from pHBCaCHβ$_1$bA (see Example III.B.3) were separately subcloned into plasmid pCMVβgal. Plasmid pCMVβgal was digested with NotI to remove the lacZ gene. The remaining vector portion of the plasmid, referred to as pCMV, was blunt-ended at the NotI sites. The full-length $\alpha_2$ and β cDNAs, contained on separate EcoRI fragments, were isolated, blunt-ended and separately ligated to the blunt-ended vector fragment of pCMV locating the cDNAs between the CMV promoter and SV40 polyadenylation sites in pCMV. To ligate the VDCCIII cDNA with pCMV, the restriction sites in the polylinkers immediately 5' of the CMV promoter and immediately 3' of the SV40 polyadenylation site were removed from pCMV. A polylinker was added at the NotI site. The polylinker had the following sequence:

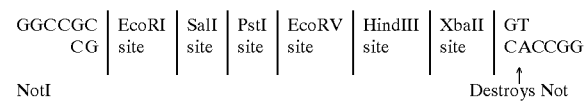

The VCCCIII cDNA, isolated as a BamHI/XhoI fragment from pVDCCIII(A), was then ligated to BglII/SalI-digested PCMV to place it between the CMV promoter and SV40 polyadenylation site.

Plasmid pCMV contains the CMV promoter as does pcDNA1, but differs from pcDNA1 in the location of splice donor/splice acceptor sites relative to the inserted subunit cDNA. After inserting the subunit cDNA into pCMV, the splice donor/splice acceptor sites are located 3' of the CMV promoter and 5' of the subunit cDNA start codon. After inserting the subunit cDNA into pcDNA1, the splice donor/splice acceptor sites are located 3' of the subunit cDNA stop codon.

2. Transfection of HEK 293 cells

HEK 293 cells were transiently co-transfected with the VDCC III, $\alpha_2$ and β-subunit cDNAs contained in pCMV or with the VDCC III, $\alpha_2$ and β-subunit cDNAs contained in pcDNA2, (i.e., vectors pVDCCIII(A), pHBCaCH$\alpha_2$ A and pHBCaCHβ$_1$bA) as described in Example VII.B.1.a. Plasmid pCMVβgal was included in each transfection to enable determination of transfection efficiency. Based on the results of β-galactosidase assays of the transfectants (see Example VII.B.2. a), HEK 293 cells were transfected equally efficiently with PCMV- and pcDNA1- based plasmids.

3. Northern analysis

Total and polyA$^+$ RNA was isolated from the transiently transfected cells as described in Examples VII.A.2 and VII.B.2. b. Northern blots of the RNA were hybridized with the following radiolabeled probes: VDCC III cDNA, human neuronal calcium channel $\alpha_2$-subunit cDNA and a human neuronal calcium channel β-subunit cDNA. Messenger RNAs of the size expected for VDCC III, $\alpha_2$ and β-subunit transcripts were detected in all transfectants. However, a greater amount of the VDCC III transcript was present in cells that were co-transfected with pCMV-based plasmids then in cells that were co-transfected with pcDNA1-based plasmids. Equivalent amounts of $\alpha_2$ and β-subunit transcripts were detected in all transfectants.

D. Recombinant Expression of Transcripts Prepared In Vitro from Human Neuronal Calcium Channel Subunit cDNAs in Xenopus laevis Oocytes Various combinations of the transcripts of cDNAs encoding the human neuronal $\alpha_1$ (VDCC III), $\alpha_2$ and β-subunits prepared in vitro were injected into Xenopus laevis oocytes which were then analyzed by two-electrode voltage clamp recording techniques for the presence of voltage-activated barium currents.

1. Preparation of transcripts

In vitro transcripts of human neuronal calcium channel $\alpha_1$, $\alpha_2$ and β-subunit cDNAs were synthesized according to the instructions of the mCAP mRNA CAPPING KIT (Strategene, La Jolla, Calif. catalog #200350). Plasmids containing these cDNAs [i.e., plasmid pVDCC III.RBS(A), consisting of pcDNA1 and the VDCC III cDNA that begins with a ribosome binding site and the eighth ATG codon of the coding sequence (see Example III.A.3. d), plasmid pHBCaCH$\alpha_1$A consisting of pcDNA1 and an $\alpha_2$-subunit cDNA (see Example IV), and plasmid pHBCaCHβ$_1$bA consisting of pcDNA1 and the β cDNA lacking intron sequence and containing a ribosome binding site (see Example III)], where linearized by restriction digestion. The VDCC III cDNA- and $\alpha_2$-subunit cDNA-containing plasmids were digested with XhoI, whereas the β-subunit cDNA-containing plasmid was digested with EcoRV. T7 RNA polymerase was used to transcribe the cDNA in each case.

2. Injection of oocytes

*Xenopus laevis* oocytes were isolated and defolliculated by collagenase treatment and maintained in 100 mM NaCl, 2 mM KCl, 1.8 mM $CaCl_2$, 1 mM $MgCl_2$, 5 mM HEPES,, pH 7.6, 20 µg/ml ampicillin and 25 µg/ml streptomycin at 19°–25° C. for 2 to 5 days after injection and prior to recording. For each transcript that was injected into the oocyte, 6 ng of the specific mRNA was injected per cell in a total volume of 50 nl.

3. Intracellular voltage recordings

Injected oocytes were examined for voltage-dependent barium currents using two-electrode voltage clamp methods [Dascal, N. (1987) *CRC Crit. Rev. Biochem.* 22:317]. The pClamp (Axon Instruments) software package was used in conjunction with a Labmaster 125 kHz data acquisition interface to generate voltage commands and to acquire and analyze data. Quattro Professional was also used in this analysis. Current signals were digitized at 1–5 kHz, and filtered appropriately. The bath solution consisted of the following: 40 mM $BaCl_2$, 36 mM tetraethylammonium chloride (TEA-Cl), 2 mM KCl, 5 mM 4-amnopyridine, 0.15 mM niflumic acid, 5 mM HEPES, pH 7.6.

a. Electrophysiological analysis of oocytes injected with transcripts of human neuronal calcium channel $\alpha_1$, $\alpha_2$ and β-subunit cDNAs It has been reported that *Xenopus laevis* oocytes express endogenous voltage-dependent calcium channels [Dascal, N. (1987). *CRC Crit. Rev. Biochem.* 22:317]. Therefore, negative control uninjected oocytes were examined by two-electrode voltage clamp methods to determine if these cells express voltage-activated barium currents that are detectable in these recordings. A very small (25 nA) endogenous inward $Ba^{2+}$ current was detected in only one of seven analyzed cells.

Figure 10A:
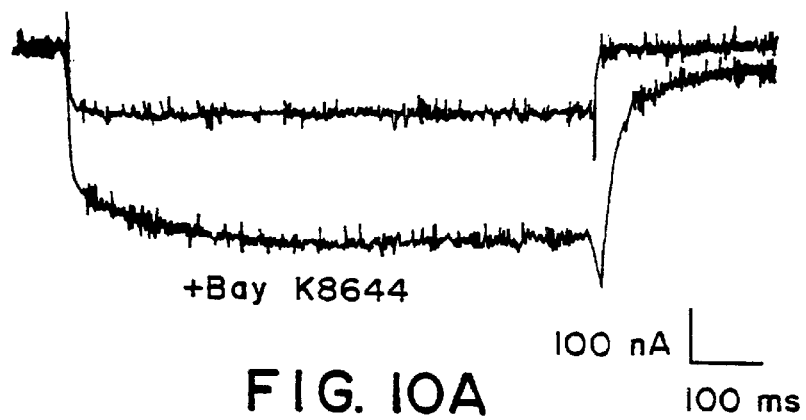
FIG. 10A–F show recordings and IV curve depicting currents measured in oocytes injected with combinations of in vitro transcripts of the α1-, α2-, and β-subunit-encoding cDNAs.
Figure 10B:
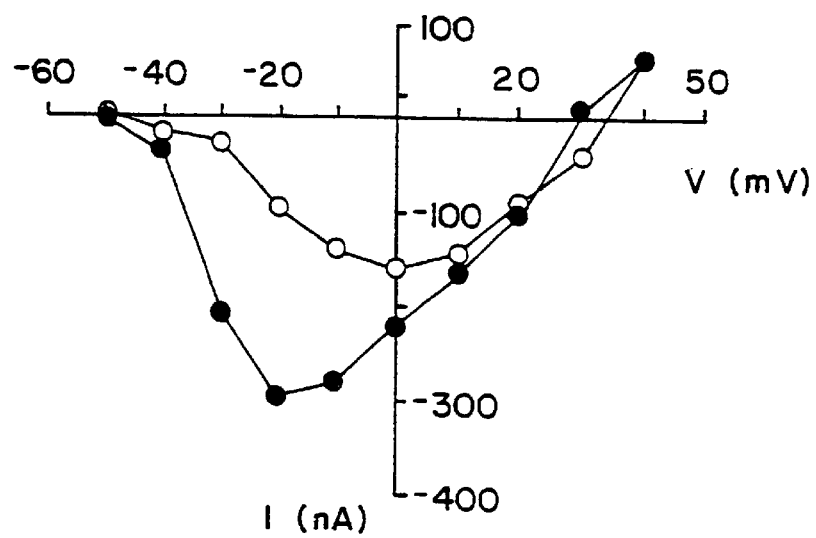
Figure 10C:
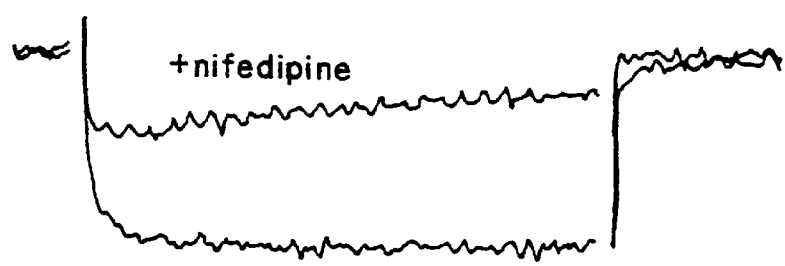

Oocytes coinjected with VDCC III, $\alpha_2$ and β-subunit transcripts expressed sustained inward barium currents upon depolarization of the membrane from a holding potential of –90 mV or –50 mV (154±129 nA, n=21). These currents typically showed little inactivation when test pulses ranging from 140 to 700 msec. were administered (FIG. 10A). Depolarization to a series of voltages revealed currents that first appeared at approximately –30 mV and peaked at approximately 0 mV (see I-V curve in FIG. 10B represented by open circles). Application of the dihydrophyridine Bay K 8644 increased the magnitude of the currents, prolonged the tail currents present upon repolarization of the cell and induced a hyperpolarizing shift in current activation (FIG. 10A and 11B, I-V curve represented by solid circles). (Bay K 8644 was prepared fresh from a stock solution in DMSO and diluted into the bath solution. Thus, Bay K 8644 was applied as a 10× concentrate directly into the 60 µl bath while the perfusion pump was turned off. The DMSO concentration of the final diluted drug solutions in contact with the cell never exceeded 0.1%. Control experiments showed that 0.1% DMSO had no effect on membrane currents.) Application of the dihydropyridine antagonist nifedipine (stock solution prepared in DMSO and applied to the cell as described for application of Bay K 8644) blocked a substantial fraction (91±6%, n=7) of the inward barium current in oocytes coinjected with transcripts of the VDCC III, $\alpha_2$ and β-subunits (FIG. 10C). A residual inactivating component of the inward barium current typically remained after nifedipine application (see FIG. 10C). The inward barium current was blocked completely by 50 µM $Cd^{2+}$, but only approximately 15% by 100 µM $Ni^{2+}$.

Figure 10D:
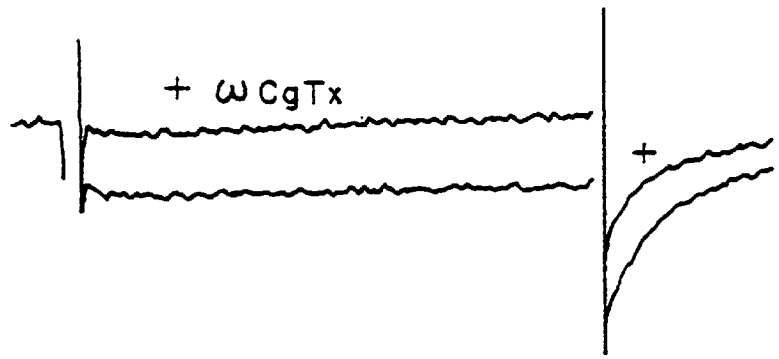

The effect of ωCgTX on the inward barium currents in oocytes co-injected with transcripts of the VDCC III, $\alpha_2$ and β-sub units was investigated. ωCgTX (Bachem, Inc., Torrance Calif.) was prepared in the 15 mM $BaCl_2$ bath solution plus 0.1% cytochrome C (Sigma) to serve as a carrier protein. Control experiments showed that cytochrome C had no effect on currents. A series of voltage pulses from a –90 mV holding potential to 0 mV were recorded at 20 msec. intervals. To reduce the inhibition of ωCgTX binding by divalent cations, recordings were made in 15 mM $BaCl_2$, 73.5 mM tetraethylammonium chloride, and the remaining ingredients identical to the 40 mM $Ba^{2+}$ recording solution. Bay K 8644 was applied to the cell prior to addition to ωCgTX in order to determine the effect of ωCgTX on the DHP-sensitive current component that was distinguished by the prolonged tail currents. The inward barium current was blocked weakly (54±29%, n=7) and reversibly by relatively high concentrations (10–15 µM) of ωCgTX (FIG. 10D). Both the test currents and the accompanying tail currents were blocked progressively within two to three minutes after application of ωCgTX, but both recovered partially as the ωCgTX was flushed from the bath.

b. Analysis of oocytes injected with transcripts of a human neuronal calcium channel $\alpha_1$ (VDCC III) subunit cDNA only or transcripts of an $\alpha_1$ and other subunit cDNAs The contribution of the $\alpha_2$ and β-subunits to the inward barium current in oocytes injected with transcripts of VDCC III, $\alpha_2$ and β cDNAs was assessed by expression of the VDCC III subunit alone or in combination with either the β-subunit or the $\alpha_2$-subunit. In oocytes injected with only the transcript of a VDCC III cDNA, no $Ba^{2+}$ currents were detected (n=3). In oocytes injected with transcripts of VDCC III $\alpha_1$ and β cDNAs, small (108±39 nA) $Ba^{2+}$ currents were detected upon depolarization of the membrane from a holding potential of –90 mV that resembled the currents observed in cells injected with transcripts of VDCC III, $\alpha_2$ and β cDNAs, although the magnitude of the current was less. In two of the four oocytes injected with transcripts of the VDCC III and β cDNAs, the $Ba^{2+}$ currents exhibited a sensitivity to Bay K 8644 that was similar to the Bay K 8644 sensitivity of $Ba_{2+}$ currents expressed in oocytes injected with transcripts of VDCC III $\alpha_1$-, $\alpha_2$- and β-subunits cDNAs.

Three of five oocytes injected with transcripts of VDCC III and $\alpha_2$ cDNAs exhibited very small $Ba^{2+}$ currents (15–30 nA) upon depolarization of the membrane from a holding potential of –90 mV. These barium currents showed little or no response to Bay K 8644.

c. Analysis of oocytes injected with transcripts of human neuronal calcium channel $\alpha_2$ and/or β-subunit cDNAS To evaluate the contribution of the VDCC III $\alpha_1$-subunit to the inward barium currents detected in oocytes co-injected with transcripts of VDCC III, $\alpha_2$ and β cDNAs, oocytes injected with transcripts of human neuronal calcium channel $\alpha_2$ and/or β cDNAs were assayed for barium currents. Oocytes injected with transcripts of the $\alpha_2$ cDNA displayed no detectable inward barium currents (n=5). Surprisingly, oocytes injected with transcripts of a β cDNA displayed measurable (54±23 nA, n=5) inward barium currents upon depolarization. Oocytes injected with transcripts of the $\alpha_2$ and β cDNAs displayed inward barium currents that were approximately 50% larger (80±61 nA, n=18) than those detected in oocytes injected with transcripts of the β cDNA only.

Figure 10E:
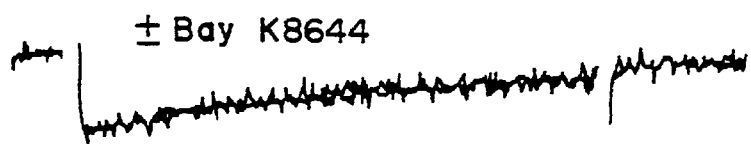
Figure 10F:
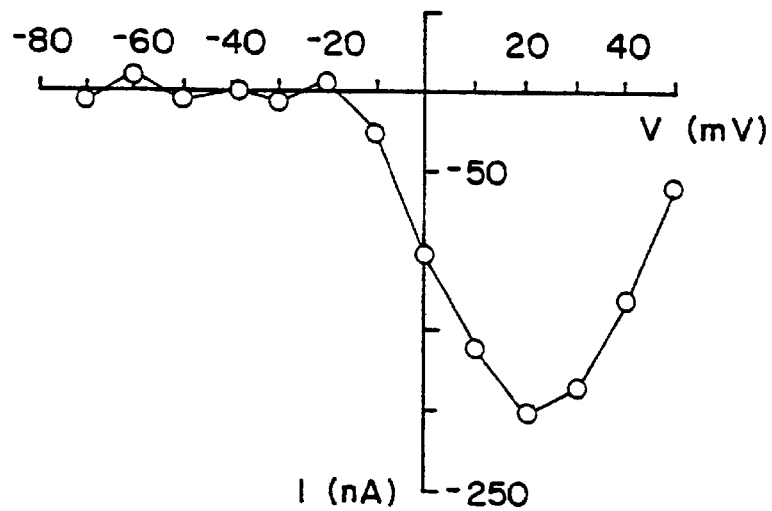

The inward barium currents in oocytes injected with transcripts of a β cDNA or of $\alpha_2$ and β cDNAs typically were first observed when the membrane was depolarized to −30 mV from a holding potential of -90 mV and peaked when the membrane was depolarized to 10 to 20 mV (FIG. 10F). Macroscopically, the currents in oocytes injected with transcripts of the $\alpha_2$ and β cDNAs or with transcripts of the β cDNA were indistinguishable. In contrast to the currents in oocytes co-injected with transcripts of VDCC III, $\alpha_2$ and β-subunit cDNAs, these currents showed both a significant inactivation during the test pulse and a strong sensitivity to the holding potential. The inward barium currents in oocytes co-injected with transcripts of the $\beta_2$ and β cDNAs usually inactivated to 10–60% of the peak magnitude during a 140-msec pulse (FIG. 10E) and were significantly more sensitive to holding potential than those in oocytes co-injected with transcripts of VDCC III, $\alpha_2$ and β cDNAs. Changing the holding potential of the membranes of oocytes co-injected with transcripts of the $\alpha_2$ and β cDNAs from −90 to −50 mV resulted in an approximately 81% (n=11) reduction in the magnitude of the inward barium current of these cells. In contrast, the inward barium current measured in oocytes co-injected with transcripts of the VDCC III, $\alpha_2$ and β cDNAs were reduced approximately 24% (n=11) when the holding potential was changed from −90 to −50 mV.

The inward barium currents detected in oocytes injected with transcripts of the $\alpha_2$ and β cDNAs were pharmacologically distinct from those observed in oocytes co-injected with transcripts of the VDCC III, $\alpha_2$ and β cDNAs. Oocytes injected with transcripts of the $\alpha_2$ and β cDNAs displayed inward barium currents that were insensitive to Bay K 8644 (n=11) (FIG. 10E). Nifedipine sensitivity was difficult to measure because of the holding potential sensitivity of both nifedipine and the current observed in oocytes injected with transcripts of the $\alpha_2$ and β cDNAs. Nevertheless, two oocytes that were co-injected with transcripts of the $\alpha_2$ and β cDNAs displayed measurable (25 to 45 nA) inward barium currents when depolarized from a holding potential of −50 mv. These currents were insensitive to nifedipine (5 to 10 μM). The inward barium currents in oocytes injected with transcripts of the $\alpha_2$ and β cDNAs showed the same sensitivity to heavy metals as the currents detected in oocytes injected with transcripts of VDCC III, $\alpha_2$ and a cDNAs.

The inward barium current detected in oocytes injected with transcripts of human neuronal $\alpha_2$ and β-subunit cDNAs has pharmacological and biophysical properties that resemble calcium currents in uninjected Xenopus oocytes. Because the amino acid sequence encoded by this human neuronal calcium channel β-subunit cDNA lacks hydrophobic segments capable of forming transmembrane domains, it is unlikely that recombinant β-sub units alone can form an ion channel. It is more probable that a homologous $\alpha_1$-subunit exists in oocytes comprising an endogenous calcium channel and that the activity mediated by such an $\alpha_1$-subunit is enhanced by expression of a human neuronal β-subunit.

d. Summary of data

Data presented in Example VII.C. demonstrates that a VDCC III $\alpha_1$-subunit mediates DHP-sensitive, high-voltage-activated, long-lasting calcium channel activity. This calcium channel activity detected when oocytes were co-injected with transcripts of VDCC III and β or VDCC III, $\alpha_2$ and β-subunit cDNAs was distinguished from $Ba^{2+}$ currents detected when oocytes were injected with transcripts of β±$\alpha_2$-subunit cDNAs (which resembled $Ca^{2+}$ currents reported 5 for uninjected oocytes) both pharmacologically and biophysically.

While the invention has been described with some specificity, modifications apparent to those with ordinary skill in the art may be made without departing from the scope of the invention.

Various features of the invention are set forth in the claims which follow the nucleotide sequence ID listing.

What is claimed is:

1. A method for testing a compound for activity as an agonist or antagonist of a calcium channel, comprising the steps of:

suspending a eukaryotic cell expressing functional, heterologous calcium channels in a solution which contains the compound and an ion or molecule capable of entering the cell through a functional calcium channel;

depolarizing the cell membrane of the cell;

detecting the current flowing into the cell; and comparing the current thus detected to a current produced by cells in a control experiment;

wherein:

the only heterologous ion channels expressed by the cells are calcium channels which comprise one or more sub units;

each heterologously expressed calcium channel subunit has the amino acid sequence of a naturally occurring human calcium channel subunit; and the heterologous calcium channels comprise at least a heterologous $\alpha_1$ subunit that is selected from the group consisting of a VDCC type IV ($\alpha_{1B}$) subunit having an amino acid sequence comprising the sequence of amino acids set forth in SEQ ID NO: 15 or 17, and a calcium channel α1 subunit encoded by DNA capable of hybridizing under conditions of high stringency with DNA that is complementary to an mRNA transcript present in a human cell and that encodes the aforesaid VDCC type IV subunit.

2. The method of claim 1, wherein:

the heterologous calcium channels further comprise one or more subunits selected from the group consisting of an $\alpha_2$ subunit which is
  a protein having the sequence of amino acids set forth as the translation of the DNA shown in SEQ ID NO: 24, or
  a calcium channel $\beta_2$ subunit encoded by DNA capable of hybridizing under conditions of high stringency with DNA which is complementary to an mRNA transcript present in a human cell and which comprises the sequence of nucleotides shown as nucleotides 1–3273 of SEQ ID NO: 24;

a $\beta$ subunit which is
  a protein having the sequence of amino acids set forth as the translation of the DNA shown in SEQ ID NO: 18, a protein having an amino acid sequence comprising the sequence of amino acids shown in SEQ ID NO: 23, or
  a calcium channel $\beta$ subunit encoded by DNA capable of hybridizing under conditions of high stringency with DNA which is complementary to an mRNA transcript present in a human cell and which comprises the sequence of nucleotides shown as nucleotides 1–1434 of SEQ ID NO: 18 or encodes the sequence of amino acids shown in SEQ ID NO: 23; and a $\gamma$ subunit which is
  a protein having an amino acid sequence comprising the sequence of amino acids set forth as the translation of the DNA shown in SEQ ID NO: 29, or
  a calcium channel $\gamma$ subunit encoded by DNA capable of hybridizing under conditions of high stringency with DNA which is complementary to an mRNA transcript present in a human cell and which comprises the sequence of nucleotides shown as nucleotides 1–129 of SEQ ID NO: 29.

3. The method of claim 1, wherein the calcium channel $\alpha_1$ subunit comprises the sequence of amino acids set forth in SEQ ID NO. 15.

4. The method of claim 1, wherein the calcium channel $\alpha_1$ subunit comprises the sequence of amino acids set forth in SEQ ID NO. 17.

* * * * *

UNITED STATES PATENT AND TRADEMARK OFFICE
CERTIFICATE OF CORRECTION

PATENT NO. : 5,876,958  
DATED : Mar. 2, 1999  
INVENTOR(S) : Michael M. Harpold, et al Page 1 of 2

It is certified that error appears in the above-identified patent and that said Letters Patent is hereby corrected as shown below:

On TITLE PAGE, item [54] and col. 1, line 2,
   "$a_1\beta$" should read as —$a_{1B}$—;

At column 5, line 3, insert —The results of studies of recombinant expression— in between "*aperta*." and "of";
   at column 7, line 27, insert —of— between "map" and "a";
   Col. 7, line 45, replace ";" with —.—;
   at column 7, line 49, replace "is" with —are—;
   at column 7, line 66, replace "inventions" with —invention—;
   at column 9, line 16, delete "which";
   at column 10, line 28, replace "antagonis" with ––agonist––
   at column 10, line 35, insert —are— between "channels" and "open";
   at column 11, line 63, replace "a subunit" with —$a$ subunit—;
   at column 11, line 67, insert —an— in between "with" and "$a_1$";
   at column 12, line 1, insert —an— between "and" and "$a_2$-subunit";
   at column 12, line 55, delete "an";
   at column 13, line 47, delete "." after "1987";
   at column 13, line 63, replace "Four" with ––The four––;
   at column 14, line 57, delete "the";
   at column 15, lines 54-55, insert —and— between "cells," and "human";
   at column 19, line 62, replace "nligated" with —ligated—;
   at column 30, line 1, replace "No. 482,384" with —No. 08/482,384, now U.S. Patent No. 5,386,025—;
   at column 33, line 15, please insert —acid— between "amino" and "insertion";
   at column 41, line 29, replace "amnopyridine" with —aminopyridine—;
   at column 41, line 56, replace "11B" with —10B—;

UNITED STATES PATENT AND TRADEMARK OFFICE
CERTIFICATE OF CORRECTION

PATENT NO. : 5,876,958
DATED : Mar. 2, 1999
INVENTOR(S) : Michael M. Harpold, et al It is certified that error appears in the above-identified patent and that said Letters Patent is hereby corrected as shown below:

IN THE CLAIMS:

at column 152, line 64, replace "sub units" with —subunits—;
at column 153, line 19, replace "$\beta_2$" with —$\alpha_2$—;

Signed and Sealed this

Seventh Day of September, 1999

Attest:

Q. TODD DICKINSON

Attesting Officer

Acting Commissioner of Patents and Trademarks

SEQUENCE LISTING ( 1 ) GENERAL INFORMATION:

( i i i ) NUMBER OF SEQUENCES: 32

( 2 ) INFORMATION FOR SEQ ID NO:1:

( i ) SEQUENCE CHARACTERISTICS:
        ( A ) LENGTH: 7125 base pairs
        ( B ) TYPE: nucleic acid
        ( C ) STRANDEDNESS: unknown
        ( D ) TOPOLOGY: unknown ( i i ) MOLECULE TYPE: DNA (genomic)

( i x ) FEATURE:
        ( A ) NAME/KEY: CDS
        ( B ) LOCATION: 1..6483

( x i ) SEQUENCE DESCRIPTION: SEQ ID NO:1:

```
ATG  ATG  ATG  ATG  ATG  ATG  ATG  AAA  AAA  ATG  CAG  CAT  CAA  CGG  CAG  CAG        48
Met  Met  Met  Met  Met  Met  Met  Lys  Lys  Met  Gln  His  Gln  Arg  Gln  Gln
 1                    5                   10                       15

CAA  GCG  GAC  CAC  GCG  AAC  GAG  GCA  AAC  TAT  GCA  AGA  GGC  ACC  AGA  CTT        96
Gln  Ala  Asp  His  Ala  Asn  Glu  Ala  Asn  Tyr  Ala  Arg  Gly  Thr  Arg  Leu
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     | 20  |     |     |     |     |     | 25  |     |     |     |     |     | 30  |     |      |
| CCT | CTT | TCT | GGT | GAA | GGA | CCA | ACT | TCT | CAG | CCG | AAT | AGC | TCC | AAG | CAA | 144  |
| Pro | Leu | Ser | Gly | Glu | Gly | Pro | Thr | Ser | Gln | Pro | Asn | Ser | Ser | Lys | Gln |      |
|     |     | 35  |     |     |     | 40  |     |     |     |     |     | 45  |     |     |     |      |
| ACT | GTC | CTG | TCT | TGG | CAA | GCT | GCA | ATC | GAT | GCT | GCT | AGA | CAG | GCC | AAG | 192  |
| Thr | Val | Leu | Ser | Trp | Gln | Ala | Ala | Ile | Asp | Ala | Ala | Arg | Gln | Ala | Lys |      |
|     | 50  |     |     |     |     | 55  |     |     |     |     |     | 60  |     |     |     |      |
| GCT | GCC | CAA | ACT | ATG | AGC | ACC | TCT | GCA | CCC | CCA | CCT | GTA | GGA | TCT | CTC | 240  |
| Ala | Ala | Gln | Thr | Met | Ser | Thr | Ser | Ala | Pro | Pro | Pro | Val | Gly | Ser | Leu |      |
| 65  |     |     |     |     | 70  |     |     |     |     | 75  |     |     |     |     | 80  |      |
| TCC | CAA | AGA | AAA | CGT | CAG | CAA | TAC | GCC | AAG | AGC | AAA | AAA | CAG | GGT | AAC | 288  |
| Ser | Gln | Arg | Lys | Arg | Gln | Gln | Tyr | Ala | Lys | Ser | Lys | Lys | Gln | Gly | Asn |      |
|     |     |     |     | 85  |     |     |     |     |     | 90  |     |     |     | 95  |     |      |
| TCG | TCC | AAC | AGC | CGA | CCT | GCC | CGC | GCC | CTT | TTC | TGT | TTA | TCA | CTC | AAT | 336  |
| Ser | Ser | Asn | Ser | Arg | Pro | Ala | Arg | Ala | Leu | Phe | Cys | Leu | Ser | Leu | Asn |      |
|     |     |     | 100 |     |     |     |     | 105 |     |     |     |     | 110 |     |     |      |
| AAC | CCC | ATC | CGA | AGA | GCC | TGC | ATT | AGT | ATA | GTG | GAA | TGG | AAA | CCA | TTT | 384  |
| Asn | Pro | Ile | Arg | Arg | Ala | Cys | Ile | Ser | Ile | Val | Glu | Trp | Lys | Pro | Phe |      |
|     |     | 115 |     |     |     |     | 120 |     |     |     |     | 125 |     |     |     |      |
| GAC | ATA | TTT | ATA | TTA | TTG | GCT | ATT | TTT | GCC | AAT | TGT | GTG | GCC | TTA | GCT | 432  |
| Asp | Ile | Phe | Ile | Leu | Leu | Ala | Ile | Phe | Ala | Asn | Cys | Val | Ala | Leu | Ala |      |
| 130 |     |     |     |     | 135 |     |     |     |     | 140 |     |     |     |     |     |      |
| ATT | TAC | ATC | CCA | TTC | CCT | GAA | GAT | GAT | TCT | AAT | TCA | ACA | AAT | CAT | AAC | 480  |
| Ile | Tyr | Ile | Pro | Phe | Pro | Glu | Asp | Asp | Ser | Asn | Ser | Thr | Asn | His | Asn |      |
| 145 |     |     |     |     | 150 |     |     |     |     | 155 |     |     |     |     | 160 |      |
| TTG | GAA | AAA | GTA | GAA | TAT | GCC | TTC | CTG | ATT | ATT | TTT | ACA | GTC | GAG | ACA | 528  |
| Leu | Glu | Lys | Val | Glu | Tyr | Ala | Phe | Leu | Ile | Ile | Phe | Thr | Val | Glu | Thr |      |
|     |     |     |     | 165 |     |     |     |     | 170 |     |     |     |     | 175 |     |      |
| TTT | TTG | AAG | ATT | ATA | GCG | TAT | GGA | TTA | TTG | CTA | CAT | CCT | AAT | GCT | TAT | 576  |
| Phe | Leu | Lys | Ile | Ile | Ala | Tyr | Gly | Leu | Leu | Leu | His | Pro | Asn | Ala | Tyr |      |
|     |     |     | 180 |     |     |     |     | 185 |     |     |     |     | 190 |     |     |      |
| GTT | AGG | AAT | GGA | TGG | AAT | TTA | CTG | GAT | TTT | GTT | ATA | GTA | ATA | GTA | GGA | 624  |
| Val | Arg | Asn | Gly | Trp | Asn | Leu | Leu | Asp | Phe | Val | Ile | Val | Ile | Val | Gly |      |
|     |     | 195 |     |     |     |     | 200 |     |     |     |     | 205 |     |     |     |      |
| TTG | TTT | AGT | GTA | ATT | TTG | GAA | CAA | TTA | ACC | AAA | GAA | ACA | GAA | GGC | GGG | 672  |
| Leu | Phe | Ser | Val | Ile | Leu | Glu | Gln | Leu | Thr | Lys | Glu | Thr | Glu | Gly | Gly |      |
| 210 |     |     |     |     | 215 |     |     |     |     | 220 |     |     |     |     |     |      |
| AAC | CAC | TCA | AGC | GGC | AAA | TCT | GGA | GGC | TTT | GAT | GTC | AAA | GCC | CTC | CGT | 720  |
| Asn | His | Ser | Ser | Gly | Lys | Ser | Gly | Gly | Phe | Asp | Val | Lys | Ala | Leu | Arg |      |
| 225 |     |     |     |     | 230 |     |     |     |     | 235 |     |     |     |     | 240 |      |
| GCC | TTT | CGA | GTG | TTG | CGA | CCA | CTT | CGA | CTA | GTG | TCA | GGA | GTG | CCC | AGT | 768  |
| Ala | Phe | Arg | Val | Leu | Arg | Pro | Leu | Arg | Leu | Val | Ser | Gly | Val | Pro | Ser |      |
|     |     |     |     | 245 |     |     |     |     | 250 |     |     |     |     | 255 |     |      |
| TTA | CAA | GTT | GTC | CTG | AAC | TCC | ATT | ATA | AAA | GCC | ATG | GTT | CCC | CTC | CTT | 816  |
| Leu | Gln | Val | Val | Leu | Asn | Ser | Ile | Ile | Lys | Ala | Met | Val | Pro | Leu | Leu |      |
|     |     |     | 260 |     |     |     |     | 265 |     |     |     |     | 270 |     |     |      |
| CAC | ATA | GCC | CTT | TTG | GTA | TTA | TTT | GTA | ATC | ATA | ATC | TAT | GCT | ATT | ATA | 864  |
| His | Ile | Ala | Leu | Leu | Val | Leu | Phe | Val | Ile | Ile | Ile | Tyr | Ala | Ile | Ile |      |
|     |     | 275 |     |     |     |     | 280 |     |     |     |     | 285 |     |     |     |      |
| GGA | TTG | GAA | CTT | TTT | ATT | GGA | AAA | ATG | CAC | AAA | ACA | TGT | TTT | TTT | GCT | 912  |
| Gly | Leu | Glu | Leu | Phe | Ile | Gly | Lys | Met | His | Lys | Thr | Cys | Phe | Phe | Ala |      |
|     | 290 |     |     |     |     | 295 |     |     |     |     | 300 |     |     |     |     |      |
| GAC | TCA | GAT | ATC | GTA | GCT | GAA | GAG | GAC | CCA | GCT | CCA | TGT | GCG | TTC | TCA | 960  |
| Asp | Ser | Asp | Ile | Val | Ala | Glu | Glu | Asp | Pro | Ala | Pro | Cys | Ala | Phe | Ser |      |
| 305 |     |     |     |     | 310 |     |     |     |     | 315 |     |     |     |     | 320 |      |
| GGG | AAT | GGA | CGC | CAG | TGT | ACT | GCC | AAT | GGC | ACG | GAA | TGT | AGG | AGT | GGC | 1008 |
| Gly | Asn | Gly | Arg | Gln | Cys | Thr | Ala | Asn | Gly | Thr | Glu | Cys | Arg | Ser | Gly |      |
|     |     |     |     | 325 |     |     |     |     | 330 |     |     |     |     | 335 |     |      |
| TGG | GTT | GGC | CCG | AAC | GGA | GGC | ATC | ACC | AAC | TTT | GAT | AAC | TTT | GCC | TTT | 1056 |
| Trp | Val | Gly | Pro | Asn | Gly | Gly | Ile | Thr | Asn | Phe | Asp | Asn | Phe | Ala | Phe |      |

```
                    340                         345                         350
GCC  ATG  CTT  ACT  GTG  TTT  CAG  TGC  ATC  ACC  ATG  GAG  GGC  TGG  ACA  GAC    1104
Ala  Met  Leu  Thr  Val  Phe  Gln  Cys  Ile  Thr  Met  Glu  Gly  Trp  Thr  Asp
          355                         360                         365

GTG  CTC  TAC  TGG  ATG  AAT  GAT  GCT  ATG  GGA  TTT  GAA  TTG  CCC  TGG  GTG    1152
Val  Leu  Tyr  Trp  Met  Asn  Asp  Ala  Met  Gly  Phe  Glu  Leu  Pro  Trp  Val
          370                         375                         380

TAT  TTT  GTC  AGT  CTC  GTC  ATC  TTT  GGG  TCA  TTT  TTC  GTA  CTA  AAT  CTT    1200
Tyr  Phe  Val  Ser  Leu  Val  Ile  Phe  Gly  Ser  Phe  Phe  Val  Leu  Asn  Leu
385                      390                         395                      400

GTA  CTT  GGT  GTA  TTG  AGC  GGA  GAA  TTC  TCA  AAG  GAA  AGA  GAG  AAG  GCA    1248
Val  Leu  Gly  Val  Leu  Ser  Gly  Glu  Phe  Ser  Lys  Glu  Arg  Glu  Lys  Ala
                    405                         410                         415

AAA  GCA  CGG  GGA  GAT  TTC  CAG  AAG  CTC  CGG  GAG  AAG  CAG  CAG  CTG  GAG    1296
Lys  Ala  Arg  Gly  Asp  Phe  Gln  Lys  Leu  Arg  Glu  Lys  Gln  Gln  Leu  Glu
               420                         425                         430

GAG  GAT  CTA  AAG  GGC  TAC  TTG  GAT  TGG  ATC  ACC  CAA  GCT  GAG  GAC  ATC    1344
Glu  Asp  Leu  Lys  Gly  Tyr  Leu  Asp  Trp  Ile  Thr  Gln  Ala  Glu  Asp  Ile
          435                         440                         445

GAT  CCG  GAG  AAT  GAG  GAA  GAA  GGA  GGA  GAG  GAA  GGC  AAA  CGA  AAT  ACT    1392
Asp  Pro  Glu  Asn  Glu  Glu  Glu  Gly  Gly  Glu  Glu  Gly  Lys  Arg  Asn  Thr
450                      455                         460

AGC  ATG  CCC  ACC  AGC  GAG  ACT  GAG  TCT  GTG  AAC  ACA  GAG  AAC  GTC  AGC    1440
Ser  Met  Pro  Thr  Ser  Glu  Thr  Glu  Ser  Val  Asn  Thr  Glu  Asn  Val  Ser
465                      470                         475                      480

GGT  GAA  GGC  GAG  AAC  CGA  GGC  TGC  TGT  GGA  AGT  CTC  TGT  CAA  GCC  ATC    1488
Gly  Glu  Gly  Glu  Asn  Arg  Gly  Cys  Cys  Gly  Ser  Leu  Cys  Gln  Ala  Ile
                    485                         490                         495

TCA  AAA  TCC  AAA  CTC  AGC  CGA  CGC  TGG  CGT  CGC  TGG  AAC  CGA  TTC  AAT    1536
Ser  Lys  Ser  Lys  Leu  Ser  Arg  Arg  Trp  Arg  Arg  Trp  Asn  Arg  Phe  Asn
               500                         505                         510

CGC  AGA  AGA  TGT  AGG  GCC  GCC  GTG  AAG  TCT  GTC  ACG  TTT  TAC  TGG  CTG    1584
Arg  Arg  Arg  Cys  Arg  Ala  Ala  Val  Lys  Ser  Val  Thr  Phe  Tyr  Trp  Leu
          515                         520                         525

GTT  ATC  GTC  CTG  GTG  TTT  CTG  AAC  ACC  TTA  ACC  ATT  TCC  TCT  GAG  CAC    1632
Val  Ile  Val  Leu  Val  Phe  Leu  Asn  Thr  Leu  Thr  Ile  Ser  Ser  Glu  His
          530                         535                         540

TAC  AAT  CAG  CCA  GAT  TGG  TTG  ACA  CAG  ATT  CAA  GAT  ATT  GCC  AAC  AAA    1680
Tyr  Asn  Gln  Pro  Asp  Trp  Leu  Thr  Gln  Ile  Gln  Asp  Ile  Ala  Asn  Lys
545                      550                         555                      560

GTC  CTC  TTG  GCT  CTG  TTC  ACC  TGC  GAG  ATG  CTG  GTA  AAA  ATG  TAC  AGC    1728
Val  Leu  Leu  Ala  Leu  Phe  Thr  Cys  Glu  Met  Leu  Val  Lys  Met  Tyr  Ser
                    565                         570                         575

TTG  GGC  CTC  CAA  GCA  TAT  TTC  GTC  TCT  CTT  TTC  AAC  CGG  TTT  GAT  TGC    1776
Leu  Gly  Leu  Gln  Ala  Tyr  Phe  Val  Ser  Leu  Phe  Asn  Arg  Phe  Asp  Cys
               580                         585                         590

TTC  GTG  GTG  TGT  GGT  GGA  ATC  ACT  GAG  ACG  ATC  TTG  GTG  GAA  CTG  GAA    1824
Phe  Val  Val  Cys  Gly  Gly  Ile  Thr  Glu  Thr  Ile  Leu  Val  Glu  Leu  Glu
          595                         600                         605

ATC  ATG  TCT  CCC  CTG  GGG  ATC  TCT  GTG  TTT  CGG  TGT  GTG  CGC  CTC  TTA    1872
Ile  Met  Ser  Pro  Leu  Gly  Ile  Ser  Val  Phe  Arg  Cys  Val  Arg  Leu  Leu
          610                         615                         620

AGA  ATC  TTC  AAA  GTG  ACC  AGG  CAC  TGG  ACT  TCC  CTG  AGC  AAC  TTA  GTG    1920
Arg  Ile  Phe  Lys  Val  Thr  Arg  His  Trp  Thr  Ser  Leu  Ser  Asn  Leu  Val
625                      630                         635                      640

GCA  TCC  TTA  TTA  AAC  TCC  ATG  AAG  TCC  ATC  GCT  TCG  CTG  TTG  CTT  CTG    1968
Ala  Ser  Leu  Leu  Asn  Ser  Met  Lys  Ser  Ile  Ala  Ser  Leu  Leu  Leu  Leu
                    645                         650                         655

CTT  TTT  CTC  TTC  ATT  ATC  ATC  TTT  TCC  TTG  CTT  GGG  ATG  CAG  CTG  TTT    2016
Leu  Phe  Leu  Phe  Ile  Ile  Ile  Phe  Ser  Leu  Leu  Gly  Met  Gln  Leu  Phe
```

```
                        660                           665                           670
GGC   GGC   AAG   TTT   AAT   TTT   GAT   GAA   ACG   CAA   ACC   AAG   CGG   AGC   ACC   TTT        2064
Gly   Gly   Lys   Phe   Asn   Phe   Asp   Glu   Thr   Gln   Thr   Lys   Arg   Ser   Thr   Phe
                  675               680                     685

GAC   AAT   TTC   CCT   CAA   GCA   CTT   CTC   ACA   GTG   TTC   CAG   ATC   CTG   ACA   GGC        2112
Asp   Asn   Phe   Pro   Gln   Ala   Leu   Leu   Thr   Val   Phe   Gln   Ile   Leu   Thr   Gly
      690                     695                           700

GAA   GAC   TGG   AAT   GCT   GTG   ATG   TAC   GAT   GGC   ATC   ATG   GCT   TAC   GGG   GGC        2160
Glu   Asp   Trp   Asn   Ala   Val   Met   Tyr   Asp   Gly   Ile   Met   Ala   Tyr   Gly   Gly
705                           710                     715                           720

CCA   TCC   TCT   TCA   GGA   ATG   ATC   GTC   TGC   ATC   TAC   TTC   ATC   ATC   CTC   TTC        2208
Pro   Ser   Ser   Ser   Gly   Met   Ile   Val   Cys   Ile   Tyr   Phe   Ile   Ile   Leu   Phe
                        725                     730                           735

ATT   TGT   GGT   AAC   TAT   ATT   CTA   CTG   AAT   GTC   TTC   TTG   GCC   ATC   GCT   GTA        2256
Ile   Cys   Gly   Asn   Tyr   Ile   Leu   Leu   Asn   Val   Phe   Leu   Ala   Ile   Ala   Val
                  740                           745                     750

GAC   AAT   TTG   GCT   GAT   GCT   GAA   AGT   CTG   AAC   ACT   GCT   CAG   AAA   GAA   GAA        2304
Asp   Asn   Leu   Ala   Asp   Ala   Glu   Ser   Leu   Asn   Thr   Ala   Gln   Lys   Glu   Glu
            755                           760                     765

GCG   GAA   GAA   AAG   GAG   AGG   AAA   AAG   ATT   GCC   AGA   AAA   GAG   AGC   CTA   GAA        2352
Ala   Glu   Glu   Lys   Glu   Arg   Lys   Lys   Ile   Ala   Arg   Lys   Glu   Ser   Leu   Glu
770                           775                     780

AAT   AAA   AAG   AAC   AAC   AAA   CCA   GAA   GTC   AAC   CAG   ATA   GCC   AAC   AGT   GAC        2400
Asn   Lys   Lys   Asn   Asn   Lys   Pro   Glu   Val   Asn   Gln   Ile   Ala   Asn   Ser   Asp
785                     790                           795                           800

AAC   AAG   GTT   ACA   ATT   GAT   GAC   TAT   AGA   GAA   GAG   GAT   GAA   GAC   AAG   GAC        2448
Asn   Lys   Val   Thr   Ile   Asp   Asp   Tyr   Arg   Glu   Glu   Asp   Glu   Asp   Lys   Asp
                        805                     810                           815

CCC   TAT   CCG   CCT   TGC   GAT   GTG   CCA   GTA   GGG   GAA   GAG   GAA   GAG   GAA   GAG        2496
Pro   Tyr   Pro   Pro   Cys   Asp   Val   Pro   Val   Gly   Glu   Glu   Glu   Glu   Glu   Glu
                  820                           825                           830

GAG   GAG   GAT   GAA   CCT   GAG   GTT   CCT   GCC   GGA   CCC   CGT   CCT   CGA   AGG   ATC        2544
Glu   Glu   Asp   Glu   Pro   Glu   Val   Pro   Ala   Gly   Pro   Arg   Pro   Arg   Arg   Ile
                  835                           840                     845

TCG   GAG   TTG   AAC   ATG   AAG   GAA   AAA   ATT   GCC   CCC   ATC   CCT   GAA   GGG   AGC        2592
Ser   Glu   Leu   Asn   Met   Lys   Glu   Lys   Ile   Ala   Pro   Ile   Pro   Glu   Gly   Ser
850                           855                     860

GCT   TTC   TTC   ATT   CTT   AGC   AAG   ACC   AAC   CCG   ATC   CGC   GTA   GGC   TGC   CAC        2640
Ala   Phe   Phe   Ile   Leu   Ser   Lys   Thr   Asn   Pro   Ile   Arg   Val   Gly   Cys   His
865                     870                           875                           880

AAG   CTC   ATC   AAC   CAC   CAC   ATC   TTC   ACC   AAC   CTC   ATC   CTT   GTC   TTC   ATC        2688
Lys   Leu   Ile   Asn   His   His   Ile   Phe   Thr   Asn   Leu   Ile   Leu   Val   Phe   Ile
                        885                     890                           895

ATG   CTG   AGC   AGT   GCT   GCC   CTG   GCC   GCA   GAG   GAC   CCC   ATC   CGC   AGC   CAC        2736
Met   Leu   Ser   Ser   Ala   Ala   Leu   Ala   Ala   Glu   Asp   Pro   Ile   Arg   Ser   His
                  900                           905                           910

TCC   TTC   CGG   AAC   ACG   ATA   CTG   GGT   TAC   TTT   GAC   TAT   GCC   TTC   ACA   GCC        2784
Ser   Phe   Arg   Asn   Thr   Ile   Leu   Gly   Tyr   Phe   Asp   Tyr   Ala   Phe   Thr   Ala
            915                           920                     925

ATC   TTT   ACT   GTT   GAG   ATC   CTG   TTG   AAG   ATG   ACA   ACT   TTT   GGA   GCT   TTC        2832
Ile   Phe   Thr   Val   Glu   Ile   Leu   Leu   Lys   Met   Thr   Thr   Phe   Gly   Ala   Phe
      930                           935                     940

CTC   CAC   AAA   GGG   GCC   TTC   TGC   AGG   AAC   TAC   TTC   AAT   TTG   CTG   GAT   ATG        2880
Leu   His   Lys   Gly   Ala   Phe   Cys   Arg   Asn   Tyr   Phe   Asn   Leu   Leu   Asp   Met
945                     950                           955                           960

CTG   GTG   GTT   GGG   GTG   TCT   CTG   GTG   TCA   TTT   GGG   ATT   CAA   TCC   AGT   GCC        2928
Leu   Val   Val   Gly   Val   Ser   Leu   Val   Ser   Phe   Gly   Ile   Gln   Ser   Ser   Ala
                        965                     970                           975

ATC   TCC   GTT   GTG   AAG   ATT   CTG   AGG   GTC   TTA   AGG   GTC   CTG   CGT   CCC   CTC        2976
Ile   Ser   Val   Val   Lys   Ile   Leu   Arg   Val   Leu   Arg   Val   Leu   Arg   Pro   Leu
```

-continued

|     |     |     | 980 |     |     |     |     | 985 |     |     |     |     | 990 |     |     |      |
|-----|-----|-----|-----|-----|-----|-----|-----|-----|-----|-----|-----|-----|-----|-----|-----|------|
| AGG | GCC | ATC | AAC | AGA | GCA | AAA | GGA | CTT | AAG | CAC | GTG | GTC | CAG | TGC | GTC | 3024 |
| Arg | Ala | Ile | Asn | Arg | Ala | Lys | Gly | Leu | Lys | His | Val | Val | Gln | Cys | Val |      |
|     |     |     | 995 |     |     |     |     | 1000|     |     |     |     | 1005|     |     |      |
| TTC | GTG | GCC | ATC | CGG | ACC | ATC | GGC | AAC | ATC | ATG | ATC | GTC | ACC | ACC | CTC | 3072 |
| Phe | Val | Ala | Ile | Arg | Thr | Ile | Gly | Asn | Ile | Met | Ile | Val | Thr | Thr | Leu |      |
|     |     |     | 1010|     |     |     |     | 1015|     |     |     |     | 1020|     |     |      |
| CTG | CAG | TTC | ATG | TTT | GCC | TGT | ATC | GGG | GTC | CAG | TTG | TTC | AAG | GGG | AAG | 3120 |
| Leu | Gln | Phe | Met | Phe | Ala | Cys | Ile | Gly | Val | Gln | Leu | Phe | Lys | Gly | Lys |      |
|     |     |     | 1025|     |     |     |     | 1030|     |     |     |     | 1035|     |     | 1040 |
| TTC | TAT | CGC | TGT | ACG | GAT | GAA | GCC | AAA | AGT | AAC | CCT | GAA | GAA | TGC | AGG | 3168 |
| Phe | Tyr | Arg | Cys | Thr | Asp | Glu | Ala | Lys | Ser | Asn | Pro | Glu | Glu | Cys | Arg |      |
|     |     |     |     |     | 1045|     |     |     |     | 1050|     |     |     |     | 1055|      |
| GGA | CTT | TTC | ATC | CTC | TAC | AAG | GAT | GGG | GAT | GTT | GAC | AGT | CCT | GTG | GTC | 3216 |
| Gly | Leu | Phe | Ile | Leu | Tyr | Lys | Asp | Gly | Asp | Val | Asp | Ser | Pro | Val | Val |      |
|     |     |     |     | 1060|     |     |     |     | 1065|     |     |     |     | 1070|     |      |
| CGT | GAA | CGG | ATC | TGG | CAA | AAC | AGT | GAT | TTC | AAC | TTC | GAC | AAC | GTC | CTC | 3264 |
| Arg | Glu | Arg | Ile | Trp | Gln | Asn | Ser | Asp | Phe | Asn | Phe | Asp | Asn | Val | Leu |      |
|     |     |     |     | 1075|     |     |     |     | 1080|     |     |     |     | 1085|     |      |
| TCT | GCT | ATG | ATG | GCG | CTC | TTC | ACA | GTC | TCC | ACG | TTT | GAG | GGC | TGG | CCT | 3312 |
| Ser | Ala | Met | Met | Ala | Leu | Phe | Thr | Val | Ser | Thr | Phe | Glu | Gly | Trp | Pro |      |
|     |     |     |     | 1090|     |     |     |     | 1095|     |     |     |     | 1100|     |      |
| GCG | TTG | CTG | TAT | AAA | GCC | ATC | GAC | TCG | AAT | GGA | GAG | AAC | ATC | GGC | CCA | 3360 |
| Ala | Leu | Leu | Tyr | Lys | Ala | Ile | Asp | Ser | Asn | Gly | Glu | Asn | Ile | Gly | Pro |      |
| 1105|     |     |     |     | 1110|     |     |     |     | 1115|     |     |     |     | 1120|      |
| ATC | TAC | AAC | CAC | CGC | GTG | GAG | ATC | TCC | ATC | TTC | TTC | ATC | ATC | TAC | ATC | 3408 |
| Ile | Tyr | Asn | His | Arg | Val | Glu | Ile | Ser | Ile | Phe | Phe | Ile | Ile | Tyr | Ile |      |
|     |     |     |     | 1125|     |     |     |     | 1130|     |     |     |     | 1135|     |      |
| ATC | ATT | GTA | GCT | TTC | TTC | ATG | ATG | AAC | ATC | TTT | GTG | GGC | TTT | GTC | ATC | 3456 |
| Ile | Ile | Val | Ala | Phe | Phe | Met | Met | Asn | Ile | Phe | Val | Gly | Phe | Val | Ile |      |
|     |     |     |     | 1140|     |     |     |     | 1145|     |     |     |     | 1150|     |      |
| GTT | ACA | TTT | CAG | GAA | CAA | GGA | GAA | AAA | GAG | TAT | AAG | AAC | TGT | GAG | CTG | 3504 |
| Val | Thr | Phe | Gln | Glu | Gln | Gly | Glu | Lys | Glu | Tyr | Lys | Asn | Cys | Glu | Leu |      |
|     |     |     | 1155|     |     |     |     | 1160|     |     |     |     | 1165|     |     |      |
| GAC | AAA | AAT | CAG | CGT | CAG | TGT | GTT | GAA | TAC | GCC | TTG | AAA | GCA | CGT | CCC | 3552 |
| Asp | Lys | Asn | Gln | Arg | Gln | Cys | Val | Glu | Tyr | Ala | Leu | Lys | Ala | Arg | Pro |      |
|     |     |     | 1170|     |     |     |     | 1175|     |     |     |     | 1180|     |     |      |
| TTG | CGG | AGA | TAC | ATC | CCC | AAA | AAC | CCC | TAC | CAG | TAC | AAG | TTC | TGG | TAC | 3600 |
| Leu | Arg | Arg | Tyr | Ile | Pro | Lys | Asn | Pro | Tyr | Gln | Tyr | Lys | Phe | Trp | Tyr |      |
| 1185|     |     |     |     | 1190|     |     |     |     | 1195|     |     |     |     | 1200|      |
| GTG | GTG | AAC | TCT | TCG | CCT | TTC | GAA | TAC | ATG | ATG | TTT | GTC | CTC | ATC | ATG | 3648 |
| Val | Val | Asn | Ser | Ser | Pro | Phe | Glu | Tyr | Met | Met | Phe | Val | Leu | Ile | Met |      |
|     |     |     |     | 1205|     |     |     |     | 1210|     |     |     |     | 1215|     |      |
| CTC | AAC | ACA | CTC | TGC | TTG | GCC | ATG | CAG | CAC | TAC | GAG | CAG | TCC | AAG | ATG | 3696 |
| Leu | Asn | Thr | Leu | Cys | Leu | Ala | Met | Gln | His | Tyr | Glu | Gln | Ser | Lys | Met |      |
|     |     |     | 1220|     |     |     |     | 1225|     |     |     |     | 1230|     |     |      |
| TTC | AAT | GAT | GCC | ATG | GAC | ATT | CTG | AAC | ATG | GTC | TTC | ACC | GGG | GTG | TTC | 3744 |
| Phe | Asn | Asp | Ala | Met | Asp | Ile | Leu | Asn | Met | Val | Phe | Thr | Gly | Val | Phe |      |
|     |     |     | 1235|     |     |     |     | 1240|     |     |     |     | 1245|     |     |      |
| ACC | GTC | GAG | ATG | GTT | TTG | AAA | GTC | ATC | GCA | TTT | AAG | CCT | AAG | GGG | TAT | 3792 |
| Thr | Val | Glu | Met | Val | Leu | Lys | Val | Ile | Ala | Phe | Lys | Pro | Lys | Gly | Tyr |      |
|     |     |     | 1250|     |     |     |     | 1255|     |     |     |     | 1260|     |     |      |
| TTT | AGT | GAC | GCC | TGG | AAC | ACG | TTT | GAC | TCC | CTC | ATC | GTA | ATC | GGC | AGC | 3840 |
| Phe | Ser | Asp | Ala | Trp | Asn | Thr | Phe | Asp | Ser | Leu | Ile | Val | Ile | Gly | Ser |      |
| 1265|     |     |     |     | 1270|     |     |     |     | 1275|     |     |     |     | 1280|      |
| ATT | ATA | GAC | GTG | GCC | CTC | AGC | GAA | GCA | GAC | CCA | ACT | GAA | AGT | GAA | AAT | 3888 |
| Ile | Ile | Asp | Val | Ala | Leu | Ser | Glu | Ala | Asp | Pro | Thr | Glu | Ser | Glu | Asn |      |
|     |     |     |     | 1285|     |     |     |     | 1290|     |     |     |     | 1295|     |      |
| GTC | CCT | GTC | CCA | ACT | GCT | ACA | CCT | GGG | AAC | TCT | GAA | GAG | AGC | AAT | AGA | 3936 |
| Val | Pro | Val | Pro | Thr | Ala | Thr | Pro | Gly | Asn | Ser | Glu | Glu | Ser | Asn | Arg |      |

```
                    1300                      1305                      1310
ATC  TCC  ATC  ACC  TTT  TTC  CGT  CTT  TTC  CGA  GTG  ATG  CGA  TTG  GTG  AAG    3984
Ile  Ser  Ile  Thr  Phe  Phe  Arg  Leu  Phe  Arg  Val  Met  Arg  Leu  Val  Lys
          1315                     1320                     1325

CTT  CTC  AGC  AGG  GGG  GAA  GGC  ATC  CGG  ACA  TTG  CTG  TGG  ACT  TTT  ATT    4032
Leu  Leu  Ser  Arg  Gly  Glu  Gly  Ile  Arg  Thr  Leu  Leu  Trp  Thr  Phe  Ile
          1330                     1335                     1340

AAG  TTC  TTT  CAG  GCG  CTC  CCG  TAT  GTG  GCC  CTC  CTC  ATA  GCC  ATG  CTG    4080
Lys  Phe  Phe  Gln  Ala  Leu  Pro  Tyr  Val  Ala  Leu  Leu  Ile  Ala  Met  Leu
1345                     1350                     1355                     1360

TTC  TTC  ATC  TAT  GCG  GTC  ATT  GGC  ATG  CAG  ATG  TTT  GGG  AAA  GTT  GCC    4128
Phe  Phe  Ile  Tyr  Ala  Val  Ile  Gly  Met  Gln  Met  Phe  Gly  Lys  Val  Ala
               1365                     1370                     1375

ATG  AGA  GAT  AAC  AAC  CAG  ATC  AAT  AGG  AAC  AAT  AAC  TTC  CAG  ACG  TTT    4176
Met  Arg  Asp  Asn  Asn  Gln  Ile  Asn  Arg  Asn  Asn  Asn  Phe  Gln  Thr  Phe
                    1380                     1385                     1390

CCC  CAG  GCG  GTG  CTG  CTG  CTC  TTC  AGG  TGT  GCA  ACA  GGT  GAG  GCC  TGG    4224
Pro  Gln  Ala  Val  Leu  Leu  Leu  Phe  Arg  Cys  Ala  Thr  Gly  Glu  Ala  Trp
          1395                     1400                     1405

CAG  GAG  ATC  ATG  CTG  GCC  TGT  CTC  CCA  GGG  AAG  CTC  TGT  GAC  CCT  GAG    4272
Gln  Glu  Ile  Met  Leu  Ala  Cys  Leu  Pro  Gly  Lys  Leu  Cys  Asp  Pro  Glu
          1410                     1415                     1420

TCA  GAT  TAC  AAC  CCC  GGG  GAG  GAG  CAT  ACA  TGT  GGG  AGC  AAC  TTT  GCC    4320
Ser  Asp  Tyr  Asn  Pro  Gly  Glu  Glu  His  Thr  Cys  Gly  Ser  Asn  Phe  Ala
1425                     1430                     1435                     1440

ATT  GTC  TAT  TTC  ATC  AGT  TTT  TAC  ATG  CTC  TGT  GCA  TTT  CTG  ATC  ATC    4368
Ile  Val  Tyr  Phe  Ile  Ser  Phe  Tyr  Met  Leu  Cys  Ala  Phe  Leu  Ile  Ile
                    1445                     1450                     1455

AAT  CTG  TTT  GTG  GCT  GTC  ATC  ATG  GAT  AAT  TTC  GAC  TAT  CTG  ACC  CGG    4416
Asn  Leu  Phe  Val  Ala  Val  Ile  Met  Asp  Asn  Phe  Asp  Tyr  Leu  Thr  Arg
               1460                     1465                     1470

GAC  TGG  TCT  ATT  TTG  GGG  CCT  CAC  CAT  TTA  GAT  GAA  TTC  AAA  AGA  ATA    4464
Asp  Trp  Ser  Ile  Leu  Gly  Pro  His  His  Leu  Asp  Glu  Phe  Lys  Arg  Ile
          1475                     1480                     1485

TGG  TCA  GAA  TAT  GAC  CCT  GAG  GCA  AAG  GGA  AGG  ATA  AAA  CAC  CTT  GAT    4512
Trp  Ser  Glu  Tyr  Asp  Pro  Glu  Ala  Lys  Gly  Arg  Ile  Lys  His  Leu  Asp
          1490                     1495                     1500

GTG  GTC  ACT  CTG  CTT  CGA  CGC  ATC  CAG  CCT  CCC  CTG  GGG  TTT  GGG  AAG    4560
Val  Val  Thr  Leu  Leu  Arg  Arg  Ile  Gln  Pro  Pro  Leu  Gly  Phe  Gly  Lys
1505                     1510                     1515                     1520

TTA  TGT  CCA  CAC  AGG  GTA  GCG  TGC  AAG  AGA  TTA  GTT  GCC  ATG  AAC  ATG    4608
Leu  Cys  Pro  His  Arg  Val  Ala  Cys  Lys  Arg  Leu  Val  Ala  Met  Asn  Met
                    1525                     1530                     1535

CCT  CTC  AAC  AGT  GAC  GGG  ACA  GTC  ATG  TTT  AAT  GCA  ACC  CTG  TTT  GCT    4656
Pro  Leu  Asn  Ser  Asp  Gly  Thr  Val  Met  Phe  Asn  Ala  Thr  Leu  Phe  Ala
               1540                     1545                     1550

TTG  GTT  CGA  ACG  GCT  CTT  AAG  ATC  AAG  ACC  GAA  GGG  AAC  CTG  GAG  CAA    4704
Leu  Val  Arg  Thr  Ala  Leu  Lys  Ile  Lys  Thr  Glu  Gly  Asn  Leu  Glu  Gln
          1555                     1560                     1565

GCT  AAT  GAA  GAA  CTT  CGG  GCT  GTG  ATA  AAG  AAA  ATT  TGG  AAG  AAA  ACC    4752
Ala  Asn  Glu  Glu  Leu  Arg  Ala  Val  Ile  Lys  Lys  Ile  Trp  Lys  Lys  Thr
          1570                     1575                     1580

AGC  ATG  AAA  TTA  CTT  GAC  CAA  GTT  GTC  CCT  CCA  GCT  GGT  GAT  GAT  GAG    4800
Ser  Met  Lys  Leu  Leu  Asp  Gln  Val  Val  Pro  Pro  Ala  Gly  Asp  Asp  Glu
1585                     1590                     1595                     1600

GTA  ACC  GTG  GGG  AAG  TTC  TAT  GCC  ACT  TTC  CTG  ATA  CAG  GAC  TAC  TTT    4848
Val  Thr  Val  Gly  Lys  Phe  Tyr  Ala  Thr  Phe  Leu  Ile  Gln  Asp  Tyr  Phe
                    1605                     1610                     1615

AGG  AAA  TTC  AAG  AAA  CGG  AAA  GAA  CAA  GGA  CTG  GTG  GGA  AAG  TAC  CCT    4896
Arg  Lys  Phe  Lys  Lys  Arg  Lys  Glu  Gln  Gly  Leu  Val  Gly  Lys  Tyr  Pro
```

-continued

```
                    1620                       1625                       1630

GCG AAG AAC ACC ACA ATT GCC CTA CAG GCG GGA TTA AGG ACA CTG CAT        4944
Ala Lys Asn Thr Thr Ile Ala Leu Gln Ala Gly Leu Arg Thr Leu His
            1635                    1640                    1645

GAC ATT GGG CCA GAA ATC CGG CGT GCT ATA TCG TGT GAT TTG CAA GAT        4992
Asp Ile Gly Pro Glu Ile Arg Arg Ala Ile Ser Cys Asp Leu Gln Asp
            1650                    1655                    1660

GAC GAG CCT GAG GAA ACA AAA CGA GAA GAA GAA GAT GAT GTG TTC AAA        5040
Asp Glu Pro Glu Glu Thr Lys Arg Glu Glu Glu Asp Asp Val Phe Lys
1665                    1670                    1675                    1680

AGA AAT GGT GCC CTG CTT GGA AAC CAT GTC AAT CAT GTT AAT AGT GAT        5088
Arg Asn Gly Ala Leu Leu Gly Asn His Val Asn His Val Asn Ser Asp
            1685                    1690                    1695

AGG AGA GAT TCC CTT CAG CAG ACC AAT ACC ACC CAC CGT CCC CTG CAT        5136
Arg Arg Asp Ser Leu Gln Gln Thr Asn Thr Thr His Arg Pro Leu His
            1700                    1705                    1710

GTC CAA AGG CCT TCA ATT CCA CCT GCA AGT GAT ACT GAG AAA CCG CTG        5184
Val Gln Arg Pro Ser Ile Pro Pro Ala Ser Asp Thr Glu Lys Pro Leu
            1715                    1720                    1725

TTT CCT CCA GCA GGA AAT TCG GTG TGT CAT AAC CAT CAT AAC CAT AAT        5232
Phe Pro Pro Ala Gly Asn Ser Val Cys His Asn His His Asn His Asn
            1730                    1735                    1740

TCC ATA GGA AAG CAA GTT CCC ACC TCA ACA AAT GCC AAT CTC AAT AAT        5280
Ser Ile Gly Lys Gln Val Pro Thr Ser Thr Asn Ala Asn Leu Asn Asn
1745                    1750                    1755                    1760

GCC AAT ATG TCC AAA GCT GCC CAT GGA AAG CGG CCC AGC ATT GGG AAC        5328
Ala Asn Met Ser Lys Ala Ala His Gly Lys Arg Pro Ser Ile Gly Asn
                    1765                    1770                    1775

CTT GAG CAT GTG TCT GAA AAT GGG CAT CAT TCT TCC CAC AAG CAT GAC        5376
Leu Glu His Val Ser Glu Asn Gly His His Ser Ser His Lys His Asp
            1780                    1785                    1790

CGG GAG CCT CAG AGA AGG TCC AGT GTG AAA AGA ACC CGC TAT TAT GAA        5424
Arg Glu Pro Gln Arg Arg Ser Ser Val Lys Arg Thr Arg Tyr Tyr Glu
            1795                    1800                    1805

ACT TAC ATT AGG TCC GAC TCA GGA GAT GAA CAG CTC CCA ACT ATT TGC        5472
Thr Tyr Ile Arg Ser Asp Ser Gly Asp Glu Gln Leu Pro Thr Ile Cys
            1810                    1815                    1820

CGG GAA GAC CCA GAG ATA CAT GGC TAT TTC AGG GAC CCC CAC TGC TTG        5520
Arg Glu Asp Pro Glu Ile His Gly Tyr Phe Arg Asp Pro His Cys Leu
1825                    1830                    1835                    1840

GGG GAG CAG GAG TAT TTC AGT AGT GAG GAA TGC TAC GAG GAT GAC AGC        5568
Gly Glu Gln Glu Tyr Phe Ser Ser Glu Glu Cys Tyr Glu Asp Asp Ser
                    1845                    1850                    1855

TCG CCC ACC TGG AGC AGG CAA AAC TAT GGC TAC TAC AGC AGA TAC CCA        5616
Ser Pro Thr Trp Ser Arg Gln Asn Tyr Gly Tyr Tyr Ser Arg Tyr Pro
                    1860                    1865                    1870

GGC AGA AAC ATC GAC TCT GAG AGG CCC CGA GGC TAC CAT CAT CCC CAA        5664
Gly Arg Asn Ile Asp Ser Glu Arg Pro Arg Gly Tyr His His Pro Gln
            1875                    1880                    1885

GGA TTC TTG GAG GAC GAT GAC TCG CCC GTT TGC TAT GAT TCA CGG AGA        5712
Gly Phe Leu Glu Asp Asp Asp Ser Pro Val Cys Tyr Asp Ser Arg Arg
            1890                    1895                    1900

TCT CCA AGG AGA CGC CTA CTA CCT CCC ACC CCA GCA TCC CAC CGG AGA        5760
Ser Pro Arg Arg Arg Leu Leu Pro Pro Thr Pro Ala Ser His Arg Arg
1905                    1910                    1915                    1920

TCC TCC TTC AAC TTT GAG TGC CTG CGC CGG CAG AGC AGC CAG GAA GAG        5808
Ser Ser Phe Asn Phe Glu Cys Leu Arg Arg Gln Ser Ser Gln Glu Glu
                    1925                    1930                    1935

GTC CCG TCG TCT CCC ATC TTC CCC CAT CGC ACG GCC CTG CCT CTG CAT        5856
Val Pro Ser Ser Pro Ile Phe Pro His Arg Thr Ala Leu Pro Leu His
```

```
                            1940                        1945                        1950
CTA  ATG  CAG  CAA  CAG  ATC  ATG  GCA  GTT  GCC  GGC  CTA  GAT  TCA  AGT  AAA              5904
Leu  Met  Gln  Gln  Gln  Ile  Met  Ala  Val  Ala  Gly  Leu  Asp  Ser  Ser  Lys
          1955                     1960                     1965

GCC  CAG  AAG  TAC  TCA  CCG  AGT  CAC  TCG  ACC  CGG  TCG  TGG  GCC  ACC  CCT              5952
Ala  Gln  Lys  Tyr  Ser  Pro  Ser  His  Ser  Thr  Arg  Ser  Trp  Ala  Thr  Pro
     1970                     1975                     1980

CCA  GCA  ACC  CCT  CCC  TAC  CGG  GAC  TGG  ACA  CCG  TGC  TAC  ACC  CCC  CTG              6000
Pro  Ala  Thr  Pro  Pro  Tyr  Arg  Asp  Trp  Thr  Pro  Cys  Tyr  Thr  Pro  Leu
1985                     1990                     1995                     2000

ATC  CAA  GTG  GAG  CAG  TCA  GAG  GCC  CTG  GAC  CAG  GTG  AAC  GGC  AGC  CTG              6048
Ile  Gln  Val  Glu  Gln  Ser  Glu  Ala  Leu  Asp  Gln  Val  Asn  Gly  Ser  Leu
               2005                     2010                     2015

CCG  TCC  CTG  CAC  CGC  AGC  TCC  TGG  TAC  ACA  GAC  GAG  CCC  GAC  ATC  TCC              6096
Pro  Ser  Leu  His  Arg  Ser  Ser  Trp  Tyr  Thr  Asp  Glu  Pro  Asp  Ile  Ser
          2020                     2025                     2030

TAC  CGG  ACT  TTC  ACA  CCA  GCC  AGC  CTG  ACT  GTC  CCC  AGC  AGC  TTC  CGG              6144
Tyr  Arg  Thr  Phe  Thr  Pro  Ala  Ser  Leu  Thr  Val  Pro  Ser  Ser  Phe  Arg
     2035                     2040                     2045

AAC  AAA  AAC  AGC  GAC  AAG  CAG  AGG  AGT  GCG  GAC  AGC  TTG  GTG  GAG  GCA              6192
Asn  Lys  Asn  Ser  Asp  Lys  Gln  Arg  Ser  Ala  Asp  Ser  Leu  Val  Glu  Ala
2050                     2055                     2060

GTC  CTG  ATA  TCC  GAA  GGC  TTG  GGA  CGC  TAT  GCA  AGG  GAC  CCA  AAA  TTT              6240
Val  Leu  Ile  Ser  Glu  Gly  Leu  Gly  Arg  Tyr  Ala  Arg  Asp  Pro  Lys  Phe
2065                     2070                     2075                     2080

GTG  TCA  GCA  ACA  AAA  CAC  GAA  ATC  GCT  GAT  GCC  TGT  GAC  CTC  ACC  ATC              6288
Val  Ser  Ala  Thr  Lys  His  Glu  Ile  Ala  Asp  Ala  Cys  Asp  Leu  Thr  Ile
               2085                     2090                     2095

GAC  GAG  ATG  GAG  AGT  GCA  GCC  AGC  ACC  CTG  CTT  AAT  GGG  AAC  GTG  CGT              6336
Asp  Glu  Met  Glu  Ser  Ala  Ala  Ser  Thr  Leu  Leu  Asn  Gly  Asn  Val  Arg
          2100                     2105                     2110

CCC  CGA  GCC  AAC  GGG  GAT  GTG  GGC  CCC  CTC  TCA  CAC  CGG  CAG  GAC  TAT              6384
Pro  Arg  Ala  Asn  Gly  Asp  Val  Gly  Pro  Leu  Ser  His  Arg  Gln  Asp  Tyr
     2115                     2120                     2125

GAG  CTA  CAG  GAC  TTT  GGT  CCT  GGC  TAC  AGC  GAC  GAA  GAG  CCA  GAC  CCT              6432
Glu  Leu  Gln  Asp  Phe  Gly  Pro  Gly  Tyr  Ser  Asp  Glu  Glu  Pro  Asp  Pro
2130                     2135                     2140

GGG  AGG  GAT  GAG  GAG  GAC  CTG  GCG  GAT  GAA  ATG  ATA  TGC  ATC  ACC  ACC              6480
Gly  Arg  Asp  Glu  Glu  Asp  Leu  Ala  Asp  Glu  Met  Ile  Cys  Ile  Thr  Thr
2145                     2150                     2155                     2160

TTG  TAGCCCCCAG  CGAGGGGCAG  ACTGGCTCTG  GCCTCAGGTG  GGGCGCAGGA                              6533
Leu

GAGCCAGGGG  AAAAGTGCCT  CATAGTTAGG  AAAGTTTAGG  CACTAGTTGG  GAGTAATATT                      6593

CAATTAATTA  GACTTTTGTA  TAAGAGATGT  CATGCCTCAA  GAAAGCCATA  AACCTGGTAG                      6653

GAACAGGTCC  CAAGCGGTTG  AGCCTGGCAG  AGTACCATGC  GCTCGGCCCC  AGCTGCAGGA                      6713

AACAGCAGGC  CCCGCCCTCT  CACAGAGGAT  GGGTGAGGAG  GCCAGACCTG  CCCTGCCCCA                      6773

TTGTCCAGAT  GGGCACTGCT  GTGGAGTCTG  CTTCTCCCAT  GTACCAGGGC  ACCAGGCCCA                      6833

CCCAACTGAA  GGCATGGCGG  CGGGGTGCAG  GGGAAAGTTA  AAGGTGATGA  CGATCATCAC                      6893

ACCTGTGTCG  TTACCTCAGC  CATCGGTCTA  GCATATCAGT  CACTGGGCCC  AACATATCCA                      6953

TTTTTAAACC  CTTTCCCCCA  AATACACTGC  GTCCTGGTTC  CTGTTTAGCT  GTTCTGAAAT                      7013

ACGGTGTGTA  AGTAAGTCAG  AACCCAGCTA  CCAGTGATTA  TTGCGAGGGC  AATGGGACCT                      7073

CATAAATAAG  GTTTCTGTG   ATGTGACGCC  AGTTTACATA  AGAGAATATC  AC                              7125
```

( 2 ) INFORMATION FOR SEQ ID NO:2:

(i) SEQUENCE CHARACTERISTICS:
(A) LENGTH: 2161 amino acids
(B) TYPE: amino acid
(D) TOPOLOGY: linear (ii) MOLECULE TYPE: protein (xi) SEQUENCE DESCRIPTION: SEQ ID NO:2:

```
Met Met Met Met Met Met Met Lys Lys Met Gln His Gln Arg Gln Gln
 1               5                  10                  15
Gln Ala Asp His Ala Asn Glu Ala Asn Tyr Ala Arg Gly Thr Arg Leu
                20                  25                  30
Pro Leu Ser Gly Glu Gly Pro Thr Ser Gln Pro Asn Ser Ser Lys Gln
            35                  40                  45
Thr Val Leu Ser Trp Gln Ala Ile Asp Ala Ala Arg Gln Ala Lys
    50                  55                  60
Ala Ala Gln Thr Met Ser Thr Ser Ala Pro Pro Pro Val Gly Ser Leu
 65                  70                  75                  80
Ser Gln Arg Lys Arg Gln Gln Tyr Ala Lys Ser Lys Lys Gln Gly Asn
                85                  90                  95
Ser Ser Asn Ser Arg Pro Ala Arg Ala Leu Phe Cys Leu Ser Leu Asn
               100                 105                 110
Asn Pro Ile Arg Arg Ala Cys Ile Ser Ile Val Glu Trp Lys Pro Phe
           115                 120                 125
Asp Ile Phe Ile Leu Leu Ala Ile Phe Ala Asn Cys Val Ala Leu Ala
   130                 135                 140
Ile Tyr Ile Pro Phe Pro Glu Asp Asp Ser Asn Ser Thr Asn His Asn
145                 150                 155                 160
Leu Glu Lys Val Glu Tyr Ala Phe Leu Ile Ile Phe Thr Val Glu Thr
                165                 170                 175
Phe Leu Lys Ile Ile Ala Tyr Gly Leu Leu Leu His Pro Asn Ala Tyr
            180                 185                 190
Val Arg Asn Gly Trp Asn Leu Leu Asp Phe Val Ile Val Ile Val Gly
    195                 200                 205
Leu Phe Ser Val Ile Leu Glu Gln Leu Thr Lys Thr Glu Gly Gly
210                 215                 220
Asn His Ser Ser Gly Lys Ser Gly Gly Phe Asp Val Lys Ala Leu Arg
225                 230                 235                 240
Ala Phe Arg Val Leu Arg Pro Leu Arg Leu Val Ser Gly Val Pro Ser
                245                 250                 255
Leu Gln Val Val Leu Asn Ser Ile Ile Lys Ala Met Val Pro Leu Leu
            260                 265                 270
His Ile Ala Leu Leu Val Leu Phe Val Ile Ile Ile Tyr Ala Ile Ile
    275                 280                 285
Gly Leu Glu Leu Phe Ile Gly Lys Met His Lys Thr Cys Phe Phe Ala
    290                 295                 300
Asp Ser Asp Ile Val Ala Glu Glu Asp Pro Ala Pro Cys Ala Phe Ser
305                 310                 315                 320
Gly Asn Gly Arg Gln Cys Thr Ala Asn Gly Thr Glu Cys Arg Ser Gly
                325                 330                 335
Trp Val Gly Pro Asn Gly Gly Ile Thr Asn Phe Asp Asn Phe Ala Phe
            340                 345                 350
Ala Met Leu Thr Val Phe Gln Cys Ile Thr Met Glu Gly Trp Thr Asp
    355                 360                 365
Val Leu Tyr Trp Met Asn Asp Ala Met Gly Phe Glu Leu Pro Trp Val
    370                 375                 380
```

| | | | | | | | | | | | | | | |
|---|---|---|---|---|---|---|---|---|---|---|---|---|---|---|
| Tyr 385 | Phe | Val | Ser | Leu | Val 390 | Ile | Phe | Gly | Ser | Phe 395 | Phe | Val | Leu | Asn | Leu 400 |
| Val | Leu | Gly | Val | Leu 405 | Ser | Gly | Glu | Phe | Ser 410 | Lys | Glu | Arg | Glu | Lys 415 | Ala |
| Lys | Ala | Arg | Gly 420 | Asp | Phe | Gln | Lys | Leu 425 | Arg | Glu | Lys | Gln | Gln 430 | Leu | Glu |
| Glu | Asp | Leu 435 | Lys | Gly | Tyr | Leu | Asp 440 | Trp | Ile | Thr | Gln | Ala 445 | Glu | Asp | Ile |
| Asp | Pro 450 | Glu | Asn | Glu | Glu | Glu 455 | Gly | Gly | Glu | Glu | Gly 460 | Lys | Arg | Asn | Thr |
| Ser 465 | Met | Pro | Thr | Ser | Glu 470 | Thr | Glu | Ser | Val | Asn 475 | Thr | Glu | Asn | Val | Ser 480 |
| Gly | Glu | Gly | Glu | Asn 485 | Arg | Gly | Cys | Cys | Gly 490 | Ser | Leu | Cys | Gln | Ala 495 | Ile |
| Ser | Lys | Ser | Lys 500 | Leu | Ser | Arg | Arg | Trp 505 | Arg | Arg | Trp | Asn | Arg 510 | Phe | Asn |
| Arg | Arg | Arg 515 | Cys | Arg | Ala | Ala | Val 520 | Lys | Ser | Val | Thr | Phe 525 | Tyr | Trp | Leu |
| Val | Ile 530 | Val | Leu | Val | Phe | Leu 535 | Asn | Thr | Leu | Thr | Ile 540 | Ser | Ser | Glu | His |
| Tyr 545 | Asn | Gln | Pro | Asp | Trp 550 | Leu | Thr | Gln | Ile | Gln 555 | Asp | Ile | Ala | Asn | Lys 560 |
| Val | Leu | Leu | Ala | Leu 565 | Phe | Thr | Cys | Glu | Met 570 | Leu | Val | Lys | Met | Tyr 575 | Ser |
| Leu | Gly | Leu | Gln 580 | Ala | Tyr | Phe | Val | Ser 585 | Leu | Phe | Asn | Arg | Phe 590 | Asp | Cys |
| Phe | Val | Val 595 | Cys | Gly | Gly | Ile | Thr 600 | Glu | Thr | Ile | Leu | Val 605 | Glu | Leu | Glu |
| Ile | Met | Ser 610 | Pro | Leu | Gly | Ile | Ser 615 | Val | Phe | Arg | Cys | Val 620 | Arg | Leu | Leu |
| Arg 625 | Ile | Phe | Lys | Val | Thr 630 | Arg | His | Trp | Thr | Ser 635 | Leu | Ser | Asn | Leu | Val 640 |
| Ala | Ser | Leu | Leu | Asn 645 | Ser | Met | Lys | Ser | Ile 650 | Ala | Ser | Leu | Leu | Leu 655 | Leu |
| Leu | Phe | Leu | Phe 660 | Ile | Ile | Ile | Phe | Ser 665 | Leu | Leu | Gly | Met | Gln 670 | Leu | Phe |
| Gly | Gly | Lys 675 | Phe | Asn | Phe | Asp | Glu 680 | Thr | Gln | Thr | Lys | Arg 685 | Ser | Thr | Phe |
| Asp | Asn 690 | Phe | Pro | Gln | Ala | Leu 695 | Leu | Thr | Val | Phe | Gln 700 | Ile | Leu | Thr | Gly |
| Glu 705 | Asp | Trp | Asn | Ala | Val 710 | Met | Tyr | Asp | Gly | Ile 715 | Met | Ala | Tyr | Gly | Gly 720 |
| Pro | Ser | Ser | Ser | Gly 725 | Met | Ile | Val | Cys | Ile 730 | Tyr | Phe | Ile | Ile | Leu 735 | Phe |
| Ile | Cys | Gly | Asn 740 | Tyr | Ile | Leu | Leu | Asn 745 | Val | Phe | Leu | Ala | Ile 750 | Ala | Val |
| Asp | Asn | Leu 755 | Ala | Asp | Ala | Glu | Ser 760 | Leu | Asn | Thr | Ala | Gln 765 | Lys | Glu | Glu |
| Ala | Glu 770 | Glu | Lys | Glu | Arg | Lys 775 | Lys | Ile | Ala | Arg | Lys 780 | Glu | Ser | Leu | Glu |
| Asn 785 | Lys | Lys | Asn | Asn | Lys 790 | Pro | Glu | Val | Asn | Gln 795 | Ile | Ala | Asn | Ser | Asp 800 |
| Asn | Lys | Val | Thr | Ile | Asp | Asp | Tyr | Arg | Glu | Glu | Asp | Glu | Asp | Lys | Asp |

```
                                805                     810                     815
Pro   Tyr   Pro   Pro   Cys   Asp   Val   Pro   Val   Gly   Glu   Glu   Glu   Glu   Glu
                  820                     825                     830

Glu   Glu   Asp   Glu   Pro   Glu   Val   Pro   Ala   Gly   Pro   Arg   Pro   Arg   Ile
                  835                     840                     845

Ser   Glu   Leu   Asn   Met   Lys   Glu   Lys   Ile   Ala   Pro   Ile   Pro   Glu   Gly   Ser
      850                     855                     860

Ala   Phe   Phe   Ile   Leu   Ser   Lys   Thr   Asn   Pro   Ile   Arg   Val   Gly   Cys   His
865                           870                     875                           880

Lys   Leu   Ile   Asn   His   His   Ile   Phe   Thr   Asn   Leu   Ile   Leu   Val   Phe   Ile
                        885                     890                           895

Met   Leu   Ser   Ser   Ala   Ala   Leu   Ala   Ala   Glu   Asp   Pro   Ile   Arg   Ser   His
                  900                     905                           910

Ser   Phe   Arg   Asn   Thr   Ile   Leu   Gly   Tyr   Phe   Asp   Tyr   Ala   Phe   Thr   Ala
                  915                     920                     925

Ile   Phe   Thr   Val   Glu   Ile   Leu   Leu   Lys   Met   Thr   Thr   Phe   Gly   Ala   Phe
            930                     935                     940

Leu   His   Lys   Gly   Ala   Phe   Cys   Arg   Asn   Tyr   Phe   Asn   Leu   Leu   Asp   Met
945                           950                     955                           960

Leu   Val   Val   Gly   Val   Ser   Leu   Val   Ser   Phe   Gly   Ile   Gln   Ser   Ser   Ala
                  965                     970                           975

Ile   Ser   Val   Val   Lys   Ile   Leu   Arg   Val   Leu   Arg   Val   Leu   Arg   Pro   Leu
                  980                     985                           990

Arg   Ala   Ile   Asn   Arg   Ala   Lys   Gly   Leu   Lys   His   Val   Val   Gln   Cys   Val
                  995                     1000                    1005

Phe   Val   Ala   Ile   Arg   Thr   Ile   Gly   Asn   Ile   Met   Ile   Val   Thr   Thr   Leu
      1010                    1015                          1020

Leu   Gln   Phe   Met   Phe   Ala   Cys   Ile   Gly   Val   Gln   Leu   Phe   Lys   Gly   Lys
1025                          1030                    1035                          1040

Phe   Tyr   Arg   Cys   Thr   Asp   Glu   Ala   Lys   Ser   Asn   Pro   Glu   Glu   Cys   Arg
                  1045                    1050                          1055

Gly   Leu   Phe   Ile   Leu   Tyr   Lys   Asp   Gly   Asp   Val   Asp   Ser   Pro   Val   Val
                  1060                    1065                          1070

Arg   Glu   Arg   Ile   Trp   Gln   Asn   Ser   Asp   Phe   Asn   Phe   Asp   Asn   Val   Leu
                  1075                    1080                          1085

Ser   Ala   Met   Met   Ala   Leu   Phe   Thr   Val   Ser   Thr   Phe   Glu   Gly   Trp   Pro
                  1090                    1095                          1100

Ala   Leu   Leu   Tyr   Lys   Ala   Ile   Asp   Ser   Asn   Gly   Glu   Asn   Ile   Gly   Pro
1105                          1110                    1115                          1120

Ile   Tyr   Asn   His   Arg   Val   Glu   Ile   Ser   Ile   Phe   Phe   Ile   Ile   Tyr   Ile
                        1125                    1130                          1135

Ile   Ile   Val   Ala   Phe   Phe   Met   Met   Asn   Ile   Phe   Val   Gly   Phe   Val   Ile
                        1140                    1145                          1150

Val   Thr   Phe   Gln   Glu   Gln   Gly   Glu   Lys   Glu   Tyr   Lys   Asn   Cys   Glu   Leu
            1155                    1160                          1165

Asp   Lys   Asn   Gln   Arg   Gln   Cys   Val   Glu   Tyr   Ala   Leu   Lys   Ala   Arg   Pro
      1170                    1175                          1180

Leu   Arg   Arg   Tyr   Ile   Pro   Lys   Asn   Pro   Tyr   Gln   Tyr   Lys   Phe   Trp   Tyr
1185                          1190                    1195                          1200

Val   Val   Asn   Ser   Ser   Pro   Phe   Glu   Tyr   Met   Met   Phe   Val   Leu   Ile   Met
                  1205                    1210                          1215

Leu   Asn   Thr   Leu   Cys   Leu   Ala   Met   Gln   His   Tyr   Glu   Gln   Ser   Lys   Met
                  1220                    1225                          1230
```

```
Phe Asn Asp Ala Met Asp Ile Leu Asn Met Val Phe Thr Gly Val Phe
            1235                1240                1245

Thr Val Glu Met Val Leu Lys Val Ile Ala Phe Lys Pro Lys Gly Tyr
    1250                1255                1260

Phe Ser Asp Ala Trp Asn Thr Phe Asp Ser Ile Val Ile Gly Ser
1265                1270                1275                1280

Ile Ile Asp Val Ala Leu Ser Glu Ala Asp Pro Thr Glu Ser Glu Asn
            1285                1290                1295

Val Pro Val Pro Thr Ala Thr Pro Gly Asn Ser Glu Glu Ser Asn Arg
                1300                1305                1310

Ile Ser Ile Thr Phe Phe Arg Leu Phe Arg Val Met Arg Leu Val Lys
            1315                1320                1325

Leu Leu Ser Arg Gly Glu Gly Ile Arg Thr Leu Leu Trp Thr Phe Ile
        1330                1335                1340

Lys Phe Phe Gln Ala Leu Pro Tyr Val Ala Leu Leu Ile Ala Met Leu
1345                1350                1355                1360

Phe Phe Ile Tyr Ala Val Ile Gly Met Gln Met Phe Gly Lys Val Ala
            1365                1370                1375

Met Arg Asp Asn Asn Gln Ile Asn Arg Asn Asn Asn Phe Gln Thr Phe
            1380                1385                1390

Pro Gln Ala Val Leu Leu Leu Phe Arg Cys Ala Thr Gly Glu Ala Trp
            1395                1400                1405

Gln Glu Ile Met Leu Ala Cys Leu Pro Gly Lys Leu Cys Asp Pro Glu
            1410                1415                1420

Ser Asp Tyr Asn Pro Gly Glu Glu His Thr Cys Gly Ser Asn Phe Ala
1425                1430                1435                1440

Ile Val Tyr Phe Ile Ser Phe Tyr Met Leu Cys Ala Phe Leu Ile Ile
            1445                1450                1455

Asn Leu Phe Val Ala Val Ile Met Asp Asn Phe Asp Tyr Leu Thr Arg
            1460                1465                1470

Asp Trp Ser Ile Leu Gly Pro His His Leu Asp Glu Phe Lys Arg Ile
            1475                1480                1485

Trp Ser Glu Tyr Asp Pro Glu Ala Lys Gly Arg Ile Lys His Leu Asp
            1490                1495                1500

Val Val Thr Leu Leu Arg Arg Ile Gln Pro Pro Leu Gly Phe Gly Lys
1505                1510                1515                1520

Leu Cys Pro His Arg Val Ala Cys Lys Arg Leu Val Ala Met Asn Met
                1525                1530                1535

Pro Leu Asn Ser Asp Gly Thr Val Met Phe Asn Ala Thr Leu Phe Ala
                1540                1545                1550

Leu Val Arg Thr Ala Leu Lys Ile Lys Thr Glu Gly Asn Leu Glu Gln
            1555                1560                1565

Ala Asn Glu Glu Leu Arg Ala Val Ile Lys Lys Ile Trp Lys Lys Thr
1570                1575                1580

Ser Met Lys Leu Leu Asp Gln Val Val Pro Pro Ala Gly Asp Asp Glu
1585                1590                1595                1600

Val Thr Val Gly Lys Phe Tyr Ala Thr Phe Leu Ile Gln Asp Tyr Phe
                1605                1610                1615

Arg Lys Phe Lys Lys Arg Lys Glu Gln Gly Leu Val Gly Lys Tyr Pro
            1620                1625                1630

Ala Lys Asn Thr Thr Ile Ala Leu Gln Ala Gly Leu Arg Thr Leu His
            1635                1640                1645

Asp Ile Gly Pro Glu Ile Arg Arg Ala Ile Ser Cys Asp Leu Gln Asp
1650                1655                1660
```

```
Asp Glu Pro Glu Glu Thr Lys Arg Glu Glu Asp Asp Val Phe Lys
1665                1670                1675                1680

Arg Asn Gly Ala Leu Leu Gly Asn His Val Asn His Val Asn Ser Asp
            1685                1690                1695

Arg Arg Asp Ser Leu Gln Gln Thr Asn Thr Thr His Arg Pro Leu His
        1700                1705                1710

Val Gln Arg Pro Ser Ile Pro Pro Ala Ser Asp Thr Glu Lys Pro Leu
            1715                1720                1725

Phe Pro Pro Ala Gly Asn Ser Val Cys His Asn His His Asn His Asn
        1730                1735                1740

Ser Ile Gly Lys Gln Val Pro Thr Ser Thr Asn Ala Asn Leu Asn Asn
1745                1750                1755                1760

Ala Asn Met Ser Lys Ala Ala His Gly Lys Arg Pro Ser Ile Gly Asn
            1765                1770                1775

Leu Glu His Val Ser Glu Asn Gly His His Ser Ser His Lys His Asp
            1780                1785                1790

Arg Glu Pro Gln Arg Arg Ser Ser Val Lys Arg Thr Arg Tyr Tyr Glu
            1795                1800                1805

Thr Tyr Ile Arg Ser Asp Ser Gly Asp Glu Gln Leu Pro Thr Ile Cys
            1810                1815                1820

Arg Glu Asp Pro Glu Ile His Gly Tyr Phe Arg Asp Pro His Cys Leu
1825                1830                1835                1840

Gly Glu Gln Glu Tyr Phe Ser Ser Glu Glu Cys Tyr Glu Asp Asp Ser
            1845                1850                1855

Ser Pro Thr Trp Ser Arg Gln Asn Tyr Gly Tyr Tyr Ser Arg Tyr Pro
            1860                1865                1870

Gly Arg Asn Ile Asp Ser Glu Arg Pro Arg Gly Tyr His His Pro Gln
            1875                1880                1885

Gly Phe Leu Glu Asp Asp Asp Ser Pro Val Cys Tyr Asp Ser Arg Arg
            1890                1895                1900

Ser Pro Arg Arg Arg Leu Leu Pro Pro Thr Pro Ala Ser His Arg Arg
1905                1910                1915                1920

Ser Ser Phe Asn Phe Glu Cys Leu Arg Arg Gln Ser Ser Gln Glu Glu
            1925                1930                1935

Val Pro Ser Ser Pro Ile Phe Pro His Arg Thr Ala Leu Pro Leu His
            1940                1945                1950

Leu Met Gln Gln Gln Ile Met Ala Val Ala Gly Leu Asp Ser Ser Lys
            1955                1960                1965

Ala Gln Lys Tyr Ser Pro Ser His Ser Thr Arg Ser Trp Ala Thr Pro
1970                1975                1980

Pro Ala Thr Pro Pro Tyr Arg Asp Trp Thr Pro Cys Tyr Thr Pro Leu
1985                1990                1995                2000

Ile Gln Val Glu Gln Ser Glu Ala Leu Asp Gln Val Asn Gly Ser Leu
            2005                2010                2015

Pro Ser Leu His Arg Ser Ser Trp Tyr Thr Asp Glu Pro Asp Ile Ser
            2020                2025                2030

Tyr Arg Thr Phe Thr Pro Ala Ser Leu Thr Val Pro Ser Ser Phe Arg
            2035                2040                2045

Asn Lys Asn Ser Asp Lys Gln Arg Ser Ala Asp Ser Leu Val Glu Ala
2050                2055                2060

Val Leu Ile Ser Glu Gly Leu Gly Arg Tyr Ala Arg Asp Pro Lys Phe
2065                2070                2075                2080

Val Ser Ala Thr Lys His Glu Ile Ala Asp Ala Cys Asp Leu Thr Ile
```

```
                            2085                    2090                    2095
Asp  Glu  Met  Glu  Ser  Ala  Ala  Ser  Thr  Leu  Leu  Asn  Gly  Asn  Val  Arg
                    2100                 2105                 2110

Pro  Arg  Ala  Asn  Gly  Asp  Val  Gly  Pro  Leu  Ser  His  Arg  Gln  Asp  Tyr
                    2115                 2120                 2125

Glu  Leu  Gln  Asp  Phe  Gly  Pro  Gly  Tyr  Ser  Asp  Glu  Glu  Pro  Asp  Pro
                    2130                 2135                 2140

Gly  Arg  Asp  Glu  Glu  Asp  Leu  Ala  Asp  Glu  Met  Ile  Cys  Ile  Thr  Thr
2145                      2150                 2155                      2160

Leu
```

( 2 ) INFORMATION FOR SEQ ID NO:3:

( i ) SEQUENCE CHARACTERISTICS:
    ( A ) LENGTH: 510 base pairs
    ( B ) TYPE: nucleic acid
    ( C ) STRANDEDNESS: unknown
    ( D ) TOPOLOGY: unknown ( i i ) MOLECULE TYPE: DNA (genomic)

( x i ) SEQUENCE DESCRIPTION: SEQ ID NO:3:

```
GGGCGAGCGC  CTCCGTCCCC  GGATGTGAGC  TCCGGCTGCC  CGCGGTCCCG  AGCCAGCGGC      60

GCGCGGGCGG  CGGCGGCGGG  CACCGGGCAC  CGCGGCGGGC  GGGCAGACGG  GCGGGCATGG     120

GGGGAGCGCC  GAGCGGCCCC  GGCGGCCGGG  CCGGCATCAC  CGCGGCGTCT  CTCCGCTAGA     180

GGAGGGGACA  AGCCAGTTCT  CCTTTGCAGC  AAAAAATTAC  ATGTATATAT  TATTAAGATA     240

ATATATACAT  TGGATTTTAT  TTTTTAAAA   AGTTTATTTT  GCTCCATTTT  TGAAAAAGAG     300

AGAGCTTGGG  TGGCGAGCGG  TTTTTTTTA   AAATCAATTA  TCCTTATTTT  CTGTTATTTG     360

TCCCCGTCCC  TCCCCACCCC  CCTGCTGAAG  CGAGAATAAG  GGCAGGGACC  GCGGCTCCTA     420

CCTCTTGGTG  ATCCCCTTCC  CCATTCCGCC  CCCGCCCCAA  CGCCCAGCAC  AGTGCCCTGC     480

ACACAGTAGT  CGCTCAATAA  ATGTTCGTGG                                        510
```

( 2 ) INFORMATION FOR SEQ ID NO:4:

( i ) SEQUENCE CHARACTERISTICS:
    ( A ) LENGTH: 104 base pairs
    ( B ) TYPE: nucleic acid
    ( C ) STRANDEDNESS: unknown
    ( D ) TOPOLOGY: unknown ( i i ) MOLECULE TYPE: DNA (genomic)

( i x ) FEATURE:
    ( A ) NAME/KEY: CDS
    ( B ) LOCATION: 1..102

( x i ) SEQUENCE DESCRIPTION: SEQ ID NO:4:

```
GTA  AAT  GAT  GCG  ATA  GGA  TGG  GAA  TGG  CCA  TGG  GTG  TAT  TTT  GTT  AGT      48
Val  Asn  Asp  Ala  Ile  Gly  Trp  Glu  Trp  Pro  Trp  Val  Tyr  Phe  Val  Ser
 1                   5                        10                       15

CTG  ATC  ATC  CTT  GGC  TCA  TTT  TTC  GTC  CTT  AAC  CTG  GTT  CTT  GGT  GTC      96
Leu  Ile  Ile  Leu  Gly  Ser  Phe  Phe  Val  Leu  Asn  Leu  Val  Leu  Gly  Val
                    20                       25                       30

CTT  AGT  GG                                                                        104
Leu  Ser
```

( 2 ) INFORMATION FOR SEQ ID NO:5:

( i ) SEQUENCE CHARACTERISTICS:
    ( A ) LENGTH: 34 amino acids (B) TYPE: amino acid
(D) TOPOLOGY: linear (ii) MOLECULE TYPE: protein (xi) SEQUENCE DESCRIPTION: SEQ ID NO:5:

```
Val Asn Asp Ala Ile Gly Trp Glu Trp Pro Trp Val Tyr Phe Val Ser
 1               5                  10                  15
Leu Ile Ile Leu Gly Ser Phe Phe Val Leu Asn Leu Val Leu Gly Val
                20                  25                  30
Leu Ser
```

(2) INFORMATION FOR SEQ ID NO:6:

(i) SEQUENCE CHARACTERISTICS:
(A) LENGTH: 5904 base pairs
(B) TYPE: nucleic acid
(C) STRANDEDNESS: unknown
(D) TOPOLOGY: unknown (ii) MOLECULE TYPE: DNA (genomic)

(xi) SEQUENCE DESCRIPTION: SEQ ID NO:6:

| | | | | | | |
|---|---|---|---|---|---|---|
| ATGGTCAATG | AGAATACGAG | GATGTACATT | CCAGAGGAAA | ACCACCAAGG | TTCCAACTAT | 60 |
| GGGAGCCCAC | GCCCCGCCCA | TGCCAACATG | AATGCCAATG | CGGCAGCGGG | GCTGGCCCCT | 120 |
| GAGCACATCC | CCACCCCGGG | GGCTGCCCTG | TCGTGGCAGG | CGGCCATCGA | CGCAGCCCGG | 180 |
| CAGGCTAAGC | TGATGGGCAG | CGCTGGCAAT | GCGACCATCT | CCACAGTCAG | CTCCACGCAG | 240 |
| CGGAAGCGCC | AGCAATATGG | GAAACCCAAG | AAGCAGGGCA | GCACCACGGC | CACACGCCCG | 300 |
| CCCCGAGCCC | TGCTCTGCCT | GACCCTGAAG | AACCCCATCC | GGAGGGCCTG | CATCAGCATT | 360 |
| GTCGAATGGA | AACCATTTGA | AATAATTATT | TTACTGACTA | TTTTTGCCAA | TTGTGTGGCC | 420 |
| TTAGCGATCT | ATATTCCCTT | TCCAGAAGAT | GATTCCAACG | CCACCAATTC | CAACCTGGAA | 480 |
| CGAGTGGAAT | ATCTCTTTCT | CATAATTTTT | ACGGTGGAAG | CGTTTTAAA | AGTAATCGCC | 540 |
| TATGGACTCC | TCTTTCACCC | CAATGCCTAC | CTCCGCAACG | GCTGGAACCT | ACTAGATTTT | 600 |
| ATAATTGTGG | TTGTGGGGCT | TTTTAGTGCA | ATTTTAGAAC | AAGCAACCAA | AGCAGATGGG | 660 |
| GCAAACGCTC | TCGGAGGGAA | AGGGGCCGGA | TTTGATGTGA | AGGCGCTGAG | GGCCTTCCGC | 720 |
| GTGCTGCGCC | CCCTGCGGCT | GGTGTCCGGA | GTCCCAAGTC | TCCAGGTGGT | CCTGAATTCC | 780 |
| ATCATCAAGG | CCATGGTCCC | CCTGCTGCAC | ATCGCCCTGC | TTGTGCTGTT | TGTCATCATC | 840 |
| ATCTACGCCA | TCATCGGCTT | GGAGCTCTTC | ATGGGGAAGA | TGCACAAGAC | CTGCTACAAC | 900 |
| CAGGAGGGCA | TAGCAGATGT | TCCAGCAGAA | GATGACCCTT | CCCCTTGTGC | GCTGGAAACG | 960 |
| GGCCACGGGC | GGCAGTGCCA | GAACGGCACG | GTGTGCAAGC | CCGGCTGGGA | TGGTCCCAAG | 1020 |
| CACGGCATCA | CCAACTTTGA | CAACTTTGCC | TTCGCCATGC | TCACGGTGTT | CCAGTGCATC | 1080 |
| ACCATGGAGG | GCTGGACGGA | CGTGCTGTAC | TGGGTCAATG | ATGCCGTAGG | AAGGGACTGG | 1140 |
| CCCTGGATCT | ATTTTGTTAC | ACTAATCATC | ATAGGGTCAT | TTTTTGTACT | TAACTTGGTT | 1200 |
| CTCGGTGTGC | TTAGCGGAGA | GTTTTCCAAA | GAGAGGGAGA | AGGCCAAGGC | CCGGGGAGAT | 1260 |
| TTCCAGAAGC | TGCGGGAGAA | GCAGCAGCTA | GAAGAGGATC | TCAAAGGCTA | CCTGGATTGG | 1320 |
| ATCACTCAGG | CCGAAGACAT | CGNTCCTGAG | AATGAGGACG | AAGGCATGGA | TGAGGAGAAG | 1380 |
| CCCCGAAACA | GAGGCACTCC | GGCGGGCATG | CTTGATCAGA | AGAAAGGGAA | GTTTGCTTGG | 1440 |
| TTTAGTCACT | CCACAGAAAC | CCATGTGAGC | ATGCCACCA | GTGAGACCGA | GTCCGTCAAC | 1500 |
| ACCGAAAACG | TGGCTGGAGG | TGACATCGAG | GGAGAAAACT | GCGGGGCCAG | GCTGGCCCAC | 1560 |

-continued

| | | | | | | |
|---|---|---|---|---|---|---|
| CGGATCTCCA | AGTCAAAGTT | CAGCCGCTAC | TGGCGCCGGT | GGAATCGGTT | CTGCAGAAGG | 1620 |
| AAGTGCCGCG | CCGCAGTCAA | GTCTAATGTC | TTCTACTGGC | TGGTGATTTT | CCTGGTGTTC | 1680 |
| CTCAACACGC | TCACCATTGC | CTCTGAGCAC | TACAACCAGC | CCAACTGGCT | CACAGAAGTC | 1740 |
| CAAGACACGG | CAAACAAGGC | CCTGCTGGCC | CTGTTCACGG | CAGAGATGCT | CCTGAAGATG | 1800 |
| TACAGCCTGG | GCCTGCAGGC | CTACTTCGTG | TCCCTCTTCA | ACCGCTTTGA | CTGCTTCGTC | 1860 |
| GTGTGTGGCG | GCATCCTGGA | GACCATCCTG | GTGGAGACCA | AGATCATGTC | CCCACTGGGC | 1920 |
| ATCTCCGTGC | TCAGATGCGT | CCGGCTGCTG | AGGATTTTCA | AGATCACGAG | GTACTGGAAC | 1980 |
| TCCTTGAGCA | ACCTGGTGGC | ATCCTTGCTG | AACTCTGTGC | GCTCCATCGC | CTCCCTGCTC | 2040 |
| CTTCTCCTCT | TCCTCTTCAT | CATCATCTTC | TCCCTCCTGG | GGATGCAGCT | CTTTGGAGGA | 2100 |
| AAGTTCAACT | TTGATGAGAT | GCAGACCCGG | AGGAGCACAT | TCGATAACTT | CCCCCAGTCC | 2160 |
| CTCCTCACTG | TGTTTNNNNN | NNNNNNNNNN | NNNNNNNNNN | NNNGGTGAT | GTATGATGGG | 2220 |
| ATCATGGCTT | ATGGGGCCC | CTCTTTTCCA | GGGATGTTAG | TCTGTATTTA | CTTCATCATC | 2280 |
| CTCTTCATCT | CTGGAAACTA | TATCCTACTG | AATGTGTTCT | TGGCCATTGC | TGTGGACAAC | 2340 |
| CTGGCTGATG | CTGAGAGCCT | CACATCTGCC | CTAAAGGAGG | AGGAAGAGGA | GAAGGAGAGA | 2400 |
| AAGAAGCTGG | CCAGGACTGC | CAGCCCAGAG | AAGAAACAAG | AGTTGGTGGA | GAAGCCGGCA | 2460 |
| GTGGGGGAAT | CCAAGGAGGA | GAAGATTGAG | CTGAAATCCA | TCACGGCTGA | CGGAGAGTCT | 2520 |
| CCACCCGCCA | CCAAGATCAA | CATGGATGAC | CTCCAGCCCA | ATGAAAATGA | GGATAAGAGC | 2580 |
| CCCTACCCCA | ACCCAGAAAC | TACAGGAGAA | GAGGATGAGG | AGGAGCCAGA | GATGCCTGTC | 2640 |
| GGCCCTCGCC | CACGACCACT | CTCTGAGCTT | CACCTTAAGG | AAAAGGCAGT | GCCCATGCCA | 2700 |
| GAAGCCAGCG | CGTTTTTCAT | CTTCAGCTCT | AACAACAGGT | TTCGCCTCCA | GTGCCACCGC | 2760 |
| ATTGTCAATG | ACACGATCTT | CACCAACCTG | ATCCTCTTCT | TCATTCTGCT | CAGCAGCATT | 2820 |
| TCCCTGGCTG | CTGAGGACCC | GGTCCAGCAC | ACCTCCTTCA | GGAACCATAT | TCTGTTTTAT | 2880 |
| TTTGATATTG | TTTTTACCAC | CATTTTCACC | ATTGAAATTG | CTCTGAAGAT | GACTGCTTAT | 2940 |
| GGGGCTTTCT | TGCACAAGGG | TTCTTTCTGC | CGGAACTACT | TCAACATCCT | GGACCTGCTG | 3000 |
| GTGGTCAGCG | TGTCCCTCAT | CTCCTTTGGC | ATCCAGTCCA | GTGCAATCAA | TGTCGTGAAG | 3060 |
| ATCTTGCGAG | TCCTGCGAGT | ACTCAGGCCC | CTGAGGGCCA | TCAACAGGGC | CAAGGGGCTA | 3120 |
| AAGCATGTGG | TTCAGTGTGT | GTTTGTCGCC | ATCCGGACCA | TCGGGAACAT | CGTGATTGTC | 3180 |
| ACCACCCTGC | TGCAGTTCAT | GTTTGCCTGC | ATCGGGGTCC | AGCTCTTCAA | GGGAAAGCTG | 3240 |
| TACACCTGTT | CAGACAGTTC | CAAGCAGACA | GAGGCGGAAT | GCAAGGGCAA | CTACATCACG | 3300 |
| TACAAAGACG | GGGAGGTTGA | CCACCCCATC | ATCCAACCCC | GCAGCTGGGA | GAACAGCAAG | 3360 |
| TTTGACTTTG | ACAATGTTCT | GGCAGCCATG | ATGGCCCTCT | TCACCGTCTC | CACCTTCGAA | 3420 |
| GGGTGGCCAG | AGCTGCTGTA | CCGCTCCATC | GACTCCACA | CGGAAGACAA | GGGCCCCATC | 3480 |
| TACAACTACC | GTGTGGAGAT | CTCCATCTTC | TTCATCATCT | ACATCATCAT | CATCGCCTTC | 3540 |
| TTCATGATGA | ACATCTTCGT | GGGCTTCGTC | ATCGTCACCT | TCAGGAGCA | GGGGGAGCAG | 3600 |
| GAGTACAAGA | ACTGTGAGCT | GGACAAGAAC | CAGCGACAGT | GCGTGGAATA | CGCCCTCAAG | 3660 |
| GCCCGGCCCC | TGCGGAGGTA | CATCCCCAAG | AACCAGCACC | AGTACAAAGT | GTGGTACGTG | 3720 |
| GTCAACTCCA | CCTACTTCGA | GTACCTGATG | TTCGTCCTCA | TCCTGCTCAA | CACCATCTGC | 3780 |
| CTGGCCATGC | AGCACTACGG | CCAGAGCTGC | CTGTTCAAAA | TCGCCATGAA | CATCCTCAAC | 3840 |
| ATGCTCTTCA | CTGGCCTCTT | CACCGTGGAG | ATGATCCTGA | AGCTCATTGC | CTTCAAACCC | 3900 |
| AAGGGTTACT | TTAGTGATCC | CTGGAATGTT | TTTGACTTCC | TCATCGTAAT | TGGCAGCATA | 3960 |

| | | | | | |
|---|---|---|---|---|---|
| ATTGACGTCA | TTCTCAGTGA | GACTAATCCA | GCTGAACATA | CCCAATGCTC | TCCCTCTATG 4020 |
| AACGCAGAGG | AAAACTCCCG | CATCTCCATC | ACCTTCTTCC | GCCTGTTCCG | GGTCATGCGT 4080 |
| CTGGTGAAGC | TGCTGAGCCG | TGGGGAGGGC | ATCCGGACGC | TGCTGTGGAC | CTTCATCAAG 4140 |
| TCCTTCCAGG | CCCTGCCCTA | TGTGGCCCTC | CTGATCGTGA | TGCTGTTCTT | CATCTACGCG 4200 |
| GTGATCGGGA | TGCAGGTGTT | TGGGAAAATT | GCCCTGAATG | ATACCACAGA | GATCAACCGG 4260 |
| AACAACAACT | TTCAGACCTT | CCCCCAGGCC | GTGCTGCTCC | TCTTCAGGTG | TGCCACCGGG 4320 |
| GAGGCCTGGC | AGGACATCAT | GCTGGCCTGC | ATGCCAGGCA | AGAAGTGTGC | CCCAGAGTCC 4380 |
| GAGCCCAGCA | ACAGCACGGA | GGGTGAAACA | CCCTGTGGTA | GCAGCTTTGC | TGTCTTCTAC 4440 |
| TTCATCAGCT | TCTACATGCG | CTGTGCCTTC | CTGATCATCA | ACCTCTTTGT | AGCTGTCATC 4500 |
| ATGGACAACT | TTGACTACCT | GACAAGGGAC | TGGTCCATCC | TTGGTCCCCA | CCACCTGGAT 4560 |
| GAGTTTAAAA | GAATCTGGGC | AGAGTATGAC | CCTGAAGCCA | AGGGTCGTAT | CAAACACCTG 4620 |
| GATGTGGTGA | CCCTCCTCCG | GCGGATTCAG | CCGCCACTAG | GTTTTGGGAA | GCTGTGCCCT 4680 |
| CACCGCGTGG | CTTGCAAACG | CCTGGTCTCC | ATGAACATGC | CTCTGAACAG | CGACGGGACA 4740 |
| GTCATGTTCA | ATGCCACCCT | GTTTGCCCTG | GTCAGGACGG | CCCTGAGGAT | CAAAACAGAA 4800 |
| GGGAACCTAG | AACAAGCCAA | TGAGGAGCTG | CGGGCGATCA | TCAAGAAGAT | CTGGAAGCGG 4860 |
| ACCAGCATGA | AGCTGCTGGA | CCAGGTGGTG | CCCCCTGCAG | GTGATGATGA | GGTCACCGTT 4920 |
| GGCAAGTTCT | ACGCCACGTT | CCTGATCCAG | GAGTACTTCC | GGAAGTTCAA | GAAGCGCAAA 4980 |
| GAGCAGGGCC | TTGTGGGCAA | GCCCTCCCAG | AGGAACGCGC | TGTCTCTGCA | GGCTGGCTTG 5040 |
| CGCACACTGC | ATGACATCGG | GCCTGAGATC | CGACGGGCCA | TCTCTGGAGA | TCTCACCGCT 5100 |
| GAGGAGGAGC | TGGACAAGGC | CATGAAGGAG | GCTGTGTCCG | CTGCTTCTGA | AGATGACATC 5160 |
| TTCAGGAGGG | CCGGTGGCCT | GTTCGGCAAC | CACGTCAGCT | ACTACCAAAG | CGACGGCCGG 5220 |
| AGCGCCTTCC | CCCAGACCTT | CACCACTCAG | CGCCCGCTGC | ACATCAACAA | GGCGGGCAGC 5280 |
| AGCCAGGGCG | ACACTGAGTC | GCCATCCCAC | GAGAAGCTGG | TGGACTCCAC | CTTCACCCCG 5340 |
| AGCAGCTACT | CGTCCACCGG | CTCCAACGCC | AACATCAACA | ACGCCAACAA | CACCGCCCTG 5400 |
| GGTCGCCTCC | CTCGCCCCGC | CGGCTACCCC | AGCACAGTCA | GCACTGTGGA | GGGCCACGGG 5460 |
| CCCCCCTTGT | CCCCTGCCAT | CCGGGTGCAG | GAGGTGGCGT | GGAAGCTCAG | CTCCAACAGG 5520 |
| TGCCACTCCC | GGGAGAGCCA | GGCAGCCATG | GCGCGTCAGG | AGGAGACGTC | TCAGGATGAG 5580 |
| ACCTATGAAG | TGAAGATGAA | CCATGACACG | GAGGCCTGCA | GTGAGCCCAG | CCTGCTCTCC 5640 |
| ACAGAGATGC | TCTCCTACCA | GGATGACGAA | AATCGGCAAC | TGACGCTCCC | AGAGGAGGAC 5700 |
| AAGAGGGACA | TCCGGCAATC | TCCGAAGAGG | GGTTTCCTCC | GCTCTTCCTC | ACTAGGTCGA 5760 |
| AGGGCCTCCT | TCCACCTGGA | ATGTCTGAAG | CGACAGAAGG | ACCGAGGGGG | AGACATCTCT 5820 |
| CAGAAGACAG | TCCTGCCCTT | GCATCTGGTT | CATCATCAGG | CATTGGCAGT | GGCAGGCCTG 5880 |
| AGCCCCCTCC | TCCAGAGAAG | CCAT | | | 5904 |

( 2 ) INFORMATION FOR SEQ ID NO:7:

( i ) SEQUENCE CHARACTERISTICS:
        ( A ) LENGTH: 1968 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:7:

Met  Val  Asn  Glu  Asn  Thr  Arg  Met  Tyr  Ile  Pro  Glu  Glu  Asn  His  Gln

```
  1                    5                          10                          15

Gly  Ser  Asn  Tyr  Gly  Ser  Pro  Arg  Pro  Ala  His  Ala  Asn  Met  Asn  Ala
                    20                       25                  30

Asn  Ala  Ala  Ala  Gly  Leu  Ala  Pro  Glu  His  Ile  Pro  Thr  Pro  Gly  Ala
          35                       40                           45

Ala  Leu  Ser  Trp  Gln  Ala  Ala  Ile  Asp  Ala  Ala  Arg  Gln  Ala  Lys  Leu
     50                       55                       60

Met  Gly  Ser  Ala  Gly  Asn  Ala  Thr  Ile  Ser  Thr  Val  Ser  Ser  Thr  Gln
65                       70                  75                            80

Arg  Lys  Arg  Gln  Gln  Tyr  Gly  Lys  Pro  Lys  Lys  Gln  Gly  Ser  Thr  Thr
                    85                       90                       95

Ala  Thr  Arg  Pro  Pro  Arg  Ala  Leu  Leu  Cys  Leu  Thr  Leu  Lys  Asn  Pro
               100                      105                      110

Ile  Arg  Arg  Ala  Cys  Ile  Ser  Ile  Val  Glu  Trp  Lys  Pro  Phe  Glu  Ile
          115                      120                      125

Ile  Ile  Leu  Leu  Thr  Ile  Phe  Ala  Asn  Cys  Val  Ala  Leu  Ala  Ile  Tyr
     130                      135                      140

Ile  Pro  Phe  Pro  Glu  Asp  Asp  Ser  Asn  Ala  Thr  Asn  Ser  Asn  Leu  Glu
145                      150                      155                      160

Arg  Val  Glu  Tyr  Leu  Phe  Leu  Ile  Ile  Phe  Thr  Val  Glu  Ala  Phe  Leu
                    165                      170                      175

Lys  Val  Ile  Ala  Tyr  Gly  Leu  Leu  Phe  His  Pro  Asn  Ala  Tyr  Leu  Arg
               180                      185                      190

Asn  Gly  Trp  Asn  Leu  Leu  Asp  Phe  Ile  Ile  Val  Val  Val  Gly  Leu  Phe
          195                      200                      205

Ser  Ala  Ile  Leu  Glu  Gln  Ala  Thr  Lys  Ala  Asp  Gly  Ala  Asn  Ala  Leu
     210                      215                      220

Gly  Gly  Lys  Gly  Ala  Gly  Phe  Asp  Val  Lys  Ala  Leu  Arg  Ala  Phe  Arg
225                      230                      235                      240

Val  Leu  Arg  Pro  Leu  Arg  Leu  Val  Ser  Gly  Val  Pro  Ser  Leu  Gln  Val
               245                      250                      255

Val  Leu  Asn  Ser  Ile  Ile  Lys  Ala  Met  Val  Pro  Leu  Leu  His  Ile  Ala
          260                      265                      270

Leu  Leu  Val  Leu  Phe  Val  Ile  Ile  Ile  Tyr  Ala  Ile  Ile  Gly  Leu  Glu
     275                      280                      285

Leu  Phe  Met  Gly  Lys  Met  His  Lys  Thr  Cys  Tyr  Asn  Gln  Glu  Gly  Ile
     290                      295                      300

Ala  Asp  Val  Pro  Ala  Glu  Asp  Asp  Pro  Ser  Pro  Cys  Ala  Leu  Glu  Thr
305                      310                      315                      320

Gly  His  Gly  Arg  Gln  Cys  Gln  Asn  Gly  Thr  Val  Cys  Lys  Pro  Gly  Trp
                    325                      330                      335

Asp  Gly  Pro  Lys  His  Gly  Ile  Thr  Asn  Phe  Asp  Asn  Phe  Ala  Phe  Ala
               340                      345                      350

Met  Leu  Thr  Val  Phe  Gln  Cys  Ile  Thr  Met  Glu  Gly  Trp  Thr  Asp  Val
          355                      360                      365

Leu  Tyr  Trp  Val  Asn  Asp  Ala  Val  Gly  Arg  Asp  Trp  Pro  Trp  Ile  Tyr
     370                      375                      380

Phe  Val  Thr  Leu  Ile  Ile  Ile  Gly  Ser  Phe  Phe  Val  Leu  Asn  Leu  Val
385                      390                      395                      400

Leu  Gly  Val  Leu  Ser  Gly  Glu  Phe  Ser  Lys  Glu  Arg  Glu  Lys  Ala  Lys
                    405                      410                      415

Ala  Arg  Gly  Asp  Phe  Gln  Lys  Leu  Arg  Glu  Lys  Gln  Gln  Leu  Glu  Glu
               420                      425                      430
```

```
Asp  Leu  Lys  Gly  Tyr  Leu  Asp  Trp  Ile  Thr  Gln  Ala  Glu  Asp  Ile  Xaa
          435                     440                     445

Pro  Glu  Asn  Glu  Asp  Glu  Gly  Met  Asp  Glu  Glu  Lys  Pro  Arg  Asn  Arg
     450                     455                     460

Gly  Thr  Pro  Ala  Gly  Met  Leu  Asp  Gln  Lys  Lys  Gly  Lys  Phe  Ala  Trp
465                      470                     475                      480

Phe  Ser  His  Ser  Thr  Glu  Thr  His  Val  Ser  Met  Pro  Thr  Ser  Glu  Thr
                    485                     490                     495

Glu  Ser  Val  Asn  Thr  Glu  Asn  Val  Ala  Gly  Gly  Asp  Ile  Glu  Gly  Glu
               500                     505                     510

Asn  Cys  Gly  Ala  Arg  Leu  Ala  His  Arg  Ile  Ser  Lys  Ser  Lys  Phe  Ser
               515                     520                     525

Arg  Tyr  Trp  Arg  Arg  Trp  Asn  Arg  Phe  Cys  Arg  Arg  Lys  Cys  Arg  Ala
     530                     535                     540

Ala  Val  Lys  Ser  Asn  Val  Phe  Tyr  Trp  Leu  Val  Ile  Phe  Leu  Val  Phe
545                      550                     555                      560

Leu  Asn  Thr  Leu  Thr  Ile  Ala  Ser  Glu  His  Tyr  Asn  Gln  Pro  Asn  Trp
                    565                     570                     575

Leu  Thr  Glu  Val  Gln  Asp  Thr  Ala  Asn  Lys  Ala  Leu  Leu  Ala  Leu  Phe
               580                     585                     590

Thr  Ala  Glu  Met  Leu  Leu  Lys  Met  Tyr  Ser  Leu  Gly  Leu  Gln  Ala  Tyr
          595                     600                     605

Phe  Val  Ser  Leu  Phe  Asn  Arg  Phe  Asp  Cys  Phe  Val  Val  Cys  Gly  Gly
     610                     615                     620

Ile  Leu  Glu  Thr  Ile  Leu  Val  Glu  Thr  Lys  Ile  Met  Ser  Pro  Leu  Gly
625                      630                     635                      640

Ile  Ser  Val  Leu  Arg  Cys  Val  Arg  Leu  Leu  Arg  Ile  Phe  Lys  Ile  Thr
                    645                     650                     655

Arg  Tyr  Trp  Asn  Ser  Leu  Ser  Asn  Leu  Val  Ala  Ser  Leu  Leu  Asn  Ser
               660                     665                     670

Val  Arg  Ser  Ile  Ala  Ser  Leu  Leu  Leu  Leu  Leu  Phe  Leu  Phe  Ile  Ile
          675                     680                     685

Ile  Phe  Ser  Leu  Leu  Gly  Met  Gln  Leu  Phe  Gly  Gly  Lys  Phe  Asn  Phe
     690                     695                     700

Asp  Glu  Met  Gln  Thr  Arg  Arg  Ser  Thr  Phe  Asp  Asn  Phe  Pro  Gln  Ser
705                      710                     715                      720

Leu  Leu  Thr  Val  Phe  Xaa  Xaa  Xaa  Xaa  Xaa  Xaa  Xaa  Xaa  Xaa  Xaa  Val
                    725                     730                     735

Met  Tyr  Asp  Gly  Ile  Met  Ala  Tyr  Gly  Gly  Pro  Ser  Phe  Pro  Gly  Met
               740                     745                     750

Leu  Val  Cys  Ile  Tyr  Phe  Ile  Ile  Leu  Phe  Ile  Ser  Gly  Asn  Tyr  Ile
          755                     760                     765

Leu  Leu  Asn  Val  Phe  Leu  Ala  Ile  Ala  Val  Asp  Asn  Leu  Ala  Asp  Ala
     770                     775                     780

Glu  Ser  Leu  Thr  Ser  Ala  Leu  Lys  Glu  Glu  Glu  Glu  Glu  Lys  Glu  Arg
785                      790                     795                      800

Lys  Lys  Leu  Ala  Arg  Thr  Ala  Ser  Pro  Glu  Lys  Lys  Gln  Glu  Leu  Val
                    805                     810                     815

Glu  Lys  Pro  Ala  Val  Gly  Glu  Ser  Lys  Glu  Glu  Lys  Ile  Glu  Leu  Lys
               820                     825                     830

Ser  Ile  Thr  Ala  Asp  Gly  Glu  Ser  Pro  Pro  Ala  Thr  Lys  Ile  Asn  Met
          835                     840                     845

Asp  Asp  Leu  Gln  Pro  Asn  Glu  Asn  Glu  Asp  Lys  Ser  Pro  Tyr  Pro  Asn
     850                     855                     860
```

```
Pro Glu Thr Thr Gly Glu Glu Asp Glu Glu Glu Pro Glu Met Pro Val
865                 870                 875                 880

Gly Pro Arg Pro Arg Pro Leu Ser Glu Leu His Leu Lys Glu Lys Ala
                885                 890                 895

Val Pro Met Pro Glu Ala Ser Ala Phe Ile Phe Ser Ser Asn Asn
            900                 905                 910

Arg Phe Arg Leu Gln Cys His Arg Ile Val Asn Asp Thr Ile Phe Thr
        915                 920                 925

Asn Leu Ile Leu Phe Phe Ile Leu Leu Ser Ser Ile Ser Leu Ala Ala
    930                 935                 940

Glu Asp Pro Val Gln His Thr Ser Phe Arg Asn His Ile Leu Phe Tyr
945                 950                 955                 960

Phe Asp Ile Val Phe Thr Thr Ile Phe Thr Ile Glu Ile Ala Leu Lys
                965                 970                 975

Met Thr Ala Tyr Gly Ala Phe Leu His Lys Gly Ser Phe Cys Arg Asn
            980                 985                 990

Tyr Phe Asn Ile Leu Asp Leu Leu Val Val Ser Val Ser Leu Ile Ser
        995                 1000                1005

Phe Gly Ile Gln Ser Ser Ala Ile Asn Val Val Lys Ile Leu Arg Val
    1010                1015                1020

Leu Arg Val Leu Arg Pro Leu Arg Ala Ile Asn Arg Ala Lys Gly Leu
1025                1030                1035                1040

Lys His Val Val Gln Cys Val Phe Val Ala Ile Arg Thr Ile Gly Asn
                1045                1050                1055

Ile Val Ile Val Thr Thr Leu Leu Gln Phe Met Phe Ala Cys Ile Gly
            1060                1065                1070

Val Gln Leu Phe Lys Gly Lys Leu Tyr Thr Cys Ser Asp Ser Ser Lys
        1075                1080                1085

Gln Thr Glu Ala Glu Cys Lys Gly Asn Tyr Ile Thr Tyr Lys Asp Gly
    1090                1095                1100

Glu Val Asp His Pro Ile Ile Gln Pro Arg Ser Trp Glu Asn Ser Lys
1105                1110                1115                1120

Phe Asp Phe Asp Asn Val Leu Ala Ala Met Met Ala Leu Phe Thr Val
                1125                1130                1135

Ser Thr Phe Glu Gly Trp Pro Glu Leu Leu Tyr Arg Ser Ile Asp Ser
            1140                1145                1150

His Thr Glu Asp Lys Gly Pro Ile Tyr Asn Tyr Arg Val Glu Ile Ser
        1155                1160                1165

Ile Phe Phe Ile Ile Tyr Ile Ile Ile Ile Ala Phe Phe Met Met Asn
    1170                1175                1180

Ile Phe Val Gly Phe Val Ile Val Thr Phe Gln Glu Gln Gly Glu Gln
1185                1190                1195                1200

Glu Tyr Lys Asn Cys Glu Leu Asp Lys Asn Gln Arg Gln Cys Val Glu
                1205                1210                1215

Tyr Ala Leu Lys Ala Arg Pro Leu Arg Arg Tyr Ile Pro Lys Asn Gln
            1220                1225                1230

His Gln Tyr Lys Val Trp Tyr Val Val Asn Ser Thr Tyr Phe Glu Tyr
        1235                1240                1245

Leu Met Phe Val Leu Ile Leu Leu Asn Thr Ile Cys Leu Ala Met Gln
    1250                1255                1260

His Tyr Gly Gln Ser Cys Leu Phe Lys Ile Ala Met Asn Ile Leu Asn
1265                1270                1275                1280

Met Leu Phe Thr Gly Leu Phe Thr Val Glu Met Ile Leu Lys Leu Ile
```

```
                        1285                      1290                     1295
    Ala  Phe  Lys  Pro  Lys  Gly  Tyr  Phe  Ser  Asp  Pro  Trp  Asn  Val  Phe  Asp
                   1300                      1305                     1310

Phe  Leu  Ile  Val  Ile  Gly  Ser  Ile  Ile  Asp  Val  Ile  Leu  Ser  Glu  Thr
              1315                       1320                      1325

Asn  Pro  Ala  Glu  His  Thr  Gln  Cys  Ser  Pro  Ser  Met  Asn  Ala  Glu  Glu
                   1330                      1335                     1340

Asn  Ser  Arg  Ile  Ser  Ile  Thr  Phe  Phe  Arg  Leu  Phe  Arg  Val  Met  Arg
    1345                      1350                      1355                     1360

Leu  Val  Lys  Leu  Leu  Ser  Arg  Gly  Glu  Gly  Ile  Arg  Thr  Leu  Leu  Trp
                        1365                      1370                     1375

Thr  Phe  Ile  Lys  Ser  Phe  Gln  Ala  Leu  Pro  Tyr  Val  Ala  Leu  Leu  Ile
                   1380                      1385                     1390

Val  Met  Leu  Phe  Phe  Ile  Tyr  Ala  Val  Ile  Gly  Met  Gln  Val  Phe  Gly
                   1395                      1400                     1405

Lys  Ile  Ala  Leu  Asn  Asp  Thr  Thr  Glu  Ile  Asn  Arg  Asn  Asn  Asn  Phe
              1410                       1415                      1420

Gln  Thr  Phe  Pro  Gln  Ala  Val  Leu  Leu  Leu  Phe  Arg  Cys  Ala  Thr  Gly
    1425                      1430                      1435                     1440

Glu  Ala  Trp  Gln  Asp  Ile  Met  Leu  Ala  Cys  Met  Pro  Gly  Lys  Lys  Cys
                        1445                      1450                     1455

Ala  Pro  Glu  Ser  Glu  Pro  Ser  Asn  Ser  Thr  Glu  Gly  Glu  Thr  Pro  Cys
                        1460                      1465                     1470

Gly  Ser  Ser  Phe  Ala  Val  Phe  Tyr  Phe  Ile  Ser  Phe  Tyr  Met  Arg  Cys
                        1475                      1480                     1485

Ala  Phe  Leu  Ile  Ile  Asn  Leu  Phe  Val  Ala  Val  Ile  Met  Asp  Asn  Phe
                   1490                      1495                     1500

Asp  Tyr  Leu  Thr  Arg  Asp  Trp  Ser  Ile  Leu  Gly  Pro  His  His  Leu  Asp
    1505                      1510                      1515                     1520

Glu  Phe  Lys  Arg  Ile  Trp  Ala  Glu  Tyr  Asp  Pro  Glu  Ala  Lys  Gly  Arg
                        1525                      1530                     1535

Ile  Lys  His  Leu  Asp  Val  Val  Thr  Leu  Leu  Arg  Arg  Ile  Gln  Pro  Pro
                   1540                      1545                     1550

Leu  Gly  Phe  Gly  Lys  Leu  Cys  Pro  His  Arg  Val  Ala  Cys  Lys  Arg  Leu
                        1555                      1560                     1565

Val  Ser  Met  Asn  Met  Pro  Leu  Asn  Ser  Asp  Gly  Thr  Val  Met  Phe  Asn
    1570                      1575                      1580

Ala  Thr  Leu  Phe  Ala  Leu  Val  Arg  Thr  Ala  Leu  Arg  Ile  Lys  Thr  Glu
    1585                      1590                      1595                     1600

Gly  Asn  Leu  Glu  Gln  Ala  Asn  Glu  Glu  Leu  Arg  Ala  Ile  Ile  Lys  Lys
                        1605                      1610                     1615

Ile  Trp  Lys  Arg  Thr  Ser  Met  Lys  Leu  Leu  Asp  Gln  Val  Val  Pro  Pro
                   1620                      1625                     1630

Ala  Gly  Asp  Asp  Glu  Val  Thr  Val  Gly  Lys  Phe  Tyr  Ala  Thr  Phe  Leu
                   1635                      1640                     1645

Ile  Gln  Glu  Tyr  Phe  Arg  Lys  Phe  Lys  Lys  Arg  Lys  Glu  Gln  Gly  Leu
                   1650                      1655                     1660

Val  Gly  Lys  Pro  Ser  Gln  Arg  Asn  Ala  Leu  Ser  Leu  Gln  Ala  Gly  Leu
    1665                      1670                      1675                     1680

Arg  Thr  Leu  His  Asp  Ile  Gly  Pro  Glu  Ile  Arg  Arg  Ala  Ile  Ser  Gly
                        1685                      1690                     1695

Asp  Leu  Thr  Ala  Glu  Glu  Glu  Leu  Asp  Lys  Ala  Met  Lys  Glu  Ala  Val
                   1700                      1705                     1710
```

| | | | | | | | | | | | | | | |
|---|---|---|---|---|---|---|---|---|---|---|---|---|---|---|
| Ser | Ala | Ala | Ser | Glu | Asp | Asp | Ile | Phe | Arg | Arg | Ala | Gly | Gly | Leu | Phe |
| | | | 1715 | | | | 1720 | | | | 1725 | | | | |
| Gly | Asn | His | Val | Ser | Tyr | Tyr | Gln | Ser | Asp | Gly | Arg | Ser | Ala | Phe | Pro |
| | | | 1730 | | | | 1735 | | | | 1740 | | | | |
| Gln | Thr | Phe | Thr | Thr | Gln | Arg | Pro | Leu | His | Ile | Asn | Lys | Ala | Gly | Ser |
| 1745 | | | | | 1750 | | | | 1755 | | | | | | 1760 |
| Ser | Gln | Gly | Asp | Thr | Glu | Ser | Pro | Ser | His | Glu | Lys | Leu | Val | Asp | Ser |
| | | | | 1765 | | | | | 1770 | | | | | 1775 | |
| Thr | Phe | Thr | Pro | Ser | Ser | Tyr | Ser | Ser | Thr | Gly | Ser | Asn | Ala | Asn | Ile |
| | | | | 1780 | | | | | 1785 | | | | | 1790 | |
| Asn | Asn | Ala | Asn | Asn | Thr | Ala | Leu | Gly | Arg | Leu | Pro | Arg | Pro | Ala | Gly |
| | | | | 1795 | | | | 1800 | | | | | 1805 | | |
| Tyr | Pro | Ser | Thr | Val | Ser | Thr | Val | Glu | Gly | His | Gly | Pro | Pro | Leu | Ser |
| | | | 1810 | | | | 1815 | | | | 1820 | | | | |
| Pro | Ala | Ile | Arg | Val | Gln | Glu | Val | Ala | Trp | Lys | Leu | Ser | Ser | Asn | Arg |
| 1825 | | | | | 1830 | | | | 1835 | | | | | | 1840 |
| Cys | His | Ser | Arg | Glu | Ser | Gln | Ala | Ala | Met | Ala | Arg | Gln | Glu | Glu | Thr |
| | | | | 1845 | | | | | 1850 | | | | | 1855 | |
| Ser | Gln | Asp | Glu | Thr | Tyr | Glu | Val | Lys | Met | Asn | His | Asp | Thr | Glu | Ala |
| | | | | 1860 | | | | | 1865 | | | | | 1870 | |
| Cys | Ser | Glu | Pro | Ser | Leu | Leu | Ser | Thr | Glu | Met | Leu | Ser | Tyr | Gln | Asp |
| | | | | 1875 | | | | | 1880 | | | | | 1885 | |
| Asp | Glu | Asn | Arg | Gln | Leu | Thr | Leu | Pro | Glu | Glu | Asp | Lys | Arg | Asp | Ile |
| | | | | 1890 | | | | | 1895 | | | | | 1900 | |
| Arg | Gln | Ser | Pro | Lys | Arg | Gly | Phe | Leu | Arg | Ser | Ser | Ser | Leu | Gly | Arg |
| 1905 | | | | | 1910 | | | | 1915 | | | | | | 1920 |
| Arg | Ala | Ser | Phe | His | Leu | Glu | Cys | Leu | Lys | Arg | Gln | Lys | Asp | Arg | Gly |
| | | | | 1925 | | | | | 1930 | | | | | 1935 | |
| Gly | Asp | Ile | Ser | Gln | Lys | Thr | Val | Leu | Pro | Leu | His | Leu | Val | His | His |
| | | | | 1940 | | | | | 1945 | | | | | 1950 | |
| Gln | Ala | Leu | Ala | Val | Ala | Gly | Leu | Ser | Pro | Leu | Leu | Gln | Arg | Ser | His |
| | | | | 1955 | | | | | 1960 | | | | | 1965 | |

(2) INFORMATION FOR SEQ ID NO:8:

(i) SEQUENCE CHARACTERISTICS:
        (A) LENGTH: 132 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:8:

```
AGACCACGGC  TTCCTCGAAT  CTTGCGCGAA  GCCGCCGGCC  TCGGAGGAGG  GATTAATCCA      60
GACCCGCCGG  GGGGTGTTTT  CACATTTCTT  CCTCTTCGTG  GCTGCTCCTC  CTATTAAAAC     120
CATTTTTGGT  CC                                                             132
```

(2) INFORMATION FOR SEQ ID NO:9:

(i) SEQUENCE CHARACTERISTICS:
        (A) LENGTH: 89 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:9:

(2) INFORMATION FOR SEQ ID NO:10:

(i) SEQUENCE CHARACTERISTICS:
        (A) LENGTH: 84 base pairs
        (B) TYPE: nucleic acid
        (C) STRANDEDNESS: unknown
        (D) TOPOLOGY: unknown (ii) MOLECULE TYPE: DNA (genomic)

(ix) FEATURE:
        (A) NAME/KEY: CDS
        (B) LOCATION: 1..84

(xi) SEQUENCE DESCRIPTION: SEQ ID NO:10:

```
CAC TAT TTC TGT GAT GCA TGG AAT ACA TTT GAC GCC TTG ATT GTT GTG      48
His Tyr Phe Cys Asp Ala Trp Asn Thr Phe Asp Ala Leu Ile Val Val
 1               5                  10                  15

GGT AGC ATT GTT GAT ATA GCA ATC ACC GAG GTA AAC                      84
Gly Ser Ile Val Asp Ile Ala Ile Thr Glu Val Asn
         20                  25
```

(2) INFORMATION FOR SEQ ID NO:11:

(i) SEQUENCE CHARACTERISTICS:
        (A) LENGTH: 28 amino acids
        (B) TYPE: amino acid
        (D) TOPOLOGY: linear (ii) MOLECULE TYPE: protein (xi) SEQUENCE DESCRIPTION: SEQ ID NO:11:

```
His Tyr Phe Cys Asp Ala Trp Asn Thr Phe Asp Ala Leu Ile Val Val
 1               5                  10                  15

Gly Ser Ile Val Asp Ile Ala Ile Thr Glu Val Asn
         20                  25
```

(2) INFORMATION FOR SEQ ID NO:12:

(i) SEQUENCE CHARACTERISTICS:
        (A) LENGTH: 5467 base pairs
        (B) TYPE: nucleic acid
        (C) STRANDEDNESS: unknown
        (D) TOPOLOGY: unknown (ii) MOLECULE TYPE: DNA (genomic)

(ix) FEATURE:
        (A) NAME/KEY: CDS
        (B) LOCATION: join(144..3164, 3168..3245, 3249..3386, 3390
            ..3392, 3396..3488, 3495..3539, 3543..3581, 3585
            ..3587, 3591..3626, 3630..3689, 3693..3737, 3744
            ..3746, 3750..4823, 4827..4841, 4845..5006, 5010
            ..5096, 5100..5306, 5310..5366, 5370..5465)

(xi) SEQUENCE DESCRIPTION: SEQ ID NO:12:

```
GCGGCGGCGG CTGCGGCGGT GGGGCCGGGC GAGGTCCGTG CGGTCCCGGC GGCTCCGTGG          60

CTGCTCCGCT CTGAGCGCCT GCGCGCCCCG CGCCCTCCCT GCCGGGGCCG CTGGGCCGGG         120

GATGCACGCG GGGCCCGGGA GCC ATG GTC CGC TTC GGG GAC GAG CTG GGC            170
                        Met Val Arg Phe Gly Asp Glu Leu Gly
                         1               5

GGC CGC TAT GGA GGC CCC GGC GGC GGA GAG CGG GCC CGG GGC GGC GGG          218
Gly Arg Tyr Gly Gly Pro Gly Gly Gly Glu Arg Ala Arg Gly Gly Gly
 10              15                  20                  25
```

| | | | | | | | | | | | | | | | | |
|---|---|---|---|---|---|---|---|---|---|---|---|---|---|---|---|---|
| GCC | GGC | GGG | GCG | GGG | GGC | CCG | GGT | CCC | GGG | GGG | CTG | CAG | CCC | GGC | CAG | 266 |
| Ala | Gly | Gly | Ala | Gly | Gly | Pro | Gly | Pro | Gly | Gly | Leu | Gln | Pro | Gly | Gln | |
| | | | | 30 | | | | 35 | | | | | | 40 | | |
| CGG | GTC | CTC | TAC | AAG | CAA | TCG | ATG | GCC | CAG | CGC | GCG | CGG | ACC | ATG | GCG | 314 |
| Arg | Val | Leu | Tyr | Lys | Gln | Ser | Met | Ala | Gln | Arg | Ala | Arg | Thr | Met | Ala | |
| | | | | 45 | | | | 50 | | | | | 55 | | | |
| CTG | TAC | AAC | CCC | ATC | CCG | GTC | AAG | CAG | AAC | TGC | TTC | ACC | GTC | AAC | CGC | 362 |
| Leu | Tyr | Asn | Pro | Ile | Pro | Val | Lys | Gln | Asn | Cys | Phe | Thr | Val | Asn | Arg | |
| | | | 60 | | | | 65 | | | | | 70 | | | | |
| TCG | CTC | TTC | GTC | TTT | AGC | GAG | GAC | AAC | GTC | GTC | CGC | AAA | TAC | GCG | AAG | 410 |
| Ser | Leu | Phe | Val | Phe | Ser | Glu | Asp | Asn | Val | Val | Arg | Lys | Tyr | Ala | Lys | |
| | 75 | | | | | 80 | | | | | 85 | | | | | |
| CGC | ATC | ACC | GAG | TGG | CCT | CCA | TTC | GAG | AAT | ATG | ATC | CTG | GCC | ACC | ATC | 458 |
| Arg | Ile | Thr | Glu | Trp | Pro | Pro | Phe | Glu | Asn | Met | Ile | Leu | Ala | Thr | Ile | |
| 90 | | | | | 95 | | | | | 100 | | | | | 105 | |
| ATC | GCC | AAC | TGC | ATC | GTG | CTG | GCC | CTG | GAG | CAG | CAC | CTC | CCT | GAT | GGG | 506 |
| Ile | Ala | Asn | Cys | Ile | Val | Leu | Ala | Leu | Glu | Gln | His | Leu | Pro | Asp | Gly | |
| | | | | 110 | | | | | 115 | | | | | 120 | | |
| GAC | AAA | ACG | CCC | ATG | TCC | GAG | CGG | CTG | GAC | GAC | ACG | GAG | CCC | TAT | TTC | 554 |
| Asp | Lys | Thr | Pro | Met | Ser | Glu | Arg | Leu | Asp | Asp | Thr | Glu | Pro | Tyr | Phe | |
| | | | 125 | | | | 130 | | | | | 135 | | | | |
| ATC | GGG | ATC | TTT | TGC | TTC | GAG | GCA | GGG | ATC | AAA | ATC | ATC | GCT | CTG | GGC | 602 |
| Ile | Gly | Ile | Phe | Cys | Phe | Glu | Ala | Gly | Ile | Lys | Ile | Ile | Ala | Leu | Gly | |
| | | | 140 | | | | | 145 | | | | | 150 | | | |
| TTT | GTC | TTC | CAC | AAG | GGC | TCT | TAC | CTG | CGG | AAC | GGC | TGG | AAC | GTC | ATG | 650 |
| Phe | Val | Phe | His | Lys | Gly | Ser | Tyr | Leu | Arg | Asn | Gly | Trp | Asn | Val | Met | |
| | 155 | | | | | 160 | | | | | 165 | | | | | |
| GAC | TTC | GTG | GTC | GTC | CTC | ACA | GGG | ATC | CTT | GCC | ACG | GCT | GGA | ACT | GAC | 698 |
| Asp | Phe | Val | Val | Val | Leu | Thr | Gly | Ile | Leu | Ala | Thr | Ala | Gly | Thr | Asp | |
| 170 | | | | | 175 | | | | | 180 | | | | | 185 | |
| TTC | GAC | CTG | CGA | ACA | CTG | AGG | GCT | GTG | CGT | GTG | CTG | AGG | CCC | CTG | AAG | 746 |
| Phe | Asp | Leu | Arg | Thr | Leu | Arg | Ala | Val | Arg | Val | Leu | Arg | Pro | Leu | Lys | |
| | | | | 190 | | | | | 195 | | | | | 200 | | |
| CTG | GTG | TCT | GGG | ATT | CCA | AGT | TTG | CAG | GTG | GTG | CTC | AAG | TCC | ATC | ATG | 794 |
| Leu | Val | Ser | Gly | Ile | Pro | Ser | Leu | Gln | Val | Val | Leu | Lys | Ser | Ile | Met | |
| | | | 205 | | | | | 210 | | | | | 215 | | | |
| AAG | GCC | ATG | GTT | CCA | CTC | CTG | CAG | ATT | GGG | CTG | CTT | CTC | TTC | TTT | GCC | 842 |
| Lys | Ala | Met | Val | Pro | Leu | Leu | Gln | Ile | Gly | Leu | Leu | Leu | Phe | Phe | Ala | |
| | | | 220 | | | | | 225 | | | | | 230 | | | |
| ATC | CTC | ATG | TTT | GCC | ATC | ATT | GGC | CTG | GAG | TTC | TAC | ATG | GGC | AAG | TTC | 890 |
| Ile | Leu | Met | Phe | Ala | Ile | Ile | Gly | Leu | Glu | Phe | Tyr | Met | Gly | Lys | Phe | |
| | | 235 | | | | | 240 | | | | | 245 | | | | |
| CAC | AAG | GCC | TGT | TTC | CCC | AAC | AGC | ACA | GAT | GCG | GAG | CCC | GTG | GGT | GAC | 938 |
| His | Lys | Ala | Cys | Phe | Pro | Asn | Ser | Thr | Asp | Ala | Glu | Pro | Val | Gly | Asp | |
| 250 | | | | | 255 | | | | | 260 | | | | | 265 | |
| TTC | CCC | TGT | GGC | AAG | GAG | GCC | CCA | GCC | CGG | CTG | TGC | GAG | GGC | GAC | ACT | 986 |
| Phe | Pro | Cys | Gly | Lys | Glu | Ala | Pro | Ala | Arg | Leu | Cys | Glu | Gly | Asp | Thr | |
| | | | | 270 | | | | | 275 | | | | | 280 | | |
| GAG | TGC | CGG | GAG | TAC | TGG | CCA | GGA | CCC | AAC | TTT | GGC | ATC | ACC | AAC | TTT | 1034 |
| Glu | Cys | Arg | Glu | Tyr | Trp | Pro | Gly | Pro | Asn | Phe | Gly | Ile | Thr | Asn | Phe | |
| | | | 285 | | | | | 290 | | | | | 295 | | | |
| GAC | AAT | ATC | CTG | TTT | GCC | ATC | TTG | ACG | GTG | TTC | CAG | TGC | ATC | ACC | ATG | 1082 |
| Asp | Asn | Ile | Leu | Phe | Ala | Ile | Leu | Thr | Val | Phe | Gln | Cys | Ile | Thr | Met | |
| | | | 300 | | | | | 305 | | | | | 310 | | | |
| GAG | GGC | TGG | ACT | GAC | ATC | CTC | TAT | AAT | ACA | AAC | GAT | GCG | GCC | GGC | AAC | 1130 |
| Glu | Gly | Trp | Thr | Asp | Ile | Leu | Tyr | Asn | Thr | Asn | Asp | Ala | Ala | Gly | Asn | |
| | | 315 | | | | | 320 | | | | | 325 | | | | |
| ACC | TGG | AAC | TGG | CTC | TAC | TTC | ATC | CCT | CTC | ATC | ATC | ATC | GGC | TCC | TTC | 1178 |
| Thr | Trp | Asn | Trp | Leu | Tyr | Phe | Ile | Pro | Leu | Ile | Ile | Ile | Gly | Ser | Phe | |
| 330 | | | | | 335 | | | | | 340 | | | | | 345 | |

| | | | | | | | | | | | | | | | | |
|---|---|---|---|---|---|---|---|---|---|---|---|---|---|---|---|---|
| TTC | ATG | CTC | AAC | CTG | GTG | CTG | GGC | GTG | CTC | TCG | GGG | GAG | TTT | GCC | AAG | 1226 |
| Phe | Met | Leu | Asn | Leu | Val | Leu | Gly | Val | Leu | Ser | Gly | Glu | Phe | Ala | Lys | |
| | | | 350 | | | | 355 | | | | | 360 | | | | |
| GAG | CGA | GAG | AGG | GTG | GAG | AAC | CGC | CGC | GCC | TTC | CTG | AAC | GTG | CGC | CGG | 1274 |
| Glu | Arg | Glu | Arg | Val | Glu | Asn | Arg | Arg | Ala | Phe | Leu | Asn | Val | Arg | Arg | |
| | | | 365 | | | | 370 | | | | | 375 | | | | |
| CAG | CAG | CAG | ATC | GAG | CGA | GAG | CTC | AAC | GGG | TAC | CTG | GAG | TGG | ATC | TTC | 1322 |
| Gln | Gln | Gln | Ile | Glu | Arg | Glu | Leu | Asn | Gly | Tyr | Leu | Glu | Trp | Ile | Phe | |
| | | 380 | | | | | 385 | | | | | 390 | | | | |
| AAG | GCG | GAG | GAA | GTC | ATG | CTG | GCC | GAG | GAG | GAC | AGG | AAT | GCA | GAG | GAG | 1370 |
| Lys | Ala | Glu | Glu | Val | Met | Leu | Ala | Glu | Glu | Asp | Arg | Asn | Ala | Glu | Glu | |
| | 395 | | | | | 400 | | | | | 405 | | | | | |
| AAG | TCC | CCT | TTG | GAC | GTG | CTG | AAG | AGA | GCG | GCC | ACC | AAG | AAG | AGC | AGA | 1418 |
| Lys | Ser | Pro | Leu | Asp | Val | Leu | Lys | Arg | Ala | Ala | Thr | Lys | Lys | Ser | Arg | |
| 410 | | | | | 415 | | | | | 420 | | | | | 425 | |
| AAT | GAC | CTG | ATC | CAC | GCA | GAG | GAG | GGA | GAG | GAC | CGG | TTT | GCA | GAT | CTC | 1466 |
| Asn | Asp | Leu | Ile | His | Ala | Glu | Glu | Gly | Glu | Asp | Arg | Phe | Ala | Asp | Leu | |
| | | | | 430 | | | | | 435 | | | | | 440 | | |
| TGT | GCT | GTT | GGA | TCC | CCC | TTC | GCC | CGC | GCC | AGC | CTC | AAG | AGC | GGG | AAG | 1514 |
| Cys | Ala | Val | Gly | Ser | Pro | Phe | Ala | Arg | Ala | Ser | Leu | Lys | Ser | Gly | Lys | |
| | | | 445 | | | | | 450 | | | | | 455 | | | |
| ACA | GAG | AGC | TCG | TCA | TAC | TTC | CGG | AGG | AAG | GAG | AAG | ATG | TTC | CGG | TTT | 1562 |
| Thr | Glu | Ser | Ser | Ser | Tyr | Phe | Arg | Arg | Lys | Glu | Lys | Met | Phe | Arg | Phe | |
| | | 460 | | | | | 465 | | | | | 470 | | | | |
| TTT | ATC | CGG | CGC | ATG | GTG | AAG | GCT | CAG | AGC | TTC | TAC | TGG | GTG | GTG | CTG | 1610 |
| Phe | Ile | Arg | Arg | Met | Val | Lys | Ala | Gln | Ser | Phe | Tyr | Trp | Val | Val | Leu | |
| | 475 | | | | | 480 | | | | | 485 | | | | | |
| TGC | GTG | GTG | GCC | CTG | AAC | ACA | CTG | TGT | GTG | GCC | ATG | GTG | CAT | TAC | AAC | 1658 |
| Cys | Val | Val | Ala | Leu | Asn | Thr | Leu | Cys | Val | Ala | Met | Val | His | Tyr | Asn | |
| 490 | | | | | 495 | | | | | 500 | | | | | 505 | |
| CAG | CCG | CGG | CGG | CTT | ACC | ACG | ACC | CTG | TAT | TTT | GCA | GAG | TTT | GTT | TTC | 1706 |
| Gln | Pro | Arg | Arg | Leu | Thr | Thr | Thr | Leu | Tyr | Phe | Ala | Glu | Phe | Val | Phe | |
| | | | | 510 | | | | | 515 | | | | | 520 | | |
| CTG | GGT | CTC | TTC | CTC | ACA | GAG | ATG | TCC | CTG | AAG | ATG | TAT | GGC | CTG | GGG | 1754 |
| Leu | Gly | Leu | Phe | Leu | Thr | Glu | Met | Ser | Leu | Lys | Met | Tyr | Gly | Leu | Gly | |
| | | | 525 | | | | | 530 | | | | | 535 | | | |
| CCC | AGA | AGC | TAC | TTC | CGG | TCC | TCC | TTC | AAC | TGC | TTC | GAC | TTT | GGG | GTC | 1802 |
| Pro | Arg | Ser | Tyr | Phe | Arg | Ser | Ser | Phe | Asn | Cys | Phe | Asp | Phe | Gly | Val | |
| | | 540 | | | | | 545 | | | | | 550 | | | | |
| ATC | GTG | GGG | AGC | GTC | TTT | GAA | GTG | GTC | TGG | GCG | GCC | ATC | AAG | CCG | GGA | 1850 |
| Ile | Val | Gly | Ser | Val | Phe | Glu | Val | Val | Trp | Ala | Ala | Ile | Lys | Pro | Gly | |
| | 555 | | | | | 560 | | | | | 565 | | | | | |
| AGC | TCC | TTT | GGG | ATC | AGT | GTG | CTG | CGG | GCC | CTC | CGC | CTG | CTG | AGG | ATC | 1898 |
| Ser | Ser | Phe | Gly | Ile | Ser | Val | Leu | Arg | Ala | Leu | Arg | Leu | Leu | Arg | Ile | |
| 570 | | | | | 575 | | | | | 580 | | | | | 585 | |
| TTC | AAA | GTC | ACG | AAG | TAC | TGG | AGC | TCC | CTG | CGG | AAC | CTG | GTG | GTG | TCC | 1946 |
| Phe | Lys | Val | Thr | Lys | Tyr | Trp | Ser | Ser | Leu | Arg | Asn | Leu | Val | Val | Ser | |
| | | | | 590 | | | | | 595 | | | | | 600 | | |
| CTG | CTG | AAC | TCC | ATG | AAG | TCC | ATC | ATC | AGC | CTG | CTC | TTC | TTG | CTC | TTC | 1994 |
| Leu | Leu | Asn | Ser | Met | Lys | Ser | Ile | Ile | Ser | Leu | Leu | Phe | Leu | Leu | Phe | |
| | | | 605 | | | | | 610 | | | | | 615 | | | |
| CTG | TTC | ATT | GTG | GTC | TTC | GCC | CTG | CTG | GGG | ATG | CAG | CTG | TTT | GGG | GGA | 2042 |
| Leu | Phe | Ile | Val | Val | Phe | Ala | Leu | Leu | Gly | Met | Gln | Leu | Phe | Gly | Gly | |
| | | 620 | | | | | 625 | | | | | 630 | | | | |
| CAG | TTC | AAC | TTC | CAG | GAT | GAG | ACT | CCC | ACA | ACC | AAC | TTC | GAC | ACC | TTC | 2090 |
| Gln | Phe | Asn | Phe | Gln | Asp | Glu | Thr | Pro | Thr | Thr | Asn | Phe | Asp | Thr | Phe | |
| | 635 | | | | | 640 | | | | | 645 | | | | | |
| CCT | GCC | GCC | ATC | CTC | ACT | GTC | TTC | CAG | ATC | CTG | ACG | GGA | GAG | GAC | TGG | 2138 |
| Pro | Ala | Ala | Ile | Leu | Thr | Val | Phe | Gln | Ile | Leu | Thr | Gly | Glu | Asp | Trp | |
| 650 | | | | | 655 | | | | | 660 | | | | | 665 | |

```
AAT  GCA  GTG  ATG  TAT  CAC  GGG  ATC  GAA  TCG  CAA  GGC  GGC  GTC  AGC  AAA       2186
Asn  Ala  Val  Met  Tyr  His  Gly  Ile  Glu  Ser  Gln  Gly  Gly  Val  Ser  Lys
                    670                 675                      680

GGC  ATG  TTC  TCG  TCC  TTT  TAC  TTC  ATT  GTC  CTG  ACA  CTG  TTC  GGA  AAC       2234
Gly  Met  Phe  Ser  Ser  Phe  Tyr  Phe  Ile  Val  Leu  Thr  Leu  Phe  Gly  Asn
               685                      690                      695

TAC  ACT  CTG  CTG  AAT  GTC  TTT  CTG  GCC  ATC  GCT  GTG  GAC  AAC  CTG  GCC       2282
Tyr  Thr  Leu  Leu  Asn  Val  Phe  Leu  Ala  Ile  Ala  Val  Asp  Asn  Leu  Ala
          700                      705                      710

AAC  GCC  CAA  GAG  CTG  ACC  AAG  GAT  GAA  GAG  GAG  ATG  GAA  GAA  GCA  GCC       2330
Asn  Ala  Gln  Glu  Leu  Thr  Lys  Asp  Glu  Glu  Glu  Met  Glu  Glu  Ala  Ala
     715                      720                      725

AAT  CAG  AAG  CTT  GCT  CTG  CAA  AAG  GCC  AAA  GAA  GTG  GCT  GAA  GTC  AGC       2378
Asn  Gln  Lys  Leu  Ala  Leu  Gln  Lys  Ala  Lys  Glu  Val  Ala  Glu  Val  Ser
730                      735                      740                      745

CCC  ATG  TCT  GCC  GCG  AAC  ATC  TCC  ATC  GCC  GCC  AGC  GAG  CAG  AAC  TCG       2426
Pro  Met  Ser  Ala  Ala  Asn  Ile  Ser  Ile  Ala  Ala  Ser  Glu  Gln  Asn  Ser
                    750                      755                      760

GCC  AAG  GCG  CGC  TCG  GTG  TGG  GAG  CAG  CGG  GCC  AGC  CAG  CTA  CGG  CTG       2474
Ala  Lys  Ala  Arg  Ser  Val  Trp  Glu  Gln  Arg  Ala  Ser  Gln  Leu  Arg  Leu
               765                      770                      775

CAG  AAC  CTG  CGG  GCC  AGC  TGC  GAG  GCG  CTG  TAC  AGC  GAG  ATG  GAC  CCC       2522
Gln  Asn  Leu  Arg  Ala  Ser  Cys  Glu  Ala  Leu  Tyr  Ser  Glu  Met  Asp  Pro
          780                      785                      790

GAG  GAG  CGG  CTG  CGC  TTC  GCC  ACT  ACG  CGC  CAC  CTG  CGG  CCC  GAC  ATG       2570
Glu  Glu  Arg  Leu  Arg  Phe  Ala  Thr  Thr  Arg  His  Leu  Arg  Pro  Asp  Met
     795                      800                      805

AAG  ACG  CAC  CTG  GAC  CGG  CCG  CTG  GTG  GTG  GAG  CTG  GGC  CGC  GAC  GGC       2618
Lys  Thr  His  Leu  Asp  Arg  Pro  Leu  Val  Val  Glu  Leu  Gly  Arg  Asp  Gly
810                      815                      820                      825

GCG  CGG  GGG  CCC  GTG  GGA  GGC  AAA  GCC  CGA  CCT  GAG  GCT  GCG  GAG  GCC       2666
Ala  Arg  Gly  Pro  Val  Gly  Gly  Lys  Ala  Arg  Pro  Glu  Ala  Ala  Glu  Ala
                    830                      835                      840

CCC  GAG  GGC  GTC  GAC  CCT  CCG  CGC  AGG  CAC  CAC  CGG  CAC  CGC  GAC  AAG       2714
Pro  Glu  Gly  Val  Asp  Pro  Pro  Arg  Arg  His  His  Arg  His  Arg  Asp  Lys
               845                      850                      855

GAC  AAG  ACC  CCC  GCG  GCG  GGG  GAC  CAG  GAC  CGA  GCA  GAG  GCC  CCG  AAG       2762
Asp  Lys  Thr  Pro  Ala  Ala  Gly  Asp  Gln  Asp  Arg  Ala  Glu  Ala  Pro  Lys
          860                      865                      870

GCG  GAG  AGC  GGG  GAG  CCC  GGT  GCC  CGG  GAG  GAG  CGG  CCG  CGC  GCC  GAC       2810
Ala  Glu  Ser  Gly  Glu  Pro  Gly  Ala  Arg  Glu  Glu  Arg  Pro  Arg  Ala  Asp
     875                      880                      885

CGC  AGC  CAC  AGC  AAG  GAG  GCC  GCG  GGG  CCC  CCG  GAG  GCG  CGG  ACG  AGC       2858
Arg  Ser  His  Ser  Lys  Glu  Ala  Ala  Gly  Pro  Pro  Glu  Ala  Arg  Thr  Ser
890                      895                      900                      905

GCG  GCC  GAG  GCC  CAG  GCC  CCG  AGG  GCG  GCC  GGC  GGC  ACC  ACC  GGC  GCG       2906
Ala  Ala  Glu  Ala  Gln  Ala  Pro  Arg  Ala  Ala  Gly  Gly  Thr  Thr  Gly  Ala
                    910                      915                      920

GCT  CCC  CGG  AGG  AGG  CGG  CCG  AGC  GGG  AGC  CCC  GAC  GCC  ACC  GCG  CGC       2954
Ala  Pro  Arg  Arg  Arg  Arg  Pro  Ser  Gly  Ser  Pro  Asp  Ala  Thr  Ala  Arg
               925                      930                      935

ACC  GGC  ACC  AGG  ATC  CGA  GCA  AGG  AGT  GCG  CCG  GCG  CCA  AGG  GCG  AGC       3002
Thr  Gly  Thr  Arg  Ile  Arg  Ala  Arg  Ser  Ala  Pro  Ala  Pro  Arg  Ala  Ser
          940                      945                      950

GGC  GCG  CGC  GGC  ACC  GCG  GCG  GCC  CCC  GAG  CGG  GGC  CCC  GGG  AGG  CGG       3050
Gly  Ala  Arg  Gly  Thr  Ala  Ala  Ala  Pro  Glu  Arg  Gly  Pro  Gly  Arg  Arg
     955                      960                      965

AGA  GCG  GGG  AGG  AGC  CGG  CGC  GGC  GGC  ACC  GGG  CCC  GGC  ACA  AGG  CGC       3098
Arg  Ala  Gly  Arg  Ser  Arg  Arg  Gly  Gly  Thr  Gly  Pro  Gly  Thr  Arg  Arg
970                      975                      980                      985
```

| | | | | | | | | | | | | | | | | |
|---|---|---|---|---|---|---|---|---|---|---|---|---|---|---|---|---|
| AGC | CTG | CTC | ACG | AGG | CTG | TGG | AGA | AGG | AGA | CCA | CGG | AGA | AGG | AGG | CCA | 3146 |
| Ser | Leu | Leu | Thr | Arg | Leu | Trp | Arg | Arg | Arg | Pro | Arg | Arg | Arg | Arg | Pro | |
| | | | | 990 | | | | 995 | | | | | | | 1000 | |

| | | | | | | | | | | | | | | | | |
|---|---|---|---|---|---|---|---|---|---|---|---|---|---|---|---|---|
| CGG | AGA | AGG | AGG | CTG | AGA | TAG | TGG | AAG | CCG | ACA | AGG | AAA | AGG | AGC | TCC | 3194 |
| Arg | Arg | Arg | Arg | Leu | Arg | | Trp | Lys | Pro | Thr | Arg | Lys | Arg | Ser | Ser | |
| | | | 1005 | | | | | 1010 | | | | | 1015 | | | |

| | | | | | | | | | | | | | | | | |
|---|---|---|---|---|---|---|---|---|---|---|---|---|---|---|---|---|
| GGA | ACC | ACC | AGC | CCC | GGG | AGC | CAC | ACT | GTG | ACC | TGG | AGA | CCA | GTG | GGA | 3242 |
| Gly | Thr | Thr | Ser | Pro | Gly | Ser | His | Thr | Val | Thr | Trp | Arg | Pro | Val | Gly | |
| | | | | 1020 | | | | 1025 | | | | | 1030 | | | |

| | | | | | | | | | | | | | | | | |
|---|---|---|---|---|---|---|---|---|---|---|---|---|---|---|---|---|
| CTG | TGA | CTG | TGG | GTC | CAT | GCA | CAC | ACT | GCC | CAG | CAA | CCT | GTC | TCC | AGA | 3290 |
| Leu | | Leu | Trp | Val | His | Ala | His | Thr | Ala | Gln | Gln | Pro | Val | Ser | Arg | |
| | | | | 1035 | | | | 1040 | | | | | 1045 | | | |

| | | | | | | | | | | | | | | | | |
|---|---|---|---|---|---|---|---|---|---|---|---|---|---|---|---|---|
| AGG | TGG | AGG | AAC | AGC | CAG | AGG | ATG | CAG | ACA | ATC | AGC | GGA | ACG | TCA | CTC | 3338 |
| Arg | Trp | Arg | Asn | Ser | Gln | Arg | Met | Gln | Thr | Ile | Ser | Gly | Thr | Ser | Leu | |
| 1050 | | | | | 1055 | | | | | 1060 | | | | | 1065 | |

| | | | | | | | | | | | | | | | | |
|---|---|---|---|---|---|---|---|---|---|---|---|---|---|---|---|---|
| GCA | TGG | GCA | GTC | AGC | CCC | CAG | ACC | CGA | ACA | CTA | TTG | TAC | ATA | TCC | CAG | 3386 |
| Ala | Trp | Ala | Val | Ser | Pro | Gln | Thr | Arg | Thr | Leu | Leu | Tyr | Ile | Ser | Gln | |
| | | | | 1070 | | | | | 1075 | | | | | | 1080 | |

| | | | | | | | | | | | | | | | | |
|---|---|---|---|---|---|---|---|---|---|---|---|---|---|---|---|---|
| TGA | TGC | TGA | CGG | GCC | CTC | TTG | GGG | AAG | CCA | CGG | TCG | TTC | CCA | GTG | GTA | 3434 |
| | Cys | | Arg | Ala | Leu | Leu | Gly | Lys | Pro | Arg | Ser | Phe | Pro | Val | Val | |
| | | | 1085 | | | | | 1090 | | | | | 1095 | | | |

| | | | | | | | | | | | | | | | | |
|---|---|---|---|---|---|---|---|---|---|---|---|---|---|---|---|---|
| ACG | TGG | ACC | TGG | AAA | GCC | AAG | CAG | AGG | GGA | AGA | AGG | AGG | TGG | AAG | CGG | 3482 |
| Thr | Trp | Thr | Trp | Lys | Ala | Lys | Gln | Arg | Gly | Arg | Arg | Arg | Trp | Lys | Arg | |
| | | | | 1100 | | | | | 1105 | | | | | 1110 | | |

| | | | | | | | | | | | | | | | | |
|---|---|---|---|---|---|---|---|---|---|---|---|---|---|---|---|---|
| ATG | ACG | TGA | TGA | GGA | GCG | GCC | CCC | GGC | CTA | TCG | TCC | CAT | ACA | GCT | CCA | 3530 |
| Met | Thr | | | Gly | Ala | Ala | Pro | Gly | Leu | Ser | Ser | His | Thr | Ala | Pro | |
| | 1115 | | | | | 1120 | | | | | 1125 | | | | | |

| | | | | | | | | | | | | | | | | |
|---|---|---|---|---|---|---|---|---|---|---|---|---|---|---|---|---|
| TGT | TCT | GTT | TAA | GCC | CCA | CCA | ACC | TGC | TCC | GCC | GCT | TCT | GCC | ACT | ACA | 3578 |
| Cys | Ser | Val | | Ala | Pro | Pro | Thr | Cys | Ser | Ala | Ala | Ser | Ala | Thr | Thr | |
| 1130 | | | | | 1135 | | | | | 1140 | | | | | 1145 | |

| | | | | | | | | | | | | | | | | |
|---|---|---|---|---|---|---|---|---|---|---|---|---|---|---|---|---|
| TCG | TGA | CCA | TGA | GGT | ACT | TCG | AGG | TGG | TCA | TTC | TCG | TGG | TCA | TCG | CCT | 3626 |
| Ser | | Pro | | Gly | Thr | Ser | Arg | Trp | Ser | Phe | Ser | Trp | Ser | Ser | Pro | |
| | | | | | 1150 | | | | | 1155 | | | | | 1160 | |

| | | | | | | | | | | | | | | | | |
|---|---|---|---|---|---|---|---|---|---|---|---|---|---|---|---|---|
| TGA | GCA | GCA | TCG | CCC | TGG | CTG | CTG | AGG | ACC | CAG | TGC | GCA | CAG | ACT | CGC | 3674 |
| | Ala | Ala | Ser | Pro | Trp | Leu | Leu | Arg | Thr | Gln | Cys | Ala | Gln | Thr | Arg | |
| | | | | 1165 | | | | | 1170 | | | | | 1175 | | |

| | | | | | | | | | | | | | | | | |
|---|---|---|---|---|---|---|---|---|---|---|---|---|---|---|---|---|
| CCA | GGA | ACA | ACG | CTC | TGA | AAT | ACC | TGG | ATT | ACA | TTT | TCA | CTG | GTG | TCT | 3722 |
| Pro | Gly | Thr | Thr | Leu | | Asn | Thr | Trp | Ile | Thr | Phe | Ser | Leu | Val | Ser | |
| | | | 1180 | | | | | 1185 | | | | | 1190 | | | |

| | | | | | | | | | | | | | | | | |
|---|---|---|---|---|---|---|---|---|---|---|---|---|---|---|---|---|
| TTA | CCT | TTG | AGA | TGG | TGA | TAA | AGA | TGA | TCG | ACT | TGG | GAC | TGC | TGC | TTC | 3770 |
| Leu | Pro | Leu | Arg | Trp | | | Arg | | Ser | Thr | Trp | Asp | Cys | Cys | Phe | |
| | | 1195 | | | | | 1200 | | | | 1205 | | | | | |

| | | | | | | | | | | | | | | | | |
|---|---|---|---|---|---|---|---|---|---|---|---|---|---|---|---|---|
| ACC | CTG | GAG | CCT | ATT | TCC | GGG | ACT | TGT | GGA | ACA | TTC | TGG | ACT | TCA | TTG | 3818 |
| Thr | Leu | Glu | Pro | Ile | Ser | Gly | Thr | Cys | Gly | Thr | Phe | Trp | Thr | Ser | Leu | |
| 1210 | | | | | 1215 | | | | | 1220 | | | | | 1225 | |

| | | | | | | | | | | | | | | | | |
|---|---|---|---|---|---|---|---|---|---|---|---|---|---|---|---|---|
| TGG | TCA | GTG | GCG | CCC | TGG | TGG | CGT | TTG | CTT | TCT | CGA | TCC | AAA | GGG | AAA | 3866 |
| Trp | Ser | Val | Ala | Pro | Trp | Trp | Arg | Leu | Leu | Ser | Arg | Ser | Lys | Gly | Lys | |
| | | | | 1230 | | | | | 1235 | | | | | 1240 | | |

| | | | | | | | | | | | | | | | | |
|---|---|---|---|---|---|---|---|---|---|---|---|---|---|---|---|---|
| GAC | ATC | AAT | ACC | ATC | AAG | TCT | CTG | AGA | GTC | CTT | CGT | GTC | CTG | CGG | CCC | 3914 |
| Asp | Ile | Asn | Thr | Ile | Lys | Ser | Leu | Arg | Val | Leu | Arg | Val | Leu | Arg | Pro | |
| | | | 1245 | | | | | 1250 | | | | | 1255 | | | |

| | | | | | | | | | | | | | | | | |
|---|---|---|---|---|---|---|---|---|---|---|---|---|---|---|---|---|
| CTC | AAG | ACC | ATC | AAA | CGG | CTG | CCC | AAG | CTC | AAG | GCT | GTG | TTT | GAC | TGT | 3962 |
| Leu | Lys | Thr | Ile | Lys | Arg | Leu | Pro | Lys | Leu | Lys | Ala | Val | Phe | Asp | Cys | |
| | | | 1260 | | | | | 1265 | | | | | 1270 | | | |

| | | | | | | | | | | | | | | | | |
|---|---|---|---|---|---|---|---|---|---|---|---|---|---|---|---|---|
| GTG | GTG | AAC | TCC | CTG | AAG | AAT | GTC | CTC | AAC | ATC | TTG | ATT | GTC | TAC | ATG | 4010 |
| Val | Val | Asn | Ser | Leu | Lys | Asn | Val | Leu | Asn | Ile | Leu | Ile | Val | Tyr | Met | |
| | | | 1275 | | | | | 1280 | | | | | 1285 | | | |

| | | | | | | | | | | | | | | | | |
|---|---|---|---|---|---|---|---|---|---|---|---|---|---|---|---|---|
| CTC | TTC | ATG | TTC | ATA | TTT | GCC | GTC | ATT | GCG | GTG | CAG | CTC | TTC | AAA | GGG | 4058 |
| Leu | Phe | Met | Phe | Ile | Phe | Ala | Val | Ile | Ala | Val | Gln | Leu | Phe | Lys | Gly | |
| 1290 | | | | | 1295 | | | | | 1300 | | | | | 1305 | |

| | | | | | | | | | | | | | | | | |
|---|---|---|---|---|---|---|---|---|---|---|---|---|---|---|---|---|
| AAG | TTT | TTC | TAC | TGC | ACA | GAT | GAA | TCC | AAG | GAG | CTG | GAG | AGG | GAC | TGC | 4106 |
| Lys | Phe | Phe | Tyr | Cys | Thr | Asp | Glu | Ser | Lys | Glu | Leu | Glu | Arg | Asp | Cys | |
| | | | | 1310 | | | | 1315 | | | | | 1320 | | | |
| AGG | GGT | CAG | TAT | TTG | GAT | TAT | GAG | AAG | GAG | GAA | GTG | GAA | GCT | CAG | CCC | 4154 |
| Arg | Gly | Gln | Tyr | Leu | Asp | Tyr | Glu | Lys | Glu | Glu | Val | Glu | Ala | Gln | Pro | |
| | | | 1325 | | | | | 1330 | | | | | 1335 | | | |
| AGG | CAG | TGG | AAG | AAA | TAC | GAC | TTT | CAC | TAC | GAC | AAT | GTG | CTC | TGG | GCT | 4202 |
| Arg | Gln | Trp | Lys | Lys | Tyr | Asp | Phe | His | Tyr | Asp | Asn | Val | Leu | Trp | Ala | |
| | | | 1340 | | | | | 1345 | | | | | 1350 | | | |
| CTG | CTG | ACG | CTG | TTC | ACA | GTG | TCC | ACG | GGA | GAA | GGC | TGG | CCC | ATG | GTG | 4250 |
| Leu | Leu | Thr | Leu | Phe | Thr | Val | Ser | Thr | Gly | Glu | Gly | Trp | Pro | Met | Val | |
| | | | 1355 | | | | | 1360 | | | | | 1365 | | | |
| CTG | AAA | CAC | TCC | GTG | GAT | GCC | ACC | TAT | GAG | GAG | CAG | GGT | CCA | AGC | CCT | 4298 |
| Leu | Lys | His | Ser | Val | Asp | Ala | Thr | Tyr | Glu | Glu | Gln | Gly | Pro | Ser | Pro | |
| 1370 | | | | 1375 | | | | | 1380 | | | | | 1385 | | |
| GGG | TAC | CGC | ATG | GAG | CTG | TCC | ATC | TTC | TAC | GTG | GTC | TAC | TTT | GTG | GTC | 4346 |
| Gly | Tyr | Arg | Met | Glu | Leu | Ser | Ile | Phe | Tyr | Val | Val | Tyr | Phe | Val | Val | |
| | | | | 1390 | | | | | 1395 | | | | | 1400 | | |
| TTT | CCC | TTC | TTC | TTC | GTC | AAC | ATC | TTT | GTG | GCT | TTG | ATC | ATC | ATC | ACC | 4394 |
| Phe | Pro | Phe | Phe | Phe | Val | Asn | Ile | Phe | Val | Ala | Leu | Ile | Ile | Ile | Thr | |
| | | | | 1405 | | | | | 1410 | | | | | 1415 | | |
| TTC | CAG | GAG | CAG | GGG | GAC | AAG | GTG | ATG | TCT | GAA | TGC | AGC | CTG | GAG | AAG | 4442 |
| Phe | Gln | Glu | Gln | Gly | Asp | Lys | Val | Met | Ser | Glu | Cys | Ser | Leu | Glu | Lys | |
| | | | | 1420 | | | | | 1425 | | | | | 1430 | | |
| AAC | GAG | AGG | GCT | TGC | ATT | GAC | TTC | GCC | ATC | AGC | GCC | AAA | CCC | CTG | ACA | 4490 |
| Asn | Glu | Arg | Ala | Cys | Ile | Asp | Phe | Ala | Ile | Ser | Ala | Lys | Pro | Leu | Thr | |
| | | | 1435 | | | | | 1440 | | | | | 1445 | | | |
| CGG | TAC | ATG | CCC | CAA | AAC | CGG | CAG | TCG | TTC | CAG | TAT | AAG | ACG | TGG | ACA | 4538 |
| Arg | Tyr | Met | Pro | Gln | Asn | Arg | Gln | Ser | Phe | Gln | Tyr | Lys | Thr | Trp | Thr | |
| 1450 | | | | | 1455 | | | | | 1460 | | | | | 1465 | |
| TTT | GTG | GTC | TCC | CCG | CCC | TTT | GAA | TAC | TTC | ATC | ATG | GCC | ATG | ATA | GCC | 4586 |
| Phe | Val | Val | Ser | Pro | Pro | Phe | Glu | Tyr | Phe | Ile | Met | Ala | Met | Ile | Ala | |
| | | | | 1470 | | | | | 1475 | | | | | 1480 | | |
| CTC | AAC | ACT | GTG | GTG | CTG | ATG | ATG | AAG | TTC | TAT | GAT | GCA | CCC | TAT | GAG | 4634 |
| Leu | Asn | Thr | Val | Val | Leu | Met | Met | Lys | Phe | Tyr | Asp | Ala | Pro | Tyr | Glu | |
| | | | | 1485 | | | | | 1490 | | | | | 1495 | | |
| TAC | GAG | CTG | ATG | CTG | AAA | TGC | CTG | AAC | ATC | GTG | TTC | ACA | TCC | ATG | TTC | 4682 |
| Tyr | Glu | Leu | Met | Leu | Lys | Cys | Leu | Asn | Ile | Val | Phe | Thr | Ser | Met | Phe | |
| | | | | 1500 | | | | | 1505 | | | | | 1510 | | |
| TCC | ATG | GAA | TGC | GTG | CTG | AAG | ATC | ATC | GCC | TTT | GGG | GTG | CTG | AAC | TAT | 4730 |
| Ser | Met | Glu | Cys | Val | Leu | Lys | Ile | Ile | Ala | Phe | Gly | Val | Leu | Asn | Tyr | |
| | | | | 1515 | | | | | 1520 | | | | | 1525 | | |
| TTC | AGA | GAT | GCC | TGG | AAT | TTT | GTC | TTT | GAC | TTT | GTC | ACT | GTG | TTG | GGA | 4778 |
| Phe | Arg | Asp | Ala | Trp | Asn | Phe | Val | Phe | Asp | Phe | Val | Thr | Val | Leu | Gly | |
| | | | 1530 | | | | | 1535 | | | | | 1540 | | | 1545 |
| AGT | ATT | ACT | GAT | ATT | TTA | GTA | ACA | GAG | ATT | GCG | ATT | TGC | CCA | AGA | TGA | 4826 |
| Ser | Ile | Thr | Asp | Ile | Leu | Val | Thr | Glu | Ile | Ala | Ile | Cys | Pro | Arg | | |
| | | | | 1550 | | | | | 1555 | | | | | 1560 | | |
| AGG | TTT | CAG | CAG | TTT | TAA | TGC | TAC | AGC | ACA | CCA | GGA | GTT | ACC | GTC | ACC | 4874 |
| Arg | Phe | Gln | Gln | Phe | | Cys | Tyr | Ser | Thr | Pro | Gly | Val | Thr | Val | Thr | |
| | | | | 1565 | | | | | 1570 | | | | | 1575 | | |
| TCA | CTT | ACC | ACC | CAC | CAA | CAG | AGG | AGA | ATC | TGT | CCA | GTG | AGC | CAC | TCC | 4922 |
| Ser | Leu | Thr | Thr | His | Gln | Gln | Arg | Arg | Ile | Cys | Pro | Val | Ser | His | Ser | |
| | | | | 1580 | | | | | 1585 | | | | | 1590 | | |
| CCA | AGG | TCT | CCA | TCC | TTA | GAG | TCG | GCT | TCC | AAG | GAA | CCA | CCC | CTG | GTG | 4970 |
| Pro | Arg | Ser | Pro | Ser | Leu | Glu | Ser | Ala | Ser | Lys | Glu | Pro | Pro | Leu | Val | |
| | | | 1595 | | | | | 1600 | | | | | 1605 | | | |
| TCA | CCT | GTC | TTT | GGA | TCA | GAA | CGT | GTG | ATC | CAA | ATG | TGA | TTT | ACT | GGA | 5018 |
| Ser | Pro | Val | Phe | Gly | Ser | Glu | Arg | Val | Ile | Gln | Met | | Phe | Thr | Gly | |
| 1610 | | | | | 1615 | | | | | 1620 | | | | | 1625 | |

| | | | | | | | | | | | | | | | |
|---|---|---|---|---|---|---|---|---|---|---|---|---|---|---|---|
| ATC | ACA | GTT | TCC | AGG | AAT | AGT | TGG | AAA | CGA | ACA | ATT | TCA | TCA | ACC | TCA | 5066
| Ile | Thr | Val | Ser | Arg | Asn | Ser | Trp | Lys | Arg | Thr | Ile | Ser | Ser | Thr | Ser |
| | | | | 1630 | | | | 1635 | | | | | 1640 | | |

| GCT | TCC | TCC | GCC | TCT | TTC | GAG | CTG | CGC | GGC | TGA | TCA | AGC | TGC | TCC | GCC | 5114
| Ala | Ser | Ser | Ala | Ser | Phe | Glu | Leu | Arg | Gly | | Ser | Ser | Cys | Ser | Ala |
| | | | 1645 | | | | 1650 | | | | | 1655 | | | |

| AGG | GCT | ACA | CCA | TCC | GCA | TCC | TGC | TGT | GGA | CCT | TTG | TCC | AGT | CCT | TCA | 5162
| Arg | Ala | Thr | Pro | Ser | Ala | Ser | Cys | Cys | Gly | Pro | Leu | Ser | Ser | Pro | Ser |
| | | 1660 | | | | | 1665 | | | | | 1670 | | | |

| AGG | CCC | TGC | CCT | ACG | TGT | GTC | TGC | TCA | TTG | CCA | TGC | TGT | TCT | TCA | TCT | 5210
| Arg | Pro | Cys | Pro | Thr | Cys | Val | Cys | Ser | Leu | Pro | Cys | Cys | Ser | Ser | Ser |
| | 1675 | | | | | 1680 | | | | | 1685 | | | | |

| ACG | CCA | TCA | TCG | GCA | TGC | AGG | TGT | TTG | GGA | ATA | TTG | CCC | TGG | ATG | ATG | 5258
| Thr | Pro | Ser | Ser | Ala | Cys | Arg | Cys | Leu | Gly | Ile | Leu | Pro | Trp | Met | Met |
| 1690 | | | | | 1695 | | | | | 1700 | | | | | 1705 |

| ACA | CCA | GCA | TCA | ACC | GCC | ACA | ACA | ACT | TCC | GGA | CGT | TTT | TGC | AAG | CCC | 5306
| Thr | Pro | Ala | Ser | Thr | Ala | Thr | Thr | Thr | Ser | Gly | Arg | Phe | Cys | Lys | Pro |
| | | | | 1710 | | | | | 1715 | | | | | 1720 | |

| TGA | TGC | TGC | TGT | TCA | GGA | GCG | CCA | CGG | GGG | AGG | CCT | GGC | ACG | AGA | TCA | 5354
| | Cys | Cys | Cys | Ser | Gly | Ala | Pro | Arg | Gly | Arg | Pro | Gly | Thr | Arg | Ser |
| | | | 1725 | | | | | 1730 | | | | | 1735 | | |

| TGC | TGT | CCT | GCC | TGA | GCA | ACC | AGG | CCT | GTG | ATG | AGC | AGG | CCA | ATG | CCA | 5402
| Cys | Cys | Pro | Ala | | Ala | Thr | Arg | Pro | Val | Met | Ser | Arg | Pro | Met | Pro |
| | | 1740 | | | | | 1745 | | | | | 1750 | | | |

| CCG | AGT | GTG | GAA | GTG | ACT | TTG | CCT | ACT | TCT | ACT | TCG | TCT | CCT | TCA | TCG | 5450
| Pro | Ser | Val | Glu | Val | Thr | Leu | Pro | Thr | Ser | Thr | Ser | Ser | Pro | Ser | Ser |
| | 1755 | | | | | 1760 | | | | | 1765 | | | | |

| CTC | GAG | TGT | ACG | TAC | CG | | | | | | | | | | | 5467
| Leu | Glu | Cys | Thr | Tyr | | | | | | | | | | | |
| 1770 | | | | | | | | | | | | | | | |

( 2 ) INFORMATION FOR SEQ ID NO:13:

( i ) SEQUENCE CHARACTERISTICS:
        ( A ) LENGTH: 1754 amino acids
        ( B ) TYPE: amino acid
        ( D ) TOPOLOGY: linear ( i i ) MOLECULE TYPE: protein ( x i ) SEQUENCE DESCRIPTION: SEQ ID NO:13:

| Met | Val | Arg | Phe | Gly | Asp | Glu | Leu | Gly | Gly | Arg | Tyr | Gly | Gly | Pro | Gly |
|---|---|---|---|---|---|---|---|---|---|---|---|---|---|---|---|
| 1 | | | | 5 | | | | | 10 | | | | | 15 | |

| Gly | Gly | Glu | Arg | Ala | Arg | Gly | Gly | Gly | Ala | Gly | Gly | Ala | Gly | Gly | Pro |
| | | | 20 | | | | | 25 | | | | | 30 | | |

| Gly | Pro | Gly | Gly | Leu | Gln | Pro | Gly | Gln | Arg | Val | Leu | Tyr | Lys | Gln | Ser |
| | | 35 | | | | | 40 | | | | | 45 | | | |

| Met | Ala | Gln | Arg | Ala | Arg | Thr | Met | Ala | Leu | Tyr | Asn | Pro | Ile | Pro | Val |
| | 50 | | | | | 55 | | | | | 60 | | | | |

| Lys | Gln | Asn | Cys | Phe | Thr | Val | Asn | Arg | Ser | Leu | Phe | Val | Phe | Ser | Glu |
| 65 | | | | | 70 | | | | | 75 | | | | | 80 |

| Asp | Asn | Val | Val | Arg | Lys | Tyr | Ala | Lys | Arg | Ile | Thr | Glu | Trp | Pro | Pro |
| | | | | 85 | | | | | 90 | | | | | 95 | |

| Phe | Glu | Asn | Met | Ile | Leu | Ala | Thr | Ile | Ile | Ala | Asn | Cys | Ile | Val | Leu |
| | | | 100 | | | | | 105 | | | | | 110 | | |

| Ala | Leu | Glu | Gln | His | Leu | Pro | Asp | Gly | Asp | Lys | Thr | Pro | Met | Ser | Glu |
| | | | 115 | | | | | 120 | | | | | 125 | | |

| Arg | Leu | Asp | Asp | Thr | Glu | Pro | Tyr | Phe | Ile | Gly | Ile | Phe | Cys | Phe | Glu |
| | | 130 | | | | | 135 | | | | | 140 | | | |

| Ala | Gly | Ile | Lys | Ile | Ile | Ala | Leu | Gly | Phe | Val | Phe | His | Lys | Gly | Ser |

```
145                      150                      155                      160
Tyr  Leu  Arg  Asn  Gly  Trp  Asn  Val  Met  Asp  Phe  Val  Val  Val  Leu  Thr
                    165                      170                      175

Gly  Ile  Leu  Ala  Thr  Ala  Gly  Thr  Asp  Phe  Asp  Leu  Arg  Thr  Leu  Arg
                    180                      185                      190

Ala  Val  Arg  Val  Leu  Arg  Pro  Leu  Lys  Leu  Val  Ser  Gly  Ile  Pro  Ser
               195                      200                      205

Leu  Gln  Val  Val  Leu  Lys  Ser  Ile  Met  Lys  Ala  Met  Val  Pro  Leu  Leu
     210                      215                      220

Gln  Ile  Gly  Leu  Leu  Leu  Phe  Phe  Ala  Ile  Leu  Met  Phe  Ala  Ile  Ile
225                      230                      235                      240

Gly  Leu  Glu  Phe  Tyr  Met  Gly  Lys  Phe  His  Lys  Ala  Cys  Phe  Pro  Asn
                    245                      250                      255

Ser  Thr  Asp  Ala  Glu  Pro  Val  Gly  Asp  Phe  Pro  Cys  Gly  Lys  Glu  Ala
               260                      265                      270

Pro  Ala  Arg  Leu  Cys  Glu  Gly  Asp  Thr  Glu  Cys  Arg  Glu  Tyr  Trp  Pro
               275                      280                      285

Gly  Pro  Asn  Phe  Gly  Ile  Thr  Asn  Phe  Asp  Asn  Ile  Leu  Phe  Ala  Ile
          290                      295                      300

Leu  Thr  Val  Phe  Gln  Cys  Ile  Thr  Met  Glu  Gly  Trp  Thr  Asp  Ile  Leu
305                      310                      315                      320

Tyr  Asn  Thr  Asn  Asp  Ala  Ala  Gly  Asn  Thr  Asn  Trp  Leu  Tyr  Phe
                    325                      330                      335

Ile  Pro  Leu  Ile  Ile  Ile  Gly  Ser  Phe  Phe  Met  Leu  Asn  Leu  Val  Leu
               340                      345                      350

Gly  Val  Leu  Ser  Gly  Glu  Phe  Ala  Lys  Glu  Arg  Glu  Arg  Val  Glu  Asn
               355                      360                      365

Arg  Arg  Ala  Phe  Leu  Asn  Val  Arg  Arg  Gln  Gln  Gln  Ile  Glu  Arg  Glu
     370                      375                      380

Leu  Asn  Gly  Tyr  Leu  Glu  Trp  Ile  Phe  Lys  Ala  Glu  Glu  Val  Met  Leu
385                      390                      395                      400

Ala  Glu  Glu  Asp  Arg  Asn  Ala  Glu  Glu  Lys  Ser  Pro  Leu  Asp  Val  Leu
                    405                      410                      415

Lys  Arg  Ala  Ala  Thr  Lys  Lys  Ser  Arg  Asn  Asp  Leu  Ile  His  Ala  Glu
                    420                      425                      430

Glu  Gly  Glu  Asp  Arg  Phe  Ala  Asp  Leu  Cys  Ala  Val  Gly  Ser  Pro  Phe
               435                      440                      445

Ala  Arg  Ala  Ser  Leu  Lys  Ser  Gly  Lys  Thr  Glu  Ser  Ser  Ser  Tyr  Phe
     450                      455                      460

Arg  Arg  Lys  Glu  Lys  Met  Phe  Arg  Phe  Phe  Ile  Arg  Arg  Met  Val  Lys
465                      470                      475                      480

Ala  Gln  Ser  Phe  Tyr  Trp  Val  Val  Leu  Cys  Val  Val  Ala  Leu  Asn  Thr
                    485                      490                      495

Leu  Cys  Val  Ala  Met  Val  His  Tyr  Asn  Gln  Pro  Arg  Arg  Leu  Thr  Thr
               500                      505                      510

Thr  Leu  Tyr  Phe  Ala  Glu  Phe  Val  Phe  Leu  Gly  Leu  Phe  Leu  Thr  Glu
          515                      520                      525

Met  Ser  Leu  Lys  Met  Tyr  Gly  Leu  Gly  Pro  Arg  Ser  Tyr  Phe  Arg  Ser
     530                      535                      540

Ser  Phe  Asn  Cys  Phe  Asp  Phe  Gly  Val  Ile  Val  Gly  Ser  Val  Phe  Glu
545                      550                      555                      560

Val  Val  Trp  Ala  Ala  Ile  Lys  Pro  Gly  Ser  Ser  Phe  Gly  Ile  Ser  Val
                    565                      570                      575
```

| Leu | Arg | Ala | Leu | Arg | Leu | Leu | Arg | Ile | Phe | Lys | Val | Thr | Lys | Tyr | Trp |
|-----|-----|-----|-----|-----|-----|-----|-----|-----|-----|-----|-----|-----|-----|-----|-----|
|     |     |     | 580 |     |     |     | 585 |     |     |     |     |     | 590 |     |     |
| Ser | Ser | Leu | Arg | Asn | Leu | Val | Val | Ser | Leu | Leu | Asn | Ser | Met | Lys | Ser |
|     |     | 595 |     |     |     | 600 |     |     |     |     | 605 |     |     |     |     |
| Ile | Ile | Ser | Leu | Leu | Phe | Leu | Phe | Leu | Phe | Ile | Val | Val | Phe | Ala |     |
|     | 610 |     |     |     |     | 615 |     |     |     |     | 620 |     |     |     |     |
| Leu | Leu | Gly | Met | Gln | Leu | Phe | Gly | Gly | Gln | Phe | Asn | Phe | Gln | Asp | Glu |
| 625 |     |     |     |     | 630 |     |     |     |     | 635 |     |     |     |     | 640 |
| Thr | Pro | Thr | Thr | Asn | Phe | Asp | Thr | Phe | Pro | Ala | Ala | Ile | Leu | Thr | Val |
|     |     |     |     | 645 |     |     |     |     | 650 |     |     |     |     | 655 |     |
| Phe | Gln | Ile | Leu | Thr | Gly | Glu | Asp | Trp | Asn | Ala | Val | Met | Tyr | His | Gly |
|     |     |     | 660 |     |     |     |     | 665 |     |     |     |     | 670 |     |     |
| Ile | Glu | Ser | Gln | Gly | Gly | Val | Ser | Lys | Gly | Met | Phe | Ser | Ser | Phe | Tyr |
|     |     | 675 |     |     |     |     | 680 |     |     |     |     | 685 |     |     |     |
| Phe | Ile | Val | Leu | Thr | Leu | Phe | Gly | Asn | Tyr | Thr | Leu | Leu | Asn | Val | Phe |
|     | 690 |     |     |     |     | 695 |     |     |     |     | 700 |     |     |     |     |
| Leu | Ala | Ile | Ala | Val | Asp | Asn | Leu | Ala | Asn | Ala | Gln | Glu | Leu | Thr | Lys |
| 705 |     |     |     |     | 710 |     |     |     |     | 715 |     |     |     |     | 720 |
| Asp | Glu | Glu | Glu | Met | Glu | Glu | Ala | Ala | Asn | Gln | Lys | Leu | Ala | Leu | Gln |
|     |     |     |     | 725 |     |     |     |     | 730 |     |     |     |     | 735 |     |
| Lys | Ala | Lys | Glu | Val | Ala | Glu | Val | Ser | Pro | Met | Ser | Ala | Ala | Asn | Ile |
|     |     |     | 740 |     |     |     |     | 745 |     |     |     |     | 750 |     |     |
| Ser | Ile | Ala | Ala | Ser | Glu | Gln | Asn | Ser | Ala | Lys | Ala | Arg | Ser | Val | Trp |
|     |     | 755 |     |     |     |     | 760 |     |     |     |     | 765 |     |     |     |
| Glu | Gln | Arg | Ala | Ser | Gln | Leu | Arg | Leu | Gln | Asn | Leu | Arg | Ala | Ser | Cys |
|     | 770 |     |     |     |     | 775 |     |     |     |     | 780 |     |     |     |     |
| Glu | Ala | Leu | Tyr | Ser | Glu | Met | Asp | Pro | Glu | Glu | Arg | Leu | Arg | Phe | Ala |
| 785 |     |     |     |     | 790 |     |     |     |     | 795 |     |     |     |     | 800 |
| Thr | Thr | Arg | His | Leu | Arg | Pro | Asp | Met | Lys | Thr | His | Leu | Asp | Arg | Pro |
|     |     |     |     | 805 |     |     |     |     | 810 |     |     |     |     | 815 |     |
| Leu | Val | Val | Glu | Leu | Gly | Arg | Asp | Gly | Ala | Arg | Gly | Pro | Val | Gly | Gly |
|     |     |     | 820 |     |     |     |     | 825 |     |     |     |     | 830 |     |     |
| Lys | Ala | Arg | Pro | Glu | Ala | Ala | Glu | Ala | Pro | Glu | Gly | Val | Asp | Pro | Pro |
|     |     | 835 |     |     |     |     | 840 |     |     |     |     | 845 |     |     |     |
| Arg | Arg | His | His | Arg | His | Arg | Asp | Lys | Asp | Lys | Thr | Pro | Ala | Ala | Gly |
|     |     | 850 |     |     |     |     | 855 |     |     |     |     | 860 |     |     |     |
| Asp | Gln | Asp | Arg | Ala | Glu | Ala | Pro | Lys | Ala | Glu | Ser | Gly | Glu | Pro | Gly |
| 865 |     |     |     |     | 870 |     |     |     |     | 875 |     |     |     |     | 880 |
| Ala | Arg | Glu | Glu | Arg | Pro | Arg | Ala | Asp | Arg | Ser | His | Ser | Lys | Glu | Ala |
|     |     |     |     | 885 |     |     |     |     | 890 |     |     |     |     | 895 |     |
| Ala | Gly | Pro | Pro | Glu | Ala | Arg | Thr | Ser | Ala | Ala | Glu | Ala | Gln | Ala | Pro |
|     |     |     | 900 |     |     |     |     | 905 |     |     |     |     | 910 |     |     |
| Arg | Ala | Ala | Gly | Gly | Thr | Thr | Gly | Ala | Ala | Pro | Arg | Arg | Arg | Arg | Pro |
|     |     |     | 915 |     |     |     |     | 920 |     |     |     |     | 925 |     |     |
| Ser | Gly | Ser | Pro | Asp | Ala | Thr | Ala | Arg | Thr | Gly | Thr | Arg | Ile | Arg | Ala |
|     | 930 |     |     |     |     | 935 |     |     |     |     | 940 |     |     |     |     |
| Arg | Ser | Ala | Pro | Ala | Pro | Arg | Ala | Ser | Gly | Ala | Arg | Gly | Thr | Ala | Ala |
| 945 |     |     |     |     | 950 |     |     |     |     | 955 |     |     |     |     | 960 |
| Ala | Pro | Glu | Arg | Gly | Pro | Gly | Arg | Arg | Arg | Ala | Gly | Arg | Ser | Arg | Arg |
|     |     |     |     | 965 |     |     |     |     | 970 |     |     |     |     | 975 |     |
| Gly | Gly | Thr | Gly | Pro | Gly | Thr | Arg | Arg | Ser | Leu | Leu | Thr | Arg | Leu | Trp |
|     |     |     | 980 |     |     |     |     | 985 |     |     |     |     | 990 |     |     |
| Arg | Arg | Arg | Pro | Arg | Arg | Arg | Arg | Pro | Arg | Arg | Arg | Arg | Leu | Arg |     |
|     |     | 995 |     |     |     |     | 1000|     |     |     |     | 1005|     |     |     |

```
Trp Lys Pro Thr Arg Lys Arg Ser Ser Gly Thr Thr Ser Pro Gly Ser
    1010              1015              1020

His Thr Val Thr Trp Arg Pro Val Gly Leu     Leu Trp Val His Ala
1025            1030              1035              1040

His Thr Ala Gln Gln Pro Val Ser Arg Arg Trp Arg Asn Ser Gln Arg
                1045              1050              1055

Met Gln Thr Ile Ser Gly Thr Ser Leu Ala Trp Ala Val Ser Pro Gln
    1060              1065              1070

Thr Arg Thr Leu Leu Tyr Ile Ser Gln     Cys     Arg Ala Leu Leu
    1075              1080                           1085

Gly Lys Pro Arg Ser Phe Pro Val Val Thr Trp Thr Trp Lys Ala Lys
    1090              1095              1100

Gln Arg Gly Arg Arg Arg Trp Lys Arg Met Thr     Gly Ala Ala
1105              1110              1115              1120

Pro Gly Leu Ser Ser His Thr Ala Pro Cys Ser Val     Ala Pro Pro
                1125              1130              1135

Thr Cys Ser Ala Ala Ser Ala Thr Thr Ser     Pro     Gly Thr Ser
                1140              1145              1150

Arg Trp Ser Phe Ser Trp Ser Ser Pro     Ala Ala Ser Pro Trp Leu
                1155              1160              1165

Leu Arg Thr Gln Cys Ala Gln Thr Arg Pro Gly Thr Thr Leu     Asn
    1170              1175              1180

Thr Trp Ile Thr Phe Ser Leu Val Ser Leu Pro Leu Arg Trp
1185            1190              1195                    1200

Arg     Ser Thr Trp Asp Cys Cys Phe Thr Leu Glu Pro Ile Ser Gly
                1205              1210              1215

Thr Cys Gly Thr Phe Trp Thr Ser Leu Trp Ser Val Ala Pro Trp Trp
                1220              1225              1230

Arg Leu Leu Ser Arg Ser Lys Gly Lys Asp Ile Asn Thr Ile Lys Ser
                1235              1240              1245

Leu Arg Val Leu Arg Val Leu Arg Pro Leu Lys Thr Ile Lys Arg Leu
    1250              1255              1260

Pro Lys Leu Lys Ala Val Phe Asp Cys Val Val Asn Ser Leu Lys Asn
1265            1270              1275                    1280

Val Leu Asn Ile Leu Ile Val Tyr Met Leu Phe Met Phe Ile Phe Ala
                1285              1290              1295

Val Ile Ala Val Gln Leu Phe Lys Gly Lys Phe Phe Tyr Cys Thr Asp
                1300              1305              1310

Glu Ser Lys Glu Leu Glu Arg Asp Cys Arg Gly Gln Tyr Leu Asp Tyr
    1315              1320              1325

Glu Lys Glu Glu Val Glu Ala Gln Pro Arg Gln Trp Lys Lys Tyr Asp
    1330              1335              1340

Phe His Tyr Asp Asn Val Leu Trp Ala Leu Leu Thr Leu Phe Thr Val
1345            1350              1355              1360

Ser Thr Gly Glu Gly Trp Pro Met Val Leu Lys His Ser Val Asp Ala
                1365              1370              1375

Thr Tyr Glu Glu Gln Gly Pro Ser Pro Gly Tyr Arg Met Glu Leu Ser
                1380              1385              1390

Ile Phe Tyr Val Val Tyr Phe Val Val Phe Pro Phe Phe Val Asn
                1395              1400              1405

Ile Phe Val Ala Leu Ile Ile Ile Thr Phe Gln Glu Gln Gly Asp Lys
    1410              1415              1420

Val Met Ser Glu Cys Ser Leu Glu Lys Asn Glu Arg Ala Cys Ile Asp
```

|  |  |  |  |
|---|---|---|---|
| 1425 | 1430 | 1435 | 1440 |

Phe Ala Ile Ser Ala Lys Pro Leu Thr Arg Tyr Met Pro Gln Asn Arg
                    1445                1450                1455

Gln Ser Phe Gln Tyr Lys Thr Trp Thr Phe Val Val Ser Pro Pro Phe
                1460                1465                1470

Glu Tyr Phe Ile Met Ala Met Ile Ala Leu Asn Thr Val Val Leu Met
            1475                1480                1485

Met Lys Phe Tyr Asp Ala Pro Tyr Glu Tyr Glu Leu Met Leu Lys Cys
1490                    1495                1500

Leu Asn Ile Val Phe Thr Ser Met Phe Ser Met Glu Cys Val Leu Lys
1505                1510                1515                1520

Ile Ile Ala Phe Gly Val Leu Asn Tyr Phe Arg Asp Ala Trp Asn Phe
                1525                1530                1535

Val Phe Asp Phe Val Thr Val Leu Gly Ser Ile Thr Asp Ile Leu Val
            1540                1545                1550

Thr Glu Ile Ala Ile Cys Pro Arg     Arg Phe Gln Gln Phe     Cys
        1555                1560            1565

Tyr Ser Thr Pro Gly Val Thr Val Thr Ser Leu Thr Thr His Gln Gln
        1570                1575                1580

Arg Arg Ile Cys Pro Val Ser His Ser Pro Arg Ser Pro Ser Leu Glu
1585                1590                1595                1600

Ser Ala Ser Lys Glu Pro Pro Leu Val Ser Pro Val Phe Gly Ser Glu
                1605                1610                1615

Arg Val Ile Gln Met     Phe Thr Gly Ile Thr Val Ser Arg Asn Ser
            1620                1625                1630

Trp Lys Arg Thr Ile Ser Ser Thr Ser Ala Ser Ser Ala Ser Phe Glu
        1635                1640                1645

Leu Arg Gly     Ser Ser Cys Ser Ala Arg Ala Thr Pro Ser Ala Ser
        1650            1655                1660

Cys Cys Gly Pro Leu Ser Ser Pro Ser Arg Pro Cys Pro Thr Cys Val
1665                1670                1675                1680

Cys Ser Leu Pro Cys Cys Ser Ser Ser Thr Pro Ser Ser Ala Cys Arg
                1685                1690                1695

Cys Leu Gly Ile Leu Pro Trp Met Met Thr Pro Ala Ser Thr Ala Thr
            1700                1705                1710

Thr Thr Ser Gly Arg Phe Cys Lys Pro     Cys Cys Cys Ser Gly Ala
        1715                1720            1725

Pro Arg Gly Arg Pro Gly Thr Arg Ser Cys Cys Pro Ala     Ala Thr
        1730                1735                1740

Arg Pro Val Met Ser Arg Pro Met Pro Pro Ser Val Glu Val Thr Leu
1745                1750                1755                1760

Pro Thr Ser Thr Ser Ser Pro Ser Ser Leu Glu Cys Thr Tyr
                1765                1770

( 2 ) INFORMATION FOR SEQ ID NO:14:

( i ) SEQUENCE CHARACTERISTICS:
        ( A ) LENGTH: 2470 base pairs
        ( B ) TYPE: nucleic acid
        ( C ) STRANDEDNESS: unknown
        ( D ) TOPOLOGY: unknown ( i i ) MOLECULE TYPE: DNA (genomic)

( i x ) FEATURE:
        ( A ) NAME/KEY: CDS
        ( B ) LOCATION: 1..2469

( x i ) SEQUENCE DESCRIPTION: SEQ ID NO:14:

| | | | | | | | | | | | | | | | | |
|---|---|---|---|---|---|---|---|---|---|---|---|---|---|---|---|---|
| ATG | GTC | CGC | TTC | GGG | GAC | GAG | CTG | GGC | GGC | CGC | TAT | GGA | GGC | CCC | GGC | 48 |
| Met | Val | Arg | Phe | Gly | Asp | Glu | Leu | Gly | Gly | Arg | Tyr | Gly | Gly | Pro | Gly | |
| 1 | | | | 5 | | | | | 10 | | | | | 15 | | |
| GGC | GGA | GAG | CGG | GCC | CGG | GGC | GGC | GGG | GCC | GGG | GCG | GGG | GGC | CCG | | 96 |
| Gly | Gly | Glu | Arg | Ala | Arg | Gly | Gly | Gly | Ala | Gly | Ala | Gly | Gly | Pro | | |
| | | | 20 | | | | | 25 | | | | | 30 | | | |
| GGT | CCC | GGG | GGG | CTG | CAG | CCC | GGC | CAG | CGG | GTC | CTC | TAC | AAG | CAA | TCG | 144 |
| Gly | Pro | Gly | Gly | Leu | Gln | Pro | Gly | Gln | Arg | Val | Leu | Tyr | Lys | Gln | Ser | |
| | | 35 | | | | | 40 | | | | | 45 | | | | |
| ATG | GCC | CAG | CGC | GCG | CGG | ACC | ATG | GCG | CTG | TAC | AAC | CCC | ATC | CCG | GTC | 192 |
| Met | Ala | Gln | Arg | Ala | Arg | Thr | Met | Ala | Leu | Tyr | Asn | Pro | Ile | Pro | Val | |
| | 50 | | | | | 55 | | | | | 60 | | | | | |
| AAG | CAG | AAC | TGC | TTC | ACC | GTC | AAC | CGC | TCG | CTC | TTC | GTC | TTC | AGC | GAG | 240 |
| Lys | Gln | Asn | Cys | Phe | Thr | Val | Asn | Arg | Ser | Leu | Phe | Val | Phe | Ser | Glu | |
| 65 | | | | | 70 | | | | | 75 | | | | | 80 | |
| GAC | AAC | GTC | GTC | CGC | AAA | TAC | GCG | AAG | CGC | ATC | ACC | GAG | TGG | CCT | CCA | 288 |
| Asp | Asn | Val | Val | Arg | Lys | Tyr | Ala | Lys | Arg | Ile | Thr | Glu | Trp | Pro | Pro | |
| | | | | 85 | | | | | 90 | | | | | 95 | | |
| TTC | GAG | AAT | ATG | ATC | CTG | GCC | ACC | ATC | ATC | GCC | AAC | TGC | ATC | GTG | CTG | 336 |
| Phe | Glu | Asn | Met | Ile | Leu | Ala | Thr | Ile | Ile | Ala | Asn | Cys | Ile | Val | Leu | |
| | | | 100 | | | | | 105 | | | | | 110 | | | |
| GCC | CTG | GAG | CAG | CAC | CTC | CCT | GAT | GGG | GAC | AAA | ACG | CCC | ATG | TCC | GAG | 384 |
| Ala | Leu | Glu | Gln | His | Leu | Pro | Asp | Gly | Asp | Lys | Thr | Pro | Met | Ser | Glu | |
| | | 115 | | | | | 120 | | | | | 125 | | | | |
| CGG | CTG | GAC | GAC | ACG | GAG | CCC | TAT | TTC | ATC | GGG | ATC | TTT | TGC | TTC | GAG | 432 |
| Arg | Leu | Asp | Asp | Thr | Glu | Pro | Tyr | Phe | Ile | Gly | Ile | Phe | Cys | Phe | Glu | |
| | 130 | | | | | 135 | | | | | 140 | | | | | |
| GCA | GGG | ATC | AAA | ATC | ATC | GCT | CTG | GGC | TTT | GTC | TTC | CAC | AAG | GGC | TCT | 480 |
| Ala | Gly | Ile | Lys | Ile | Ile | Ala | Leu | Gly | Phe | Val | Phe | His | Lys | Gly | Ser | |
| 145 | | | | | 150 | | | | | 155 | | | | | 160 | |
| TAC | CTG | CGG | AAC | GGC | TGG | AAC | GTC | ATG | GAC | TTC | GTG | GTC | GTC | CTC | ACA | 528 |
| Tyr | Leu | Arg | Asn | Gly | Trp | Asn | Val | Met | Asp | Phe | Val | Val | Val | Leu | Thr | |
| | | | | 165 | | | | | 170 | | | | | 175 | | |
| GGG | ATC | CTT | GCC | ACG | GCT | GGA | ACT | GAC | TTC | GAC | CTG | CGA | ACA | CTG | AGG | 576 |
| Gly | Ile | Leu | Ala | Thr | Ala | Gly | Thr | Asp | Phe | Asp | Leu | Arg | Thr | Leu | Arg | |
| | | | 180 | | | | | 185 | | | | | 190 | | | |
| GCT | GTG | CGT | GTG | CTG | AGG | CCC | CTG | AAG | CTG | GTG | TCT | GGG | ATT | CCA | AGT | 624 |
| Ala | Val | Arg | Val | Leu | Arg | Pro | Leu | Lys | Leu | Val | Ser | Gly | Ile | Pro | Ser | |
| | | 195 | | | | | 200 | | | | | 205 | | | | |
| TTG | CAG | GTG | GTG | CTC | AAG | TCC | ATC | ATG | AAG | GCC | ATG | GTT | CCA | CTC | CTG | 672 |
| Leu | Gln | Val | Val | Leu | Lys | Ser | Ile | Met | Lys | Ala | Met | Val | Pro | Leu | Leu | |
| | 210 | | | | | 215 | | | | | 220 | | | | | |
| CAG | ATT | GGG | CTG | CTT | CTC | TTC | TTT | GCC | ATC | CTC | ATG | TTT | GCC | ATC | ATT | 720 |
| Gln | Ile | Gly | Leu | Leu | Leu | Phe | Phe | Ala | Ile | Leu | Met | Phe | Ala | Ile | Ile | |
| 225 | | | | | 230 | | | | | 235 | | | | | 240 | |
| GGC | CTG | GAG | TTC | TAC | ATG | GGC | AAG | TTC | CAC | AAG | GCC | TGT | TTC | CCC | AAC | 768 |
| Gly | Leu | Glu | Phe | Tyr | Met | Gly | Lys | Phe | His | Lys | Ala | Cys | Phe | Pro | Asn | |
| | | | | 245 | | | | | 250 | | | | | 255 | | |
| AGC | ACA | GAT | GCG | GAG | CCC | GTG | GGT | GAC | TTC | CCC | TGT | GGC | AAG | GAG | GCC | 816 |
| Ser | Thr | Asp | Ala | Glu | Pro | Val | Gly | Asp | Phe | Pro | Cys | Gly | Lys | Glu | Ala | |
| | | | 260 | | | | | 265 | | | | | 270 | | | |
| CCA | GCC | CGG | CTG | TGC | GAG | GGC | GAC | ACT | GAG | TGC | CGG | GAG | TAC | TGG | CCA | 864 |
| Pro | Ala | Arg | Leu | Cys | Glu | Gly | Asp | Thr | Glu | Cys | Arg | Glu | Tyr | Trp | Pro | |
| | | 275 | | | | | 280 | | | | | 285 | | | | |
| GGA | CCC | AAC | TTT | GGC | ATC | ACC | AAC | TTT | GAC | AAT | ATC | CTG | TTT | GCC | ATC | 912 |
| Gly | Pro | Asn | Phe | Gly | Ile | Thr | Asn | Phe | Asp | Asn | Ile | Leu | Phe | Ala | Ile | |
| | 290 | | | | | 295 | | | | | 300 | | | | | |
| TTG | ACG | GTG | TTC | CAG | TGC | ATC | ACC | ATG | GAG | GGC | TGG | ACT | GAC | ATC | CTC | 960 |
| Leu | Thr | Val | Phe | Gln | Cys | Ile | Thr | Met | Glu | Gly | Trp | Thr | Asp | Ile | Leu | |

```
                     305                         310                         315                         320
TAT  AAT  ACA  AAC  GAT  GCG  GCC  GGC  AAC  ACC  TGG  AAC  TGG  CTC  TAC  TTC              1008
Tyr  Asn  Thr  Asn  Asp  Ala  Ala  Gly  Asn  Thr  Trp  Asn  Trp  Leu  Tyr  Phe
                    325                         330                              335

ATC  CCT  CTC  ATC  ATC  ATC  GGC  TCC  TTC  ATG  CTC  AAC  CTG  GTG  CTG              1056
Ile  Pro  Leu  Ile  Ile  Ile  Gly  Ser  Phe  Met  Leu  Asn  Leu  Val  Leu
               340                         345                         350

GGC  GTG  CTC  TCG  GGG  GAG  TTT  GCC  AAG  GAG  CGA  GAG  AGG  GTG  GAG  AAC         1104
Gly  Val  Leu  Ser  Gly  Glu  Phe  Ala  Lys  Glu  Arg  Glu  Arg  Val  Glu  Asn
          355                         360                         365

CGC  CGC  GCC  TTC  CTG  AAC  GTG  CGC  CGG  CAG  CAG  CAG  ATC  GAG  CGA  GAG         1152
Arg  Arg  Ala  Phe  Leu  Asn  Val  Arg  Arg  Gln  Gln  Gln  Ile  Glu  Arg  Glu
     370                         375                         380

CTC  AAC  GGG  TAC  CTG  GAG  TGG  ATC  TTC  AAG  GCG  GAG  GAA  GTC  ATG  CTG         1200
Leu  Asn  Gly  Tyr  Leu  Glu  Trp  Ile  Phe  Lys  Ala  Glu  Glu  Val  Met  Leu
385                         390                         395                         400

GCC  GAG  GAG  GAC  AGG  AAT  GCA  GAG  GAG  AAG  TCC  CCT  TTG  GAC  GTG  CTG         1248
Ala  Glu  Glu  Asp  Arg  Asn  Ala  Glu  Glu  Lys  Ser  Pro  Leu  Asp  Val  Leu
                    405                         410                         415

AAG  AGA  GCG  GCC  ACC  AAG  AAG  AGC  AGA  AAT  GAC  CTG  ATC  CAC  GCA  GAG         1296
Lys  Arg  Ala  Ala  Thr  Lys  Lys  Ser  Arg  Asn  Asp  Leu  Ile  His  Ala  Glu
               420                         425                         430

GAG  GGA  GAG  GAC  CGG  TTT  GCA  GAT  CTC  TGT  GCT  GTT  GGA  TCC  CCC  TTC         1344
Glu  Gly  Glu  Asp  Arg  Phe  Ala  Asp  Leu  Cys  Ala  Val  Gly  Ser  Pro  Phe
          435                         440                         445

GCC  CGC  GCC  AGC  CTC  AAG  AGC  GGG  AAG  ACA  GAG  AGC  TCG  TCA  TAC  TTC         1392
Ala  Arg  Ala  Ser  Leu  Lys  Ser  Gly  Lys  Thr  Glu  Ser  Ser  Ser  Tyr  Phe
     450                         455                         460

CGG  AGG  AAG  GAG  AAG  ATG  TTC  CGG  TTT  TTT  ATC  CGG  CGC  ATG  GTG  AAG         1440
Arg  Arg  Lys  Glu  Lys  Met  Phe  Arg  Phe  Phe  Ile  Arg  Arg  Met  Val  Lys
465                         470                         475                         480

GCT  CAG  AGC  TTC  TAC  TGG  GTG  GTG  CTG  TGC  GTG  GTG  GCC  CTG  AAC  ACA         1488
Ala  Gln  Ser  Phe  Tyr  Trp  Val  Val  Leu  Cys  Val  Val  Ala  Leu  Asn  Thr
                    485                         490                         495

CTG  TGT  GTG  GCC  ATG  GTG  CAT  TAC  AAC  CAG  CCG  CGG  CGG  CTT  ACC  ACG         1536
Leu  Cys  Val  Ala  Met  Val  His  Tyr  Asn  Gln  Pro  Arg  Arg  Leu  Thr  Thr
               500                         505                         510

ACC  CTG  TAT  TTT  GCA  GAG  TTT  GTT  TTC  CTG  GGT  CTC  TTC  CTC  ACA  GAG         1584
Thr  Leu  Tyr  Phe  Ala  Glu  Phe  Val  Phe  Leu  Gly  Leu  Phe  Leu  Thr  Glu
          515                         520                         525

ATG  TCC  CTG  AAG  ATG  TAT  GGC  CTG  GGG  CCC  AGA  AGC  TAC  TTC  CGG  TCC         1632
Met  Ser  Leu  Lys  Met  Tyr  Gly  Leu  Gly  Pro  Arg  Ser  Tyr  Phe  Arg  Ser
     530                         535                         540

TCC  TTC  AAC  TGC  TTC  GAC  TTT  GGG  GTC  ATC  GTG  GGG  AGC  GTC  TTT  GAA         1680
Ser  Phe  Asn  Cys  Phe  Asp  Phe  Gly  Val  Ile  Val  Gly  Ser  Val  Phe  Glu
545                         550                         555                         560

GTG  GTC  TGG  GCG  GCC  ATC  AAG  CCG  GGA  AGC  TCC  TTT  GGG  ATC  AGT  GTG         1728
Val  Val  Trp  Ala  Ala  Ile  Lys  Pro  Gly  Ser  Ser  Phe  Gly  Ile  Ser  Val
                    565                         570                         575

CTG  CGG  GCC  CTC  CGC  CTG  CTG  AGG  ATC  TTC  AAA  GTC  ACG  AAG  TAC  TGG         1776
Leu  Arg  Ala  Leu  Arg  Leu  Leu  Arg  Ile  Phe  Lys  Val  Thr  Lys  Tyr  Trp
               580                         585                         590

AGC  TCC  CTG  CGG  AAC  CTG  GTG  GTG  TCC  CTG  CTG  AAC  TCC  ATG  AAG  TCC         1824
Ser  Ser  Leu  Arg  Asn  Leu  Val  Val  Ser  Leu  Leu  Asn  Ser  Met  Lys  Ser
          595                         600                         605

ATC  ATC  AGC  CTG  CTC  TTC  TTG  CTC  TTC  CTG  TTC  ATT  GTG  GTC  TTC  GCC         1872
Ile  Ile  Ser  Leu  Leu  Phe  Leu  Leu  Phe  Leu  Phe  Ile  Val  Val  Phe  Ala
     610                         615                         620

CTG  CTG  GGG  ATG  CAG  CTG  TTT  GGG  GGA  CAG  TTC  AAC  TTC  CAG  GAT  GAG         1920
Leu  Leu  Gly  Met  Gln  Leu  Phe  Gly  Gly  Gln  Phe  Asn  Phe  Gln  Asp  Glu
```

-continued

| | | | | | | | | | | | | | | | | |
|---|---|---|---|---|---|---|---|---|---|---|---|---|---|---|---|---|
| | | | 625 | | | | 630 | | | | 635 | | | | 640 | |
| ACT | CCC | ACA | ACC | AAC | TTC | GAC | ACC | TTC | CCT | GCC | GCC | ATC | CTC | ACT | GTC | 1968 |
| Thr | Pro | Thr | Thr | Asn 645 | Phe | Asp | Thr | Phe | Pro 650 | Ala | Ala | Ile | Leu | Thr 655 | Val | |
| TTC | CAG | ATC | CTG | ACG | GGA | GAG | GAC | TGG | AAT | GCA | GTG | ATG | TAT | CAC | GGG | 2016 |
| Phe | Gln | Ile | Leu 660 | Thr | Gly | Glu | Asp | Trp 665 | Asn | Ala | Val | Met | Tyr 670 | His | Gly | |
| ATC | GAA | TCG | CAA | GGC | GGC | GTC | AGC | AAA | GGC | ATG | TTC | TCG | TCC | TTT | TAC | 2064 |
| Ile | Glu | Ser 675 | Gln | Gly | Gly | Val | Ser 680 | Lys | Gly | Met | Phe | Ser 685 | Ser | Phe | Tyr | |
| TTC | ATT | GTC | CTG | ACA | CTG | TTC | GGA | AAC | TAC | ACT | CTG | CTG | AAT | GTC | TTT | 2112 |
| Phe | Ile 690 | Val | Leu | Thr | Leu | Phe 695 | Gly | Asn | Tyr | Thr | Leu 700 | Leu | Asn | Val | Phe | |
| CTG | GCC | ATC | GCT | GTG | GAC | AAC | CTG | GCC | AAC | GCC | CAA | GAG | CTG | ACC | AAG | 2160 |
| Leu 705 | Ala | Ile | Ala | Val | Asp | Asn 710 | Leu | Ala | Asn | Ala | Gln 715 | Glu | Leu | Thr | Lys 720 | |
| GAT | GAA | GAG | GAG | ATG | GAA | GAA | GCA | GCC | AAT | CAG | AAG | CTT | GCT | CTG | CAA | 2208 |
| Asp | Glu | Glu | Glu | Met 725 | Glu | Glu | Ala | Ala | Asn 730 | Gln | Lys | Leu | Ala | Leu 735 | Gln | |
| AAG | GCC | AAA | GAA | GTG | GCT | GAA | GTC | AGC | CCC | ATG | TCT | GCC | GCG | AAC | ATC | 2256 |
| Lys | Ala | Lys | Glu 740 | Val | Ala | Glu | Val | Ser 745 | Pro | Met | Ser | Ala | Ala 750 | Asn | Ile | |
| TCC | ATC | GCC | GCC | AGC | GAG | CAG | AAC | TCG | GCC | AAG | GCG | CGC | TCG | GTG | TGG | 2304 |
| Ser | Ile | Ala 755 | Ala | Ser | Glu | Gln | Asn 760 | Ser | Ala | Lys | Ala | Arg 765 | Ser | Val | Trp | |
| GAG | CAG | CGG | GCC | AGC | CAG | CTA | CGG | CTG | CAG | AAC | CTG | CGG | GCC | AGC | TGC | 2352 |
| Glu | Gln | Arg 770 | Ala | Ser | Gln | Leu | Arg 775 | Leu | Gln | Asn | Leu | Arg 780 | Ala | Ser | Cys | |
| GAG | GCG | CTG | TAC | AGC | GAG | ATG | GAC | CCC | GAG | GAG | CGG | CTG | CGC | TTC | GCC | 2400 |
| Glu 785 | Ala | Leu | Tyr | Ser | Glu 790 | Met | Asp | Pro | Glu | Glu 795 | Arg | Leu | Arg | Phe | Ala 800 | |
| ACT | ACG | CGC | CAC | CTG | CGG | CCC | GAC | ATG | AAG | ACG | CAC | CTG | GAC | CGG | CCG | 2448 |
| Thr | Thr | Arg | His | Leu 805 | Arg | Pro | Asp | Met | Lys 810 | Thr | His | Leu | Asp | Arg 815 | Pro | |
| CTG | GTG | GTG | GAG | CTG | GGC | CGC | G | | | | | | | | | 2470 |
| Leu | Val | Val | Glu | Leu | Gly | Arg | | | | | | | | | | |
| | | | 820 | | | | | | | | | | | | | |

( 2 ) INFORMATION FOR SEQ ID NO:15:

( i ) SEQUENCE CHARACTERISTICS:
        ( A ) LENGTH: 823 amino acids
        ( B ) TYPE: amino acid
        ( D ) TOPOLOGY: linear ( i i ) MOLECULE TYPE: protein ( x i ) SEQUENCE DESCRIPTION: SEQ ID NO:15:

| Met | Val | Arg | Phe | Gly | Asp | Glu | Leu | Gly | Gly | Arg | Tyr | Gly | Gly | Pro | Gly |
|---|---|---|---|---|---|---|---|---|---|---|---|---|---|---|---|
| 1 | | | | 5 | | | | | 10 | | | | | 15 | |
| Gly | Gly | Glu | Arg | Ala | Arg | Gly | Gly | Gly | Ala | Gly | Gly | Ala | Gly | Gly | Pro |
| | | | 20 | | | | | 25 | | | | | 30 | | |
| Gly | Pro | Gly | Gly | Leu | Gln | Pro | Gly | Gln | Arg | Val | Leu | Tyr | Lys | Gln | Ser |
| | | 35 | | | | | 40 | | | | | 45 | | | |
| Met | Ala | Gln | Arg | Ala | Arg | Thr | Met | Ala | Leu | Tyr | Asn | Pro | Ile | Pro | Val |
| | 50 | | | | | 55 | | | | | 60 | | | | |
| Lys | Gln | Asn | Cys | Phe | Thr | Val | Asn | Arg | Ser | Leu | Phe | Val | Phe | Ser | Glu |
| 65 | | | | | 70 | | | | | 75 | | | | | 80 |
| Asp | Asn | Val | Val | Arg | Lys | Tyr | Ala | Lys | Arg | Ile | Thr | Glu | Trp | Pro | Pro |
| | | | | 85 | | | | | 90 | | | | | 95 | |

-continued

| | | | | | | | | | | | | | | |
|---|---|---|---|---|---|---|---|---|---|---|---|---|---|---|
|Phe|Glu|Asn|Met<br>100|Ile|Leu|Ala|Thr|Ile<br>105|Ile|Ala|Asn|Cys|Ile<br>110|Val|Leu|
|Ala|Leu|Glu|Gln<br>115|His|Leu|Pro|Asp<br>120|Gly|Asp|Lys|Thr|Pro<br>125|Met|Ser|Glu|
|Arg|Leu<br>130|Asp|Asp|Thr|Glu|Pro<br>135|Tyr|Phe|Ile|Gly|Ile<br>140|Phe|Cys|Phe|Glu|
|Ala<br>145|Gly|Ile|Lys|Ile|Ile<br>150|Ala|Leu|Gly|Phe|Val<br>155|Phe|His|Lys|Gly|Ser<br>160|
|Tyr|Leu|Arg|Asn|Gly<br>165|Trp|Asn|Val|Met|Asp<br>170|Phe|Val|Val|Val|Leu<br>175|Thr|
|Gly|Ile|Leu|Ala<br>180|Thr|Ala|Gly|Thr|Asp<br>185|Phe|Asp|Leu|Arg|Thr<br>190|Leu|Arg|
|Ala|Val|Arg<br>195|Val|Leu|Arg|Pro|Leu<br>200|Lys|Leu|Val|Ser|Gly<br>205|Ile|Pro|Ser|
|Leu|Gln<br>210|Val|Val|Leu|Lys|Ser<br>215|Ile|Met|Lys|Ala|Met<br>220|Val|Pro|Leu|Leu|
|Gln<br>225|Ile|Gly|Leu|Leu|Leu<br>230|Phe|Phe|Ala|Ile|Leu<br>235|Met|Phe|Ala|Ile|Ile<br>240|
|Gly|Leu|Glu|Phe|Tyr<br>245|Met|Gly|Lys|Phe|His<br>250|Lys|Ala|Cys|Phe|Pro<br>255|Asn|
|Ser|Thr|Asp|Ala|Glu<br>260|Pro|Val|Gly|Asp|Phe<br>265|Pro|Cys|Gly|Lys|Glu<br>270|Ala|
|Pro|Ala|Arg<br>275|Leu|Cys|Glu|Gly|Asp<br>280|Thr|Glu|Cys|Arg|Glu<br>285|Tyr|Trp|Pro|
|Gly|Pro<br>290|Asn|Phe|Gly|Ile|Thr<br>295|Asn|Phe|Asp|Asn|Ile<br>300|Leu|Phe|Ala|Ile|
|Leu<br>305|Thr|Val|Phe|Gln|Cys<br>310|Ile|Thr|Met|Glu|Gly<br>315|Trp|Thr|Asp|Ile|Leu<br>320|
|Tyr|Asn|Thr|Asn|Asp<br>325|Ala|Ala|Gly|Asn|Thr<br>330|Trp|Asn|Trp|Leu|Tyr<br>335|Phe|
|Ile|Pro|Leu|Ile<br>340|Ile|Ile|Gly|Ser|Phe<br>345|Phe|Met|Leu|Asn|Leu<br>350|Val|Leu|
|Gly|Val|Leu|Ser<br>355|Gly|Glu|Phe|Ala|Lys<br>360|Glu|Arg|Glu|Arg<br>365|Val|Glu|Asn|
|Arg|Arg|Ala<br>370|Phe|Leu|Asn|Val|Arg<br>375|Arg|Gln|Gln|Gln|Ile<br>380|Glu|Arg|Glu|
|Leu|Asn<br>385|Gly|Tyr|Leu|Glu|Trp<br>390|Ile|Phe|Lys|Ala|Glu<br>395|Glu|Val|Met|Leu<br>400|
|Ala|Glu|Glu|Asp|Arg<br>405|Asn|Ala|Glu|Glu|Lys<br>410|Ser|Pro|Leu|Asp|Val<br>415|Leu|
|Lys|Arg|Ala|Ala<br>420|Thr|Lys|Lys|Ser|Arg<br>425|Asn|Asp|Leu|Ile|His<br>430|Ala|Glu|
|Glu|Gly|Glu<br>435|Asp|Arg|Phe|Ala|Asp<br>440|Leu|Cys|Ala|Val|Gly<br>445|Ser|Pro|Phe|
|Ala|Arg|Ala<br>450|Ser|Leu|Lys|Ser|Gly<br>455|Lys|Thr|Glu|Ser|Ser<br>460|Ser|Tyr|Phe|
|Arg|Arg<br>465|Lys|Glu|Lys|Met|Phe<br>470|Arg|Phe|Phe|Ile<br>475|Arg|Arg|Met|Val|Lys<br>480|
|Ala|Gln|Ser|Phe|Tyr<br>485|Trp|Val|Val|Leu|Cys<br>490|Val|Val|Ala|Leu|Asn<br>495|Thr|
|Leu|Cys|Val|Ala<br>500|Met|Val|His|Tyr|Asn<br>505|Gln|Pro|Arg|Arg|Leu<br>510|Thr|Thr|
|Thr|Leu|Tyr<br>515|Phe|Ala|Glu|Phe|Val<br>520|Phe|Leu|Gly|Leu|Phe<br>525|Leu|Thr|Glu|

|     |     |     |     |     |     |     |     |     |     |     |     |     |     |     |     |
|---|---|---|---|---|---|---|---|---|---|---|---|---|---|---|---|
| Met | Ser | Leu | Lys | Met | Tyr | Gly | Leu | Gly | Pro | Arg | Ser | Tyr | Phe | Arg | Ser |
|     | 530 |     |     |     | 535 |     |     |     |     |     | 540 |     |     |     |     |
| Ser | Phe | Asn | Cys | Phe | Asp | Phe | Gly | Val | Ile | Val | Gly | Ser | Val | Phe | Glu |
| 545 |     |     |     |     | 550 |     |     |     |     | 555 |     |     |     |     | 560 |
| Val | Val | Trp | Ala | Ala | Ile | Lys | Pro | Gly | Ser | Ser | Phe | Gly | Ile | Ser | Val |
|     |     |     |     | 565 |     |     |     |     | 570 |     |     |     |     | 575 |     |
| Leu | Arg | Ala | Leu | Arg | Leu | Leu | Arg | Ile | Phe | Lys | Val | Thr | Lys | Tyr | Trp |
|     |     |     | 580 |     |     |     |     | 585 |     |     |     |     | 590 |     |     |
| Ser | Ser | Leu | Arg | Asn | Leu | Val | Val | Ser | Leu | Leu | Asn | Ser | Met | Lys | Ser |
|     |     | 595 |     |     |     |     | 600 |     |     |     |     | 605 |     |     |     |
| Ile | Ile | Ser | Leu | Leu | Phe | Leu | Leu | Phe | Leu | Phe | Ile | Val | Val | Phe | Ala |
|     | 610 |     |     |     |     | 615 |     |     |     |     | 620 |     |     |     |     |
| Leu | Leu | Gly | Met | Gln | Leu | Phe | Gly | Gly | Gln | Phe | Asn | Phe | Gln | Asp | Glu |
| 625 |     |     |     |     | 630 |     |     |     |     | 635 |     |     |     |     | 640 |
| Thr | Pro | Thr | Thr | Asn | Phe | Asp | Thr | Phe | Pro | Ala | Ala | Ile | Leu | Thr | Val |
|     |     |     |     | 645 |     |     |     |     | 650 |     |     |     |     | 655 |     |
| Phe | Gln | Ile | Leu | Thr | Gly | Glu | Asp | Trp | Asn | Ala | Val | Met | Tyr | His | Gly |
|     |     |     | 660 |     |     |     |     | 665 |     |     |     |     | 670 |     |     |
| Ile | Glu | Ser | Gln | Gly | Gly | Val | Ser | Lys | Gly | Met | Phe | Ser | Ser | Phe | Tyr |
|     |     | 675 |     |     |     |     | 680 |     |     |     |     | 685 |     |     |     |
| Phe | Ile | Val | Leu | Thr | Leu | Phe | Gly | Asn | Tyr | Thr | Leu | Leu | Asn | Val | Phe |
|     | 690 |     |     |     |     | 695 |     |     |     |     | 700 |     |     |     |     |
| Leu | Ala | Ile | Ala | Val | Asp | Asn | Leu | Ala | Asn | Ala | Gln | Glu | Leu | Thr | Lys |
| 705 |     |     |     |     | 710 |     |     |     |     | 715 |     |     |     |     | 720 |
| Asp | Glu | Glu | Glu | Met | Glu | Glu | Ala | Ala | Asn | Gln | Lys | Leu | Ala | Leu | Gln |
|     |     |     |     | 725 |     |     |     |     | 730 |     |     |     |     | 735 |     |
| Lys | Ala | Lys | Glu | Val | Ala | Glu | Val | Ser | Pro | Met | Ser | Ala | Ala | Asn | Ile |
|     |     |     | 740 |     |     |     |     | 745 |     |     |     |     | 750 |     |     |
| Ser | Ile | Ala | Ala | Ser | Glu | Gln | Asn | Ser | Ala | Lys | Ala | Arg | Ser | Val | Trp |
|     |     | 755 |     |     |     |     | 760 |     |     |     |     | 765 |     |     |     |
| Glu | Gln | Arg | Ala | Ser | Gln | Leu | Arg | Leu | Gln | Asn | Leu | Arg | Ala | Ser | Cys |
|     | 770 |     |     |     |     | 775 |     |     |     |     | 780 |     |     |     |     |
| Glu | Ala | Leu | Tyr | Ser | Glu | Met | Asp | Pro | Glu | Glu | Arg | Leu | Arg | Phe | Ala |
| 785 |     |     |     |     | 790 |     |     |     |     | 795 |     |     |     |     | 800 |
| Thr | Thr | Arg | His | Leu | Arg | Pro | Asp | Met | Lys | Thr | His | Leu | Asp | Arg | Pro |
|     |     |     |     | 805 |     |     |     |     | 810 |     |     |     |     | 815 |     |
| Leu | Val | Val | Glu | Leu | Gly | Arg |     |     |     |     |     |     |     |     |     |
|     |     |     | 820 |     |     |     |     |     |     |     |     |     |     |     |     |

(2) INFORMATION FOR SEQ ID NO:16:

(i) SEQUENCE CHARACTERISTICS:
        (A) LENGTH: 957 base pairs
        (B) TYPE: nucleic acid
        (C) STRANDEDNESS: unknown
        (D) TOPOLOGY: unknown (ii) MOLECULE TYPE: DNA (genomic)

(ix) FEATURE:
        (A) NAME/KEY: CDS
        (B) LOCATION: 1..957

(xi) SEQUENCE DESCRIPTION: SEQ ID NO:16:

| TCC | AAA | GGG | AAA | GAC | ATC | AAT | ACC | ATC | AAG | TCT | CTG | AGA | GTC | CTT | CGT | 48 |
|---|---|---|---|---|---|---|---|---|---|---|---|---|---|---|---|---|
| Ser | Lys | Gly | Lys | Asp | Ile | Asn | Thr | Ile | Lys | Ser | Leu | Arg | Val | Leu | Arg |    |
| 1   |     |     |     | 5   |     |     |     |     | 10  |     |     |     |     | 15  |     |    |

| GTC | CTG | CGG | CCC | CTC | AAG | ACC | ATC | AAA | CGG | CTG | CCC | AAG | CTC | AAG | GCT | 96 |

| | | | | | | | | | | | | | | | | |
|---|---|---|---|---|---|---|---|---|---|---|---|---|---|---|---|---|
| Val | Leu | Arg | Pro | Leu | Lys | Thr | Ile | Lys | Arg | Leu | Pro | Lys | Leu | Lys | Ala | |
| | | | 20 | | | | | 25 | | | | | 30 | | | |
| GTG | TTT | GAC | TGT | GTG | GTG | AAC | TCC | CTG | AAG | AAT | GTC | CTC | AAC | ATC | TTG | 144 |
| Val | Phe | Asp | Cys | Val | Val | Asn | Ser | Leu | Lys | Asn | Val | Leu | Asn | Ile | Leu | |
| | | | 35 | | | | 40 | | | | | 45 | | | | |
| ATT | GTC | TAC | ATG | CTC | TTC | ATG | TTC | ATA | TTT | GCC | GTC | ATT | GCG | GTG | CAG | 192 |
| Ile | Val | Tyr | Met | Leu | Phe | Met | Phe | Ile | Phe | Ala | Val | Ile | Ala | Val | Gln | |
| | 50 | | | | | 55 | | | | | 60 | | | | | |
| CTC | TTC | AAA | GGG | AAG | TTT | TTC | TAC | TGC | ACA | GAT | GAA | TCC | AAG | GAG | CTG | 240 |
| Leu | Phe | Lys | Gly | Lys | Phe | Phe | Tyr | Cys | Thr | Asp | Glu | Ser | Lys | Glu | Leu | |
| 65 | | | | | 70 | | | | | 75 | | | | | 80 | |
| GAG | AGG | GAC | TGC | AGG | GGT | CAG | TAT | TTG | GAT | TAT | GAG | AAG | GAG | GAA | GTG | 288 |
| Glu | Arg | Asp | Cys | Arg | Gly | Gln | Tyr | Leu | Asp | Tyr | Glu | Lys | Glu | Glu | Val | |
| | | | | 85 | | | | | 90 | | | | | 95 | | |
| GAA | GCT | CAG | CCC | AGG | CAG | TGG | AAG | AAA | TAC | GAC | TTT | CAC | TAC | GAC | AAT | 336 |
| Glu | Ala | Gln | Pro | Arg | Gln | Trp | Lys | Lys | Tyr | Asp | Phe | His | Tyr | Asp | Asn | |
| | | | 100 | | | | | 105 | | | | | 110 | | | |
| GTG | CTC | TGG | GCT | CTG | CTG | ACG | CTG | TTC | ACA | GTG | TCC | ACG | GGA | GAA | GGC | 384 |
| Val | Leu | Trp | Ala | Leu | Leu | Thr | Leu | Phe | Thr | Val | Ser | Thr | Gly | Glu | Gly | |
| | | | 115 | | | | | 120 | | | | | 125 | | | |
| TGG | CCC | ATG | GTG | CTG | AAA | CAC | TCC | GTG | GAT | GCC | ACC | TAT | GAG | GAG | CAG | 432 |
| Trp | Pro | Met | Val | Leu | Lys | His | Ser | Val | Asp | Ala | Thr | Tyr | Glu | Glu | Gln | |
| | | 130 | | | | | 135 | | | | | 140 | | | | |
| GGT | CCA | AGC | CCT | GGG | TAC | CGC | ATG | GAG | CTG | TCC | ATC | TTC | TAC | GTG | GTC | 480 |
| Gly | Pro | Ser | Pro | Gly | Tyr | Arg | Met | Glu | Leu | Ser | Ile | Phe | Tyr | Val | Val | |
| 145 | | | | | 150 | | | | | 155 | | | | | 160 | |
| TAC | TTT | GTG | GTC | TTT | CCC | TTC | TTC | TTC | GTC | AAC | ATC | TTT | GTG | GCT | TTG | 528 |
| Tyr | Phe | Val | Val | Phe | Pro | Phe | Phe | Phe | Val | Asn | Ile | Phe | Val | Ala | Leu | |
| | | | | 165 | | | | | 170 | | | | | 175 | | |
| ATC | ATC | ATC | ACC | TTC | CAG | GAG | CAG | GGG | GAC | AAG | GTG | ATG | TCT | GAA | TGC | 576 |
| Ile | Ile | Ile | Thr | Phe | Gln | Glu | Gln | Gly | Asp | Lys | Val | Met | Ser | Glu | Cys | |
| | | | 180 | | | | | 185 | | | | | 190 | | | |
| AGC | CTG | GAG | AAG | AAC | GAG | AGG | GCT | TGC | ATT | GAC | TTC | GCC | ATC | AGC | GCC | 624 |
| Ser | Leu | Glu | Lys | Asn | Glu | Arg | Ala | Cys | Ile | Asp | Phe | Ala | Ile | Ser | Ala | |
| | | 195 | | | | | 200 | | | | | 205 | | | | |
| AAA | CCC | CTG | ACA | CGG | TAC | ATG | CCC | CAA | AAC | CGG | CAG | TCG | TTC | CAG | TAT | 672 |
| Lys | Pro | Leu | Thr | Arg | Tyr | Met | Pro | Gln | Asn | Arg | Gln | Ser | Phe | Gln | Tyr | |
| | 210 | | | | | 215 | | | | | 220 | | | | | |
| AAG | ACG | TGG | ACA | TTT | GTG | GTC | TCC | CCG | CCC | TTT | GAA | TAC | TTC | ATC | ATG | 720 |
| Lys | Thr | Trp | Thr | Phe | Val | Val | Ser | Pro | Pro | Phe | Glu | Tyr | Phe | Ile | Met | |
| 225 | | | | | 230 | | | | | 235 | | | | | 240 | |
| GCC | ATG | ATA | GCC | CTC | AAC | ACT | GTG | GTG | CTG | ATG | ATG | AAG | TTC | TAT | GAT | 768 |
| Ala | Met | Ile | Ala | Leu | Asn | Thr | Val | Val | Leu | Met | Met | Lys | Phe | Tyr | Asp | |
| | | | | 245 | | | | | 250 | | | | | 255 | | |
| GCA | CCC | TAT | GAG | TAC | GAG | CTG | ATG | CTG | AAA | TGC | CTG | AAC | ATC | GTG | TTC | 816 |
| Ala | Pro | Tyr | Glu | Tyr | Glu | Leu | Met | Leu | Lys | Cys | Leu | Asn | Ile | Val | Phe | |
| | | | 260 | | | | | 265 | | | | | 270 | | | |
| ACA | TCC | ATG | TTC | TCC | ATG | GAA | TGC | GTG | CTG | AAG | ATC | ATC | GCC | TTT | GGG | 864 |
| Thr | Ser | Met | Phe | Ser | Met | Glu | Cys | Val | Leu | Lys | Ile | Ile | Ala | Phe | Gly | |
| | | 275 | | | | | 280 | | | | | 285 | | | | |
| GTG | CTG | AAC | TAT | TTC | AGA | GAT | GCC | TGG | AAT | TTT | GTC | TTT | GAC | TTT | GTC | 912 |
| Val | Leu | Asn | Tyr | Phe | Arg | Asp | Ala | Trp | Asn | Phe | Val | Phe | Asp | Phe | Val | |
| | 290 | | | | | 295 | | | | | 300 | | | | | |
| ACT | GTG | TTG | GGA | AGT | ATT | ACT | GAT | ATT | TTA | GTA | ACA | GAG | ATT | GCG | | 957 |
| Thr | Val | Leu | Gly | Ser | Ile | Thr | Asp | Ile | Leu | Val | Thr | Glu | Ile | Ala | | |
| 305 | | | | | 310 | | | | | 315 | | | | | | |

( 2 ) INFORMATION FOR SEQ ID NO:17:

( i ) SEQUENCE CHARACTERISTICS:
( A ) LENGTH: 319 amino acids ( B ) TYPE: amino acid
( D ) TOPOLOGY: linear ( i i ) MOLECULE TYPE: protein ( x i ) SEQUENCE DESCRIPTION: SEQ ID NO:17:

| Ser | Lys | Gly | Lys | Asp | Ile | Asn | Thr | Ile | Lys | Ser | Leu | Arg | Val | Leu | Arg |
|---|---|---|---|---|---|---|---|---|---|---|---|---|---|---|---|
| 1 | | | | 5 | | | | | 10 | | | | | 15 | |

| Val | Leu | Arg | Pro | Leu | Lys | Thr | Ile | Lys | Arg | Leu | Pro | Lys | Leu | Lys | Ala |
|---|---|---|---|---|---|---|---|---|---|---|---|---|---|---|---|
| | | | 20 | | | | | 25 | | | | | 30 | | |

| Val | Phe | Asp | Cys | Val | Val | Asn | Ser | Leu | Lys | Asn | Val | Leu | Asn | Ile | Leu |
|---|---|---|---|---|---|---|---|---|---|---|---|---|---|---|---|
| | | 35 | | | | | 40 | | | | | 45 | | | |

| Ile | Val | Tyr | Met | Leu | Phe | Met | Phe | Ile | Phe | Ala | Val | Ile | Ala | Val | Gln |
|---|---|---|---|---|---|---|---|---|---|---|---|---|---|---|---|
| | 50 | | | | | 55 | | | | | 60 | | | | |

| Leu | Phe | Lys | Gly | Lys | Phe | Phe | Tyr | Cys | Thr | Asp | Glu | Ser | Lys | Glu | Leu |
|---|---|---|---|---|---|---|---|---|---|---|---|---|---|---|---|
| 65 | | | | | 70 | | | | | 75 | | | | | 80 |

| Glu | Arg | Asp | Cys | Arg | Gly | Gln | Tyr | Leu | Asp | Tyr | Glu | Lys | Glu | Glu | Val |
|---|---|---|---|---|---|---|---|---|---|---|---|---|---|---|---|
| | | | | 85 | | | | | 90 | | | | | 95 | |

| Glu | Ala | Gln | Pro | Arg | Gln | Trp | Lys | Lys | Tyr | Asp | Phe | His | Tyr | Asp | Asn |
|---|---|---|---|---|---|---|---|---|---|---|---|---|---|---|---|
| | | | 100 | | | | | 105 | | | | | 110 | | |

| Val | Leu | Trp | Ala | Leu | Leu | Thr | Leu | Phe | Thr | Val | Ser | Thr | Gly | Glu | Gly |
|---|---|---|---|---|---|---|---|---|---|---|---|---|---|---|---|
| | | | 115 | | | | | 120 | | | | | 125 | | |

| Trp | Pro | Met | Val | Leu | Lys | His | Ser | Val | Asp | Ala | Thr | Tyr | Glu | Glu | Gln |
|---|---|---|---|---|---|---|---|---|---|---|---|---|---|---|---|
| | | | 130 | | | | 135 | | | | | 140 | | | |

| Gly | Pro | Ser | Pro | Gly | Tyr | Arg | Met | Glu | Leu | Ser | Ile | Phe | Tyr | Val | Val |
|---|---|---|---|---|---|---|---|---|---|---|---|---|---|---|---|
| 145 | | | | | 150 | | | | | 155 | | | | | 160 |

| Tyr | Phe | Val | Val | Phe | Pro | Phe | Phe | Phe | Val | Asn | Ile | Phe | Val | Ala | Leu |
|---|---|---|---|---|---|---|---|---|---|---|---|---|---|---|---|
| | | | | 165 | | | | | 170 | | | | | 175 | |

| Ile | Ile | Ile | Thr | Phe | Gln | Glu | Gln | Gly | Asp | Lys | Val | Met | Ser | Glu | Cys |
|---|---|---|---|---|---|---|---|---|---|---|---|---|---|---|---|
| | | | 180 | | | | | 185 | | | | | 190 | | |

| Ser | Leu | Glu | Lys | Asn | Glu | Arg | Ala | Cys | Ile | Asp | Phe | Ala | Ile | Ser | Ala |
|---|---|---|---|---|---|---|---|---|---|---|---|---|---|---|---|
| | | 195 | | | | | 200 | | | | | 205 | | | |

| Lys | Pro | Leu | Thr | Arg | Tyr | Met | Pro | Gln | Asn | Arg | Gln | Ser | Phe | Gln | Tyr |
|---|---|---|---|---|---|---|---|---|---|---|---|---|---|---|---|
| | 210 | | | | | 215 | | | | | 220 | | | | |

| Lys | Thr | Trp | Thr | Phe | Val | Val | Ser | Pro | Pro | Phe | Glu | Tyr | Phe | Ile | Met |
|---|---|---|---|---|---|---|---|---|---|---|---|---|---|---|---|
| 225 | | | | | 230 | | | | | 235 | | | | | 240 |

| Ala | Met | Ile | Ala | Leu | Asn | Thr | Val | Val | Leu | Met | Met | Lys | Phe | Tyr | Asp |
|---|---|---|---|---|---|---|---|---|---|---|---|---|---|---|---|
| | | | | 245 | | | | | 250 | | | | | 255 | |

| Ala | Pro | Tyr | Glu | Tyr | Glu | Leu | Met | Leu | Lys | Cys | Leu | Asn | Ile | Val | Phe |
|---|---|---|---|---|---|---|---|---|---|---|---|---|---|---|---|
| | | | 260 | | | | | 265 | | | | | 270 | | |

| Thr | Ser | Met | Phe | Ser | Met | Glu | Cys | Val | Leu | Lys | Ile | Ile | Ala | Phe | Gly |
|---|---|---|---|---|---|---|---|---|---|---|---|---|---|---|---|
| | | 275 | | | | | 280 | | | | | 285 | | | |

| Val | Leu | Asn | Tyr | Phe | Arg | Asp | Ala | Trp | Asn | Phe | Val | Phe | Asp | Phe | Val |
|---|---|---|---|---|---|---|---|---|---|---|---|---|---|---|---|
| | 290 | | | | | 295 | | | | | 300 | | | | |

| Thr | Val | Leu | Gly | Ser | Ile | Thr | Asp | Ile | Leu | Val | Thr | Glu | Ile | Ala |
|---|---|---|---|---|---|---|---|---|---|---|---|---|---|---|
| 305 | | | | | 310 | | | | | 315 | | | | |

( 2 ) INFORMATION FOR SEQ ID NO:18:

( i ) SEQUENCE CHARACTERISTICS:
( A ) LENGTH: 1546 base pairs
( B ) TYPE: nucleic acid
( C ) STRANDEDNESS: unknown
( D ) TOPOLOGY: unknown ( i i ) MOLECULE TYPE: DNA (genomic)

( i x ) FEATURE:
( A ) NAME/KEY: CDS ( B ) LOCATION: 1..1434

( x i ) SEQUENCE DESCRIPTION: SEQ ID NO:18:

| ATG | GTC | CAG | AAG | ACC | AGC | ATG | TCC | CGG | GGC | CCT | TAC | CCA | CCC | TCC | CAG | 48 |
| Met | Val | Gln | Lys | Thr | Ser | Met | Ser | Arg | Gly | Pro | Tyr | Pro | Pro | Ser | Gln | |
| 1 | | | | 5 | | | | | 10 | | | | | 15 | | |

| GAG | ATC | CCC | ATG | GGA | GTC | TTC | GAC | CCC | AGC | CCG | CAG | GGC | AAA | TAC | AGC | 96 |
| Glu | Ile | Pro | Met | Gly | Val | Phe | Asp | Pro | Ser | Pro | Gln | Gly | Lys | Tyr | Ser | |
| | | | 20 | | | | | 25 | | | | | 30 | | | |

| AAG | AGG | AAA | GGG | CGA | TTC | AAA | CGG | TCA | GAT | GGG | AGC | ACG | TCC | TCG | GAT | 144 |
| Lys | Arg | Lys | Gly | Arg | Phe | Lys | Arg | Ser | Asp | Gly | Ser | Thr | Ser | Ser | Asp | |
| | | 35 | | | | | 40 | | | | | 45 | | | | |

| ACC | ACA | TCC | AAC | AGC | TTT | GTC | CGC | CAG | GGC | TCA | GCG | GAG | TCC | TAC | ACC | 192 |
| Thr | Thr | Ser | Asn | Ser | Phe | Val | Arg | Gln | Gly | Ser | Ala | Glu | Ser | Tyr | Thr | |
| | 50 | | | | | 55 | | | | | 60 | | | | | |

| AGC | CGT | CCA | TCA | GAC | TCT | GAT | GTA | TCT | CTG | GAG | GAG | GAC | CGG | GAA | GCC | 240 |
| Ser | Arg | Pro | Ser | Asp | Ser | Asp | Val | Ser | Leu | Glu | Glu | Asp | Arg | Glu | Ala | |
| 65 | | | | | 70 | | | | | 75 | | | | | 80 | |

| TTA | AGG | AAG | GAA | GCA | GAG | CGC | CAG | GCA | TTA | GCG | CAG | CTC | GAG | AAG | GCC | 288 |
| Leu | Arg | Lys | Glu | Ala | Glu | Arg | Gln | Ala | Leu | Ala | Gln | Leu | Glu | Lys | Ala | |
| | | | | 85 | | | | | 90 | | | | | 95 | | |

| AAG | ACC | AAG | CCA | GTG | GCA | TTT | GCT | GTG | CGG | ACA | AAT | GTT | GGC | TAC | AAT | 336 |
| Lys | Thr | Lys | Pro | Val | Ala | Phe | Ala | Val | Arg | Thr | Asn | Val | Gly | Tyr | Asn | |
| | | | 100 | | | | | 105 | | | | | 110 | | | |

| CCG | TCT | CCA | GGG | GAT | GAG | GTG | CCT | GTG | CAG | GGA | GTG | GCC | ATC | ACC | TTC | 384 |
| Pro | Ser | Pro | Gly | Asp | Glu | Val | Pro | Val | Gln | Gly | Val | Ala | Ile | Thr | Phe | |
| | | 115 | | | | | 120 | | | | | 125 | | | | |

| GAG | CCC | AAA | GAC | TTC | CTG | CAC | ATC | AAG | GAG | AAA | TAC | AAT | AAT | GAC | TGG | 432 |
| Glu | Pro | Lys | Asp | Phe | Leu | His | Ile | Lys | Glu | Lys | Tyr | Asn | Asn | Asp | Trp | |
| | 130 | | | | | 135 | | | | | 140 | | | | | |

| TGG | ATC | GGG | CGG | CTG | GTG | AAG | GAG | GGC | TGT | GAG | GTT | GGC | TTC | ATT | CCC | 480 |
| Trp | Ile | Gly | Arg | Leu | Val | Lys | Glu | Gly | Cys | Glu | Val | Gly | Phe | Ile | Pro | |
| 145 | | | | | 150 | | | | | 155 | | | | | 160 | |

| AGC | CCC | GTC | AAA | CTG | GAC | AGC | CTT | CGC | CTG | CTG | CAG | GAA | CAG | AAG | CTG | 528 |
| Ser | Pro | Val | Lys | Leu | Asp | Ser | Leu | Arg | Leu | Leu | Gln | Glu | Gln | Lys | Leu | |
| | | | | 165 | | | | | 170 | | | | | 175 | | |

| CGC | CAG | AAC | CGC | CTC | GGC | TCC | AGC | AAA | TCA | GGC | GAT | AAC | TCC | AGT | TCC | 576 |
| Arg | Gln | Asn | Arg | Leu | Gly | Ser | Ser | Lys | Ser | Gly | Asp | Asn | Ser | Ser | Ser | |
| | | | 180 | | | | | 185 | | | | | 190 | | | |

| AGT | CTG | GGA | GAT | GTG | GTG | ACT | GGC | ACC | CGC | CGC | CCC | ACA | CCC | CCT | GCC | 624 |
| Ser | Leu | Gly | Asp | Val | Val | Thr | Gly | Thr | Arg | Arg | Pro | Thr | Pro | Pro | Ala | |
| | | 195 | | | | | 200 | | | | | 205 | | | | |

| AGT | GCC | AAA | CAG | AAG | CAG | AAG | TCG | ACA | GAG | CAT | GTG | CCC | CCC | TAT | GAC | 672 |
| Ser | Ala | Lys | Gln | Lys | Gln | Lys | Ser | Thr | Glu | His | Val | Pro | Pro | Tyr | Asp | |
| | 210 | | | | | 215 | | | | | 220 | | | | | |

| GTG | GTG | CCT | TCC | ATG | AGG | CCC | ATC | ATC | CTG | GTG | GGA | CCG | TCG | CTC | AAG | 720 |
| Val | Val | Pro | Ser | Met | Arg | Pro | Ile | Ile | Leu | Val | Gly | Pro | Ser | Leu | Lys | |
| 225 | | | | | 230 | | | | | 235 | | | | | 240 | |

| GGC | TAC | GAG | GTT | ACA | GAC | ATG | ATG | CAG | AAA | GCT | TTA | TTT | GAC | TTC | TTG | 768 |
| Gly | Tyr | Glu | Val | Thr | Asp | Met | Met | Gln | Lys | Ala | Leu | Phe | Asp | Phe | Leu | |
| | | | | 245 | | | | | 250 | | | | | 255 | | |

| AAG | CAT | CGG | TTT | GAT | GGC | AGG | ATC | TCC | ATC | ACT | CGT | GTG | ACG | GCA | GAT | 816 |
| Lys | His | Arg | Phe | Asp | Gly | Arg | Ile | Ser | Ile | Thr | Arg | Val | Thr | Ala | Asp | |
| | | | 260 | | | | | 265 | | | | | 270 | | | |

| ATT | TCC | CTG | GCT | AAG | CGC | TCA | GTT | CTC | AAC | AAC | CCC | AGC | AAA | CAC | ATC | 864 |
| Ile | Ser | Leu | Ala | Lys | Arg | Ser | Val | Leu | Asn | Asn | Pro | Ser | Lys | His | Ile | |
| | | 275 | | | | | 280 | | | | | 285 | | | | |

| ATC | ATT | GAG | CGC | TCC | AAC | ACA | CGC | TCC | AGC | CTG | GCT | GAG | GTG | CAG | AGT | 912 |
| Ile | Ile | Glu | Arg | Ser | Asn | Thr | Arg | Ser | Ser | Leu | Ala | Glu | Val | Gln | Ser | |
| | 290 | | | | | 295 | | | | | 300 | | | | | |

| | | | | | | | | | | | | | | | | |
|---|---|---|---|---|---|---|---|---|---|---|---|---|---|---|---|---|
| GAA | ATC | GAG | CGA | ATC | TTC | GAG | CTG | GCC | CGG | ACC | CTT | CAG | TTG | GTC | GCT | 960 |
| Glu | Ile | Glu | Arg | Ile | Phe | Glu | Leu | Ala | Arg | Thr | Leu | Gln | Leu | Val | Ala | |
| 305 | | | | 310 | | | | | 315 | | | | | | 320 | |
| CTG | GAT | GCT | GAC | ACC | ATC | AAT | CAC | CCA | GCC | CAG | CTG | TCC | AAG | ACC | TCG | 1008 |
| Leu | Asp | Ala | Asp | Thr | Ile | Asn | His | Pro | Ala | Gln | Leu | Ser | Lys | Thr | Ser | |
| | | | | 325 | | | | | 330 | | | | | 335 | | |
| CTG | GCC | CCC | ATC | ATT | GTT | TAC | ATC | AAG | ATC | ACC | TCT | CCC | AAG | GTA | CTT | 1056 |
| Leu | Ala | Pro | Ile | Ile | Val | Tyr | Ile | Lys | Ile | Thr | Ser | Pro | Lys | Val | Leu | |
| | | | 340 | | | | | 345 | | | | | 350 | | | |
| CAA | AGG | CTC | ATC | AAG | TCC | CGA | GGA | AAG | TCT | CAG | TCC | AAA | CAC | CTC | AAT | 1104 |
| Gln | Arg | Leu | Ile | Lys | Ser | Arg | Gly | Lys | Ser | Gln | Ser | Lys | His | Leu | Asn | |
| | | 355 | | | | | 360 | | | | | 365 | | | | |
| GTC | CAA | ATA | GCG | GCC | TCG | GAA | AAG | CTG | GCA | CAG | TGC | CCC | CCT | GAA | ATG | 1152 |
| Val | Gln | Ile | Ala | Ala | Ser | Glu | Lys | Leu | Ala | Gln | Cys | Pro | Pro | Glu | Met | |
| | 370 | | | | | 375 | | | | | 380 | | | | | |
| TTT | GAC | ATC | ATC | CTG | GAT | GAG | AAC | CAA | TTG | GAG | GAT | GCC | TGC | GAG | CAT | 1200 |
| Phe | Asp | Ile | Ile | Leu | Asp | Glu | Asn | Gln | Leu | Glu | Asp | Ala | Cys | Glu | His | |
| 385 | | | | | 390 | | | | | 395 | | | | | 400 | |
| CTG | GCG | GAG | TAC | TTG | GAA | GCC | TAT | TGG | AAG | GCC | ACA | CAC | CCG | CCC | AGC | 1248 |
| Leu | Ala | Glu | Tyr | Leu | Glu | Ala | Tyr | Trp | Lys | Ala | Thr | His | Pro | Pro | Ser | |
| | | | | 405 | | | | | 410 | | | | | 415 | | |
| AGC | ACG | CCA | CCC | AAT | CCG | CTG | CTG | AAC | CGC | ACC | ATG | GCT | ACC | GCA | GCC | 1296 |
| Ser | Thr | Pro | Pro | Asn | Pro | Leu | Leu | Asn | Arg | Thr | Met | Ala | Thr | Ala | Ala | |
| | | | 420 | | | | | 425 | | | | | 430 | | | |
| CTG | GCT | GCC | AGC | CCT | GCC | CCT | GTC | TCC | AAC | CTC | CAG | GTA | CAG | GTG | CTC | 1344 |
| Leu | Ala | Ala | Ser | Pro | Ala | Pro | Val | Ser | Asn | Leu | Gln | Val | Gln | Val | Leu | |
| | | 435 | | | | | 440 | | | | | 445 | | | | |
| ACC | TCG | CTC | AGG | AGA | AAC | CTC | GGC | TTC | TGG | GGC | GGG | CTG | GAG | TCC | TCA | 1392 |
| Thr | Ser | Leu | Arg | Arg | Asn | Leu | Gly | Phe | Trp | Gly | Gly | Leu | Glu | Ser | Ser | |
| | 450 | | | | | 455 | | | | | 460 | | | | | |
| CAG | CGG | GGC | AGT | GTG | GTG | CCC | CAG | GAG | CAG | GAA | CAT | GCC | ATG | | | 1434 |
| Gln | Arg | Gly | Ser | Val | Val | Pro | Gln | Glu | Gln | Glu | His | Ala | Met | | | |
| 465 | | | | 470 | | | | | 475 | | | | | | | |

TAGTGGGCGC CCTGCCCGTC TTCCCTCCTG CTCTGGGGTC GGAACTGGAG TGCAGGGAAC    1494

ATGGAGGAGG AAGGGAAGAG CTTTATTTTG TAAAAAAATA AGATGAGCGG CA            1546

( 2 ) INFORMATION FOR SEQ ID NO:19:

( i ) SEQUENCE CHARACTERISTICS:
        ( A ) LENGTH: 478 amino acids
        ( B ) TYPE: amino acid
        ( D ) TOPOLOGY: linear ( i i ) MOLECULE TYPE: protein ( x i ) SEQUENCE DESCRIPTION: SEQ ID NO:19:

| | | | | | | | | | | | | | | |
|---|---|---|---|---|---|---|---|---|---|---|---|---|---|---|
| Met | Val | Gln | Lys | Thr | Ser | Met | Ser | Arg | Gly | Pro | Tyr | Pro | Pro | Ser | Gln |
| 1 | | | | 5 | | | | | 10 | | | | | 15 | |
| Glu | Ile | Pro | Met | Gly | Val | Phe | Asp | Pro | Ser | Pro | Gln | Gly | Lys | Tyr | Ser |
| | | | 20 | | | | | 25 | | | | | 30 | | |
| Lys | Arg | Lys | Gly | Arg | Phe | Lys | Arg | Ser | Asp | Gly | Ser | Thr | Ser | Ser | Asp |
| | | 35 | | | | | 40 | | | | | 45 | | | |
| Thr | Thr | Ser | Asn | Ser | Phe | Val | Arg | Gln | Gly | Ser | Ala | Glu | Ser | Tyr | Thr |
| | 50 | | | | | 55 | | | | | 60 | | | | |
| Ser | Arg | Pro | Ser | Asp | Ser | Asp | Val | Ser | Leu | Glu | Glu | Asp | Arg | Glu | Ala |
| 65 | | | | | 70 | | | | | 75 | | | | | 80 |
| Leu | Arg | Lys | Glu | Ala | Glu | Arg | Gln | Ala | Leu | Ala | Gln | Leu | Glu | Lys | Ala |
| | | | | 85 | | | | | 90 | | | | | 95 | |
| Lys | Thr | Lys | Pro | Val | Ala | Phe | Ala | Val | Arg | Thr | Asn | Val | Gly | Tyr | Asn |
| | | | 100 | | | | | 105 | | | | | 110 | | |

| | | | | | | | | | | | | | |
|---|---|---|---|---|---|---|---|---|---|---|---|---|---|
|Pro|Ser|Pro|Gly|Asp|Glu|Val|Pro|Val|Gln|Gly|Val|Ala|Ile|Thr|Phe|
| | |115| | | |120| | | | |125| | | |
|Glu|Pro|Lys|Asp|Phe|Leu|His|Ile|Lys|Glu|Lys|Tyr|Asn|Asn|Asp|Trp|
| |130| | | | |135| | | |140| | | | |
|Trp|Ile|Gly|Arg|Leu|Val|Lys|Glu|Gly|Cys|Glu|Val|Gly|Phe|Ile|Pro|
|145| | | | |150| | | |155| | | | |160|
|Ser|Pro|Val|Lys|Leu|Asp|Ser|Leu|Arg|Leu|Leu|Gln|Glu|Gln|Lys|Leu|
| | | | |165| | | |170| | | | |175| |
|Arg|Gln|Asn|Arg|Leu|Gly|Ser|Ser|Lys|Ser|Gly|Asp|Asn|Ser|Ser|Ser|
| | | |180| | | |185| | | | |190| | |
|Ser|Leu|Gly|Asp|Val|Val|Thr|Gly|Thr|Arg|Arg|Pro|Thr|Pro|Pro|Ala|
| | |195| | | |200| | | | |205| | | |
|Ser|Ala|Lys|Gln|Lys|Gln|Lys|Ser|Thr|Glu|His|Val|Pro|Pro|Tyr|Asp|
| |210| | | | |215| | | |220| | | | |
|Val|Val|Pro|Ser|Met|Arg|Pro|Ile|Ile|Leu|Val|Gly|Pro|Ser|Leu|Lys|
|225| | | | |230| | | |235| | | | |240|
|Gly|Tyr|Glu|Val|Thr|Asp|Met|Met|Gln|Lys|Ala|Leu|Phe|Asp|Phe|Leu|
| | | |245| | | |250| | | | |255| | |
|Lys|His|Arg|Phe|Asp|Gly|Arg|Ile|Ser|Ile|Thr|Arg|Val|Thr|Ala|Asp|
| | |260| | | |265| | | | |270| | | |
|Ile|Ser|Leu|Ala|Lys|Arg|Ser|Val|Leu|Asn|Pro|Ser|Lys|His|Ile|
| | |275| | | |280| | | |285| | | | |
|Ile|Ile|Glu|Arg|Ser|Asn|Thr|Arg|Ser|Ser|Leu|Ala|Glu|Val|Gln|Ser|
| |290| | | | |295| | | | |300| | | |
|Glu|Ile|Glu|Arg|Ile|Phe|Glu|Leu|Ala|Arg|Thr|Leu|Gln|Leu|Val|Ala|
|305| | | | |310| | | | |315| | | | |320|
|Leu|Asp|Ala|Asp|Thr|Ile|Asn|His|Pro|Ala|Gln|Leu|Ser|Lys|Thr|Ser|
| | | |325| | | |330| | | | |335| | |
|Leu|Ala|Pro|Ile|Ile|Val|Tyr|Ile|Lys|Ile|Thr|Ser|Pro|Lys|Val|Leu|
| | | |340| | | |345| | | | |350| | |
|Gln|Arg|Leu|Ile|Lys|Ser|Arg|Gly|Lys|Ser|Gln|Ser|Lys|His|Leu|Asn|
| |355| | | | |360| | | | |365| | | |
|Val|Gln|Ile|Ala|Ala|Ser|Glu|Lys|Leu|Ala|Gln|Cys|Pro|Pro|Glu|Met|
| |370| | | | |375| | | | |380| | | |
|Phe|Asp|Ile|Ile|Leu|Asp|Glu|Asn|Gln|Leu|Glu|Asp|Ala|Cys|Glu|His|
|385| | | | |390| | | | |395| | | | |400|
|Leu|Ala|Glu|Tyr|Leu|Glu|Ala|Tyr|Trp|Lys|Ala|Thr|His|Pro|Pro|Ser|
| | | | |405| | | |410| | | | |415| |
|Ser|Thr|Pro|Pro|Asn|Pro|Leu|Leu|Asn|Arg|Thr|Met|Ala|Thr|Ala|Ala|
| | | |420| | | |425| | | | |430| | |
|Leu|Ala|Ala|Ser|Pro|Ala|Pro|Val|Ser|Asn|Leu|Gln|Val|Gln|Val|Leu|
| | |435| | | |440| | | | |445| | | |
|Thr|Ser|Leu|Arg|Arg|Asn|Leu|Gly|Phe|Trp|Gly|Gly|Leu|Glu|Ser|Ser|
| |450| | | | |455| | | | |460| | | |
|Gln|Arg|Gly|Ser|Val|Val|Pro|Gln|Glu|Gln|Glu|His|Ala|Met|
|465| | | | |470| | | | |475| | | |

( 2 ) INFORMATION FOR SEQ ID NO:20:

( i ) SEQUENCE CHARACTERISTICS:
        ( A ) LENGTH: 65 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:20:

| TAAGTTGGGT | GCTTTGTGTT | AAGCAACACT | CTGGTTCGTC | CAAGTGCACT | TTCCAGTCCC | 60 |
| TCTCC | | | | | | 65 |

( 2 ) INFORMATION FOR SEQ ID NO:21:

( i ) SEQUENCE CHARACTERISTICS:
        ( A ) LENGTH: 448 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:21:

| GTGAGTGCCT | AGATCCCAGA | GAAGGGAATG | GAGGGAGAAC | ATTTGGGTTG | TCCTGGTTTC | 60 |
| CTCTGGCCTA | CATGAGAGAC | AGGGTGACCA | GGAACACCTG | GGTCAGGCCT | GTGGGTGCAG | 120 |
| ACTGGTCTTC | TGGGAAGAGC | GCAGGTCCCG | TCAGTCAAAG | ACTGGGTTCA | AGCCCAGAA | 180 |
| GCACCCTTCT | GCGTGGAGAG | TCAAGCCCTG | TCTCCCAGCC | TTGGTTGCCT | TATCTCTAGA | 240 |
| ATGAGGGAGT | TGGACTGAGT | GCCAAAACTT | CTTGCAGTTC | TGCCAATCTG | TAGATCTGAG | 300 |
| AGCTCTCCTT | CCCTTCTACA | TCCAGAGGCC | TCTTTTTAAC | CTTGTCCTTC | AATCCCTTGA | 360 |
| CTCTACCCAC | TGCACCCAGG | CCACACCCTC | AACCCCTTG | GCCATGCCCC | ACTCATCCA | 420 |
| GCCCTGCCCC | CTAACCCCGC | CTTCACAG | | | | 448 |

( 2 ) INFORMATION FOR SEQ ID NO:22:

( i ) SEQUENCE CHARACTERISTICS:
        ( A ) LENGTH: 1515 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:22:

| AAGGAAGCAG | AGCGCCAGGC | ATTAGCGCAC | GTCGAGAAGG | CCAAGACCAA | GCCAGTGGCA | 60 |
| TTTGCTGTGC | GGACAAATGT | TGGCTACAAT | CCGTCTCCAG | GGGATGAGGT | GCCTGTGCAG | 120 |
| GGAGTGGCCA | TCACCTTCGA | GCCCAAAGAC | TTCCTGCACA | TCAAGGAGAA | ATACAATAAT | 180 |
| GACTGGTGGA | TCGGGCGGCT | GGTGAAGGAG | GGCTGTGAGG | TTGGCTTCAT | TCCCAGCCCC | 240 |
| GTCAAACTGG | ACAGCCTTCG | CCTGCTGCAG | GAACAGAAGC | TGCGCCAGAA | CCGCCTCGGC | 300 |
| TCCAGCAAAT | CAGGCGATAA | CTCCAGTTCC | AGTCTGGGAG | ATGTGGTGAC | TGGCACCCGC | 360 |
| CGCCCCACAC | CCCCTGCCAG | TGCCAAACAG | AAGCAGAAGT | CGACAGAGCA | TGTGCCCCCC | 420 |
| TATGACGTGG | TGCCTTCCAT | GAGGCCCATC | ATCCTGGTGG | GACCGTCGCT | CAAGGGCTAC | 480 |
| GAGGTTACAG | ACATGATGCA | GAAAGCTTTA | TTTGACTTCT | TGAAGCATCG | GTTTGATGGC | 540 |
| AGGATCTCCA | TCACTCGTGT | GACGGCAGAT | ATTTCCCTGG | CTAAGCGCTC | AGTTCTCAAC | 600 |
| AACCCCAGCA | AACACATCAT | CATTGAGCGC | TCCAACACAC | GCTCCAGCCT | GGCTGAGGTG | 660 |
| CAGAGTGAAA | TCGAGCGAAT | CTTCGAGCTG | GCCCGGACCC | TTCAGTTGGT | CGCTCTGGAT | 720 |
| GCTGACACCA | TCAATCACCC | AGCCCAGCTG | TCCAAGACCT | CGCTGGCCCC | CATCATTGTT | 780 |
| TACATCAAGA | TCACCTCTCC | CAAGGTACTT | CAAAGGCTCA | TCAAGTCCCG | AGGAAAGTCT | 840 |
| CAGTCCAAAC | ACCTCAATGT | CCAAATAGCG | GCCTCGGAAA | AGCTGGCACA | GTGCCCCCCT | 900 |
| GAAATGTTTG | ACATCATCCT | GGATGAGAAC | CAATTGGAGG | ATGCCTGCGA | GCATCTGGCG | 960 |

-continued

```
GAGTACTTGG   AAGCCTATTG   GAAGGCCACA   CACCCGCCCA   GCAGCACGCC   ACCCAATCCG       1 0 2 0

CTGCTGAACC   GCACCATGGC   TACCGCAGCC   CTGGCTGCCA   GCCCTGCCCC   TGTCTCCAAC       1 0 8 0

CTCCAGCCAC   CCTACCTTCC   TTCCGGGACC   AGCCACTGGA   ACGGCCCACC   NNGGAGCACG       1 1 4 0

CCAGCATGCA   CGAGTACTCA   GGGGAGCTGG   GCCAGCCCCA   GGCCTTTACC   CCAGCAGCCA       1 2 0 0

CCCACCAGGC   CGGGCAGGCA   CGCTAGGGCA   CTGTCCCGCC   AAGACACTTT   TGATGCCGAC       1 2 6 0

ACCCCCGGCA   GCCGAAACTC   TGCCTACACG   GAGCTGGGAG   ACTCATGTGT   GGACATGGAG       1 3 2 0

ACTGACCCCT   CAGAGGGGCC   AGGGCTTGGA   GACCCTGCAG   GGGGCGGCAC   GCCCCCAGCC       1 3 8 0

CGACAGGGAT   CCTGGGAGGA   CGAGGAAGAA   GACTATGAGG   AAGAGCTGAC   CGACAACCGG       1 4 4 0

AACCGGGGCC   GGAATAAGGC   CCGCTACTGC   GCTGAGGGTG   GGGTCCAGT    TTTGGGGCGC       1 5 0 0

AACAAGAATG   AGGGA                                                               1 5 1 5
```

( 2 ) INFORMATION FOR SEQ ID NO:23:

( i ) SEQUENCE CHARACTERISTICS:
( A ) LENGTH: 505 amino acids
( B ) TYPE: amino acid
( C ) STRANDEDNESS: unknown
( D ) TOPOLOGY: unknown ( i i ) MOLECULE TYPE: peptide ( x i ) SEQUENCE DESCRIPTION: SEQ ID NO:23:

```
Lys  Glu  Ala  Glu  Arg  Gln  Ala  Leu  Ala  His  Val  Glu  Lys  Ala  Lys  Thr
 1              5                         10                          15

Lys  Pro  Val  Ala  Phe  Ala  Val  Arg  Thr  Asn  Val  Gly  Tyr  Asn  Pro  Ser
                20                        25                        30

Pro  Gly  Asp  Glu  Val  Pro  Val  Gln  Gly  Val  Ala  Ile  Thr  Phe  Glu  Pro
           35                        40                        45

Lys  Asp  Phe  Leu  His  Ile  Lys  Glu  Lys  Tyr  Asn  Asn  Asp  Trp  Trp  Ile
      50                        55                        60

Gly  Arg  Leu  Val  Lys  Glu  Gly  Cys  Glu  Val  Gly  Phe  Ile  Pro  Ser  Pro
 65                      70                        75                       80

Val  Lys  Leu  Asp  Ser  Leu  Arg  Leu  Leu  Gln  Glu  Gln  Lys  Leu  Arg  Gln
                85                        90                        95

Asn  Arg  Leu  Gly  Ser  Ser  Lys  Ser  Gly  Asp  Asn  Ser  Ser  Ser  Ser  Leu
               100                       105                       110

Gly  Asp  Val  Val  Thr  Gly  Thr  Arg  Arg  Pro  Thr  Pro  Pro  Ala  Ser  Ala
               115                       120                       125

Lys  Gln  Lys  Gln  Lys  Ser  Thr  Glu  His  Val  Pro  Pro  Tyr  Asp  Val  Val
          130                       135                       140

Pro  Ser  Met  Arg  Pro  Ile  Ile  Leu  Val  Gly  Pro  Ser  Leu  Lys  Gly  Tyr
145                       150                       155                       160

Glu  Val  Thr  Asp  Met  Met  Gln  Lys  Ala  Leu  Phe  Asp  Phe  Leu  Lys  His
                     165                       170                       175

Arg  Phe  Asp  Gly  Arg  Ile  Ser  Ile  Thr  Arg  Val  Thr  Ala  Asp  Ile  Ser
               180                       185                       190

Leu  Ala  Lys  Arg  Ser  Val  Leu  Asn  Asn  Pro  Ser  Lys  His  Ile  Ile  Ile
          195                       200                       205

Glu  Arg  Ser  Asn  Thr  Arg  Ser  Ser  Leu  Ala  Glu  Val  Gln  Ser  Glu  Ile
     210                       215                       220

Glu  Arg  Ile  Phe  Glu  Leu  Ala  Arg  Thr  Leu  Gln  Leu  Val  Ala  Leu  Asp
225                       230                       235                       240

Ala  Asp  Thr  Ile  Asn  His  Pro  Ala  Gln  Leu  Ser  Lys  Thr  Ser  Leu  Ala
```

|   |   |   |   | 245 |   |   |   | 250 |   |   |   | 255 |   |   |
|---|---|---|---|---|---|---|---|---|---|---|---|---|---|---|
| Pro | Ile | Ile | Val | Tyr | Ile | Lys | Ile | Thr | Ser | Pro | Lys | Val | Leu | Gln | Arg |
|   |   |   | 260 |   |   |   | 265 |   |   |   | 270 |   |   |   |
| Leu | Ile | Lys | Ser | Arg | Gly | Lys | Ser | Gln | Ser | Lys | His | Leu | Asn | Val | Gln |
|   |   | 275 |   |   |   | 280 |   |   |   | 285 |   |   |   |   |
| Ile | Ala | Ala | Ser | Glu | Lys | Leu | Ala | Gln | Cys | Pro | Pro | Glu | Met | Phe | Asp |
|   | 290 |   |   |   | 295 |   |   |   | 300 |   |   |   |   |   |
| Ile | Ile | Leu | Asp | Glu | Asn | Gln | Leu | Glu | Asp | Ala | Cys | Glu | His | Leu | Ala |
| 305 |   |   |   | 310 |   |   |   | 315 |   |   |   |   |   | 320 |
| Glu | Tyr | Leu | Glu | Ala | Tyr | Trp | Lys | Ala | Thr | His | Pro | Pro | Ser | Ser | Thr |
|   |   |   | 325 |   |   |   | 330 |   |   |   |   | 335 |   |   |
| Pro | Pro | Asn | Pro | Leu | Leu | Asn | Arg | Thr | Met | Ala | Thr | Ala | Ala | Leu | Ala |
|   |   |   | 340 |   |   |   | 345 |   |   |   | 350 |   |   |   |
| Ala | Ser | Pro | Ala | Pro | Val | Ser | Asn | Leu | Gln | Pro | Pro | Tyr | Leu | Pro | Ser |
|   |   | 355 |   |   |   | 360 |   |   |   |   | 365 |   |   |   |
| Gly | Thr | Ser | His | Trp | Asn | Gly | Pro | Pro | Xaa | Ser | Thr | Pro | Ala | Cys | Thr |
|   | 370 |   |   |   |   | 375 |   |   |   | 380 |   |   |   |   |
| Ser | Thr | Gln | Gly | Ser | Trp | Ala | Ser | Pro | Arg | Pro | Leu | Pro | Gln | Gln | Pro |
| 385 |   |   |   |   | 390 |   |   |   | 395 |   |   |   |   | 400 |
| Pro | Thr | Arg | Pro | Gly | Arg | His | Ala | Arg | Ala | Leu | Ser | Arg | Gln | Asp | Thr |
|   |   |   | 405 |   |   |   | 410 |   |   |   | 415 |   |   |   |
| Phe | Asp | Ala | Asp | Thr | Pro | Gly | Ser | Arg | Asn | Ser | Ala | Tyr | Thr | Glu | Leu |
|   |   | 420 |   |   |   | 425 |   |   |   | 430 |   |   |   |   |
| Gly | Asp | Ser | Cys | Val | Asp | Met | Glu | Thr | Asp | Pro | Ser | Glu | Gly | Pro | Gly |
|   | 435 |   |   |   | 440 |   |   |   | 445 |   |   |   |   |   |
| Leu | Gly | Asp | Pro | Ala | Gly | Gly | Thr | Pro | Pro | Ala | Arg | Gln | Gly | Ser |   |
|   | 450 |   |   |   | 455 |   |   |   | 460 |   |   |   |   |   |
| Trp | Glu | Asp | Glu | Glu | Glu | Asp | Tyr | Glu | Glu | Glu | Leu | Thr | Asp | Asn | Arg |
| 465 |   |   |   | 470 |   |   |   | 475 |   |   |   |   | 480 |   |
| Asn | Arg | Gly | Arg | Asn | Lys | Ala | Arg | Tyr | Cys | Ala | Glu | Gly | Gly | Gly | Pro |
|   |   |   | 485 |   |   |   | 490 |   |   |   |   | 495 |   |   |
| Val | Leu | Gly | Arg | Asn | Lys | Asn | Glu | Gly |   |   |   |   |   |   |
|   |   |   | 500 |   |   |   | 505 |   |   |   |   |   |   |   |

( 2 ) INFORMATION FOR SEQ ID NO:24:

( i ) SEQUENCE CHARACTERISTICS:
        ( A ) LENGTH: 3566 base pairs
        ( B ) TYPE: nucleic acid
        ( C ) STRANDEDNESS: unknown
        ( D ) TOPOLOGY: unknown ( i i ) MOLECULE TYPE: DNA (genomic)

( i x ) FEATURE:
        ( A ) NAME/KEY: CDS
        ( B ) LOCATION: 1..3273

( x i ) SEQUENCE DESCRIPTION: SEQ ID NO:24:

| ATG | GCT | GCT | GGC | TGC | CTG | CTG | GCC | TTG | ACT | CTG | ACA | CTT | TTC | CAA | TCT | 48 |
|---|---|---|---|---|---|---|---|---|---|---|---|---|---|---|---|---|
| Met | Ala | Ala | Gly | Cys | Leu | Leu | Ala | Leu | Thr | Leu | Thr | Leu | Phe | Gln | Ser |   |
| 1 |   |   |   | 5 |   |   |   |   | 10 |   |   |   |   | 15 |   |   |

| TTG | CTC | ATC | GGC | CCC | TCG | TCG | GAG | GAG | CCG | TTC | CCT | TCG | GCC | GTC | ACT | 96 |
|---|---|---|---|---|---|---|---|---|---|---|---|---|---|---|---|---|
| Leu | Leu | Ile | Gly | Pro | Ser | Ser | Glu | Glu | Pro | Phe | Pro | Ser | Ala | Val | Thr |   |
|   |   |   | 20 |   |   |   | 25 |   |   |   |   | 30 |   |   |   |   |

| ATC | AAA | TCA | TGG | GTG | GAT | AAG | ATG | CAA | GAA | GAC | CTT | GTC | ACA | CTG | GCA | 144 |
|---|---|---|---|---|---|---|---|---|---|---|---|---|---|---|---|---|
| Ile | Lys | Ser | Trp | Val | Asp | Lys | Met | Gln | Glu | Asp | Leu | Val | Thr | Leu | Ala |   |
|   |   | 35 |   |   |   |   | 40 |   |   |   |   | 45 |   |   |   |   |

| AAA | ACA | GCA | AGT | GGA | GTC | AAT | CAG | CTT | GTT | GAT | ATT | TAT | GAG | AAA | TAT | 192 |

|  |  |  |  |  |  |  |  |  |  |  |  |  |  |  |  |  |
|---|---|---|---|---|---|---|---|---|---|---|---|---|---|---|---|---|
| Lys | Thr | Ala | Ser | Gly | Val | Asn | Gln | Leu | Val | Asp | Ile | Tyr | Glu | Lys | Tyr | |
| | 50 | | | | 55 | | | | | 60 | | | | | | |

```
CAA  GAT  TTG  TAT  ACT  GTG  GAA  CCA  AAT  AAT  GCA  CGC  CAG  CTG  GTA  GAA      240
Gln  Asp  Leu  Tyr  Thr  Val  Glu  Pro  Asn  Asn  Ala  Arg  Gln  Leu  Val  Glu
65                   70                   75                        80

ATT  GCA  GCC  AGG  GAT  ATT  GAG  AAA  CTT  CTG  AGC  AAC  AGA  TCT  AAA  GCC      288
Ile  Ala  Ala  Arg  Asp  Ile  Glu  Lys  Leu  Leu  Ser  Asn  Arg  Ser  Lys  Ala
                    85                        90                        95

CTG  GTG  AGC  CTG  GCA  TTG  GAA  GCG  GAG  AAA  GTT  CAA  GCA  GCT  CAC  CAG      336
Leu  Val  Ser  Leu  Ala  Leu  Glu  Ala  Glu  Lys  Val  Gln  Ala  Ala  His  Gln
                    100                       105                       110

TGG  AGA  GAA  GAT  TTT  GCA  AGC  AAT  GAA  GTT  GTC  TAC  TAC  AAT  GCA  AAG      384
Trp  Arg  Glu  Asp  Phe  Ala  Ser  Asn  Glu  Val  Val  Tyr  Tyr  Asn  Ala  Lys
               115                       120                       125

GAT  GAT  CTC  GAT  CCT  GAG  AAA  AAT  GAC  AGT  GAG  CCA  GGC  AGC  CAG  AGG      432
Asp  Asp  Leu  Asp  Pro  Glu  Lys  Asn  Asp  Ser  Glu  Pro  Gly  Ser  Gln  Arg
130                      135                       140

ATA  AAA  CCT  GTT  TTC  ATT  GAA  GAT  GCT  AAT  TTT  GGA  CGA  CAA  ATA  TCT      480
Ile  Lys  Pro  Val  Phe  Ile  Glu  Asp  Ala  Asn  Phe  Gly  Arg  Gln  Ile  Ser
145                      150                       155                       160

TAT  CAG  CAC  GCA  GCA  GTC  CAT  ATT  CCT  ACT  GAC  ATC  TAT  GAG  GGC  TCA      528
Tyr  Gln  His  Ala  Ala  Val  His  Ile  Pro  Thr  Asp  Ile  Tyr  Glu  Gly  Ser
                    165                       170                       175

ACA  ATT  GTG  TTA  AAT  GAA  CTC  AAC  TGG  ACA  AGT  GCC  TTA  GAT  GAA  GTT      576
Thr  Ile  Val  Leu  Asn  Glu  Leu  Asn  Trp  Thr  Ser  Ala  Leu  Asp  Glu  Val
                    180                       185                       190

TTC  AAA  AAG  AAT  CGC  GAG  GAA  GAC  CCT  TCA  TTA  TTG  TGG  CAG  GTT  TTT      624
Phe  Lys  Lys  Asn  Arg  Glu  Glu  Asp  Pro  Ser  Leu  Leu  Trp  Gln  Val  Phe
               195                       200                       205

GGC  AGT  GCC  ACT  GGC  CTA  GCT  CGA  TAT  TAT  CCA  GCT  TCA  CCA  TGG  GTT      672
Gly  Ser  Ala  Thr  Gly  Leu  Ala  Arg  Tyr  Tyr  Pro  Ala  Ser  Pro  Trp  Val
     210                       215                       220

GAT  AAT  AGT  AGA  ACT  CCA  AAT  AAG  ATT  GAC  CTT  TAT  GAT  GTA  CGC  AGA      720
Asp  Asn  Ser  Arg  Thr  Pro  Asn  Lys  Ile  Asp  Leu  Tyr  Asp  Val  Arg  Arg
225                      230                       235                       240

AGA  CCA  TGG  TAC  ATC  CAA  GGA  GCT  GCA  TCT  CCT  AAA  GAC  ATG  CTT  ATT      768
Arg  Pro  Trp  Tyr  Ile  Gln  Gly  Ala  Ala  Ser  Pro  Lys  Asp  Met  Leu  Ile
                    245                       250                       255

CTG  GTG  GAT  GTG  AGT  GGA  AGT  GTT  AGT  GGA  TTG  ACA  CTT  AAA  CTG  ATC      816
Leu  Val  Asp  Val  Ser  Gly  Ser  Val  Ser  Gly  Leu  Thr  Leu  Lys  Leu  Ile
                    260                       265                       270

CGA  ACA  TCT  GTC  TCC  GAA  ATG  TTA  GAA  ACC  CTC  TCA  GAT  GAT  GAT  TTC      864
Arg  Thr  Ser  Val  Ser  Glu  Met  Leu  Glu  Thr  Leu  Ser  Asp  Asp  Asp  Phe
          275                       280                       285

GTG  AAT  GTA  GCT  TCA  TTT  AAC  AGC  AAT  GCT  CAG  GAT  GTA  AGC  TGT  TTT      912
Val  Asn  Val  Ala  Ser  Phe  Asn  Ser  Asn  Ala  Gln  Asp  Val  Ser  Cys  Phe
     290                       295                       300

CAG  CAC  CTT  GTC  CAA  GCA  AAT  GTA  AGA  AAT  AAA  AAA  GTG  TTG  AAA  GAC      960
Gln  His  Leu  Val  Gln  Ala  Asn  Val  Arg  Asn  Lys  Lys  Val  Leu  Lys  Asp
305                      310                       315                       320

GCG  GTG  AAT  AAT  ATC  ACA  GCC  AAA  GGA  ATT  ACA  GAT  TAT  AAG  AAG  GGC     1008
Ala  Val  Asn  Asn  Ile  Thr  Ala  Lys  Gly  Ile  Thr  Asp  Tyr  Lys  Lys  Gly
                    325                       330                       335

TTT  AGT  TTT  GCT  TTT  GAA  CAG  CTG  CTT  AAT  TAT  AAT  GTT  TCC  AGA  GCA     1056
Phe  Ser  Phe  Ala  Phe  Glu  Gln  Leu  Leu  Asn  Tyr  Asn  Val  Ser  Arg  Ala
               340                       345                       350

AAC  TGC  AAT  AAG  ATT  ATT  ATG  CTA  TTC  ACG  GAT  GGA  GGA  GAA  GAG  AGA     1104
Asn  Cys  Asn  Lys  Ile  Ile  Met  Leu  Phe  Thr  Asp  Gly  Gly  Glu  Glu  Arg
          355                       360                       365

GCC  CAG  GAG  ATA  TTT  AAC  AAA  TAC  AAT  AAA  GAT  AAA  AAA  GTA  CGT  GTA     1152
```

|  |  |  |  |  |  |  |  |  |  |  |  |  |  |  |  |
|---|---|---|---|---|---|---|---|---|---|---|---|---|---|---|---|
| Ala | Gln | Glu | Ile | Phe | Asn | Lys | Tyr | Asn | Lys | Asp | Lys | Lys | Val | Arg | Val |
|  | 370 |  |  |  | 375 |  |  |  |  | 380 |  |  |  |  |  |

| TTC | AGG | TTT | TCA | GTT | GGT | CAA | CAC | AAT | TAT | GAG | AGA | GGA | CCT | ATT | CAG | 1200 |
|---|---|---|---|---|---|---|---|---|---|---|---|---|---|---|---|---|
| Phe | Arg | Phe | Ser | Val | Gly | Gln | His | Asn | Tyr | Glu | Arg | Gly | Pro | Ile | Gln |  |
| 385 |  |  |  | 390 |  |  |  |  | 395 |  |  |  |  |  | 400 |  |

| TGG | ATG | GCC | TGT | GAA | AAC | AAA | GGT | TAT | TAT | TAT | GAA | ATT | CCT | TCC | ATT | 1248 |
|---|---|---|---|---|---|---|---|---|---|---|---|---|---|---|---|---|
| Trp | Met | Ala | Cys | Glu | Asn | Lys | Gly | Tyr | Tyr | Tyr | Glu | Ile | Pro | Ser | Ile |  |
|  |  |  |  | 405 |  |  |  |  | 410 |  |  |  |  | 415 |  |  |

| GGT | GCA | ATA | AGA | ATC | AAT | ACT | CAG | GAA | TAT | TTG | GAT | GTT | TTG | GGA | AGA | 1296 |
|---|---|---|---|---|---|---|---|---|---|---|---|---|---|---|---|---|
| Gly | Ala | Ile | Arg | Ile | Asn | Thr | Gln | Glu | Tyr | Leu | Asp | Val | Leu | Gly | Arg |  |
|  |  |  | 420 |  |  |  | 425 |  |  |  |  |  | 430 |  |  |  |

| CCA | ATG | GTT | TTA | GCA | GGA | GAC | AAA | GCT | AAG | CAA | GTC | CAA | TGG | ACA | AAT | 1344 |
|---|---|---|---|---|---|---|---|---|---|---|---|---|---|---|---|---|
| Pro | Met | Val | Leu | Ala | Gly | Asp | Lys | Ala | Lys | Gln | Val | Gln | Trp | Thr | Asn |  |
|  | 435 |  |  |  |  | 440 |  |  |  |  | 445 |  |  |  |  |  |

| GTG | TAC | CTG | GAT | GCA | TTG | GAA | CTG | GGA | CTT | GTC | ATT | ACT | GGA | ACT | CTT | 1392 |
|---|---|---|---|---|---|---|---|---|---|---|---|---|---|---|---|---|
| Val | Tyr | Leu | Asp | Ala | Leu | Glu | Leu | Gly | Leu | Val | Ile | Thr | Gly | Thr | Leu |  |
|  | 450 |  |  |  |  | 455 |  |  |  |  | 460 |  |  |  |  |  |

| CCG | GTC | TTC | AAC | ATA | ACC | GGC | CAA | TTT | GAA | AAT | AAG | ACA | AAC | TTA | AAG | 1440 |
|---|---|---|---|---|---|---|---|---|---|---|---|---|---|---|---|---|
| Pro | Val | Phe | Asn | Ile | Thr | Gly | Gln | Phe | Glu | Asn | Lys | Thr | Asn | Leu | Lys |  |
| 465 |  |  |  |  | 470 |  |  |  |  | 475 |  |  |  |  | 480 |  |

| AAC | CAG | CTG | ATT | CTT | GGT | GTG | ATG | GGA | GTA | GAT | GTG | TCT | TTG | GAA | GAT | 1488 |
|---|---|---|---|---|---|---|---|---|---|---|---|---|---|---|---|---|
| Asn | Gln | Leu | Ile | Leu | Gly | Val | Met | Gly | Val | Asp | Val | Ser | Leu | Glu | Asp |  |
|  |  |  |  | 485 |  |  |  |  | 490 |  |  |  |  | 495 |  |  |

| ATT | AAA | AGA | CTG | ACA | CCA | CGT | TTT | ACA | CTG | TGC | CCC | AAT | GGG | TAT | TAC | 1536 |
|---|---|---|---|---|---|---|---|---|---|---|---|---|---|---|---|---|
| Ile | Lys | Arg | Leu | Thr | Pro | Arg | Phe | Thr | Leu | Cys | Pro | Asn | Gly | Tyr | Tyr |  |
|  |  |  | 500 |  |  |  | 505 |  |  |  |  | 510 |  |  |  |  |

| TTT | GCA | ATC | GAT | CCT | AAT | GGT | TAT | GTT | TTA | TTA | CAT | CCA | AAT | CTT | CAG | 1584 |
|---|---|---|---|---|---|---|---|---|---|---|---|---|---|---|---|---|
| Phe | Ala | Ile | Asp | Pro | Asn | Gly | Tyr | Val | Leu | Leu | His | Pro | Asn | Leu | Gln |  |
|  |  | 515 |  |  |  |  | 520 |  |  |  |  | 525 |  |  |  |  |

| CCA | AAG | AAC | CCC | AAA | TCT | CAG | GAG | CCA | GTA | ACA | TTG | GAT | TTC | CTT | GAT | 1632 |
|---|---|---|---|---|---|---|---|---|---|---|---|---|---|---|---|---|
| Pro | Lys | Asn | Pro | Lys | Ser | Gln | Glu | Pro | Val | Thr | Leu | Asp | Phe | Leu | Asp |  |
|  | 530 |  |  |  |  | 535 |  |  |  |  | 540 |  |  |  |  |  |

| GCA | GAG | TTA | GAG | AAT | GAT | ATT | AAA | GTG | GAG | ATT | CGA | AAT | AAG | ATG | ATT | 1680 |
|---|---|---|---|---|---|---|---|---|---|---|---|---|---|---|---|---|
| Ala | Glu | Leu | Glu | Asn | Asp | Ile | Lys | Val | Glu | Ile | Arg | Asn | Lys | Met | Ile |  |
| 545 |  |  |  |  | 550 |  |  |  |  | 555 |  |  |  |  | 560 |  |

| GAT | GGG | GAA | AGT | GGA | GAA | AAA | ACA | TTC | AGA | ACT | CTG | GTT | AAA | TCT | CAA | 1728 |
|---|---|---|---|---|---|---|---|---|---|---|---|---|---|---|---|---|
| Asp | Gly | Glu | Ser | Gly | Glu | Lys | Thr | Phe | Arg | Thr | Leu | Val | Lys | Ser | Gln |  |
|  |  |  |  | 565 |  |  |  |  | 570 |  |  |  |  | 575 |  |  |

| GAT | GAG | AGA | TAT | ATT | GAC | AAA | GGA | AAC | AGG | ACA | TAC | ACA | TGG | ACA | CCT | 1776 |
|---|---|---|---|---|---|---|---|---|---|---|---|---|---|---|---|---|
| Asp | Glu | Arg | Tyr | Ile | Asp | Lys | Gly | Asn | Arg | Thr | Tyr | Thr | Trp | Thr | Pro |  |
|  |  |  | 580 |  |  |  |  | 585 |  |  |  |  | 590 |  |  |  |

| GTC | AAT | GGC | ACA | GAT | TAC | AGT | TTG | GCC | TTG | GTA | TTA | CCA | ACC | TAC | AGT | 1824 |
|---|---|---|---|---|---|---|---|---|---|---|---|---|---|---|---|---|
| Val | Asn | Gly | Thr | Asp | Tyr | Ser | Leu | Ala | Leu | Val | Leu | Pro | Thr | Tyr | Ser |  |
|  |  | 595 |  |  |  |  | 600 |  |  |  |  | 605 |  |  |  |  |

| TTT | TAC | TAT | ATA | AAA | GCC | AAA | CTA | GAA | GAG | ACA | ATA | ACT | CAG | GCC | AGA | 1872 |
|---|---|---|---|---|---|---|---|---|---|---|---|---|---|---|---|---|
| Phe | Tyr | Tyr | Ile | Lys | Ala | Lys | Leu | Glu | Glu | Thr | Ile | Thr | Gln | Ala | Arg |  |
| 610 |  |  |  |  | 615 |  |  |  |  | 620 |  |  |  |  |  |  |

| TCA | AAA | AAG | GGC | AAA | ATG | AAG | GAT | TCG | GAA | ACC | CTG | AAG | CCA | GAT | AAT | 1920 |
|---|---|---|---|---|---|---|---|---|---|---|---|---|---|---|---|---|
| Ser | Lys | Lys | Gly | Lys | Met | Lys | Asp | Ser | Glu | Thr | Leu | Lys | Pro | Asp | Asn |  |
| 625 |  |  |  |  | 630 |  |  |  |  | 635 |  |  |  |  | 640 |  |

| TTT | GAA | GAA | TCT | GGC | TAT | ACA | TTC | ATA | GCA | CCA | AGA | GAT | TAC | TGC | AAT | 1968 |
|---|---|---|---|---|---|---|---|---|---|---|---|---|---|---|---|---|
| Phe | Glu | Glu | Ser | Gly | Tyr | Thr | Phe | Ile | Ala | Pro | Arg | Asp | Tyr | Cys | Asn |  |
|  |  |  |  | 645 |  |  |  |  | 650 |  |  |  |  | 655 |  |  |

| GAC | CTG | AAA | ATA | TCG | GAT | AAT | AAC | ACT | GAA | TTT | CTT | TTA | AAT | TTC | AAC | 2016 |
|---|---|---|---|---|---|---|---|---|---|---|---|---|---|---|---|---|
| Asp | Leu | Lys | Ile | Ser | Asp | Asn | Asn | Thr | Glu | Phe | Leu | Leu | Asn | Phe | Asn |  |
|  |  |  | 660 |  |  |  |  | 665 |  |  |  |  | 670 |  |  |  |

| GAG | TTT | ATT | GAT | AGA | AAA | ACT | CCA | AAC | AAC | CCA | TCA | TGT | AAC | GCG | GAT | 2064 |
|---|---|---|---|---|---|---|---|---|---|---|---|---|---|---|---|---|
| Glu | Phe | Ile | Asp | Arg | Lys | Thr | Pro | Asn | Asn | Pro | Ser | Cys | Asn | Ala | Asp |  |
|  |  | 675 |  |  |  |  | 680 |  |  |  |  | 685 |  |  |  |  |

| TTG | ATT | AAT | AGA | GTC | TTG | CTT | GAT | GCA | GGC | TTT | ACA | AAT | GAA | CTT | GTC | 2112 |

```
                Leu  Ile  Asn  Arg  Val  Leu  Leu  Asp  Ala  Gly  Phe  Thr  Asn  Glu  Leu  Val
                     690                 695                      700

CAA  AAT  TAC  TGG  AGT  AAG  CAG  AAA  AAT  ATC  AAG  GGA  GTG  AAA  GCA  CGA          2160
Gln  Asn  Tyr  Trp  Ser  Lys  Gln  Lys  Asn  Ile  Lys  Gly  Val  Lys  Ala  Arg
705                 710                 715                      720

TTT  GTT  GTG  ACT  GAT  GGT  GGG  ATT  ACC  AGA  GTT  TAT  CCC  AAA  GAG  GCT          2208
Phe  Val  Val  Thr  Asp  Gly  Gly  Ile  Thr  Arg  Val  Tyr  Pro  Lys  Glu  Ala
                    725                 730                      735

GGA  GAA  AAT  TGG  CAA  GAA  AAC  CCA  GAG  ACA  TAT  GAG  GAC  AGC  TTC  TAT          2256
Gly  Glu  Asn  Trp  Gln  Glu  Asn  Pro  Glu  Thr  Tyr  Glu  Asp  Ser  Phe  Tyr
               740                 745                      750

AAA  AGG  AGC  CTA  GAT  AAT  GAT  AAC  TAT  GTT  TTC  ACT  GCT  CCC  TAC  TTT          2304
Lys  Arg  Ser  Leu  Asp  Asn  Asp  Asn  Tyr  Val  Phe  Thr  Ala  Pro  Tyr  Phe
               755                 760                      765

AAC  AAA  AGT  GGA  CCT  GGT  GCC  TAT  GAA  TCG  GGC  ATT  ATG  GTA  AGC  AAA          2352
Asn  Lys  Ser  Gly  Pro  Gly  Ala  Tyr  Glu  Ser  Gly  Ile  Met  Val  Ser  Lys
          770                 775                      780

GCT  GTA  GAA  ATA  TAT  ATT  CAA  GGG  AAA  CTT  CTT  AAA  CCT  GCA  GTT  GTT          2400
Ala  Val  Glu  Ile  Tyr  Ile  Gln  Gly  Lys  Leu  Leu  Lys  Pro  Ala  Val  Val
785                 790                 795                      800

GGA  ATT  AAA  ATT  GAT  GTA  AAT  TCC  TGG  ATA  GAG  AAT  TTC  ACC  AAA  ACC          2448
Gly  Ile  Lys  Ile  Asp  Val  Asn  Ser  Trp  Ile  Glu  Asn  Phe  Thr  Lys  Thr
                    805                 810                      815

TCA  ATC  AGA  GAT  CCG  TGT  GCT  GGT  CCA  GTT  TGT  GAC  TGC  AAA  AGA  AAC          2496
Ser  Ile  Arg  Asp  Pro  Cys  Ala  Gly  Pro  Val  Cys  Asp  Cys  Lys  Arg  Asn
               820                 825                      830

AGT  GAC  GTA  ATG  GAT  TGT  GTG  ATT  CTG  GAT  GAT  GGT  GGG  TTT  CTT  CTG          2544
Ser  Asp  Val  Met  Asp  Cys  Val  Ile  Leu  Asp  Asp  Gly  Gly  Phe  Leu  Leu
          835                 840                      845

ATG  GCA  AAT  CAT  GAT  GAT  TAT  ACT  AAT  CAG  ATT  GGA  AGA  TTT  TTT  GGA          2592
Met  Ala  Asn  His  Asp  Asp  Tyr  Thr  Asn  Gln  Ile  Gly  Arg  Phe  Phe  Gly
850                 855                      860

GAG  ATT  GAT  CCC  AGC  TTG  ATG  AGA  CAC  CTG  GTT  AAT  ATA  TCA  GTT  TAT          2640
Glu  Ile  Asp  Pro  Ser  Leu  Met  Arg  His  Leu  Val  Asn  Ile  Ser  Val  Tyr
865                 870                 875                      880

GCT  TTT  AAC  AAA  TCT  TAT  GAT  TAT  CAG  TCA  GTA  TGT  GAG  CCC  GGT  GCT          2688
Ala  Phe  Asn  Lys  Ser  Tyr  Asp  Tyr  Gln  Ser  Val  Cys  Glu  Pro  Gly  Ala
               885                 890                      895

GCA  CCA  AAA  CAA  GGA  GCA  GGA  CAT  CGC  TCA  GCA  TAT  GTG  CCA  TCA  GTA          2736
Ala  Pro  Lys  Gln  Gly  Ala  Gly  His  Arg  Ser  Ala  Tyr  Val  Pro  Ser  Val
          900                 905                      910

GCA  GAC  ATA  TTA  CAA  ATT  GGC  TGG  TGG  GCC  ACT  GCT  GCT  GCC  TGG  TCT          2784
Ala  Asp  Ile  Leu  Gln  Ile  Gly  Trp  Trp  Ala  Thr  Ala  Ala  Ala  Trp  Ser
               915                 920                      925

ATT  CTA  CAG  CAG  TTT  CTC  TTG  AGT  TTG  ACC  TTT  CCA  CGA  CTC  CTT  GAG          2832
Ile  Leu  Gln  Gln  Phe  Leu  Leu  Ser  Leu  Thr  Phe  Pro  Arg  Leu  Leu  Glu
     930                 935                      940

GCA  GTT  GAG  ATG  GAG  GAT  GAT  GAC  TTC  ACG  GCC  TCC  CTG  TCC  AAG  CAG          2880
Ala  Val  Glu  Met  Glu  Asp  Asp  Asp  Phe  Thr  Ala  Ser  Leu  Ser  Lys  Gln
945                 950                      955                 960

AGC  TGC  ATT  ACT  GAA  CAA  ACC  CAG  TAT  TTC  TTC  GAT  AAC  GAC  AGT  AAA          2928
Ser  Cys  Ile  Thr  Glu  Gln  Thr  Gln  Tyr  Phe  Phe  Asp  Asn  Asp  Ser  Lys
               965                 970                      975

TCA  TTC  AGT  GGT  GTA  TTA  GAC  TGT  GGA  AAC  TGT  TCC  AGA  ATC  TTT  CAT          2976
Ser  Phe  Ser  Gly  Val  Leu  Asp  Cys  Gly  Asn  Cys  Ser  Arg  Ile  Phe  His
          980                 985                      990

GGA  GAA  AAG  CTT  ATG  AAC  ACC  AAC  TTA  ATA  TTC  ATA  ATG  GTT  GAG  AGC          3024
Gly  Glu  Lys  Leu  Met  Asn  Thr  Asn  Leu  Ile  Phe  Ile  Met  Val  Glu  Ser
               995                 1000                    1005

AAA  GGG  ACA  TGT  CCA  TGT  GAC  ACA  CGA  CTG  CTC  ATA  CAA  GCG  GAG  CAG          3072
```

|     |     |     |     |     |     |     |     |     |     |     |     |     |     |     |     |
| --- | --- | --- | --- | --- | --- | --- | --- | --- | --- | --- | --- | --- | --- | --- | --- |
| Lys | Gly | Thr | Cys | Pro | Cys | Asp | Thr | Arg | Leu | Leu | Ile | Gln | Ala | Glu | Gln |
|     |     | 1010 |     |     |     | 1015 |     |     |     |     | 1020 |     |     |     |     |

```
ACT TCT GAC GGT CCA AAT CCT TGT GAC ATG GTT AAG CAA CCT AGA TAC      3120
Thr Ser Asp Gly Pro Asn Pro Cys Asp Met Val Lys Gln Pro Arg Tyr
1025            1030                1035                1040

CGA AAA GGG CCT GAT GTC TGC TTT GAT AAC AAT GTC TTG GAG GAT TAT      3168
Arg Lys Gly Pro Asp Val Cys Phe Asp Asn Asn Val Leu Glu Asp Tyr
                1045                1050                1055

ACT GAC TGT GGT GGT GTT TCT GGA TTA AAT CCC TCC CTG TGG TAT ATC      3216
Thr Asp Cys Gly Gly Val Ser Gly Leu Asn Pro Ser Leu Trp Tyr Ile
            1060                1065                1070

ATT GGA ATC CAG TTT CTA CTA CTT TGG CTG GTA TCT GGC AGC ACA CAC      3264
Ile Gly Ile Gln Phe Leu Leu Leu Trp Leu Val Ser Gly Ser Thr His
        1075                1080                1085

CGG CTG TTA TGACCTTCTA AAAACCAAAT CTGCATAGTT AAACTCCAGA              3313
Arg Leu Leu
    1090

CCCTGCCAAA ACATGAGCCC TGCCCTCAAT TACAGTAACG TAGGGTCAGC TATAAAATCA    3373
GACAAACATT AGCTGGGCCT GTTCCATGGC ATAACACTAA GGCGCAGACT CCTAAGGCAC    3433
CCACTGGCTG CATGTCAGGG TGTCAGATCC TTAAACGTGT GTGAATGCTG CATCATCTAT    3493
GTGTAACATC AAAGCAAAAT CCTATACGTG TCCTCTATTG GAAAATTTGG GCGTTTGTTG    3553
TTGCATTGTT GGT                                                       3566
```

( 2 ) INFORMATION FOR SEQ ID NO:25:

( i ) SEQUENCE CHARACTERISTICS:
        ( A ) LENGTH: 1091 amino acids
        ( B ) TYPE: amino acid
        ( D ) TOPOLOGY: linear ( i i ) MOLECULE TYPE: protein ( x i ) SEQUENCE DESCRIPTION: SEQ ID NO:25:

```
Met Ala Ala Gly Cys Leu Leu Ala Leu Thr Leu Thr Leu Phe Gln Ser
 1               5                  10                  15

Leu Leu Ile Gly Pro Ser Ser Glu Glu Pro Phe Pro Ser Ala Val Thr
            20                  25                  30

Ile Lys Ser Trp Val Asp Lys Met Gln Glu Asp Leu Val Thr Leu Ala
        35                  40                  45

Lys Thr Ala Ser Gly Val Asn Gln Leu Val Asp Ile Tyr Glu Lys Tyr
    50                  55                  60

Gln Asp Leu Tyr Thr Val Glu Pro Asn Asn Ala Arg Gln Leu Val Glu
65                  70                  75                  80

Ile Ala Ala Arg Asp Ile Glu Lys Leu Leu Ser Asn Arg Ser Lys Ala
                85                  90                  95

Leu Val Ser Leu Ala Leu Glu Ala Glu Lys Val Gln Ala Ala His Gln
            100                 105                 110

Trp Arg Glu Asp Phe Ala Ser Asn Glu Val Val Tyr Tyr Asn Ala Lys
        115                 120                 125

Asp Asp Leu Asp Pro Glu Lys Asn Asp Ser Glu Pro Gly Ser Gln Arg
    130                 135                 140

Ile Lys Pro Val Phe Ile Glu Asp Ala Asn Phe Gly Arg Gln Ile Ser
145                 150                 155                 160

Tyr Gln His Ala Ala Val His Ile Pro Thr Asp Ile Tyr Glu Gly Ser
                165                 170                 175

Thr Ile Val Leu Asn Glu Leu Asn Trp Thr Ser Ala Leu Asp Glu Val
            180                 185                 190
```

Phe Lys Lys Asn Arg Glu Glu Asp Pro Ser Leu Leu Trp Gln Val Phe
            195                     200                 205

Gly Ser Ala Thr Gly Leu Ala Arg Tyr Tyr Pro Ala Ser Pro Trp Val
        210                 215                 220

Asp Asn Ser Arg Thr Pro Asn Lys Ile Asp Leu Tyr Asp Val Arg Arg
225                 230                 235                 240

Arg Pro Trp Tyr Ile Gln Gly Ala Ala Ser Pro Lys Asp Met Leu Ile
                245                 250                 255

Leu Val Asp Val Ser Gly Ser Val Ser Gly Leu Thr Leu Lys Leu Ile
            260                 265                 270

Arg Thr Ser Val Ser Glu Met Leu Glu Thr Leu Ser Asp Asp Phe
        275                 280                 285

Val Asn Val Ala Ser Phe Asn Ser Asn Ala Gln Asp Val Ser Cys Phe
    290                 295                 300

Gln His Leu Val Gln Ala Asn Val Arg Asn Lys Lys Val Leu Lys Asp
305                 310                 315                 320

Ala Val Asn Asn Ile Thr Ala Lys Gly Ile Thr Asp Tyr Lys Lys Gly
                325                 330                 335

Phe Ser Phe Ala Phe Glu Gln Leu Leu Asn Tyr Asn Val Ser Arg Ala
            340                 345                 350

Asn Cys Asn Lys Ile Ile Met Leu Phe Thr Asp Gly Gly Glu Glu Arg
        355                 360                 365

Ala Gln Glu Ile Phe Asn Lys Tyr Asn Lys Asp Lys Lys Val Arg Val
    370                 375                 380

Phe Arg Phe Ser Val Gly Gln His Asn Tyr Glu Arg Gly Pro Ile Gln
385                 390                 395                 400

Trp Met Ala Cys Glu Asn Lys Gly Tyr Tyr Tyr Glu Ile Pro Ser Ile
                405                 410                 415

Gly Ala Ile Arg Ile Asn Thr Gln Glu Tyr Leu Asp Val Leu Gly Arg
            420                 425                 430

Pro Met Val Leu Ala Gly Asp Lys Ala Lys Gln Val Gln Trp Thr Asn
        435                 440                 445

Val Tyr Leu Asp Ala Leu Glu Leu Gly Leu Val Ile Thr Gly Thr Leu
    450                 455                 460

Pro Val Phe Asn Ile Thr Gly Gln Phe Glu Asn Lys Thr Asn Leu Lys
465                 470                 475                 480

Asn Gln Leu Ile Leu Gly Val Met Gly Val Asp Val Ser Leu Glu Asp
                485                 490                 495

Ile Lys Arg Leu Thr Pro Arg Phe Thr Leu Cys Pro Asn Gly Tyr Tyr
            500                 505                 510

Phe Ala Ile Asp Pro Asn Gly Tyr Val Leu Leu His Pro Asn Leu Gln
        515                 520                 525

Pro Lys Asn Pro Lys Ser Gln Glu Pro Val Thr Leu Asp Phe Leu Asp
    530                 535                 540

Ala Glu Leu Glu Asn Asp Ile Lys Val Glu Ile Arg Asn Lys Met Ile
545                 550                 555                 560

Asp Gly Glu Ser Gly Glu Lys Thr Phe Arg Thr Leu Val Lys Ser Gln
                565                 570                 575

Asp Glu Arg Tyr Ile Asp Lys Gly Asn Arg Thr Tyr Thr Trp Thr Pro
            580                 585                 590

Val Asn Gly Thr Asp Tyr Ser Leu Ala Leu Val Leu Pro Thr Tyr Ser
        595                 600                 605

Phe Tyr Tyr Ile Lys Ala Lys Leu Glu Glu Thr Ile Thr Gln Ala Arg

-continued

|     | 610 |     |     |     | 615 |     |     |     | 620 |     |     |     |     |
|-----|-----|-----|-----|-----|-----|-----|-----|-----|-----|-----|-----|-----|-----|
| Ser 625 | Lys | Lys | Gly | Lys | Met 630 | Lys | Asp | Ser | Glu | Thr 635 | Leu | Lys | Pro | Asp 640 |
| Phe | Glu | Glu | Ser | Gly 645 | Tyr | Thr | Phe | Ile | Ala 650 | Pro | Arg | Asp | Tyr | Cys 655 | Asn |
| Asp | Leu | Lys | Ile 660 | Ser | Asp | Asn | Asn | Thr 665 | Glu | Phe | Leu | Leu 670 | Asn | Phe | Asn |
| Glu | Phe | Ile 675 | Asp | Arg | Lys | Thr | Pro 680 | Asn | Asn | Pro | Ser | Cys 685 | Asn | Ala | Asp |
| Leu | Ile | Asn 690 | Arg | Val | Leu | Leu 695 | Asp | Ala | Gly | Phe | Thr 700 | Asn | Glu | Leu | Val |
| Gln 705 | Asn | Tyr | Trp | Ser | Lys 710 | Gln | Lys | Asn | Ile | Lys 715 | Gly | Val | Lys | Ala | Arg 720 |
| Phe | Val | Val | Thr | Asp 725 | Gly | Gly | Ile | Thr | Arg 730 | Val | Tyr | Pro | Lys | Glu 735 | Ala |
| Gly | Glu | Asn | Trp 740 | Gln | Glu | Asn | Pro | Glu 745 | Thr | Tyr | Glu | Asp | Ser 750 | Phe | Tyr |
| Lys | Arg | Ser 755 | Leu | Asp | Asn | Asp | Asn 760 | Tyr | Val | Phe | Thr | Ala 765 | Pro | Tyr | Phe |
| Asn | Lys 770 | Ser | Gly | Pro | Gly | Ala 775 | Tyr | Glu | Ser | Gly | Ile 780 | Met | Val | Ser | Lys |
| Ala 785 | Val | Glu | Ile | Tyr | Ile 790 | Gln | Gly | Lys | Leu | Leu 795 | Lys | Pro | Ala | Val | Val 800 |
| Gly | Ile | Lys | Ile | Asp 805 | Val | Asn | Ser | Trp | Ile 810 | Glu | Asn | Phe | Thr | Lys 815 | Thr |
| Ser | Ile | Arg | Asp 820 | Pro | Cys | Ala | Gly | Pro 825 | Val | Cys | Asp | Cys | Lys 830 | Arg | Asn |
| Ser | Asp | Val 835 | Met | Asp | Cys | Val | Ile 840 | Leu | Asp | Asp | Gly | Gly 845 | Phe | Leu | Leu |
| Met | Ala 850 | Asn | His | Asp | Asp | Tyr 855 | Thr | Asn | Gln | Ile | Gly 860 | Arg | Phe | Phe | Gly |
| Glu 865 | Ile | Asp | Pro | Ser | Leu 870 | Met | Arg | His | Leu | Val 875 | Asn | Ile | Ser | Val | Tyr 880 |
| Ala | Phe | Asn | Lys | Ser 885 | Tyr | Asp | Tyr | Gln | Ser 890 | Val | Cys | Glu | Pro | Gly 895 | Ala |
| Ala | Pro | Lys | Gln 900 | Gly | Ala | Gly | His | Arg 905 | Ser | Ala | Tyr | Val | Pro 910 | Ser | Val |
| Ala | Asp | Ile 915 | Leu | Gln | Ile | Gly | Trp 920 | Trp | Ala | Thr | Ala | Ala 925 | Trp | Ser |
| Ile | Leu | Gln 930 | Gln | Phe | Leu | Leu 935 | Ser | Leu | Thr | Phe | Pro 940 | Arg | Leu | Leu | Glu |
| Ala | Val 945 | Glu | Met | Glu | Asp 950 | Asp | Phe | Thr | Ala | Ser 955 | Leu | Ser | Lys | Gln 960 |
| Ser | Cys | Ile | Thr | Glu 965 | Gln | Thr | Gln | Tyr | Phe 970 | Phe | Asp | Asn | Asp | Ser 975 | Lys |
| Ser | Phe | Ser | Gly 980 | Val | Leu | Asp | Cys | Gly 985 | Asn | Cys | Ser | Arg | Ile 990 | Phe | His |
| Gly | Glu | Lys 995 | Leu | Met | Asn | Thr | Asn 1000 | Leu | Ile | Phe | Ile | Met 1005 | Val | Glu | Ser |
| Lys | Gly | Thr 1010 | Cys | Pro | Cys | Asp | Thr 1015 | Arg | Leu | Leu | Ile | Gln 1020 | Ala | Glu | Gln |
| Thr 1025 | Ser | Asp | Gly | Pro | Asn 1030 | Pro | Cys | Asp | Met | Val 1035 | Lys | Gln | Pro | Arg | Tyr 1040 |

```
Arg  Lys  Gly  Pro  Asp  Val  Cys  Phe  Asp  Asn  Asn  Val  Leu  Glu  Asp  Tyr
               1045                1050                     1055

Thr  Asp  Cys  Gly  Gly  Val  Ser  Gly  Leu  Asn  Pro  Ser  Leu  Trp  Tyr  Ile
               1060                1065                     1070

Ile  Gly  Ile  Gln  Phe  Leu  Leu  Leu  Trp  Leu  Val  Ser  Gly  Ser  Thr  His
               1075                1080                     1085

Arg  Leu  Leu
     1090
```

( 2 ) INFORMATION FOR SEQ ID NO:26:

( i ) SEQUENCE CHARACTERISTICS:
        ( A ) LENGTH: 34 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:26:

```
GCGGGGGAGG  GGGCATTGAT  CTTCGATCGC  GAAG                                        34
```

( 2 ) INFORMATION FOR SEQ ID NO:27:

( i ) SEQUENCE CHARACTERISTICS:
        ( A ) LENGTH: 156 base pairs
        ( B ) TYPE: nucleic acid
        ( C ) STRANDEDNESS: unknown
        ( D ) TOPOLOGY: unknown ( i i ) MOLECULE TYPE: DNA (genomic)

( i x ) FEATURE:
        ( A ) NAME/KEY: CDS
        ( B ) LOCATION: 1..156

( x i ) SEQUENCE DESCRIPTION: SEQ ID NO:27:

```
GGT  AAT  GAA  ATG  ACT  AAC  TTA  GCC  TTT  GAA  CTA  GAC  CCC  CTA  GAG  TTA     48
Gly  Asn  Glu  Met  Thr  Asn  Leu  Ala  Phe  Glu  Leu  Asp  Pro  Leu  Glu  Leu
  1                  5                      10                      15

GAG  GAG  GAA  GAG  GCT  GAG  CTT  GGT  GAG  CAG  AGT  GGC  TCT  GCC  AAG  ACT     96
Glu  Glu  Glu  Glu  Ala  Glu  Leu  Gly  Glu  Gln  Ser  Gly  Ser  Ala  Lys  Thr
                    20                      25                      30

AGT  GTT  AGC  AGT  GTC  ACC  ACC  CCG  CCA  CCC  CAT  GGC  AAA  CGC  ATC  CCC    144
Ser  Val  Ser  Ser  Val  Thr  Thr  Pro  Pro  Pro  His  Gly  Lys  Arg  Ile  Pro
               35                      40                      45

TTC  TTT  AAG  AAG                                                                 156
Phe  Phe  Lys  Lys
 50
```

( 2 ) INFORMATION FOR SEQ ID NO:28:

( i ) SEQUENCE CHARACTERISTICS:
        ( A ) LENGTH: 52 amino acids
        ( B ) TYPE: amino acid
        ( D ) TOPOLOGY: linear ( i i ) MOLECULE TYPE: protein ( x i ) SEQUENCE DESCRIPTION: SEQ ID NO:28:

```
Gly  Asn  Glu  Met  Thr  Asn  Leu  Ala  Phe  Glu  Leu  Asp  Pro  Leu  Glu  Leu
  1                  5                      10                      15

Glu  Glu  Glu  Glu  Ala  Glu  Leu  Gly  Glu  Gln  Ser  Gly  Ser  Ala  Lys  Thr
                    20                      25                      30

Ser  Val  Ser  Ser  Val  Thr  Thr  Pro  Pro  Pro  His  Gly  Lys  Arg  Ile  Pro
               35                      40                      45
```

Phe Phe Lys Lys
    50

(2) INFORMATION FOR SEQ ID NO:29:

(i) SEQUENCE CHARACTERISTICS:
        (A) LENGTH: 180 base pairs
        (B) TYPE: nucleic acid
        (C) STRANDEDNESS: unknown
        (D) TOPOLOGY: unknown (ii) MOLECULE TYPE: DNA (genomic)

(ix) FEATURE:
        (A) NAME/KEY: CDS
        (B) LOCATION: 1..129

(xi) SEQUENCE DESCRIPTION: SEQ ID NO:29:

```
TGG  TCC  TTT  GCC  TGC  GCC  TGT  GCC  GCC  TTC  ATC  CTC  CTC  TTT  CTC  GGC         48
Trp  Ser  Phe  Ala  Cys  Ala  Cys  Ala  Ala  Phe  Ile  Leu  Leu  Phe  Leu  Gly
 1                  5                        10                      15

GGT  CTC  GCC  CTC  CTG  CTG  TTC  TCC  CTG  CCT  CGA  ATG  CCC  CGG  AAC  CCA         96
Gly  Leu  Ala  Leu  Leu  Leu  Phe  Ser  Leu  Pro  Arg  Met  Pro  Arg  Asn  Pro
                20                       25                      30

TGG  GAG  TCC  TGC  ATG  GAT  GCT  GAG  CCC  GAG  CAC  TAACCCTCCT  GCGGCCCTAG         149
Trp  Glu  Ser  Cys  Met  Asp  Ala  Glu  Pro  Glu  His
           35                      40

CGACCCTCAG  GCTTCTTCCC  AGGAAGCGGG  G                                                 180
```

(2) INFORMATION FOR SEQ ID NO:30:

(i) SEQUENCE CHARACTERISTICS:
        (A) LENGTH: 43 amino acids
        (B) TYPE: amino acid
        (D) TOPOLOGY: linear (ii) MOLECULE TYPE: protein (xi) SEQUENCE DESCRIPTION: SEQ ID NO:30:

```
Trp  Ser  Phe  Ala  Cys  Ala  Cys  Ala  Ala  Phe  Ile  Leu  Leu  Phe  Leu  Gly
 1                  5                        10                      15

Gly  Leu  Ala  Leu  Leu  Leu  Phe  Ser  Leu  Pro  Arg  Met  Pro  Arg  Asn  Pro
                20                       25                      30

Trp  Glu  Ser  Cys  Met  Asp  Ala  Glu  Pro  Glu  His
           35                      40
```

(2) INFORMATION FOR SEQ ID NO:31:

(i) SEQUENCE CHARACTERISTICS:
        (A) LENGTH: 411 base pairs
        (B) TYPE: nucleic acid
        (C) STRANDEDNESS: unknown
        (D) TOPOLOGY: unknown (ii) MOLECULE TYPE: DNA (genomic)

(ix) FEATURE:
        (A) NAME/KEY: CDS
        (B) LOCATION: 1..411

(xi) SEQUENCE DESCRIPTION: SEQ ID NO:31:

```
CTC  GGC  TCC  AGC  AAA  TCA  GGC  GAT  AAC  TCC  AGT  TCC  AGT  CTG  GGA  GAT         48
Leu  Gly  Ser  Ser  Lys  Ser  Gly  Asp  Asn  Ser  Ser  Ser  Ser  Leu  Gly  Asp
 1                  5                        10                      15

GTG  GTG  ACT  GGC  ACC  CGC  CGC  CCC  ACA  CCC  CCT  GCC  AGT  ACA  GAG  CAT         96
Val  Val  Thr  Gly  Thr  Arg  Arg  Pro  Thr  Pro  Pro  Ala  Ser  Thr  Glu  His
                20                       25                      30
```

-continued

| GTG | CCC | CCC | TAT | GAC | GTG | GTG | CCT | TCC | ATG | AGG | CCC | ATC | ATC | CTG | GTG | 144 |
| Val | Pro | Pro | Tyr | Asp | Val | Val | Pro | Ser | Met | Arg | Pro | Ile | Ile | Leu | Val | |
| | | 35 | | | | | 40 | | | | | 45 | | | | |
| GGA | CCG | TCG | CTC | AAG | GGC | TAC | GAG | GTT | ACA | GAC | ATG | ATG | CAG | AAA | GCT | 192 |
| Gly | Pro | Ser | Leu | Lys | Gly | Tyr | Glu | Val | Thr | Asp | Met | Met | Gln | Lys | Ala | |
| | 50 | | | | | 55 | | | | | 60 | | | | | |
| TTA | TTT | GAC | TTC | TTG | AAG | CAT | CGG | TTT | GAT | GGC | AGG | ATC | TCC | ATC | ACT | 240 |
| Leu | Phe | Asp | Phe | Leu | Lys | His | Arg | Phe | Asp | Gly | Arg | Ile | Ser | Ile | Thr | |
| 65 | | | | | 70 | | | | | 75 | | | | | 80 | |
| CGT | GTG | ACG | GCA | GAT | ATT | TCC | CTG | GCT | AAG | CGC | TCA | GTT | CTC | AAC | AAC | 288 |
| Arg | Val | Thr | Ala | Asp | Ile | Ser | Leu | Ala | Lys | Arg | Ser | Val | Leu | Asn | Asn | |
| | | | | 85 | | | | | 90 | | | | | 95 | | |
| CCC | AGC | AAA | CAC | ATC | ATC | ATT | GAG | CGC | TCC | AAC | ACA | CGC | TCC | AGC | CTG | 336 |
| Pro | Ser | Lys | His | Ile | Ile | Ile | Glu | Arg | Ser | Asn | Thr | Arg | Ser | Ser | Leu | |
| | | | 100 | | | | | 105 | | | | | 110 | | | |
| GCT | GAG | GTG | CAG | AGT | GAA | ATC | GAG | CGA | ATC | TTC | GAG | CTG | GCC | CGG | ACC | 384 |
| Ala | Glu | Val | Gln | Ser | Glu | Ile | Glu | Arg | Ile | Phe | Glu | Leu | Ala | Arg | Thr | |
| | | 115 | | | | | 120 | | | | | 125 | | | | |
| CTT | CAG | TTG | GTC | GCT | CTG | GAT | GCT | GAC | | | | | | | | 411 |
| Leu | Gln | Leu | Val | Ala | Leu | Asp | Ala | Asp | | | | | | | | |
| | 130 | | | | | 135 | | | | | | | | | | |

(2) INFORMATION FOR SEQ ID NO:32:

(i) SEQUENCE CHARACTERISTICS:
        (A) LENGTH: 137 amino acids
        (B) TYPE: amino acid
        (D) TOPOLOGY: linear (ii) MOLECULE TYPE: protein (xi) SEQUENCE DESCRIPTION: SEQ ID NO:32:

| Leu | Gly | Ser | Ser | Lys | Ser | Gly | Asp | Asn | Ser | Ser | Ser | Ser | Leu | Gly | Asp |
| 1 | | | | 5 | | | | | 10 | | | | | 15 | |
| Val | Val | Thr | Gly | Thr | Arg | Arg | Pro | Thr | Pro | Pro | Ala | Ser | Thr | Glu | His |
| | | | 20 | | | | | 25 | | | | | 30 | | |
| Val | Pro | Pro | Tyr | Asp | Val | Val | Pro | Ser | Met | Arg | Pro | Ile | Ile | Leu | Val |
| | | 35 | | | | | 40 | | | | | 45 | | | |
| Gly | Pro | Ser | Leu | Lys | Gly | Tyr | Glu | Val | Thr | Asp | Met | Met | Gln | Lys | Ala |
| | 50 | | | | | 55 | | | | | 60 | | | | |
| Leu | Phe | Asp | Phe | Leu | Lys | His | Arg | Phe | Asp | Gly | Arg | Ile | Ser | Ile | Thr |
| 65 | | | | | 70 | | | | | 75 | | | | | 80 |
| Arg | Val | Thr | Ala | Asp | Ile | Ser | Leu | Ala | Lys | Arg | Ser | Val | Leu | Asn | Asn |
| | | | | 85 | | | | | 90 | | | | | 95 | |
| Pro | Ser | Lys | His | Ile | Ile | Ile | Glu | Arg | Ser | Asn | Thr | Arg | Ser | Ser | Leu |
| | | | 100 | | | | | 105 | | | | | 110 | | |
| Ala | Glu | Val | Gln | Ser | Glu | Ile | Glu | Arg | Ile | Phe | Glu | Leu | Ala | Arg | Thr |
| | | 115 | | | | | 120 | | | | | 125 | | | |
| Leu | Gln | Leu | Val | Ala | Leu | Asp | Ala | Asp | | | | | | | |
| | 130 | | | | | 135 | | | | | | | | | |